US011441150B2

(12) United States Patent
Lavoie et al.

(10) Patent No.: US 11,441,150 B2
(45) Date of Patent: Sep. 13, 2022

(54) CPMV ENHANCER ELEMENTS

(71) Applicant: Medicago Inc., Quebec (CA)

(72) Inventors: Pierre-Olivier Lavoie, Quebec (CA); Marc-Andre D'Aoust, Quebec (CA)

(73) Assignee: Medicago Inc., Quebec (CA)

( * ) Notice: Subject to any disclaimer, the term of this patent is extended or adjusted under 35 U.S.C. 154(b) by 207 days.

(21) Appl. No.: 15/110,696

(22) PCT Filed: Jan. 8, 2015

(86) PCT No.: PCT/CA2015/050009
§ 371 (c)(1),
(2) Date: Jul. 8, 2016

(87) PCT Pub. No.: WO2015/103704
PCT Pub. Date: Jul. 16, 2015

(65) Prior Publication Data

US 2017/0029832 A1 Feb. 2, 2017

Related U.S. Application Data

(63) Continuation-in-part of application No. PCT/CA2014/050326, filed on Mar. 28, 2014.

(60) Provisional application No. 61/925,852, filed on Jan. 10, 2014.

(30) Foreign Application Priority Data

Mar. 28, 2014 (CA) ................. PCT/CA2014/050326

(51) Int. Cl.
*C12N 15/82* (2006.01)
*C12N 7/04* (2006.01)

(52) U.S. Cl.
CPC ......... *C12N 15/8216* (2013.01); *C12N 7/045* (2013.01); *C12N 15/8251* (2013.01)

(58) Field of Classification Search
None
See application file for complete search history.

(56) References Cited

U.S. PATENT DOCUMENTS

| | | | | |
|---|---|---|---|---|
| 5,958,422 | A | 9/1999 | Lomonossoff | |
| 6,042,832 | A | 3/2000 | Koprowski | |
| 6,287,570 | B1 | 9/2001 | Foley | |
| 6,489,537 | B1 | 12/2002 | Rea | |
| 7,125,978 | B1 | 10/2006 | Vezina | |
| 7,132,291 | B2 | 11/2006 | Cardineau | |
| 7,618,815 | B2 | 11/2009 | Ghabrial | |
| 7,763,450 | B2 | 7/2010 | Robinson | |
| 8,124,103 | B2 | 2/2012 | Yibov | |
| 8,519,113 | B2 * | 8/2013 | Lomonossoff ..... | C12N 15/8203 435/320.1 |
| 8,674,084 | B2 * | 3/2014 | Sainsbury .......... | C12N 15/8203 536/23.72 |
| 9,056,901 | B2 | 6/2015 | Song | |
| 9,555,094 | B2 | 1/2017 | Kuroda | |
| 2001/0006950 | A1 | 7/2001 | Punnonen | |
| 2004/0268442 | A1 | 12/2004 | Miller | |
| 2005/0091706 | A1 | 4/2005 | Klimyuk | |
| 2006/0252132 | A1 | 11/2006 | Yang | |
| 2009/0181460 | A1 * | 7/2009 | Lomonossoff ..... | C12N 15/8203 435/468 |
| 2010/0287670 | A1 | 11/2010 | Sainsbury | |
| 2012/0207786 | A1 | 8/2012 | Smith | |

FOREIGN PATENT DOCUMENTS

| | | |
|---|---|---|
| WO | 2001048145 | 7/2001 |
| WO | 2004/098533 | 11/2004 |
| WO | 2006/119516 | 9/2006 |
| WO | 2007/011904 | 1/2007 |
| WO | 2007/047831 | 4/2007 |
| WO | 2007/095318 | 8/2007 |
| WO | 2008/148104 | 4/2008 |
| WO | 2009/076778 | 6/2009 |
| WO | WO 2009/076778 A1 * | 6/2009 |
| WO | 2009/087391 | 7/2009 |
| WO | 2010/003225 | 1/2010 |
| WO | 2010117786 A1 | 10/2010 |
| WO | 2010/148511 | 12/2010 |
| WO | 2011/035422 | 3/2011 |
| WO | 2011028914 | 3/2011 |
| WO | 2012047941 A2 | 4/2012 |

(Continued)

OTHER PUBLICATIONS

Sainsbury et al., Plant Biotech J 7:682-93, 682 (2009).*
Sainsbury et al., Annu Rev Phytopathol 48:437-55 (2010).*
Serizawa et al., J Mol Diagn 12(4):402-08, 403 (2010).*
Sainsbury & Lomonossoff, Plant Physiol 148:1212-18 (2008).*
Fischetti, Clin Microbiol Rev 2(3):285 314 (1989).*
Merriam-Webster, Definition of Define, accessed Jun. 26, 2018.*
Sainsbury et al., Annu Rev Phtopahtol 48:437-55 (2010).*
Holness et al. (1989) Virol 172:311-20.*
Cañizares et al. (2006) Plant Biotech J 4:183-93.*
Sainsbury et al. (2009) Plant Biotech J 7:682-93.*
Sainsbury & Lomonossoff (2008) Plant Physiol 148:1212-18.*

(Continued)

*Primary Examiner* — Russell T Boggs
(74) *Attorney, Agent, or Firm* — Quarles & Brady LLP

(57) ABSTRACT

An expression enhancer comprising a CPMV 5'UTR nucleotide sequence consisting of X nucleotides (CMPVX), where X=160, 155, 150, or 114 of SEQ ID NO:1, or consisting of a nucleotide sequence comprising from about 80% to 100% sequence similarity with CMPVX, where X=160, 155, 150, or 114 of SEQ ID NO:1 SEQ ID NO:1 is provided. The expression enhancer may further comprise a stuffer sequence fused to the 3' end of the 5'UTR nucleotide sequence (CMPVX+, where X=160, 155, 150, or 114 of SEQ ID NO:1). The stuffer sequence may comprise one or more plant kozak sequences. Plants comprising the expression enhancer and methods using the expression enhancer are also described.

11 Claims, 55 Drawing Sheets

Specification includes a Sequence Listing.

(56) References Cited

FOREIGN PATENT DOCUMENTS

| | | |
|---|---|---|
| WO | 2012/083445 | 6/2012 |
| WO | 2012126123 | 9/2012 |
| WO | 2012/058762 | 10/2012 |
| WO | 2012/171104 | 12/2012 |
| WO | 2013/043067 | 3/2013 |
| WO | 2013/044390 | 4/2013 |
| WO | 2013/068593 | 5/2013 |
| WO | 2014/153674 | 10/2014 |

OTHER PUBLICATIONS

Lohman et al. (2011) "DNA ligases" in Curr Protoc Mol Biol Chapters, Unit 3.14.*
Nsil (2020) New England Biolabs (accessed Jul. 29, 2020).*
Amann & Brosius (1985) Gene 40(2-3):183-90.*
Oppmann et al. (2000) Immunity 13:715-25.*
Pushko, Influenza virus-like particles comprised of the HA, NA and M1 proteins of H9N2 influenza virus induce protective immune responses in BALB/c mice, Vaccine, (2005) vol. 23, pp. 5751-5759.
Quan, et al., Virus-like particle vaccine induces protective immunity against homologous and heterologous strains of influenza virus, Journal of Virology (2007) 81(7): 3514-3524.
Rivard, et al., An in-built proteinase inhibitor system for the protection of recombinant proteins recovered from transgenic plants, Plant Biotechnology Journal, 4, pp. 359-368, 2006.
Rohill, et al., 3'-Terminal nucleotide sequences important for the accumulation of Cowpea Mosaic Virus M-RNA, Virology, 1993, vol. 193, pp. 672-679.
Restriction Requirement in U.S. Appl. No. 12/300,922, dated Apr. 21, 2011, 11 pages.
Sainsbury, et al., Expression of multiple proteins using full-length and deleted versions of cowpea mosaic virus RNA-2, Plant Biotechnology Journal, vol. 6, 2008, pp. 82-92.
Sainsbury, et al., Cowpea Mosaic Virus: The Plant Virus-Based Biotechnology Workhorse, Ann. Rev. Phytopathol. 48, pp. 437-455, 2010.
Saint-Jore-Dupas, et al., From planta to pharma with glycosylation in the toolbox, Trends in Biotechnology (2007) 25(7) pp. 317-328.
Shoji, et al., Plant-expressed HA as a seasonal influenza vaccine candidate, Vaccine. (2008) vol. 26, pp. 2930-2934.
Shoji, et al., A plant-produced H1N1 trimeric hemagglutinin protects mice from a lethal influenza virus challenge, Human Vaccines and Immunotherapeutics, vol. 9, 2013, pp. 553-560.
Shorrosh, et al., Sequence analysis and developmental expression of an alfalfa protein disulfide isomerase, Plant Molecular Biology, vol. 19, pp. 319-321, 1992.
Shorrosh, Molecular Cloning of a Putative Plant Endomembrane Protein Resembling Vertebrate Protein Disulfide-Isomerase and a Phosphatidylinositol-Specific Phospholipase C, Proceedings of the National Academy of Sciences, (Dec. 1, 1991)vol. 88:23, pp. 10941-10945.
Song, et al., Protective Immunity against H5N1 Influenza virus by a single dose vaccination with virus-like particles, Virology, 2010, vol. 405(1), 165-175.
Sorensen, Advanced genetic strategies for recombinant protein expression in *Escherichia coli*, Journal of Biotechnology 115 (2005) pp. 113-128.
Treanor, Safety and immunogenicity of a Baculovirus-expressed hemagglutinin influenza vaccine: a randomized control trial, Journal of the American Medical Association, (2007) vol. 297:14, pp. 1577-1582.
U.S. Appl. No. 61/806,227 (No copy provided).
Van Bokhoven, et al., Cis- and trans-acting elements in cowpea mosaic virus RNA Replication, Virology, 1993, 195, 377-386.
Van Ree, et al., Beta (1,2)-Xylose and alpha (1,3)-fucose residues have a strong contribution in IgE binding to plant glycoallergens, Journal of Biological Chemistry, (2000) vol. 275:15, 11451-11458.
Verch, et al., Expression and assembly of a full-length monoclonal antibody in plants using a plant virus vector, J. Immunol. Methods 220, 69-75 (1998).
Verver, et al., Studies on movement of Cowpea Mosaic Virus using the jellyfish green fluorscent protein, Virology 242, 22-27, 1998.
Wang, et al., Viral proteins function as ion channels, Biochimica et Biophysica Acta. vol 1808:2, Feb. 2011, pp. 510-515.
Wang, et al., Role of plant heat-shock proteins and molecular chaperones in the abiotic stress response, Trends in Plant Science, vol. 9:5, 2004, pp. 244-252.
Wellink, et al., Mutational Analysis of AUG Codons of Cowpea Mosaic Virus M RNA, Biochimie 1993, 75(8), pp. 741-747.
Whitelam, The Production of Recombinant Proteins in Plants, (J Sci Food Agric, 68, pp. 1-9, 1995).
Wilson, et al., Core alpha 1,3-fucose is a key part of the epitope recognized by antibodies reacting against plant N-linked oligosaccharides and is present in a wide variety of plant extracts, Glycobiology (1998) vol. 8:7, 651-661.
Written Opinion and Search Report dated Dec. 15, 2016 re SG 1120150928Q.
Wydro, et al., Optimization of transient Agrobacterium-mediated gene expression system in leaves of Nicotiana benthamiana, Acta Biochimica Polonica (2006) 53(2), 289-298.
Yokoyama, et al., Co-expression of human chaperone Hsp70 and Hsdj or Hsp40 co-factor increases solubility of overexpressed target proteins in insect cells, Biochimica et Biophysica Acta 1493 (2000) pp. 119-124.
Yusibov, et al., Antigens produced in plants by infection with chimeric viruses immunize against rabies virus and HIB-1, Proc. Nat'l. Acad. Sci. USA vol. 94, pp. 5784-5788, 1997.
Monger, et al., An antibody derivative expressed from viral vectors passively immunizes pigs against transmissible gastroenteritis virus infection when supplied orally in crude plant extracts, Plant Biotechnology Journal, 2006, vol. 4, pp. 623-631.
Rangan, et al., Analysis of Context Sequence Surrounding Translation Initiation Site from Complete Genome of Model Plants, Mol. Biotechnol., 2008, vol. 39, pp. 207-213.
Sainsbury, et al., Extremely high-level and rapid transient protein production in plants without the use of viral replication, Plant Physiology. (2008) vol. 148, 1212-1218.
Sainsbury, et al., pEAQ: versatile expression vectors for easy and quick transient expression of heterologous proteins in plants, Plant Biotechnology Journal (2009), 7, pp. 682-693.
Sainsbury, et al., Cowpea mosaic virus-based expression vectors, In K Hefferon, ed, Virus Expression Vectors. Transworld Research Network, Kerala, India, pp. 339-555 (2007).
Sainsbury, et al., Cowpea Mosaic Virus-Based Systems for the Expression of Antigens and Antibodies in Plants, Methods in Molecular Biology, Recombinant Proteins From Plants, 2009, Chapter 2, vol. 483: 25-39.
Alamillo, et al., Use of virus vectors for the expression in plants of active full-length and single chain anti-coronavirus antibodies, Biotechnol. J., 2006, vol. 1, 1103-1111.
Bianchi, et al., Universal Influenza B Vaccine Based on the Maturational Cleavage Site of the Hemagglutinin Precursor, Journal of Virology, 2005, pp. 7380-7388.
Canizares, et al., A bipartite system for the constitutive an inducible expression of high levels of foreign proteins in plants, Plant Biotechnology Journal (2006), vol. 4, pp. 183-193.
Chandler, Influenza Hemagglutinin Expression in Nicotiana tabacum and Nicotiana benthamiana, Masters in Science Thesis, Baylor University, Waco, Texas, 2007, 70 pages.
Charland, et al., An Innovative VLP-based technology to respond to Global Influenza Vaccine Needs, Poster Abstracts, IDSA Seasonal and Pandemic Influenza Meeting, Arlington, Virginia, USA, 2008.
Chen, et al., Influenza virus hemagglutinin and neuraminidase, but not the matrix protein, are required for assembly and budding of plasmid-derived virus-like particles, J. Virol. (2007) 81: 13 7111-7123.
Chen, et al., Structure of the Hemagglutinin Precursor Cleavage Site, a Determinant of Influenza Pathogenicity and the Origin of the Labile Conformation, Cell, vol. 95, pp. 409-417, 1998.

(56) References Cited

OTHER PUBLICATIONS

D'Aoust, et al., Influenza virus-like particles produced by transient expression in Nicotiana benthamiana induce a protective immune response against a lethal viral challenge in mice, Plant Biotechnology Journal (2008) vol. 6, pp. 930-940.
Denis, et al., Immunogenicity of papaya mosaic virus-like particles fused to a hepatitis C virus epitope: Evidence for the critical function of multimerization, Virology 363 (2007) 59-68.
Ellis, The molecular chaperone concept, Seminars in Cell Biology, 1990 (1):1-9 (abstract only).
Extended European Search Report from EP 14773061.8, dated Oct. 18, 2016, 8 pages.
GenBank Accession AGX20074.1.
GenBank Accession EF541394.1 Apr. 1, 2007.
GenBank Accession GQ497237.1.
Genbank Accession No. AY289929, Influenza A virus (A/Caledonia/20/99(H1N1)) hemagglutinin (HA) gene., 2003.
Gleba, et al., Engineering viral expression vectors for plant: the full virus and the deconstructed virus strategies (2004) Curr. Opin. In Plant Biol. 7:182-188.
Gopinath, et al., Engineering Cowpea Mosaic Virus RNA-2 into a vector to express Heterologous proteins in plants, Virology, 2000, vol. 267(2), pp. 159-173.
Grgacic, et al., Virus-like particles: Passport to immune recognition, Methods (2006) 40, pp. 60-65.
Hahn, Expression of hemagglutinin-neuraminidase protein of Newcastle disease virus in transgenic tobacco, Plant Biotechnology Reporter, (2007) vol. 1, pp. 85-92.
Hartl, Molecular chaperones in cellular protein folding, Nature, (1996) vol. 381, Jun. 13, pp. 571-580.
Hoffmann, et al., Eight-plasmid system for rapid generation of influenza virus vaccines, Vaccine, vol. 20, pp. 3165-3170, 2002.
Holness, et al., Identification of the initiation codons for translation of Cowpea Mosaic Virus middle component RNA using site-directed mutagenesis of an infectious cDNA Clone, Virology, 1989, vol. 172(1), pp. 311-320.
Horimoto, et al., The development and characterization of H5 influenza virus vaccines derived from a 2003 human isolate, Vaccine (2006) vol. 24, pp. 3669-3676.
Houston, et al., Phylogenetic Analyses Identify 10 Classes of the Protein Disulfide Isomerase Family in Plants, Including Single-Domain Protein Disulfide Isomerase-Related Proteins, Plant Physiology, 2005, vol. 137, pp. 762-778.
Huang, et al., Virus-like particle expression and assembly in plants: hepatitis B and Norwalk viruses. Vaccine (2005) 23:1851-8.
International Search Report in PCT/CA2015/050240, dated Jun. 25, 2015, 11 pages.
International Search Report in PCT/CA2014/050326, dated Jul. 16, 2014, 5 pagest.
International Search Report in PCT/CA2015/050009, dated Apr. 17, 2015, 16 pages.
Kanagarajan, et al., Transient expression of hemagglutinin antigen from low pathogenic avian influenza A (H7N7) in Nicotiana benthamiana, PLoS ONE, 7/3, pp. 1-10, 2012.
Klopfleisch, et al., Neurotropism of Highly Pathogenic Avian Influenza Virus A/Chicken/Indonesia/2003 (H5N1) in Experimentally Infected Pigeons (*Columbia livia* f. domestica), Vet Pathol. vol. 43, pp. 463-470, 2006.
Kobayashi, et al., Chaperones Hsp70 and Hsp40 Suppress Aggregate Formation and Apoptosis in cultured Neuronal Cells Expressing Truncated Androgen Receptor Protein with Expanded Polyglutamine Tract (The Journal of Biological Chemistry, 275(12), pp. 8772-8778, 2000.
Kozak, At least six nucleotides preceding the AUG initiator codon enhance translation in mammalian cells, J. Mol. Biol., 1987, vol. 196(4), pp. 947-950.
Landry, et al., Preclinical and clinical development of plant-made virus-like particle vaccine against avian H5N1 influenza, PLOS One, vol. 5:12, pp. e15559, 2010.
Liu, et al., Cowpea mosaic virus-based systems for the production of antigens and antibodies in plants, Vaccine 23 (2005) pp. 1788-1792.
Lomonossoff, et al., Cowpea mosaic virus as a versatile system for the expression of foreign peptides and proteins in legumes, Molecular Farming. Proceedings of the OECD workshop, La Grande Motte, France, Sep. 3-6, 2000 (2001) pp. 151-160.
Ma, et al., The Production of Recombinant Pharmaceutical Proteins in Plants, Nature 2003, vol. 4, pp. 794-805.
Marozin, et al., Antigenic and genetic diversity among swine influenza A H1N1 and H1N2 viruses in Europe, Journal of General Virology, (2002) 83, 735-745.
Mason, Expression of Norwalk virus capsid protein in transgenic tobacco and potato and its oral immunogenicity in mice, Proceedings of the National Academy of Sciences USA, (1996) vol. 93, pp. 5335-5340.
Mechtcheriakova, et al., The use of viral vectors to produce hepatitis B virus core particles in plants, Journal of Virological Methods, Amsterdam, NL, vol. 131, No. 1, Jan. 2006 (Jan. 2006), pp. 10-15.
Mett, A plant-produced influenza subunit vaccine protects ferrets against virus challenge, Influenza Other Resp. Viruses (2008) 2(1):33-40.
Mortimer, et al., Setting up a platform for plant-based influenza virus vaccine production in South Africa, BMC Biotechnology 2012, 12:14, pp. 1-10.
Musiychuk, A launch vector for the production of vaccine antigens in plants, Influenza and other respiratory viruses. (2007) vol. 1, pp. 19-25.
Naito, et al., Involvement of Hsp90 in Assembly and Nuclear Import of Influenza Virus RNA Polymerase Subunits, Journal of Virology, 2007, pp. 1339-1349.
Notice of Allowance for U.S. Appl. No. 12/300,922, dated Jun. 11, 2013, 12 pages.
Nuttall, et al., ER-resident chaperone interactions with recombinant antibodies in transgenic plants, Eur. J. Biochem. (2002) vol. 269, pp. 6042-6051.
Office Action in Canadian Application No. 2,651,907, dated Dec. 15, 2011, 5 pages.
Office Action in U.S. Appl. No. 12/300,922, dated Feb. 16, 2012, 19 pages.
Office Action in U.S. Appl. No. 12/300,922, dated Jul. 20, 2011, 16 pages.
Office Action in U.S. Appl. No. 12/300,922, dated Nov. 15, 2012, 16 pages.
Office Action in U.S. Appl. No. 14/779,423, dated Nov. 4, 2016, 21 pages.
Extended European Search Report from European Publication No. 15735364, dated May 26, 2017, 9 pages.
Non-Final Office Action dated Jul. 19, 2017 from U.S. Appl. No. 14/779,423, 27 pages.
Genbank Accession ACU12738.1, Influenza B virus (B/Wisconsin/03/2009), 2009.
Joshi, C.P. An inspection of the domain between putative TATA box and translation start site in 79 plant genes. Nucleic Acids Research. vol. 15:16, 1987.
Genbank Accession AFD32428.2, Influenza A virus (A/Perth/16-RGcH5-3/2009(H3N1)), 2009.
Liu, et al., Agroinfection as a rapid method for propagating Cowpea mosaic virus-based constructs, Journal of Virological Methods (2002) vol. 105, pp. 343-348.
Lu, et al., Insights into Avian influenza virus pathogenicity: the hemagglutinin precursor HA0 of subtype H16 has an alpha-Helix structure in its cleavage site with inefficient HA1/HA2 cleavage. Journal of Virology, 2012, vol. 86:23, pp. 12861-12870.
Attwood, The Babel of Bioinformatics, Science (2000), vol. 290:5491, pp. 471-473.
Baker, et al., Protein Structure Prediction and Structural Genomics, Science 294, 93-96 (2001).
Genbank Accession BAO45161.1, Hypothetical Protein TBH_C2250 (hiolapillus brandeum), 2016.
Klenk, H.-D., et al. "Host cell proteases controlling virus pathogenicity." Trends in microbiology 2.2 (1994): 39-43.

(56) References Cited

OTHER PUBLICATIONS

Sun, X, et al. "Modifications to the hemagglutinin cleavage site control the virulence of a neurotropic H1N1 influenza virus." Journal of virology 84.17 (2010): 8683-8690.
Genbank Accession GQ497234, Binary vector pEQ-HT, complete sequence, 2009.
D'Aoust, et al. The production of hemagglutinin-based virus-like particles in plants: a rapid, efficient and safe response to pandemic influenza. Plant Biotech. J. (2010) 8:607-619.
Accession AFN19371, hemagglutinin (Influenza A virus (A/Singapore/GP1063/2011(H3N2))). 2012.
GenBank Accession AET22022, Hemagglutinin (Influenza B Virus (B/Wisconsin/01/2010)). 2017.

* cited by examiner

Constructs comprising CPMV1-X, when X=160; CPMV160

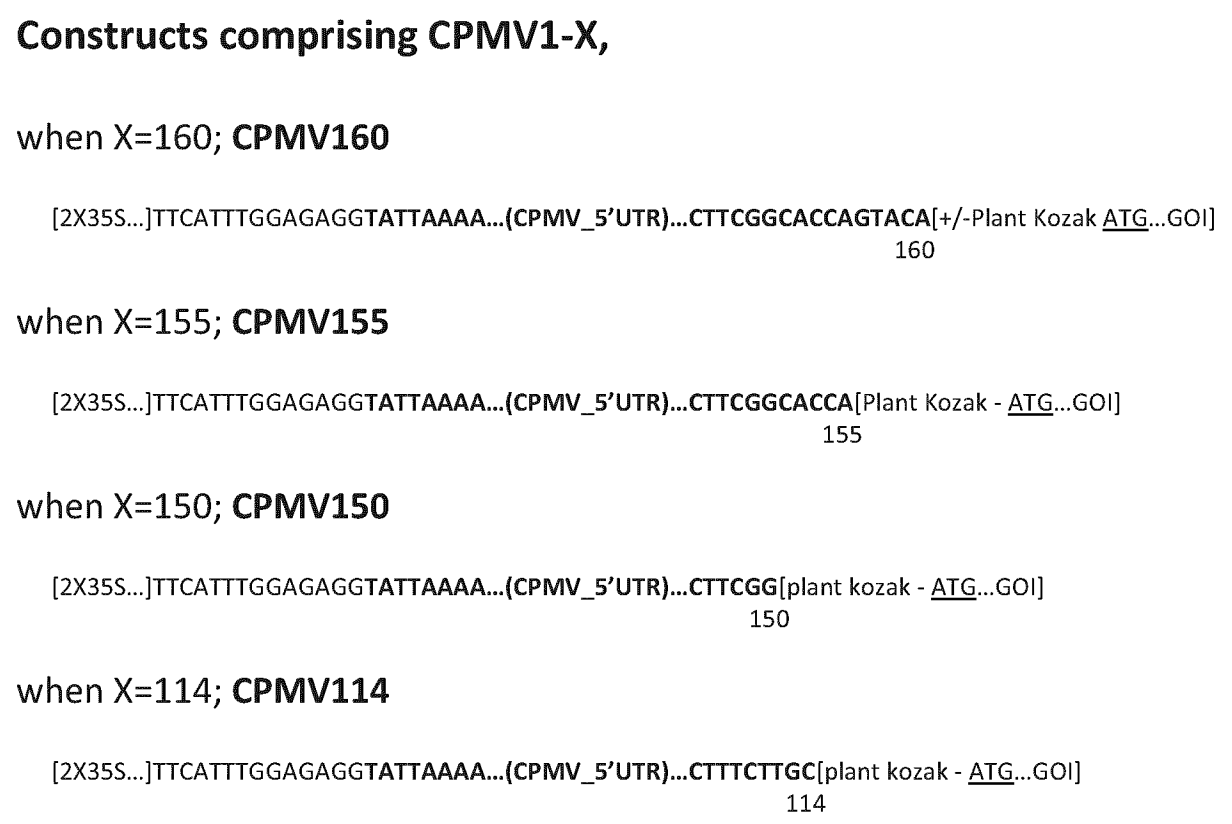

[2X35S...]TTCATTTGGAGAGGTATTAAAA...(CPMV_5'UTR)...CTTCGGCACCAGTACA[+/-Plant Kozak ATG...GOI]
160 when X=155; CPMV155

[2X35S...]TTCATTTGGAGAGGTATTAAAA...(CPMV_5'UTR)...CTTCGGCACCA[Plant Kozak - ATG...GOI]
155 when X=150; CPMV150

[2X35S...]TTCATTTGGAGAGGTATTAAAA...(CPMV_5'UTR)...CTTCGG[plant kozak - ATG...GOI]
150 when X=114; CPMV114

[2X35S...]TTCATTTGGAGAGGTATTAAAA...(CPMV_5'UTR)...CTTTCTTGC[plant kozak - ATG...GOI]
114

Figure 1b

Constructs comprising CPMV1-X+, when X=160; CPMV160+

[2X35S...]TTCATTTGGAGAGGTATTAAAA...(CPMV_5'UTR)...ACCAGTACA*GGGCCCAATACCGCGG*AGAAAATG...(GOI)

when X=155; CPMV155+

[2X35S...]TTCATTTGGAGAGGTATTAAAA...(CPMV_5'UTR)...CTTCGGCACCA*GGGCCCAATACCGCGG*AGAAAATG...GOI
155 when X=150; CPMV150+

[2X35S...]TTCATTTGGAGAGGTATTAAAA...(CPMV_5'UTR)...CTTCGG*GGGCCCAATACCGCGG*AGAAAATG...GOI
150 when X=114; CPMV114+

[2X35S...]TTCATTTGGAGAGGTATTAAAA...(CPMV_5'UTR)...CTTTCTTGC*GGGCCCAATACCGCGG*AGAAAATG...GOI

Figure 1c

Figure 6: A-2X35S/CPMV-HT/ PDISP/H3 Victoria/ NOS (Construct number 1391)

Figure 6A (SEQ ID NO: 67) IF-PDI.S1+3c

AAATTTGTCGGGCCCATGGCGAAAAACGTTGCGATTTTCGGCTTATTG

Figure 6B (SEQ ID NO: 17) IF-H3V36111.s1-4r

ACTAAAGAAAATAGGCCTTCAAATGCAAATGTTGCACCTAATGTTGCCCTT

Figure 6C (SEQ ID NO :18) Nucleotide sequence of PDISP/H3 Victoria.

ATGGCGAAAAACGTTGCGATTTTCGGCTTATTGTTTTCTCTTCTTGTGTTGGTTCCTTCTCAGATCTTCGC
CCAAAAACTTCCTGGAAATGACAACAGCACGGCAACGCTGTGCCTTGGGCACCATGCAGTACCAAACGGAA
CGATAGTGAAAACAATCACGAATGACCAAATTGAAGTTACTAATGCTACTGAGCTGGTTCAGAATTCCTCA
ATAGGTGAAATATGCGACAGTCCTCATCAGATCCTTGATGGAGAAAACTGCACACTAATAGATGCTCTATT
GGGAGACCCTCAGTGTGATGGCTTCCAAAATAAGAAATGGGACCTTTTTGTTGAACGAAGCAAAGCCTACA
GCAACTGTTACCCTTATGATGTGCCGGATTATGCCTCCCTTAGGTCACTAGTTGCCTCATCCGGCACACTG
GAGTTTAACAATGAAAGCTTCAATTGGACTGGAGTCACTCAAAACGGAACAAGTTCTGCTTGCATAAGGAG
ATCTAATAATAGTTTCTTTAGTAGATTAAATTGGTTGACCCACTTAAACTTCAAATACCCAGCATTGAACG
TGACTATGCCAAACAATGAACAATTTGACAAATTGTACATTTGGGGGGTTCACCACCCGGGTACGGACAAG
GACCAAATCTTCCTGTATGCTCAATCATCAGGAAGAATCACAGTATCTACCAAAAGAAGCCAACAAGCTGT
AATCCCGAATATCGGATCTAGACCCAGAATAAGGAATATCCCTAGCAGAATAAGCATCTATTGGACAATAG
TAAAACCGGGAGACATACTTTTGATTAACAGCACAGGGAATCTAATTGCTCCTAGGGGTTACTTCAAAATA
CGAAGTGGGAAAAGCTCAATAATGAGATCAGATGCACCCATTGGCAAATGCAATTCTGAATGCATCACTCC
AAATGGAAGCATTCCCAATGACAAACCATTCCAAAATGTAAACAGGATCACATACGGGGCCTGTCCCAGAT
ATGTTAAGCAAAGCACTCTGAAATTGGCAACAGGAATGCGAAATGTACCAGAGAAACAAACTAGAGGCATA
TTTGGCGCAATAGCGGGTTTCATAGAAAATGGTTGGGAGGGAATGGTGGATGGTTGGTACGGTTTCAGGCA
TCAAAATTCTGAGGGAAGAGGACAAGCAGCAGATCTCAAAAGCACTCAAGCAGCAATCGATCAAATCAATG
GGAAGCTGAATCGATTGATCGGGAAAACCAACGAGAAATTCCATCAGATTGAAAAAGAATTCTCAGAAGTC
GAAGGGAGAATTCAGGACCTTGAGAAATATGTTGAGGACACTAAAATAGATCTCTGGTCATACAACGCGGA
GCTTCTTGTTGCCCTGGAGAACCAACATACAATTGATCTAACTGACTCAGAAATGAACAAACTGTTTGAAA
AAACAAAGAAGCAACTAAGGGAAAATGCTGAGGATATGGGCAATGGTTGTTTCAAAATATACCACAAATGT
GACAATGCCTGCATAGGATCAATCAGAAATGGAACTTATGACCACGATGTATACAGAGATGAAGCATTAAA
CAACCGGTTCCAGATCAAGGGAGTTGAGCTGAAGTCAGGGTACAAAGATTGGATCCTATGGATTTCCTTTG
CCATATCATGTTTTTTGCTTTGTGTTGCTTTGTTGGGGTTCATCATGTGGGCCTGCCAAAAGGGCAACATT
AGGTGCAACATTTGCATTTGA

Figure 6D Schematic representation of construct 1191.
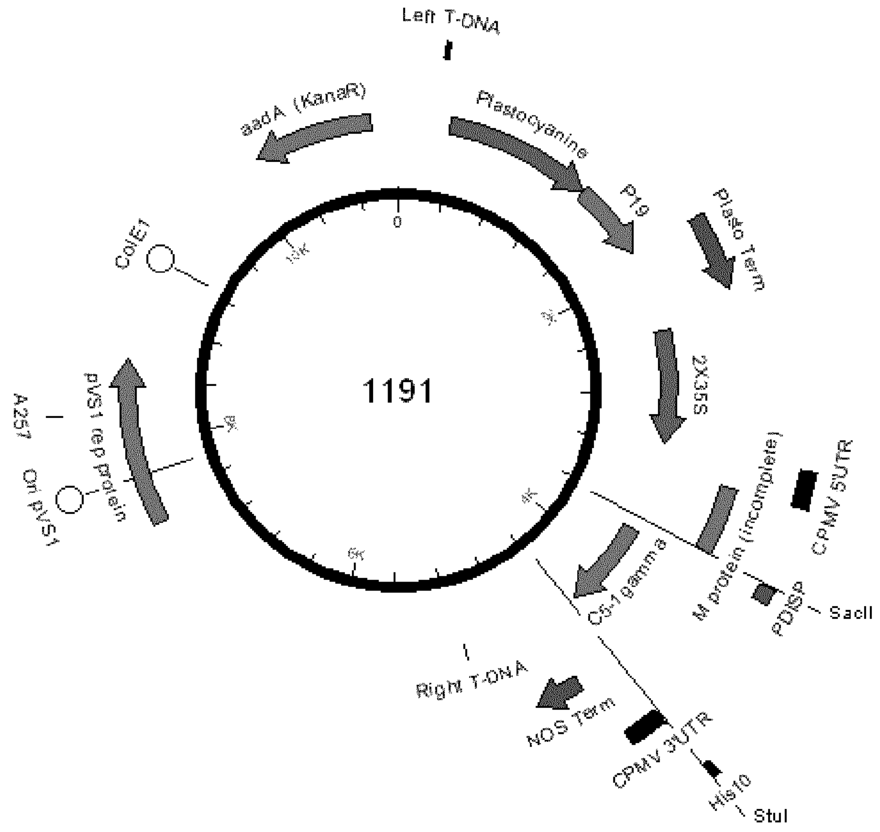

Figure 6E (SEQ ID NO: 19) Construct 1191 from left to right t-DNA borders (underlined). 2X35S/CPMV-HT/NOS with Plastocyanine-P19-Plastocyanine silencing inhibitor expression cassette TGGCAGGATATATTGTGGTGTAAACAAATTGACGCTTAGACAACTTAATAACACATTGCGGACGTTTTTAA
TGTACTGAATTAACGCCGAATCCCGGGCTGGTATATTTATATGTTGTCAAATAACTCAAAAACCATAAAAG
TTTAAGTTAGCAAGTGTGTACATTTTTACTTGAACAAAAATATTCACCTACTACTGTTATAAATCATTATT
AAACATTAGAGTAAAGAAATATGGATGATAAGAACAAGAGTAGTGATATTTTGACAACAATTTTGTTGCAA
CATTTGAGAAAATTTTGTTGTTCTCTCTTTTCATTGGTCAAAAACAATAGAGAGAGAAAAAGGAAGAGGGA
GAATAAAAACATAATGTGAGTATGAGAGAGAAAGTTGTACAAAAGTTGTACCAAAATAGTTGTACAAATAT
CATTGAGGAATTTGACAAAAGCTACACAAATAAGGGTTAATTGCTGTAAATAAATAAGGATGACGCATTAG
AGAGATGTACCATTAGAGAATTTTTGGCAAGTCATTAAAAAGAAAGAATAAATTATTTTTAAAATTAAAAG
TTGAGTCATTTGATTAAACATGTGATTATTTAATGAATTGATGAAAGAGTTGGATTAAAGTTGTATTAGTA
ATTAGAATTTGGTGTCAAATTTAATTTGACATTTGATCTTTTCCTATATATTGCCCCATAGAGTCAGTTAA
CTCATTTTTATATTTCATAGATCAAATAAGAGAAATAACGGTATATTAATCCCTCCAAAAAAAAAAAACGG
TATATTTACTAAAAAATCTAAGCCACGTAGGAGGATAACAGGATCCCCGTAGGAGGATAACATCCAATCCA
ACCAATCACAACAATCCTGATGAGATAACCCACTTTAAGCCCACGCATCTGTGGCACATCTACATTATCTA
AATCACACATTCTTCCACACATCTGAGCCACACAAAAACCAATCCACATCTTTATCACCCATTCTATAAAA
AATCACACTTTGTGAGTCTACACTTTGATTCCCTTCAAACACATACAAAGAGAAGAGACTAATTAATTAAT
TAATCATCTTGAGAGAAAATGGAACGAGCTATACAAGGAAACGACGCTAGGGAACAAGCTAACAGTGAACG
TTGGGATGGAGGATCAGGAGGTACCACTTCTCCCTTCAAACTTCCTGACGAAAGTCCGAGTTGGACTGAGT
GGCGGCTACATAACGATGAGACGAATTCGAATCAAGATAATCCCCTTGGTTTCAAGGAAAGCTGGGGTTTC
GGGAAAGTTGTATTTAAGAGATATCTCAGATACGACAGGACGGAAGCTTCACTGCACAGAGTCCTTGGATC
TTGGACGGGAGATTCGGTTAACTATGCAGCATCTCGATTTTTCGGTTTCGACCAGATCGGATGTACCTATA
GTATTCGGTTTCGAGGAGTTAGTATCACCGTTTCTGGAGGGTCGCGAACTCTTCAGCATCTCTGTGAGATG
GCAATTCGGTCTAAGCAAGAACTGCTACAGCTTGCCCCAATCGAAGTGGAAAGTAATGTATCAAGAGGATG
CCCTGAAGGTACTCAAACCTTCGAAAAAGAAAGCGAGTAAGTTAAAATGCTTCTTCGTCTCCTATTTATAA
TATGGTTTGTTATTGTTAATTTTGTTCTTGTAGAAGAGCTTAATTAATCGTTGTTGTTATGAAATACTATT
TGTATGAGATGAACTGGTGTAATGTAATTCATTTACATAAGTGGAGTCAGAATCAGAATGTTTCCTCCATA
ACTAACTAGACATGAAGACCTGCCGCGTACAATTGTCTTATATTTGAACAACTAAAATTGAACATCTTTTG
CCACAACTTTATAAGTGGTTAATATAGCTCAAATATATGGTCAAGTTCAATAGATTAATAATGGAAATATC
AGTTATCGAAATTCATTAACAATCAACTTAACGTTATTAACTACTAATTTTATATCATCCCCTTTGATAAA
TGATAGTACACCAATTAGGAAGGAGCATGCTCGCCTAGGAGATTGTCGTTTCCCGCCTTCAGTTTGCAAGC
TGCTCTAGCCGTGTAGCCAATACGCAAACCGCCTCTCCCCGCGCGTTGGGAATTACTAGCGCGTGTCGACA
AGCTTGCATGCCGGTCAACATGGTGGAGCACGACACACTTGTCTACTCCAAAAATATCAAAGATACAGTCT
CAGAAGACCAAAGGGCAATTGAGACTTTTCAACAAAGGGTAATATCCGGAAACCTCCTCGGATTCCATTGC
CCAGCTATCTGTCACTTTATTGTGAAGATAGTGGAAAAGGAAGGTGGCTCCTACAAATGCCATCATTGCGA
TAAAGGAAAGGCCATCGTTGAAGATGCCTCTGCCGACAGTGGTCCCAAAGATGGACCCCCACCCACGAGGA
GCATCGTGGAAAAAGAAGACGTTCCAACCACGTCTTCAAAGCAAGTGGATTGATGTGATAACATGGTGGAG
CACGACACACTTGTCTACTCCAAAAATATCAAAGATACAGTCTCAGAAGACCAAAGGGCAATTGAGACTTT
TCAACAAAGGGTAATATCCGGAAACCTCCTCGGATTCCATTGCCCAGCTATCTGTCACTTTATTGTGAAGA
TAGTGGAAAAGGAAGGTGGCTCCTACAAATGCCATCATTGCGATAAAGGAAAGGCCATCGTTGAAGATGCC
TCTGCCGACAGTGGTCCCAAAGATGGACCCCCACCCACGAGGAGCATCGTGGAAAAAGAAGACGTTCCAAC
CACGTCTTCAAAGCAAGTGGATTGATGTGATATCTCCACTGACGTAAGGGATGACGCACAATCCCACTATC
CTTCGCAAGACCCTTCCTCTATATAAGGAAGTTCATTTCATTTGGAGAGGTATTAAAATCTTAATAGGTTT
TGATAAAAGCGAACGTGGGGAAACCCGAACCAAACCTTCTTCTAAACTCTCTCTCATCTCTCTTAAAGCAA
ACTTCTCTCTTGTCTTTCTTGCGTGAGCGATCTTCAACGTTGTCAGATCGTGCTTCGGCACCAGTACAACG
TTTTCTTTCACTGAAGCGAAATCAAAGATCTCTTTGTGGACACGTAGTGCGGCGCCATTAAATAACGTGTA
CTTGTCCTATTCTTGTCGGTGTGGTCTTGGGAAAAGAAAGCTTGCTGGAGGCTGCTGTTCAGCCCCATACA
TTACTTGTTACGATTCTGCTGACTTTCGGCGGGTGCAATATCTCTACTTCTGCTTGACGAGGTATTGTTGC
CTGTACTTCTTTCTTCTTCTTCTTGCTGATTGGTTCTATAAGAAATCTAGTATTTTCTTTGAAACAGAGTT
TTCCCGTGGTTTTCGAACTTGGAGAAAGATTGTTAAGCTTCTGTATATTCTGCCCAAATTTGTCGGGCCCG
CGGATGGCGAAAAACGTTGCGATTTTCGGCTTATTGTTTCTCTTCTTGTGTTGGTTCCTTCTCAGATCTT
CGCCTGCAGGCTCCTCAGCCAAAACGACACCCCCATCTGTCTATCCACTGGCCCCTGGATCTGCTGCCCAA
ACTAACTCCATGGTGACCCTGGGATGCCTGGTCAAGGGCTATTTCCCTGAGCCAGTGACAGTGACCTGGAA
CTCTGGATCCCTGTCCAGCGGTGTGCACACCTTCCCAGCTGTCCTGCAGTCTGACCTCTACACTCTGAGCA
GCTCAGTGACTGTCCCCTCCAGCACCTGGCCCAGCGAGACCGTCACCTGCAACGTTGCCCACCCGGCCAGC AGCACCAAGGTGGACAAGAAAATTGTGCCCAGGGATTGTGGTTGTAAGCCTTGCATATGTACAGTCCCAGA
AGTATCATCTGTCTTCATCTTCCCCCCAAAGCCCAAGGATGTGCTCACCATTACTCTGACTCCTAAGGTCA
CGTGTGTTGTGGTAGACATCAGCAAGGATGATCCCGAGGTCCAGTTCAGCTGGTTTGTAGATGATGTGGAG
GTGCACACAGCTCAGACGCAACCCCGGGAGGAGCAGTTCAACAGCACTTTCCGCTCAGTCAGTGAACTTCC
CATCATGCACCAGGACTGGCTCAATGGCAAGGAGCGATCGCTCACCATCACCATCACCATCACCATCACCA
TTAAAGGCCTATTTTCTTTAGTTTGAATTTACTGTTATTCGGTGTGCATTTCTATGTTTGGTGAGCGGTTT
TCTGTGCTCAGAGTGTGTTTATTTTATGTAATTTAATTTCTTTGTGAGCTCCTGTTTAGCAGGTCGTCCCT
TCAGCAAGGACACAAAAAGATTTTAATTTTATTAAAAAAAAAAAAAAAAAAGACCGGGAATTCGATATCAA
GCTTATCGACCTGCAGATCGTTCAAACATTTGGCAATAAAGTTTCTTAAGATTGAATCCTGTTGCCGGTCT
TGCGATGATTATCATATAATTTCTGTTGAATTACGTTAAGCATGTAATAATTAACATGTAATGCATGACGT
TATTTATGAGATGGGTTTTTATGATTAGAGTCCCGCAATTATACATTTAATACGCGATAGAAAACAAAATA
TAGCGCGCAAACTAGGATAAATTATCGCGCGCGGTGTCATCTATGTTACTAGATCTCTAGAGTCTCAAGCT
TGGCGCGCCCACGTGACTAGTGGCACTGGCCGTCGTTTTACAACGTCGTGACTGGGAAAACCCTGGCGTTA
CCCAACTTAATCGCCTTGCAGCACATCCCCCTTTCGCCAGCTGGCGTAATAGCGAAGAGGCCCGCACCGAT
CGCCCTTCCCAACAGTTGCGCAGCCTGAATGGCGAATGCTAGAGCAGCTTGAGCTTGGATCAGATTGTCGT
TTCCCGCCTTCAGTTTAAACTATCAGTGTTTGACAGGATATATTGGCGGGTAAACCTAAGAGAAAAGAGCG
TTTA

Figure 6E (SEQ ID NO: 19) con't

Figure 6F (SEQ ID NO: 20) Expression cassette number 1391 from 2X35S promoter to NOS terminator. PDISP/H3 Victoria nucleotide sequence is underlined; CPMV 5'UTR in bold; incomplete M protein in italics GTCAACATGGTGGAGCACGACACACTTGTCTACTCCAAAAATATCAAAGATACAGTCTCAGAAGACCAAAG
GGCAATTGAGACTTTTCAACAAAGGGTAATATCCGGAAACCTCCTCGGATTCCATTGCCCAGCTATCTGTC
ACTTTATTGTGAAGATAGTGGAAAAGGAAGGTGGCTCCTACAAATGCCATCATTGCGATAAAGGAAAGGCC
ATCGTTGAAGATGCCTCTGCCGACAGTGGTCCCAAAGATGGACCCCCACCCACGAGGAGCATCGTGGAAAA
AGAAGACGTTCCAACCACGTCTTCAAAGCAAGTGGATTGATGTGATAACATGGTGGAGCACGACACACTTG
TCTACTCCAAAAATATCAAAGATACAGTCTCAGAAGACCAAAGGGCAATTGAGACTTTTCAACAAAGGGTA
ATATCCGGAAACCTCCTCGGATTCCATTGCCCAGCTATCTGTCACTTTATTGTGAAGATAGTGGAAAAGGA
AGGTGGCTCCTACAAATGCCATCATTGCGATAAAGGAAAGGCCATCGTTGAAGATGCCTCTGCCGACAGTG
GTCCCAAAGATGGACCCCCACCCACGAGGAGCATCGTGGAAAAAGAAGACGTTCCAACCACGTCTTCAAAG
CAAGTGGATTGATGTGATATCTCCACTGACGTAAGGGATGACGCACAATCCCACTATCCTTCGCAAGACCC
TTCCTCTATATAAGGAAGTTCATTTCATTTGGAGAGGTATTAAAATCTTAATAGGTTTTGATAAAAGCGAA
CGTGGGGAAACCCGAACCAAACCTTCTTCTAAACTCTCTCTCATCTCTCTTAAAGCAAACTTCTCTCTTGT
CTTTCTTGCGTGAGCGATCTTCAACGTTGTCAGATCGTGCTTCGGCACCAGTACA*ACGTTTTCTTTCACTG*
*AAGCGAAATCAAAGATCTCTTTGTGGACACGTAGTGCGGCGCCATTAAATAACGTGTACTTGTCCTATTCT*
*TGTCGGTGTGGTCTTGGGAAAAGAAAGCTTGCTGGAGGCTGCTGTTCAGCCCCATACATTACTTGTTACGA*
*TTCTGCTGACTTTCGGCGGGTGCAATATCTCTACTTCTGCTTGACGAGGTATTGTTGCCTGTACTTCTTTC*
*TTCTTCTTCTTGCTGATTGGTTCTATAAGAAATCTAGTATTTTCTTTGAAACAGAGTTTTCCCGTGGTTTT*
*CGAACTTGGAGAAAGATTGTTAAGCTTCTGTATATTCTGCCCAAATTTG*TCGGGCCCATGGCGAAAAACGT
TGCGATTTTCGGCTTATTGTTTTCTCTTCTTGTGTTGGTTCCTTCTCAGATCTTCGCCCAAAAACTTCCTG
GAAATGACAACAGCACGGCAACGCTGTGCCTTGGGCACCATGCAGTACCAAACGGAACGATAGTGAAAACA
ATCACGAATGACCAAATTGAAGTTACTAATGCTACTGAGCTGGTTCAGAATTCCTCAATAGGTGAAATATG
CGACAGTCCTCATCAGATCCTTGATGGAGAAAACTGCACACTAATAGATGCTCTATTGGGAGACCCTCAGT
GTGATGGCTTCCAAAATAAGAAATGGGACCTTTTTGTTGAACGAAGCAAAGCCTACAGCAACTGTTACCCT
TATGATGTGCCGGATTATGCCTCCCTTAGGTCACTAGTTGCCTCATCCGGCACACTGGAGTTTAACAATGA
AAGCTTCAATTGGACTGGAGTCACTCAAAACGGAACAAGTTCTGCTTGCATAAGGAGATCTAATAATAGTT
TCTTTAGTAGATTAAATTGGTTGACCCACTTAAACTTCAAATACCCAGCATTGAACGTGACTATGCCAAAC
AATGAACAATTTGACAAATTGTACATTTGGGGGGTTCACCACCCGGGTACGGACAAGGACCAAATCTTCCT
GTATGCTCAATCATCAGGAAGAATCACAGTATCTACCAAAAGAAGCCAACAAGCTGTAATCCCGAATATCG
GATCTAGACCCAGAATAAGGAATATCCCTAGCAGAATAAGCATCTATTGGACAATAGTAAAACCGGGAGAC
ATACTTTTGATTAACAGCACAGGGAATCTAATTGCTCCTAGGGGTTACTTCAAAATACGAAGTGGGAAAAG
CTCAATAATGAGATCAGATGCACCCATTGGCAAATGCAATTCTGAATGCATCACTCCAAATGGAAGCATTC
CCAATGACAAACCATTCCAAAATGTAAACAGGATCACATACGGGGCCTGTCCCAGATATGTTAAGCAAAGC
ACTCTGAAATTGGCAACAGGAATGCGAAATGTACCAGAGAAACAAACTAGAGGCATATTTGGCGCAATAGC
GGGTTTCATAGAAAATGGTTGGGAGGGAATGGTGGATGGTTGGTACGGTTTCAGGCATCAAAATTCTGAGG
GAAGAGGACAAGCAGCAGATCTCAAAAGCACTCAAGCAGCAATCGATCAAATCAATGGGAAGCTGAATCGA
TTGATCGGGAAAACCAACGAGAAATTCCATCAGATTGAAAAAGAATTCTCAGAAGTCGAAGGGAGAATTCA
GGACCTTGAGAAATATGTTGAGGACACTAAAATAGATCTCTGGTCATACAACGCGGAGCTTCTTGTTGCCC
TGGAGAACCAACATACAATTGATCTAACTGACTCAGAAATGAACAAACTGTTTGAAAAAACAAAGAAGCAA
CTAAGGGAAAATGCTGAGGATATGGGCAATGGTTGTTTCAAAATATACCACAAATGTGACAATGCCTGCAT
AGGATCAATCAGAAATGGAACTTATGACCACGATGTATACAGAGATGAAGCATTAAACAACCGGTTCCAGA
TCAAGGGAGTTGAGCTGAAGTCAGGGTACAAAGATTGGATCCTATGGATTTCCTTTGCCATATCATGTTTT
TTGCTTTGTGTTGCTTTGTTGGGGTTCATCATGTGGGCCTGCCAAAAGGGCAACATTAGGTGCAACATTTG
CATTTGAAGGCCTATTTTCTTTAGTTTGAATTTACTGTTATTCGGTGTGCATTTCTATGTTTGGTGAGCGG
TTTTCTGTGCTCAGAGTGTGTTTATTTTATGTAATTTAATTTCTTTGTGAGCTCCTGTTTAGCAGGTCGTC
CCTTCAGCAAGGACACAAAAAGATTTAATTTATTAAAAAAAAAAAAAAAAAAAAGACCGGGAATTCGATAT
CAAGCTTATCGACCTGCAGATCGTTCAAACATTTGGCAATAAAGTTTCTTAAGATTGAATCCTGTTGCCGG
TCTTGCGATGATTATCATATAATTTCTGTTGAATTACGTTAAGCATGTAATAATTAACATGTAATGCATGA
CGTTATTTATGAGATGGGTTTTTATGATTAGAGTCCCGCAATTATACATTTAATACGCGATAGAAAACAAA
ATATAGCGCGCAAACTAGGATAAATTATCGCGCGCGGTGTCATCTATGTTACTAGAT

Figure 6G ( SEQ ID NO: 21) Amino acid sequence of PDISP/H3 Victoria

```
MAKNVAIFGLLFSLLVLVPSQIFAQKLPGNDNSTATLCLGHHAVPNGTIVKTITNDQIEVTNATELVQNSS
IGEICDSPHQILDGENCTLIDALLGDPQCDGFQNKKWDLFVERSKAYSNCYPYDVPDYASLRSLVASSGTL
EFNNESFNWTGVTQNGTSSACIRRSNNSFFSRLNWLTHLNFKYPALNVTMPNNEQFDKLYIWGVHHPGTDK
DQIFLYAQSSGRITVSTKRSQQAVIPNIGSRPRIRNIPSRISIYWTIVKPGDILLINSTGNLIAPRGYFKI
RSGKSSIMRSDAPIGKCNSECITPNGSIPNDKPFQNVNRITYGACPRYVKQSTLKLATGMRNVPEKQTRGI
FGAIAGFIENGWEGMVDGWYGFRHQNSEGRGQAADLKSTQAAIDQINGKLNRLIGKTNEKFHQIEKEFSEV
EGRIQDLEKYVEDTKIDLWSYNAELLVALENQHTIDLTDSEMNKLFEKTKKQLRENAEDMGNGCFKIYHKC
DNACIGSIRNGTYDHDVYRDEALNNRFQIKGVELKSGYKDWILWISFAISCFLLCVALLGFIMWACQKGNI
RCNICI*
```

Figure 6H

Schematic representation of construct number 1391

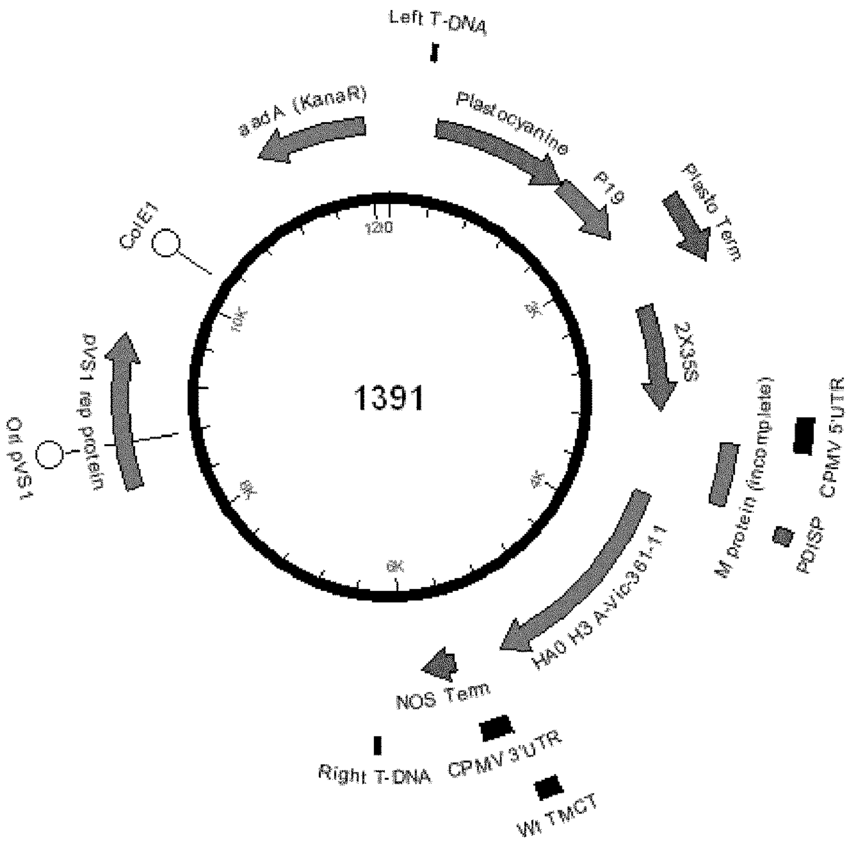

Figure 7: components for 2X35S/CPMV160/PDISP/H3 Victoria/ NOS (Construct number 1800)

Figure 7A (SEQ ID NO: 22) IF**(SacII)-PDI.s1+4c

ACAGGGCCCAATACCGCGGAGAAAATGGCGAAAAACGTTGCGATTTTCGGCT

Figure 7B (SEQ ID NO: 23) IF-H3V36111.s1-4r

ACTAAAGAAAATAGGCCTTCAAATGCAAATGTTGCACCTAATGTTGCCCTT

Figure 7C

Schematic representation of construct 2171. SacII and StuI restriction enzyme sites used for plasmid linearization are annotated on the representation.

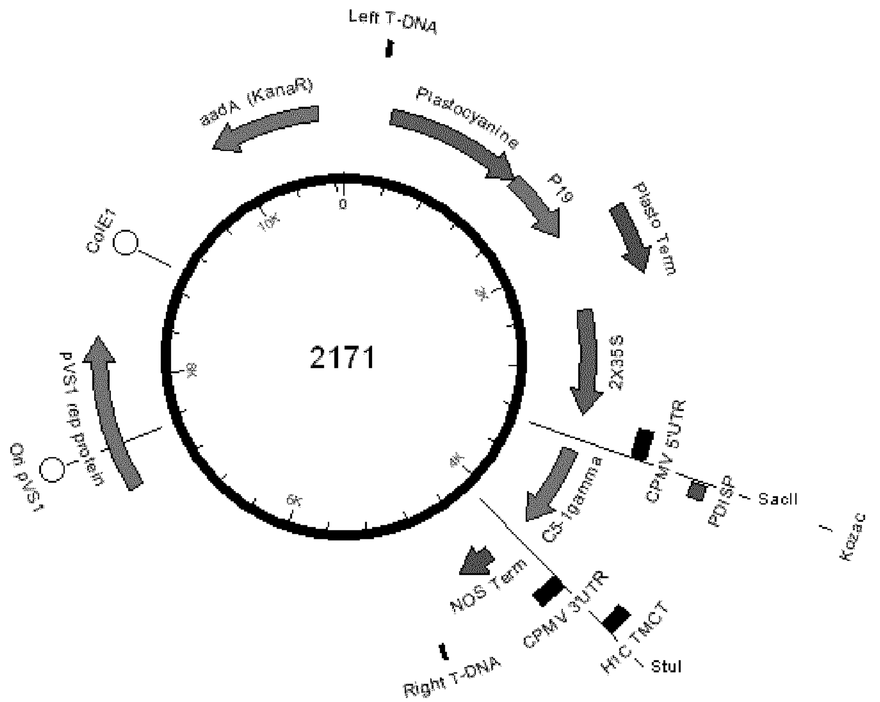

Figure 7D (SEQ ID NO: 25) Construct 2171 from left to right t-DNA borders (underlined). 2X35S/CPMV160/NOS with Plastocyanine-P19-Plastocyanine silencing inhibitor expression cassette TGGCAGGATATATTGTGGTGTAAACAAATTGACGCTTAGACAACTTAATAACACATTGCGGACGTTTTTAA
TGTACTGAATTAACGCCGAATCCCGGGCTGGTATATTTATATGTTGTCAAATAACTCAAAAACCATAAAAG
TTTAAGTTAGCAAGTGTGTACATTTTTACTTGAACAAAAATATTCACCTACTACTGTTATAAATCATTATT
AAACATTAGAGTAAAGAAATATGGATGATAAGAACAAGAGTAGTGATATTTTGACAACAATTTTGTTGCAA
CATTTGAGAAAATTTTGTTGTTCTCTCTTTTCATTGGTCAAAAACAATAGAGAGAGAAAAAGGAAGAGGGA
GAATAAAAACATAATGTGAGTATGAGAGAGAAAGTTGTACAAAAGTTGTACCAAAATAGTTGTACAAATAT
CATTGAGGAATTTGACAAAAGCTACACAAATAAGGGTTAATTGCTGTAAATAAATAAGGATGACGCATTAG
AGAGATGTACCATTAGAGAATTTTTGGCAAGTCATTAAAAAGAAAGAATAAATTATTTTTAAAATTAAAAG
TTGAGTCATTTGATTAAACATGTGATTATTTAATGAATTGATGAAAGAGTTGGATTAAAGTTGTATTAGTA
ATTAGAATTTGGTGTCAAATTTAATTTGACATTTGATCTTTTCCTATATATTGCCCCATAGAGTCAGTTAA
CTCATTTTTATATTTCATAGATCAAATAAGAGAAATAACGGTATATTAATCCCTCCAAAAAAAAAAAACGG
TATATTTACTAAAAAATCTAAGCCACGTAGGAGGATAACAGGATCCCCGTAGGAGGATAACATCCAATCCA
ACCAATCACAACAATCCTGATGAGATAACCCACTTTAAGCCCACGCATCTGTGGCACATCTACATTATCTA
AATCACACATTCTTCCACACATCTGAGCCACACAAAAACCAATCCACATCTTTATCACCCATTCTATAAAA
AATCACACTTTGTGAGTCTACACTTTGATTCCCTTCAAACACATACAAAGAGAAGAGACTAATTAATTAAT
TAATCATCTTGAGAGAAAATGGAACGAGCTATACAAGGAAACGACGCTAGGGAACAAGCTAACAGTGAACG
TTGGGATGGAGGATCAGGAGGTACCACTTCTCCCTTCAAACTTCCTGACGAAAGTCCGAGTTGGACTGAGT
GGCGGCTACATAACGATGAGACGAATTCGAATCAAGATAATCCCCTTGGTTTCAAGGAAAGCTGGGGTTTC
GGGAAAGTTGTATTTAAGAGATATCTCAGATACGACAGGACGGAAGCTTCACTGCACAGAGTCCTTGGATC
TTGGACGGGAGATTCGGTTAACTATGCAGCATCTCGATTTTTCGGTTTCGACCAGATCGGATGTACCTATA
GTATTCGGTTTCGAGGAGTTAGTATCACCGTTTCTGGAGGGTCGCGAACTCTTCAGCATCTCTGTGAGATG
GCAATTCGGTCTAAGCAAGAACTGCTACAGCTTGCCCCAATCGAAGTGGAAAGTAATGTATCAAGAGGATG
CCCTGAAGGTACTCAAACCTTCGAAAAAGAAAGCGAGTAAGTTAAAATGCTTCTTCGTCTCCTATTTATAA
TATGGTTTGTTATTGTTAATTTTGTTCTTGTAGAAGAGCTTAATTAATCGTTGTTGTTATGAAATACTATT
TGTATGAGATGAACTGGTGTAATGTAATTCATTTACATAAGTGGAGTCAGAATCAGAATGTTTCCTCCATA
ACTAACTAGACATGAAGACCTGCCGCGTACAATTGTCTTATATTTGAACAACTAAAATTGAACATCTTTTG
CCACAACTTTATAAGTGGTTAATATAGCTCAAATATATGGTCAAGTTCAATAGATTAATAATGGAAATATC
AGTTATCGAAATTCATTAACAATCAACTTAACGTTATTAACTACTAATTTTATATCATCCCCTTTGATAAA
TGATAGTACACCAATTAGGAAGGAGCATGCTCGCCTAGGAGATTGTCGTTTCCCGCCTTCAGTTTGCAAGC
TGCTCTAGCCGTGTAGCCAATACGCAAACCGCCTCTCCCCGCGCGTTGGGAATTACTAGCGCGTGTCGACA
AGCTTGCATGCCGGTCAACATGGTGGAGCACGACACACTTGTCTACTCCAAAAATATCAAAGATACAGTCT
CAGAAGACCAAAGGGCAATTGAGACTTTTCAACAAAGGGTAATATCCGGAAACCTCCTCGGATTCCATTGC
CCAGCTATCTGTCACTTTATTGTGAAGATAGTGGAAAAGGAAGGTGGCTCCTACAAATGCCATCATTGCGA
TAAAGGAAAGGCCATCGTTGAAGATGCCTCTGCCGACAGTGGTCCCAAAGATGGACCCCCACCCACGAGGA
GCATCGTGGAAAAAGAAGACGTTCCAACCACGTCTTCAAAGCAAGTGGATTGATGTGATAACATGGTGGAG
CACGACACACTTGTCTACTCCAAAAATATCAAAGATACAGTCTCAGAAGACCAAAGGGCAATTGAGACTTT
TCAACAAAGGGTAATATCCGGAAACCTCCTCGGATTCCATTGCCCAGCTATCTGTCACTTTATTGTGAAGA
TAGTGGAAAAGGAAGGTGGCTCCTACAAATGCCATCATTGCGATAAAGGAAAGGCCATCGTTGAAGATGCC
TCTGCCGACAGTGGTCCCAAAGATGGACCCCCACCCACGAGGAGCATCGTGGAAAAAGAAGACGTTCCAAC
CACGTCTTCAAAGCAAGTGGATTGATGTGATATCTCCACTGACGTAAGGGATGACGCACAATCCCACTATC
CTTCGCAAGACCCTTCCTCTATATAAGGAAGTTCATTTCATTTGGAGAGGTATTAAAATCTTAATAGGTTT
TGATAAAAGCGAACGTGGGGAAACCCGAACCAAACCTTCTTCTAAACTCTCTCTCATCTCTCTTAAAGCAA
ACTTCTCTCTTGTCTTTCTTGCGTGAGCGATCTTCAACGTTGTCAGATCGTGCTTCGGCACCAGTACAGGG
CCCAATACCGCGGAGAAAATGGCGAAAAACGTTGCGATTTTCGGCTTATTGTTTTCTCTTCTTGTGTTGGT
TCCTTCTCAGATCTTCGCGACGTCACTCCTCAGCCAAAACGACACCCCCATCTGTCTATCCACTGGCCCCT GGATCTGCTGCCCAAACTAACTCCATGGTGACCCTGGGATGCCTGGTCAAGGGCTATTTCCCTGAGCCAGT
GACAGTGACCTGGAACTCTGGATCCCTGTCCAGCGGTGTGCACACCTTCCCAGCTGTCCTGCAGTCTGACC
TCTACACTCTGAGCAGCTCAGTGACTGTCCCCTCCAGCACCTGGCCCAGCGAGACCGTCACCTGCAACGTT
GCCCACCCGGCCAGCAGCACCAAGGTGGACAAGAAAATTGTGCCCAGGGATTGTGGTTGTAAGCCTTGCAT
ATGTACAGTCCCAGAAGTATCATCTGTCTTCATCTTCCCCCCAAAGCCCAAGGATGTGCTCACCATTACTC
TGACTCCTAAGGTCACGTGTGTTGTGGTAGACATCAGCAAGGATGATCCCGAGGTCCAGTTCAGCTGGTTT
GTAGATGATGTGGAGGTGCACACAGCTCAGACGCAACCCCGGGAGGAGCAGTTCAACAGCACTTTCCGCTC
AGTCAGTGAACTTCCCATCATGCACCAGGACTGGCTCAATGGCAAGGAGACGTCCAGATTTTGGCGATCTA
TTCAACTGTCGCCAGTTCATTGGTACTGGTAGTCTCCCTGGGGGCAATCAGTTTCTGGATGTGCTCTAATG
GGTCTCTACAGTGTAGAATATGTATTTAAAGGCCTATTTTCTTTAGTTTGAATTTACTGTTATTCGGTGTG
CATTTCTATGTTTGGTGAGCGGTTTTCTGTGCTCAGAGTGTGTTTATTTTATGTAATTTAATTTCTTTGTG
AGCTCCTGTTTAGCAGGTCGTCCCTTCAGCAAGGACACAAAAAGATTTAATTTTATTAAAAAAAAAAAAA
AAAAAGACCGGGAATTCGATATCAAGCTTATCGACCTGCAGATCGTTCAAACATTTGGCAATAAAGTTTCT
TAAGATTGAATCCTGTTGCCGGTCTTGCGATGATTATCATATAATTTCTGTTGAATTACGTTAAGCATGTA
ATAATTAACATGTAATGCATGACGTTATTTATGAGATGGGTTTTTATGATTAGAGTCCCGCAATTATACAT
TTAATACGCGATAGAAAACAAAATATAGCGCGCAAACTAGGATAAATTATCGCGCGCGGTGTCATCTATGT
TACTAGATCTCTAGAGTCTCAAGCTTGGCGCGCCCACGTGACTAGTGGCACTGGCCGTCGTTTTACAACGT
CGTGACTGGGAAAACCCTGGCGTTACCCAACTTAATCGCCTTGCAGCACATCCCCCTTTCGCCAGCTGGCG
TAATAGCGAAGAGGCCCGCACCGATCGCCCTTCCCAACAGTTGCGCAGCCTGAATGGCGAATGCTAGAGCA
GCTTGAGCTTGGATCAGATTGTCGTTTCCCGCCTTCAGTTTAAACTATCAGTGTTTGACAGGATATATTGG
CGGGTAAACCTAAGAGAAAAGAGCGTTTA

Figure 7D (SEQ ID NO: 25) con't

Figure 7E (SEQ ID NO: 26) Expression cassette number 1800 from 2X35S promoter to NOS terminator. PDISP/H3 Victoria nucleotide sequence is underlined; 5'UTR in bold; plant kozak sequence double underline GTCAACATGGTGGAGCACGACACACTTGTCTACTCCAAAAATATCAAAGATACAGTCTCAGAAGACCAAAGGGCAATTG
AGACTTTTCAACAAAGGGTAATATCCGGAAACCTCCTCGGATTCCATTGCCCAGCTATCTGTCACTTTATTGTGAAGAT
AGTGGAAAAGGAAGGTGGCTCCTACAAATGCCATCATTGCGATAAAGGAAAGGCCATCGTTGAAGATGCCTCTGCCGAC
AGTGGTCCCAAAGATGGACCCCCACCCACGAGGAGCATCGTGGAAAAAGAAGACGTTCCAACCACGTCTTCAAAGCAAG
TGGATTGATGTGATAACATGGTGGAGCACGACACACTTGTCTACTCCAAAAATATCAAAGATACAGTCTCAGAAGACCA
AAGGGCAATTGAGACTTTTCAACAAAGGGTAATATCCGGAAACCTCCTCGGATTCCATTGCCCAGCTATCTGTCACTTT
ATTGTGAAGATAGTGGAAAAGGAAGGTGGCTCCTACAAATGCCATCATTGCGATAAAGGAAAGGCCATCGTTGAAGATG
CCTCTGCCGACAGTGGTCCCAAAGATGGACCCCCACCCACGAGGAGCATCGTGGAAAAAGAAGACGTTCCAACCACGTC
TTCAAAGCAAGTGGATTGATGTGATATCTCCACTGACGTAAGGGATGACGCACAATCCCACTATCCTTCGCAAGACCCT
TCCTCTATATAAGGAAGTTCATTTCATTTGGAGAGGTATTAAAATCTTAATAGGTTTTGATAAAAGCGAACGTGGGGAA
ACCCGAACCAAACCTTCTTCTAAACTCTCTCTCATCTCTCTTAAAGCAAACTTCTCTCTTGTCTTTCTTGCGTGAGCGA
TCTTCAACGTTGTCAGATCGTGCTTCGGCACCAGTACAGGGCCCAATACCGCGGAGAAAATGGCGAAAAACGTTGCGAT
TTTCGGCTTATTGTTTTCTCTTCTTGTGTTGGTTCCTTCTCAGATCTTCGCCCAAAAACTTCCTGGAAATGACAACAGC
ACGGCAACGCTGTGCCTTGGGCACCATGCAGTACCAAACGGAACGATAGTGAAAACAATCACGAATGACCAAATTGAAG
TTACTAATGCTACTGAGCTGGTTCAGAATTCCTCAATAGGTGAAATATGCGACAGTCCTCATCAGATCCTTGATGGAGA
AAACTGCACACTAATAGATGCTCTATTGGGAGACCCTCAGTGTGATGGCTTCCAAAATAAGAAATGGGACCTTTTTGTT
GAACGAAGCAAAGCCTACAGCAACTGTTACCCTTATGATGTGCCGGATTATGCCTCCCTTAGGTCACTAGTTGCCTCAT
CCGGCACACTGGAGTTTAACAATGAAAGCTTCAATTGGACTGGAGTCACTCAAAACGGAACAAGTTCTGCTTGCATAAG
GAGATCTAATAATAGTTTCTTTAGTAGATTAAATTGGTTGACCCACTTAAACTTCAAATACCCAGCATTGAACGTGACT
ATGCCAAACAATGAACAATTTGACAAATTGTACATTTGGGGGGTTCACCACCCGGGTACGGACAAGGACCAAATCTTCC
TGTATGCTCAATCATCAGGAAGAATCACAGTATCTACCAAAAGAAGCCAACAAGCTGTAATCCCGAATATCGGATCTAG
ACCCAGAATAAGGAATATCCCTAGCAGAATAAGCATCTATTGGACAATAGTAAAACCGGGAGACATACTTTTGATTAAC
AGCACAGGGAATCTAATTGCTCCTAGGGGTTACTTCAAAATACGAAGTGGGAAAAGCTCAATAATGAGATCAGATGCAC
CCATTGGCAAATGCAATTCTGAATGCATCACTCCAAATGGAAGCATTCCCAATGACAAACCATTCCAAAATGTAAACAG
GATCACATACGGGGCCTGTCCCAGATATGTTAAGCAAAGCACTCTGAAATTGGCAACAGGAATGCGAAATGTACCAGAG
AAACAAACTAGAGGCATATTTGGCGCAATAGCGGGTTTCATAGAAAATGGTTGGGAGGGAATGGTGGATGGTTGGTACG
GTTTCAGGCATCAAAATTCTGAGGGAAGAGGACAAGCAGCAGATCTCAAAAGCACTCAAGCAGCAATCGATCAAATCAA
TGGGAAGCTGAATCGATTGATCGGGAAAACCAACGAGAAATTCCATCAGATTGAAAAAGAATTCTCAGAAGTCGAAGGG
AGAATTCAGGACCTTGAGAAATATGTTGAGGACACTAAAATAGATCTCTGGTCATACAACGCGGAGCTTCTTGTTGCCC
TGGAGAACCAACATACAATTGATCTAACTGACTCAGAAATGAACAAACTGTTTGAAAAAACAAAGAAGCAACTAAGGGA
AAATGCTGAGGATATGGGCAATGGTTGTTTCAAAATATACCACAAATGTGACAATGCCTGCATAGGATCAATCAGAAAT
GGAACTTATGACCACGATGTATACAGAGATGAAGCATTAAACAACCGGTTCCAGATCAAGGGAGTTGAGCTGAAGTCAG
GGTACAAAGATTGGATCCTATGGATTTCCTTTGCCATATCATGTTTTTTGCTTTGTGTTGCTTTGTTGGGGTTCATCAT
GTGGGCCTGCCAAAAGGGCAACATTAGGTGCAACATTTGCATTTGAAGGCCTATTTTCTTTAGTTTGAATTTACTGTTA
TTCGGTGTGCATTTCTATGTTTGGTGAGCGGTTTTCTGTGCTCAGAGTGTGTTTATTTTATGTAATTTAATTTCTTTGT
GAGCTCCTGTTTAGCAGGTCGTCCCTTCAGCAAGGACACAAAAAGATTTTAATTTTATTAAAAAAAAAAAAAAAAAAAGA
CCGGGAATTCGATATCAAGCTTATCGACCTGCAGATCGTTCAAACATTTGGCAATAAAGTTTCTTAAGATTGAATCCTG
TTGCCGGTCTTGCGATGATTATCATATAATTTCTGTTGAATTACGTTAAGCATGTAATAATTAACATGTAATGCATGAC
GTTATTTATGAGATGGGTTTTTATGATTAGAGTCCCGCAATTATACATTTAATACGCGATAGAAAACAAAATATAGCGC
GCAAACTAGGATAAATTATCGCGCGCGGTGTCATCTATGTTACTAGAT Schematic representation of construct number 1800

Figure 8 Components for 2X35S/CPMV160 PDISP/H3 Victoria/ NOS (Construct number 1935)

Figure 8A (SEQ ID NO: 28) IF-CPMV(fl5'UTR)_SpPDI.c

TCGTGCTTCGGCACCAGTACAATGGCGAAAAACGTTGCGATTTTCGGCT

Schematic representation of construct 1190. SacII and StuI restriction enzyme sites used for plasmid linearization are annotated on the representation.

Figure 8C (SEQ ID NO: 29) Construct 1190 from left to right t-DNA borders (underlined). 2X35S/CPMV-HT(fl5'UTR)/NOS with Plastocyanine-P19-Plastocyanine silencing inhibitor expression cassette TGGCAGGATATATTGTGGTGTAAACAAATTGACGCTTAGACAACTTAATAACACATTGCGGACGTTTTTAA
TGTACTGAATTAACGCCGAATCCCGGGCTGGTATATTTATATGTTGTCAAATAACTCAAAAACCATAAAAG
TTTAAGTTAGCAAGTGTGTACATTTTTACTTGAACAAAAATATTCACCTACTACTGTTATAAATCATTATT
AAACATTAGAGTAAAGAAATATGGATGATAAGAACAAGAGTAGTGATATTTTGACAACAATTTTGTTGCAA
CATTTGAGAAAATTTTGTTGTTCTCTCTTTTCATTGGTCAAAAACAATAGAGAGAGAAAAAGGAAGAGGGA
GAATAAAAACATAATGTGAGTATGAGAGAGAAAGTTGTACAAAAGTTGTACCAAAATAGTTGTACAAATAT
CATTGAGGAATTTGACAAAAGCTACACAAATAAGGGTTAATTGCTGTAAATAAATAAGGATGACGCATTAG
AGAGATGTACCATTAGAGAATTTTTGGCAAGTCATTAAAAAGAAAGAATAAATTATTTTTAAAATTAAAAG
TTGAGTCATTTGATTAAACATGTGATTATTTAATGAATTGATGAAAGAGTTGGATTAAAGTTGTATTAGTA
ATTAGAATTTGGTGTCAAATTTAATTTGACATTTGATCTTTTCCTATATATTGCCCCATAGAGTCAGTTAA
CTCATTTTTATATTTCATAGATCAAATAAGAGAAATAACGGTATATTAATCCCTCCAAAAAAAAAAAAACGG
TATATTTACTAAAAAATCTAAGCCACGTAGGAGGATAACAGGATCCCCGTAGGAGGATAACATCCAATCCA
ACCAATCACAACAATCCTGATGAGATAACCCACTTTAAGCCCACGCATCTGTGGCACATCTACATTATCTA
AATCACACATTCTTCCACACATCTGAGCCACACAAAAACCAATCCACATCTTTATCACCCATTCTATAAAA
AATCACACTTTGTGAGTCTACACTTTGATTCCCTTCAAACACATACAAAGAGAAGAGACTAATTAATTAAT
TAATCATCTTGAGAGAAAATGGAACGAGCTATACAAGGAAACGACGCTAGGGAACAAGCTAACAGTGAACG
TTGGGATGGAGGATCAGGAGGTACCACTTCTCCCTTCAAACTTCCTGACGAAAGTCCGAGTTGGACTGAGT
GGCGGCTACATAACGATGAGACGAATTCGAATCAAGATAATCCCCTTGGTTTCAAGGAAAGCTGGGGTTTC
GGGAAAGTTGTATTTAAGAGATATCTCAGATACGACAGGACGGAAGCTTCACTGCACAGAGTCCTTGGATC
TTGGACGGGAGATTCGGTTAACTATGCAGCATCTCGATTTTTCGGTTTCGACCAGATCGGATGTACCTATA
GTATTCGGTTTCGAGGAGTTAGTATCACCGTTTCTGGAGGGTCGCGAACTCTTCAGCATCTCTGTGAGATG
GCAATTCGGTCTAAGCAAGAACTGCTACAGCTTGCCCCAATCGAAGTGGAAAGTAATGTATCAAGAGGATG
CCCTGAAGGTACTCAAACCTTCGAAAAAGAAAGCGAGTAAGTTAAAATGCTTCTTCGTCTCCTATTTATAA
TATGGTTTGTTATTGTTAATTTTGTTCTTGTAGAAGAGCTTAATTAATCGTTGTTGTTATGAAATACTATT
TGTATGAGATGAACTGGTGTAATGTAATTCATTTACATAAGTGGAGTCAGAATCAGAATGTTTCCTCCATA
ACTAACTAGACATGAAGACCTGCCGCGTACAATTGTCTTATATTTGAACAACTAAAATTGAACATCTTTTG
CCACAACTTTATAAGTGGTTAATATAGCTCAAATATATGGTCAAGTTCAATAGATTAATAATGGAAATATC
AGTTATCGAAATTCATTAACAATCAACTTAACGTTATTAACTACTAATTTTATATCATCCCCTTTGATAAA
TGATAGTACACCAATTAGGAAGGAGCATGCTCGCCTAGGAGATTGTCGTTTCCCGCCTTCAGTTTGCAAGC
TGCTCTAGCCGTGTAGCCAATACGCAAACCGCCTCTCCCCGCGCGTTGGGAATTACTAGCGCGTGTCGACA
AGCTTGCATGCCGGTCAACATGGTGGAGCACGACACACTTGTCTACTCCAAAAATATCAAAGATACAGTCT
CAGAAGACCAAAGGGCAATTGAGACTTTTCAACAAAGGGTAATATCCGGAAACCTCCTCGGATTCCATTGC
CCAGCTATCTGTCACTTTATTGTGAAGATAGTGGAAAAGGAAGGTGGCTCCTACAAATGCCATCATTGCGA
TAAAGGAAAGGCCATCGTTGAAGATGCCTCTGCCGACAGTGGTCCCAAAGATGGACCCCCACCCACGAGGA
GCATCGTGGAAAAAGAAGACGTTCCAACCACGTCTTCAAAGCAAGTGGATTGATGTGATAACATGGTGGAG
CACGACACACTTGTCTACTCCAAAAATATCAAAGATACAGTCTCAGAAGACCAAAGGGCAATTGAGACTTT
TCAACAAAGGGTAATATCCGGAAACCTCCTCGGATTCCATTGCCCAGCTATCTGTCACTTTATTGTGAAGA
TAGTGGAAAAGGAAGGTGGCTCCTACAAATGCCATCATTGCGATAAAGGAAAGGCCATCGTTGAAGATGCC
TCTGCCGACAGTGGTCCCAAAGATGGACCCCCACCCACGAGGAGCATCGTGGAAAAAGAAGACGTTCCAAC
CACGTCTTCAAAGCAAGTGGATTGATGTGATATCTCCACTGACGTAAGGGATGACGCACAATCCCACTATC
CTTCGCAAGACCCTTCCTCTATATAAGGAAGTTCATTTCATTTGGAGAGGTATTAAAATCTTAATAGGTTT
TGATAAAAGCGAACGTGGGGAAACCCGAACCAAACCTTCTTCTAAACTCTCTCTCATCTCTCTTAAAGCAA
ACTTCTCTCTTGTCTTTCTTGCGTGAGCGATCTTCAACGTTGTCAGATCGTGCTTCGGCACCGCGGATGGC
GAAAAACGTTGCGATTTTCGGCTTATTGTTTTCTCTTCTTGTGTTGGTTCCTTCTCAGATCTTCGCCTGCA
GGCTCCTCAGCCAAAACGACACCCCCATCTGTCTATCCACTGGCCCCTGGATCTGCTGCCCAAACTAACTC CATGGTGACCCTGGGATGCCTGGTCAAGGGCTATTTCCCTGAGCCAGTGACAGTGACCTGGAACTCTGGAT
CCCTGTCCAGCGGTGTGCACACCTTCCCAGCTGTCCTGCAGTCTGACCTCTACACTCTGAGCAGCTCAGTG
ACTGTCCCCTCCAGCACCTGGCCCAGCGAGACCGTCACCTGCAACGTTGCCCACCCGGCCAGCAGCACCAA
GGTGGACAAGAAAATTGTGCCCAGGGATTGTGGTTGTAAGCCTTGCATATGTACAGTCCCAGAAGTATCAT
CTGTCTTCATCTTCCCCCCAAAGCCCAAGGATGTGCTCACCATTACTCTGACTCCTAAGGTCACGTGTGTT
GTGGTAGACATCAGCAAGGATGATCCCGAGGTCCAGTTCAGCTGGTTTGTAGATGATGTGGAGGTGCACAC
AGCTCAGACGCAACCCCGGGAGGAGCAGTTCAACAGCACTTTCCGCTCAGTCAGTGAACTTCCCATCATGC
ACCAGGACTGGCTCAATGGCAAGGAGCGATCGCTCACCATCACCATCACCATCACCATCACCATTAAAGGC
CTATTTTCTTTAGTTTGAATTTACTGTTATTCGGTGTGCATTTCTATGTTTGGTGAGCGGTTTTCTGTGCT
CAGAGTGTGTTTATTTTATGTAATTTAATTTCTTTGTGAGCTCCTGTTTAGCAGGTCGTCCCTTCAGCAAG
GACACAAAAAGATTTTAATTTTATTAAAAAAAAAAAAAAAAAAGACCGGGAATTCGATATCAAGCTTATCG
ACCTGCAGATCGTTCAAACATTTGGCAATAAAGTTTCTTAAGATTGAATCCTGTTGCCGGTCTTGCGATGA
TTATCATATAATTTCTGTTGAATTACGTTAAGCATGTAATAATTAACATGTAATGCATGACGTTATTTATG
AGATGGGTTTTTATGATTAGAGTCCCGCAATTATACATTTAATACGCGATAGAAAACAAAATATAGCGCGC
AAACTAGGATAAATTATCGCGCGCGGTGTCATCTATGTTACTAGATCTCTAGAGTCTCAAGCTTGGCGCGC
CCACGTGACTAGTGGCACTGGCCGTCGTTTTACAACGTCGTGACTGGGAAAACCCTGGCGTTACCCAACTT
AATCGCCTTGCAGCACATCCCCCTTTCGCCAGCTGGCGTAATAGCGAAGAGGCCCGCACCGATCGCCCTTC
CCAACAGTTGCGCAGCCTGAATGGCGAATGCTAGAGCAGCTTGAGCTTGGATCAGATTGTCGTTTCCCGCC
TTCAGTTTAAACTATCAGTGTTTGACAGGATATATTGGCGGGTAAACCTAAGAGAAAAGAGCGTTTA Figure 8C (SEQ ID NO: 29) con't

Figure 8D (SEQ ID NO: 30) Expression cassette number 1935 from 2X35S promoter to NOS terminator. PDISP/H3 Victoria nucleotide sequence is underlined. 5"UTR is shown in bold GTCAACATGGTGGAGCACGACACACTTGTCTACTCCAAAAATATCAAAGATACAGTCTCAGAAGACCAAAG
GGCAATTGAGACTTTTCAACAAAGGGTAATATCCGGAAACCTCCTCGGATTCCATTGCCCAGCTATCTGTC
ACTTTATTGTGAAGATAGTGGAAAAGGAAGGTGGCTCCTACAAATGCCATCATTGCGATAAAGGAAAGGCC
ATCGTTGAAGATGCCTCTGCCGACAGTGGTCCCAAAGATGGACCCCCACCCACGAGGAGCATCGTGGAAAA
AGAAGACGTTCCAACCACGTCTTCAAAGCAAGTGGATTGATGTGATAACATGGTGGAGCACGACACACTTG
TCTACTCCAAAAATATCAAAGATACAGTCTCAGAAGACCAAAGGGCAATTGAGACTTTTCAACAAAGGGTA
ATATCCGGAAACCTCCTCGGATTCCATTGCCCAGCTATCTGTCACTTTATTGTGAAGATAGTGGAAAAGGA
AGGTGGCTCCTACAAATGCCATCATTGCGATAAAGGAAAGGCCATCGTTGAAGATGCCTCTGCCGACAGTG
GTCCCAAAGATGGACCCCCACCCACGAGGAGCATCGTGGAAAAAGAAGACGTTCCAACCACGTCTTCAAAG
CAAGTGGATTGATGTGATATCTCCACTGACGTAAGGGATGACGCACAATCCCACTATCCTTCGCAAGACCC
TTCCTCTATATAAGGAAGTTCATTTCATTTGGAGAGGTATTAAAATCTTAATAGGTTTTGATAAAAGCGAA
CGTGGGGAAACCCGAACCAAACCTTCTTCTAAACTCTCTCTCATCTCTCTTAAAGCAAACTTCTCTCTTGT
CTTTCTTGCGTGAGCGATCTTCAACGTTGTCAGATCGTGCTTCGGCACCAGTACAATGGCGAAAAACGTTG
CGATTTTCGGCTTATTGTTTTCTCTTCTTGTGTTGGTTCCTTCTCAGATCTTCGCCCAAAAACTTCCTGGA
AATGACAACAGCACGGCAACGCTGTGCCTTGGGCACCATGCAGTACCAAACGGAACGATAGTGAAAACAAT
CACGAATGACCAAATTGAAGTTACTAATGCTACTGAGCTGGTTCAGAATTCCTCAATAGGTGAAATATGCG
ACAGTCCTCATCAGATCCTTGATGGAGAAAACTGCACACTAATAGATGCTCTATTGGGAGACCCTCAGTGT
GATGGCTTCCAAAATAAGAAATGGGACCTTTTTGTTGAACGAAGCAAAGCCTACAGCAACTGTTACCCTTA
TGATGTGCCGGATTATGCCTCCCTTAGGTCACTAGTTGCCTCATCCGGCACACTGGAGTTTAACAATGAAA
GCTTCAATTGGACTGGAGTCACTCAAAACGGAACAAGTTCTGCTTGCATAAGGAGATCTAATAATAGTTTC
TTTAGTAGATTAAATTGGTTGACCCACTTAAACTTCAAATACCCAGCATTGAACGTGACTATGCCAAACAA
TGAACAATTTGACAAATTGTACATTTGGGGGGTTCACCACCCGGGTACGGACAAGGACCAAATCTTCCTGT
ATGCTCAATCATCAGGAAGAATCACAGTATCTACCAAAAGAAGCCAACAAGCTGTAATCCCGAATATCGGA
TCTAGACCCAGAATAAGGAATATCCCTAGCAGAATAAGCATCTATTGGACAATAGTAAAACCGGGAGACAT
ACTTTTGATTAACAGCACAGGGAATCTAATTGCTCCTAGGGGTTACTTCAAAATACGAAGTGGGAAAAGCT
CAATAATGAGATCAGATGCACCCATTGGCAAATGCAATTCTGAATGCATCACTCCAAATGGAAGCATTCCC
AATGACAAACCATTCCAAAATGTAAACAGGATCACATACGGGGCCTGTCCCAGATATGTTAAGCAAAGCAC
TCTGAAATTGGCAACAGGAATGCGAAATGTACCAGAGAAACAAACTAGAGGCATATTTGGCGCAATAGCGG
GTTTCATAGAAAATGGTTGGGAGGGAATGGTGGATGGTTGGTACGGTTTCAGGCATCAAAATTCTGAGGGA
AGAGGACAAGCAGCAGATCTCAAAAGCACTCAAGCAGCAATCGATCAAATCAATGGGAAGCTGAATCGATT
GATCGGGAAAACCAACGAGAAATTCCATCAGATTGAAAAAGAATTCTCAGAAGTCGAAGGGAGAATTCAGG
ACCTTGAGAAATATGTTGAGGACACTAAAATAGATCTCTGGTCATACAACGCGGAGCTTCTTGTTGCCCTG
GAGAACCAACATACAATTGATCTAACTGACTCAGAAATGAACAAACTGTTTGAAAAAACAAAGAAGCAACT
AAGGGAAAATGCTGAGGATATGGGCAATGGTTGTTTCAAAATATACCACAAATGTGACAATGCCTGCATAG
GATCAATCAGAAATGGAACTTATGACCACGATGTATACAGAGATGAAGCATTAAACAACCGGTTCCAGATC
AAGGGAGTTGAGCTGAAGTCAGGGTACAAAGATTGGATCCTATGGATTTCCTTTGCCATATCATGTTTTTT
GCTTTGTGTTGCTTTGTTGGGGTTCATCATGTGGGCCTGCCAAAAGGGCAACATTAGGTGCAACATTTGCA
TTTGAAGGCCTATTTTCTTTAGTTTGAATTTACTGTTATTCGGTGTGCATTTCTATGTTTGGTGAGCGGTT
TTCTGTGCTCAGAGTGTGTTTATTTTATGTAATTTAATTTCTTTGTGAGCTCCTGTTTAGCAGGTCGTCCC
TTCAGCAAGGACACAAAAAGATTTTAATTTTATTAAAAAAAAAAAAAAAAAAAGACCGGGAATTCGATATCA
AGCTTATCGACCTGCAGATCGTTCAAACATTTGGCAATAAAGTTTCTTAAGATTGAATCCTGTTGCCGGTC
TTGCGATGATTATCATATAATTTCTGTTGAATTACGTTAAGCATGTAATAATTAACATGTAATGCATGACG
TTATTTATGAGATGGGTTTTTATGATTAGAGTCCCGCAATTATACATTTAATACGCGATAGAAAACAAAAT
ATAGCGCGCAAACTAGGATAAATTATCGCGCGCGGTGTCATCTATGTTACTAGAT Schematic representation of construct number 1935

Figure 9 Variation of sequence between SacII restriction site and ATG of PDISP/H3 Victoria in 2X35S/CPMV HT*(-Mprot)/NOS expression system

Figure 9A (SEQ ID NO: 31) IF-HT1*(-Mprot)-PDI.c (modified sequence from original 1800 construct underlined)

ACAGGGCCCAATACCGCGGAGACAATGGCGAAAAACGTTGCGATTTTCGGCT

Figure 9B (SEQ ID NO: 32) IF-HT2*(-Mprot)-PDI.c (modified sequence from original 1800 construct underlined)

ACAGGGCCCAATACCGCGGAGGAAATGGCGAAAAACGTTGCGATTTTCGGCT

Figure 9C (SEQ ID NO: 33) IF-HT3*(-Mprot)-PDI.c (modified sequence from original 1800 construct underlined)

ACAGGGCCCAATACCGCGGAAAAAATGGCGAAAAACGTTGCGATTTTCGGCT

Figure 9D (SEQ ID NO: 34) IF-HT4*(-Mprot)-PDI.c (modified sequence from original 1800 construct underlined)

ACAGGGCCCAATACCGCGGAAACAATGGCGAAAAACGTTGCGATTTTCGGCT

Figure 9E (SEQ ID NO: 35) IF-HT5*(-Mprot)-PDI.c (modified sequence from original 1800 construct underlined)

ACAGGGCCCAATACCGCGGAAGCAATGGCGAAAAACGTTGCGATTTTCGGCT

Figure 9F (SEQ ID NO: 36) IF-HT6*(-Mprot)-PDI.c (modified sequence from original 1800 construct underlined)

ACAGGGCCCAATACCGCGGAAGAAATGGCGAAAAACGTTGCGATTTTCGGCT

Figure 9G (SEQ ID NO: 37) IF-HT7*(-Mprot)-PDI.c (modified sequence from original 1800 construct underlined)

ACAGGGCCCAATACCGCGGAAAGAAATGGCGAAAAACGTTGCGATTTTCGGCT

Figure 9H (SEQ ID NO: 38) IF-HT8*(-Mprot)-PDI.c (modified sequence from original 1800 construct underlined)

ACAGGGCCCAATACCGCGGAAAAGAAATGGCGAAAAACGTTGCGATTTTCGGCT

Schematic representation of construct number 1992. Analogous features were used to prepare constructs 1993 -1999.

Figure 10 2X35S/CPMV HT (construct no 484), and HT*(-Mprot) (construct no 1897) for PDISP/H1 California/NOS

Figure 10A (SEQ ID NO: 39) Nucleotide sequence of PDISP/H1 California.

ATGGCGAAAAACGTTGCGATTTTCGGCTTATTGTTTTCTCTTCTTGTGTTGGTTCCTTCTCAGATCTTCGC
TGACACATTATGTATAGGTTATCATGCGAACAATTCAACAGACACTGTAGACACAGTACTAGAAAAGAATG
TAACAGTAACACACTCTGTTAACCTTCTAGAAGACAAGCATAACGGGAAACTATGCAAACTAAGAGGGGTA
GCCCCATTGCATTTGGGTAAATGTAACATTGCTGGCTGGATCCTGGGAAATCCAGAGTGTGAATCACTCTC
CACAGCAAGCTCATGGTCCTACATTGTGGAAACACCTAGTTCAGACAATGGAACGTGTTACCCAGGAGATT
TCATCGATTATGAGGAGCTAAGAGAGCAATTGAGCTCAGTGTCATCATTTGAAAGGTTTGAGATATTCCCC
AAGACAAGTTCATGGCCCAATCATGACTCGAACAAAGGTGTAACGGCAGCATGTCCTCATGCTGGAGCAAA
AAGCTTCTACAAAAATTTAATATGGCTAGTTAAAAAAGGAAATTCATACCCAAAGCTCAGCAAATCCTACA
TTAATGATAAAGGGAAAGAAGTCCTCGTGCTATGGGGCATTCACCATCCATCTACTAGTGCTGACCAACAA
AGTCTCTATCAGAATGCAGATGCATATGTTTTTGTGGGGTCATCAAGATACAGCAAGAAGTTCAAGCCGGA
AATAGCAATAAGACCCAAAGTGAGGGATCAAGAAGGGAGAATGAACTATTACTGGACACTAGTAGAGCCGG
GAGACAAAATAACATTCGAAGCAACTGGAAATCTAGTGGTACCGAGATATGCATTCGCAATGGAAAGAAAT
GCTGGATCTGGTATTATCATTTCAGATACACCAGTCCACGATTGCAATACAACTTGTCAAACACCCAAGGG
TGCTATAAACACCAGCCTCCCATTTCAGAATATACATCCGATCACAATTGGAAAATGTCCAAAATATGTAA
AAAGCACAAAATTGAGACTGGCCACAGGATTGAGGAATATCCCGTCTATTCAATCTAGAGGACTATTTGGG
GCCATTGCCGGTTTCATTGAAGGGGGGTGGACAGGGATGGTAGATGGATGGTACGGTTATCACCATCAAAA
TGAGCAGGGGTCAGGATATGCAGCCGACCTGAAGAGCACACAGAATGCCATTGACGAGATTACTAACAAAG
TAAATTCTGTTATTGAAAAGATGAATACACAGTTCACAGCAGTAGGTAAAGAGTTCAACCACCTGGAAAAA
AGAATAGAGAATTTAAATAAAAAAGTTGATGATGGTTTCCTGGACATTTGGACTTACAATGCCGAACTGTT
GGTTCTATTGGAAAATGAAAGAACTTTGGACTACCACGATTCAAATGTGAAGAACTTATATGAAAAGGTAA
GAAGCCAGCTAAAAAACAATGCCAAGGAAATTGGAAACGGCTGCTTTGAATTTTACCACAAATGCGATAAC
ACGTGCATGGAAAGTGTCAAAAATGGGACTTATGACTACCCAAAATACTCAGAGGAAGCAAAATTAAACAG
AGAAGAAATAGATGGGGTAAAGCTGGAATCAACAAGGATTTACCAGATTTTGGCGATCTATTCAACTGTCG
CCAGTTCATTGGTACTGGTAGTCTCCCTGGGGGCAATCAGTTTCTGGATGTGCTCTAATGGGTCTCTACAG
TGTAGAATATGTATTTAA

Figure 10B (SEQ ID NO: 40) Amino acid sequence of PDISP/H1 California.

MAKNVAIFGLLFSLLVLVPSQIFADTLCIGYHANNSTDTVDTVLEKNVTVTHSVNLLEDKHNGKLCKLRGV
APLHLGKCNIAGWILGNPECESLSTASSWSYIVETPSSDNGTCYPGDFIDYEELREQLSSVSSFERFEIFP
KTSSWPNHDSNKGVTAACPHAGAKSFYKNLIWLVKKGNSYPKLSKSYINDKGKEVLVLWGIHHPSTSADQQ
SLYQNADAYVFVGSSRYSKKFKPEIAIRPKVRDQEGRMNYYWTLVEPGDKITFEATGNLVVPRYAFAMERN
AGSGIIISDTPVHDCNTTCQTPKGAINTSLPFQNIHPITIGKCPKYVKSTKLRLATGLRNIPSIQSRGLFG
AIAGFIEGGWTGMVDGWYGYHHQNEQGSGYAADLKSTQNAIDEITNKVNSVIEKMNTQFTAVGKEFNHLEK
RIENLNKKVDDGFLDIWTYNAELLVLLENERTLDYHDSNVKNLYEKVRSQLKNNAKEIGNGCFEFYHKCDN
TCMESVKNGTYDYPKYSEEAKLNREEIDGVKLESTRIYQILAIYSTVASSLVLVVSLGAISFWMCSNGSLQ
CRICI*

Schematic representation of construct number 484 (2X35S/CPMV HT)

Schematic representation of construct number 1897 (2X35S/CPMV HT*(-Mprot))

Figure 11: 2X35S/CPMV HT (construct no 489), HT*(-Mprot) (construct no 1880) and HT(fl5'UTR) (construct no 1885) for H5 Indonesia

Figure 11A (SEQ ID NO: 41) Nucleotide sequence of native H5 Indonesia.

ATGGAGAAAATAGTGCTTCTTCTTGCAATAGTCAGTCTTGTTAAAAGTGATCAGATTTGCATTGGTTACCA
TGCAAACAATTCAACAGAGCAGGTTGACACAATCATGGAAAAGAACGTTACTGTTACACATGCCCAAGACA
TACTGGAAAAGACACACAACGGGAAGCTCTGCGATCTAGATGGAGTGAAGCCTCTAATTTTAAGAGATTGT
AGTGTAGCTGGATGGCTCCTCGGGAACCCAATGTGTGACGAATTCATCAATGTACCGGAATGGTCTTACAT
AGTGGAGAAGGCCAATCCAACCAATGACCTCTGTTACCCAGGGAGTTTCAACGACTATGAAGAACTGAAAC
ACCTATTGAGCAGAATAAACCATTTTGAGAAAATTCAAATCATCCCCAAAAGTTCTTGGTCCGATCATGAA
GCCTCATCAGGAGTTAGCTCAGCATGTCCATACCTGGGAAGTCCCTCCTTTTTTAGAAATGTGGTATGGCT
TATCAAAAAGAACAGTACATACCCAACAATAAAGAAAAGCTACAATAATACCAACCAAGAGGATCTTTTGG
TACTGTGGGGAATTCACCATCCTAATGATGCGGCAGAGCAGACAAGGCTATATCAAAACCCAACCACCTAT
ATTTCCATTGGGACATCAACACTAAACCAGAGATTGGTACCAAAAATAGCTACTAGATCCAAAGTAAACGG
GCAAAGTGGAAGGATGGAGTTCTTCTGGACAATTTTAAAACCTAATGATGCAATCAACTTCGAGAGTAATG
GAAATTTCATTGCTCCAGAATATGCATACAAAATTGTCAAGAAAGGGGACTCAGCAATTATGAAAAGTGAA
TTGGAATATGGTAACTGCAACACCAAGTGTCAAACTCCAATGGGGGCGATAAACTCTAGTATGCCATTCCA
CAACATACACCCTCTCACCATCGGGGAATGCCCCAAATATGTGAAATCAAACAGATTAGTCCTTGCAACAG
GGCTCAGAAATAGCCCTCAAAGAGAGAGCAGAAGAAAAAAGAGAGGACTATTTGGAGCTATAGCAGGTTTT
ATAGAGGGAGGATGGCAGGGAATGGTAGATGGTTGGTATGGGTACCACCATAGCAATGAGCAGGGGAGTGG
GTACGCTGCAGACAAAGAATCCACTCAAAAGGCAATAGATGGAGTCACCAATAAGGTCAACTCAATCATTG
ACAAAATGAACACTCAGTTTGAGGCCGTTGGAAGGGAATTTAATAACTTAGAAAGGAGAATAGAGAATTTA
AACAAGAAGATGGAAGACGGGTTTCTAGATGTCTGGACTTATAATGCCGAACTTCTGGTTCTCATGGAAAA
TGAGAGAACTCTAGACTTTCATGACTCAAATGTTAAGAACCTCTACGACAAGGTCCGACTACAGCTTAGGG
ATAATGCAAAGGAGCTGGGTAACGGTTGTTTCGAGTTCTATCACAAATGTGATAATGAATGTATGGAAAGT
ATAAGAAACGGAACGTACAACTATCCGCAGTATTCAGAAGAAGCAAGATTAAAAAGAGAGGAAATAAGTGG
GGTAAAATTGGAATCAATAGGAACTTACCAAATACTGTCAATTTATTCAACAGTGGCGAGTTCCCTAGCAC
TGGCAATCATGATGGCTGGTCTATCTTTATGGATGTGCTCCAATGGATCGTTACAATGCAGAATTTGCATT
TAA

Figure 11B (SEQ ID NO: 42) Amino acid sequence of native H5 Indonesia.

MEKIVLLLAIVSLVKSDQICIGYHANNSTEQVDTIMEKNVTVTHAQDILEKTHNGKLCDLDGVKPLILRDC
SVAGWLLGNPMCDEFINVPEWSYIVEKANPTNDLCYPGSFNDYEELKHLLSRINHFEKIQIIPKSSWSDHE
ASSGVSSACPYLGSPSFFRNVVWLIKKNSTYPTIKKSYNNTNQEDLLVLWGIHHPNDAAEQTRLYQNPTTY
ISIGTSTLNQRLVPKIATRSKVNGQSGRMEFFWTILKPNDAINFESNGNFIAPEYAYKIVKKGDSAIMKSE
LEYGNCNTKCQTPMGAINSSMPFHNIHPLTIGECPKYVKSNRLVLATGLRNSPQRESRRKKRGLFGAIAGF
IEGGWQGMVDGWYGYHHSNEQGSGYAADKESTQKAIDGVTNKVNSIIDKMNTQFEAVGREFNNLERRIENL
NKKMEDGFLDVWTYNAELLVLMENERTLDFHDSNVKNLYDKVRLQLRDNAKELGNGCFEFYHKCDNECMES
IRNGTYNYPQYSEEARLKREEISGVKLESIGTYQILSIYSTVASSLALAIMMAGLSLWMCSNGSLQCRICI
*

Schematic representation of construct number 489 (2X35S/CPMV HT)

Schematic representation of construct number 1880 (2X35S/CPMV HT*(-Mprot))

Schematic representation of construct number 1885 (2X35S/CPMV HT(fl5'UTR))

Figure 12: 2X35S/CPMV HT (construct no 2140) and HT*(-Mprot) (construct no 2168) for PDISP/H7 Hangzhou

Figure 12A (SEQ ID NO: 43) Nucleotide sequence of PDISP/H7 Hangzhou.

ATGGCGAAAAACGTTGCGATTTTCGGCTTATTGTTTTCTCTTCTTGTGTTGGTTCCTTCTCAGATCTTCGC
GGACAAAATCTGCCTCGGACATCATGCCGTGTCAAACGGAACCAAAGTAAACACATTAACTGAAAGAGGAG
TGGAAGTCGTCAATGCAACTGAAACAGTGGAACGAACAAACATCCCCAGGATCTGCTCAAAAGGGAAAAGG
ACAGTTGACCTCGGTCAATGTGGACTCCTGGGGACAATCACTGGACCACCTCAATGTGACCAATTCCTAGA
ATTTTCAGCCGATTTAATTATTGAGAGGCGAGAAGGAAGTGATGTCTGTTATCCTGGGAAATTCGTGAATG
AAGAAGCTCTGAGGCAAATTCTCAGAGAATCAGGCGGAATTGACAAGGAAGCAATGGGATTCACATACAGT
GGAATAAGAACTAATGGAGCAACCAGTGCATGTAGGAGATCAGGATCTTCATTCTATGCAGAAATGAAATG
GCTCCTGTCAAACACAGATAATGCTGCATTCCCGCAGATGACTAAGTCATATAAAAATACAAGAAAAAGCC
CAGCTCTAATAGTATGGGGGATCCATCATTCCGTATCAACTGCAGAGCAAACCAAGCTATATGGGAGTGGA
AACAAACTGGTGACAGTTGGGAGTTCTAATTATCAACAATCTTTTGTACCGAGTCCAGGAGCGAGACCACA
AGTTAATGGTATATCTGGAAGAATTGACTTTCATTGGCTAATGCTAAATCCCAATGATACAGTCACTTTCA
GTTTCAATGGGGCTTTCATAGCTCCAGACCGTGCAAGCTTCCTGAGAGGAAAATCTATGGGAATCCAGAGT
GGAGTACAGGTTGATGCCAATTGTGAAGGGGACTGCTATCATAGTGGAGGGACAATAATAAGTAACTTGCC
ATTTCAGAACATAGATAGCAGGGCAGTTGGAAAATGTCCGAGATATGTTAAGCAAAGGAGTCTGCTGCTAG
CAACAGGGATGAAGAATGTTCCTGAGATTCCAAAGGGAAGAGGCCTATTTGGTGCTATAGCGGGTTTCATT
GAAAATGGATGGGAAGGCCTAATTGATGGTTGGTATGGTTTCAGACACCAGAATGCACAGGGAGAGGGAAC
TGCTGCAGATTACAAAAGCACTCAATCGGCAATTGATCAAATAACAGGAAAATTAAACCGGCTTATAGAAA
AAACCAACCAACAATTTGAGTTGATCGACAATGAATTCAATGAGGTAGAGAAGCAAATCGGTAATGTGATA
AATTGGACCAGAGATTCTATAACAGAAGTGTGGTCATACAATGCTGAACTCTTGGTAGCAATGGAGAACCA
GCATACAATTGATCTGGCTGATTCAGAAATGGACAAACTGTACGAACGAGTGAAAAGACAGCTGAGAGAGA
ATGCTGAAGAAGATGGCACTGGTTGCTTTGAAATATTTCACAAGTGTGATGATGACTGTATGGCCAGTATT
AGAAATAACACCTATGATCACAGCAAATACAGGGAAGAGGCAATGCAAAATAGAATACAGATTGACCCAGT
CAAACTAAGCAGCGGCTACAAAGATGTGATACTTTGGTTTAGCTTCGGGGCATCATGTTTCATACTTCTAG
CCATTGTAATGGGCCTTGTCTTCATATGTGTAAAGAATGGAAACATGCGGTGCACTATTTGTATATAA

Figure 12B (SEQ ID NO: 44) Amino acid sequence of PDISP/H7 Hangzhou.

MAKNVAIFGLLFSLLVLVPSQIFADKICLGHHAVSNGTKVNTLTERGVEVVNATETVERTNIPRICSKGKR
TVDLGQCGLLGTITGPPQCDQFLEFSADLIIERREGSDVCYPGKFVNEEALRQILRESGGIDKEAMGFTYS
GIRTNGATSACRRSGSSFYAEMKWLLSNTDNAAFPQMTKSYKNTRKSPALIVWGIHHSVSTAEQTKLYGSG
NKLVTVGSSNYQQSFVPSPGARPQVNGISGRIDFHWLMLNPNDTVTFSFNGAFIAPDRASFLRGKSMGIQS
GVQVDANCEGDCYHSGGTIISNLPFQNIDSRAVGKCPRYVKQRSLLLATGMKNVPEIPKGRGLFGAIAGFI
ENGWEGLIDGWYGFRHQNAQGEGTAADYKSTQSAIDQITGKLNRLIEKTNQQFELIDNEFNEVEKQIGNVI
NWTRDSITEVWSYNAELLVAMENQHTIDLADSEMDKLYERVKRQLRENAEEDGTGCFEIFHKCDDDCMASI
RNNTYDHSKYREEAMQNRIQIDPVKLSSGYKDVILWFSFGASCFILLAIVMGLVFICVKNGNMRCTICI*

Schematic representation of construct number 2140 (2X35S/CPMV HT)

Schematic representation of construct number 2168 (2X35S/CPMV HT*(-Mprot))

Figure 13: 2X35S/CPMV HT (construct no 2130) and HT*(-Mprot) (construct no 2188) for PDISP/H7 Hangzhou+H5 Indonesia TMCT

Figure 13A (SEQ ID NO: 45) Nucleotide sequence of PDISP/H7 Hangzhou+H5 Indonesia TMCT.

ATGGCGAAAAACGTTGCGATTTTCGGCTTATTGTTTTCTCTTCTTGTGTTGGTTCCTTCTCAGATCTTCGC
GGACAAAATCTGCCTCGGACATCATGCCGTGTCAAACGGAACCAAAGTAAACACATTAACTGAAAGAGGAG
TGGAAGTCGTCAATGCAACTGAAACAGTGGAACGAACAAACATCCCCAGGATCTGCTCAAAAGGGAAAAGG
ACAGTTGACCTCGGTCAATGTGGACTCCTGGGGACAATCACTGGACCACCTCAATGTGACCAATTCCTAGA
ATTTTCAGCCGATTTAATTATTGAGAGGCGAGAAGGAAGTGATGTCTGTTATCCTGGGAAATTCGTGAATG
AAGAAGCTCTGAGGCAAATTCTCAGAGAATCAGGCGGAATTGACAAGGAAGCAATGGGATTCACATACAGT
GGAATAAGAACTAATGGAGCAACCAGTGCATGTAGGAGATCAGGATCTTCATTCTATGCAGAAATGAAATG
GCTCCTGTCAAACACAGATAATGCTGCATTCCCGCAGATGACTAAGTCATATAAAAATACAAGAAAAAGCC
CAGCTCTAATAGTATGGGGGATCCATCATTCCGTATCAACTGCAGAGCAAACCAAGCTATATGGGAGTGGA
AACAAACTGGTGACAGTTGGGAGTTCTAATTATCAACAATCTTTTGTACCGAGTCCAGGAGCGAGACCACA
AGTTAATGGTATATCTGGAAGAATTGACTTTCATTGGCTAATGCTAAATCCCAATGATACAGTCACTTTCA
GTTTCAATGGGGCTTTCATAGCTCCAGACCGTGCAAGCTTCCTGAGAGGAAAATCTATGGGAATCCAGAGT
GGAGTACAGGTTGATGCCAATTGTGAAGGGGACTGCTATCATAGTGGAGGGACAATAATAAGTAACTTGCC
ATTTCAGAACATAGATAGCAGGGCAGTTGGAAAATGTCCGAGATATGTTAAGCAAAGGAGTCTGCTGCTAG
CAACAGGGATGAAGAATGTTCCTGAGATTCCAAAGGGAAGAGGCCTATTTGGTGCTATAGCGGGTTTCATT
GAAAATGGATGGGAAGGCCTAATTGATGGTTGGTATGGTTTCAGACACCAGAATGCACAGGGAGAGGGAAC
TGCTGCAGATTACAAAAGCACTCAATCGGCAATTGATCAAATAACAGGAAAATTAAACCGGCTTATAGAAA
AAACCAACCAACAATTTGAGTTGATCGACAATGAATTCAATGAGGTAGAGAAGCAAATCGGTAATGTGATA
AATTGGACCAGAGATTCTATAACAGAAGTGTGGTCATACAATGCTGAACTCTTGGTAGCAATGGAGAACCA
GCATACAATTGATCTGGCTGATTCAGAAATGGACAAACTGTACGAACGAGTGAAAAGACAGCTGAGAGAGA
ATGCTGAAGAAGATGGCACTGGTTGCTTTGAAATATTTCACAAGTGTGATGATGACTGTATGGCCAGTATT
AGAAATAACACCTATGATCACAGCAAATACAGGGAAGAGGCAATGCAAAATAGAATACAGATTGACCCAGT
CAAACTAAGCAGCGGCTACCAAATACTGTCAATTTATTCAACAGTGGCGAGTTCCCTAGCACTGGCAATCA
TGATGGCTGGTCTATCTTTATGGATGTGCTCCAATGGATCGTTACAATGCAGAATTTGCATTTAA

Figure 13B (SEQ ID NO: 46) Amino acid sequence of PDISP/H7 Hangzhou+H5 Indonesia TMCT.

MAKNVAIFGLLFSLLVLVPSQIFADKICLGHHAVSNGTKVNTLTERGVEVVNATETVERTNIPRICSKGKR
TVDLGQCGLLGTITGPPQCDQFLEFSADLIIERREGSDVCYPGKFVNEEALRQILRESGGIDKEAMGFTYS
GIRTNGATSACRRSGSSFYAEMKWLLSNTDNAAFPQMTKSYKNTRKSPALIVWGIHHSVSTAEQTKLYGSG
NKLVTVGSSNYQQSFVPSPGARPQVNGISGRIDFHWLMLNPNDTVTFSFNGAFIAPDRASFLRGKSMGIQS
GVQVDANCEGDCYHSGGTIISNLPFQNIDSRAVGKCPRYVKQRSLLLATGMKNVPEIPKGRGLFGAIAGFI
ENGWEGLIDGWYGFRHQNAQGEGTAADYKSTQSAIDQITGKLNRLIEKTNQQFELIDNEFNEVEKQIGNVI
NWTRDSITEVWSYNAELLVAMENQHTIDLADSEMDKLYERVKRQLRENAEEDGTGCFEIFHKCDDDCMASI
RNNTYDHSKYREEAMQNRIQIDPVKLSSGYQILSIYSTVASSLALAIMMAGLSLWMCSNGSLQCRICI*

Schematic representation of construct number 2130 (2X35S/CPMV HT)

Schematic representation of construct number 2188 (2X35S/CPMV HT*(-Mprot))

Figure 14: 2X35S/CPMV HT (construct no 1039) and HT*(-Mprot) (construct no 1937) for PDISP/HA B Brisbane (PrL-)

Figure 14A (SEQ ID NO: 47) Nucleotide sequence of PDISP/HA B Brisbane (PrL-).

ATGGCGAAAAACGTTGCGATTTTCGGCTTATTGTTTTCTCTTCTTGTGTTGGTTCCTTCTCAGATCTTCGC
CGATCGAATCTGCACTGGAATAACATCGTCAAACTCACCACATGTCGTCAAAACTGCTACTCAAGGGGAGG
TCAATGTGACTGGTGTAATACCACTGACAACAACACCCACCAAATCTCATTTTGCAAATCTCAAAGGAACA
GAAACCAGGGGGAAACTATGCCCAAAATGCCTCAACTGCACAGATCTGGACGTAGCCTTGGGCAGACCAAA
ATGCACGGGGAAAATACCCTCGGCAAGAGTTTCAATACTCCATGAAGTCAGACCTGTTACATCTGGGTGCT
TTCCTATAATGCACGACAGAACAAAAATTAGACAGCTGCCTAACCTTCTCCGAGGATACGAACATATCAGG
TTATCAACCCATAACGTTATCAATGCAGAAAATGCACCAGGAGGACCCTACAAAATTGGAACCTCAGGGTC
TTGCCCTAACATTACCAATGGAAACGGATTTTTCGCAACAATGGCTTGGGCCGTCCCAAAAAACGACAAAA
ACAAAACAGCAACAAATCCATTAACAATAGAAGTACCATACATTTGTACAGAAGGAGAAGACCAAATTACC
GTTTGGGGGTTCCACTCTGACAACGAGACCCAAATGGCAAAGCTCTATGGGGACTCAAAGCCCCAGAAGTT
CACCTCATCTGCCAACGGAGTGACCACACATTACGTTTCACAGATTGGTGGCTTCCCAAATCAAACAGAAG
ACGGAGGACTACCACAAAGTGGTAGAATTGTTGTTGATTACATGGTGCAAAAATCTGGGAAAACAGGAACA
ATTACCTATCAAAGGGGTATTTTATTGCCTCAAAAGGTGTGGTGCGCAAGTGGCAGGAGCAAGGTAATAAA
AGGATCCTTGCCTTTAATTGGAGAAGCAGATTGCCTCCACGAAAAATACGGTGGATTAAACAAAAGCAAGC
CTTACTACACAGGGGAACATGCAAAGGCCATAGGAAATTGCCCAATATGGGTGAAAACACCCTTGAAGCTG
GCCAATGGAACCAAATATAGACCTCCTGGTGGAGGATGGGAAGGAATGATTGCAGGTTGGCACGGATACAC
ATCCCATGGGGCACATGGAGTAGCGGTGGCAGCAGACCTTAAGAGCACTCAAGAGGCCATAAACAAGATAA
CAAAAAATCTCAACTCTTTGAGTGAGCTGGAAGTAAAGAATCTTCAAAGACTAAGCGGTGCCATGGATGAA
CTCCACAACGAAATACTAGAACTAGATGAGAAAGTGGATGATCTCAGAGCTGATACAATAAGCTCACAAAT
AGAACTCGCAGTCCTGCTTTCCAATGAAGGAATAATAAACAGTGAAGATGAACATCTCTTGGCGCTTGAAA
GAAAGCTGAAGAAAATGCTGGGCCCCTCTGCTGTAGAGATAGGGAATGGATGCTTTGAAACCAAACACAAG
TGCAACCAGACCTGTCTCGACAGAATAGCTGCTGGTACCTTTGATGCAGGAGAATTTTCTCTCCCCACCTT
TGATTCACTGAATATTACTGCTGCATCTTTAAATGACGATGGATTGGATAATCATACTATACTGCTTTACT
ACTCAACTGCTGCCTCCAGTTTGGCTGTAACACTGATGATAGCTATCTTTGTTGTTTATATGGTCTCCAGA
GACAATGTTTCTTGCTCCATCTGTCTATAA

Figure 14B (SEQ ID NO : 48) Amino acid sequence of PDISP/HA B Brisbane (PrL-).

MAKNVAIFGLLFSLLVLVPSQIFADRICTGITSSNSPHVVKTATQGEVNVTGVIPLTTTPTKSHFANLKGT
ETRGKLCPKCLNCTDLDVALGRPKCTGKIPSARVSILHEVRPVTSGCFPIMHDRTKIRQLPNLLRGYEHIR
LSTHNVINAENAPGGPYKIGTSGSCPNITNGNGFFATMAWAVPKNDKNKTATNPLTIEVPYICTEGEDQIT
VWGFHSDNETQMAKLYGDSKPQKFTSSANGVTTHYVSQIGGFPNQTEDGGLPQSGRIVVDYMVQKSGKTGT
ITYQRGILLPQKVWCASGRSKVIKGSLPLIGEADCLHEKYGGLNKSKPYYTGEHAKAIGNCPIWVKTPLKL
ANGTKYRPPGGGWEGMIAGWHGYTSHGAHGVAVAADLKSTQEAINKITKNLNSLSELEVKNLQRLSGAMDE
LHNEILELDEKVDDLRADTISSQIELAVLLSNEGIINSEDEHLLALERKLKKMLGPSAVEIGNGCFETKHK
CNQTCLDRIAAGTFDAGEFSLPTFDSLNITAASLNDDGLDNHTILLYYSTAASSLAVTLMIAIFVVYMVSR
DNVSCSICL*

Schematic representation of construct number 1039 (2X35S/CPMV HT)

Schematic representation of construct number 1937 (2X35S/CPMV HT*(-Mprot))

Figure 15: 2X35S/CPMV HT (construct no 1067) and HT*(-Mprot) (construct no 1977) for PDISP/HA B Brisbane (PrL-)+H1 California TMCT

Figure 15A (SEQ ID NO :49) Nucleotide sequence of PDISP/HA B Brisbane (PrL-)+H1 California TMCT.

ATGGCGAAAAACGTTGCGATTTTCGGCTTATTGTTTTCTCTTCTTGTGTTGGTTCCTTCTCAGATCTTCGC
CGATCGAATCTGCACTGGAATAACATCGTCAAACTCACCACATGTCGTCAAAACTGCTACTCAAGGGGAGG
TCAATGTGACTGGTGTAATACCACTGACAACAACACCCACCAAATCTCATTTTGCAAATCTCAAAGGAACA
GAAACCAGGGGGAAACTATGCCCAAAATGCCTCAACTGCACAGATCTGGACGTAGCCTTGGGCAGACCAAA
ATGCACGGGGAAAATACCCTCGGCAAGAGTTTCAATACTCCATGAAGTCAGACCTGTTACATCTGGGTGCT
TTCCTATAATGCACGACAGAACAAAAATTAGACAGCTGCCTAACCTTCTCCGAGGATACGAACATATCAGG
TTATCAACCCATAACGTTATCAATGCAGAAAATGCACCAGGAGGACCCTACAAAATTGGAACCTCAGGGTC
TTGCCCTAACATTACCAATGGAAACGGATTTTTCGCAACAATGGCTTGGGCCGTCCCAAAAAACGACAAAA
ACAAAACAGCAACAAATCCATTAACAATAGAAGTACCATACATTTGTACAGAAGGAGAAGACCAAATTACC
GTTTGGGGGTTCCACTCTGACAACGAGACCCAAATGGCAAAGCTCTATGGGGACTCAAAGCCCCAGAAGTT
CACCTCATCTGCCAACGGAGTGACCACACATTACGTTTCACAGATTGGTGGCTTCCCAAATCAAACAGAAG
ACGGAGGACTACCACAAAGTGGTAGAATTGTTGTTGATTACATGGTGCAAAAATCTGGGAAAACAGGAACA
ATTACCTATCAAAGGGGTATTTTATTGCCTCAAAAGGTGTGGTGCGCAAGTGGCAGGAGCAAGGTAATAAA
AGGATCCTTGCCTTTAATTGGAGAAGCAGATTGCCTCCACGAAAAATACGGTGGATTAAACAAAAGCAAGC
CTTACTACACAGGGGAACATGCAAAGGCCATAGGAAATTGCCCAATATGGGTGAAAACACCCTTGAAGCTG
GCCAATGGAACCAAATATAGACCTCCTGGTGGAGGATGGGAAGGAATGATTGCAGGTTGGCACGGATACAC
ATCCCATGGGGCACATGGAGTAGCGGTGGCAGCAGACCTTAAGAGCACTCAAGAGGCCATAAACAAGATAA
CAAAAAATCTCAACTCTTTGAGTGAGCTGGAAGTAAAGAATCTTCAAAGACTAAGCGGTGCCATGGATGAA
CTCCACAACGAAATACTAGAACTAGATGAGAAAGTGGATGATCTCAGAGCTGATACAATAAGCTCACAAAT
AGAACTCGCAGTCCTGCTTTCCAATGAAGGAATAATAAACAGTGAAGATGAACATCTCTTGGCGCTTGAAA
GAAAGCTGAAGAAAATGCTGGGCCCCTCTGCTGTAGAGATAGGGAATGGATGCTTTGAAACCAAACACAAG
TGCAACCAGACCTGTCTCGACAGAATAGCTGCTGGTACCTTTGATGCAGGAGAATTTTCTCTCCCCACCTT
TGATTCACTGAATATTACTGCTGCATCTTTAAATGACGATGGATTGGATAATTACCAGATTTTGGCGATCT
ATTCAACTGTCGCCAGTTCATTGGTACTGGTAGTCTCCCTGGGGGCAATCAGTTTCTGGATGTGCTCTAAT
GGGTCTCTACAGTGTAGAATATGTATTTAA

Figure 15B (SEQ ID NO : 50) Amino acid sequence of PDISP/HA B Brisbane (PrL-)+H1 California TMCT.

MAKNVAIFGLLFSLLVLVPSQIFADRICTGITSSNSPHVVKTATQGEVNVTGVIPLTTTPTKSHFANLKGT
ETRGKLCPKCLNCTDLDVALGRPKCTGKIPSARVSILHEVRPVTSGCFPIMHDRTKIRQLPNLLRGYEHIR
LSTHNVINAENAPGGPYKIGTSGSCPNITNGNGFFATMAWAVPKNDKNKTATNPLTIEVPYICTEGEDQIT
VWGFHSDNETQMAKLYGDSKPQKFTSSANGVTTHYVSQIGGFPNQTEDGGLPQSGRIVVDYMVQKSGKTGT
ITYQRGILLPQKVWCASGRSKVIKGSLPLIGEADCLHEKYGGLNKSKPYYTGEHAKAIGNCPIWVKTPLKL
ANGTKYRPPGGGWEGMIAGWHGYTSHGAHGVAVAADLKSTQEAINKITKNLNSLSELEVKNLQRLSGAMDE
LHNEILELDEKVDDLRADTISSQIELAVLLSNEGIINSEDEHLLALERKLKKMLGPSAVEIGNGCFETKHK
CNQTCLDRIAAGTFDAGEFSLPTFDSLNITAASLNDDGLDNYQILAIYSTVASSLVLVVSLGAISFWMCSN
GSLQCRICI*

Schematic representation of construct number 1067 (2X35S/CPMV HT)

Schematic representation of construct number 1977 (2X35S/CPMV HT*(-Mprot))

Figure 16: 2X35S/CPMV HT (construct no 2072) and HT*(-Mprot) (construct no 2050) for PDISP/HA B Massachussetts (PrL-)

Figure 16A (SEQ ID NO : 51) Nucleotide sequence of PDISP/HA B Massachussetts (PrL-).

ATGGCGAAAAACGTTGCGATTTTCGGCTTATTGTTTTCTCTTCTTGTGTTGGTTCCTTCTCAGATCTTCGC
CGATCGAATCTGCACTGGGATAACATCTTCAAACTCACCTCATGTGGTCAAAACAGCTACTCAAGGGGAGG
TCAATGTGACTGGTGTGATACCACTAACAACAACACCAACAAAATCTTATTTTGCAAATCTCAAAGGAACA
AAGACCAGAGGGAAACTATGCCCAGACTGTCTCAACTGTACAGATCTGGATGTGGCCCTGGGCAGGCCAAT
GTGTGTGGGAACTACACCTTCTGCGAAAGCTTCAATACTTCACGAAGTCAGACCTGTTACATCCGGGTGCT
TCCCTATAATGCACGACAGAACAAAAATCAGGCAACTAGCCAATCTTCTCAGAGGATATGAAAATATCAGG
TTATCAACCCAAAACGTTATCGATGCAGAAAAGGCACCAGGAGGACCCTACAGACTTGGAACCTCAGGATC
TTGCCCTAACGCTACCAGTAAAAGCGGATTTTTCGCAACAATGGCTTGGGCTGTCCCAAAGGACAACAACA
AAAATGCAACGAACCCATTAACAGTAGAAGTACCATACATTTGTGCAGAAGGGGAAGACCAAATTACTGTT
TGGGGGTTCCATTCAGATAACAAAACCCAAATGAAGAACCTCTATGGAGACTCAAATCCTCAAAAGTTCAC
CTCATCTGCTAATGGAGTAACCACACATTATGTTTCTCAGATTGGCGGCTTCCCAGATCAAACAGAAGACG
GAGGACTACCACAAAGCGGCAGAATTGTCGTTGATTACATGATGCAAAAACCTGGGAAAACAGGAACAATT
GTCTATCAAAGAGGTGTTTTGTTGCCTCAAAAGGTGTGGTGCGCGAGTGGCAGGAGCAAAGTAATAAAAGG
GTCCTTGCCTTTAATTGGTGAAGCAGATTGCCTTCATGAAAAATACGGTGGATTAAACAAAAGCAAGCCTT
ACTACACAGGAGAACATGCAAAAGCCATAGGAAATTGCCCAATATGGGTGAAAACACCTTTGAAGCTTGCC
AATGGAACCAAATATAGACCTCCTGGTGGAGGATGGGAAGGAATGATTGCAGGTTGGCACGGATACACATC
TCACGGAGCACATGGAGTGGCAGTTGCTGCAGACCTTAAGAGCACACAAGAAGCTATAAACAAGATAACAA
AAAATCTCAACTCTTTGAGTGAGCTAGAAGTAAAGAATCTTCAAAGGCTAAGTGGTGCCATGGATGAACTC
CACAACGAAATACTCGAGCTGGATGAGAAAGTGGATGACCTCAGAGCTGACACTATAAGTTCACAAATAGA
ACTTGCAGTCTTGCTTTCCAACGAAGGAATAATAAACAGTGAAGACGAGCATCTATTGGCACTTGAGAGAA
AACTAAAGAAAATGCTGGGTCCCTCTGCTGTAGACATAGGAAATGGATGCTTCGAAACCAAACACAAATGC
AACCAGACCTGCTTAGACAGGATAGCTGCTGGCACCTTTAATGCAGGAGAGTTTTCTCTCCCCACTTTTGA
TTCATTGAACATTACTGCTGCATCTTTAAATGATGATGGATTGGATAACCATACTATACTGCTCTATTACT
CAACTGCTGCTTCTAGTTTGGCTGTAACATTGATGCTAGCTATTTTTATTGTTTATATGGTCTCCAGAGAC
AACGTTTCATGCTCCATCTGTCTATAA

Figure 16B (SEQ ID NO : 52) Amino acid sequence of PDISP/HA B Massachussetts (PrL-).

MAKNVAIFGLLFSLLVLVPSQIFADRICTGITSSNSPHVVKTATQGEVNVTGVIPLTTTPTKSYFANLKGT
KTRGKLCPDCLNCTDLDVALGRPMCVGTTPSAKASILHEVRPVTSGCFPIMHDRTKIRQLANLLRGYENIR
LSTQNVIDAEKAPGGPYRLGTSGSCPNATSKSGFFATMAWAVPKDNNKNATNPLTVEVPYICAEGEDQITV
WGFHSDNKTQMKNLYGDSNPQKFTSSANGVTTHYVSQIGGFPDQTEDGGLPQSGRIVVDYMMQKPGKTGTI
VYQRGVLLPQKVWCASGRSKVIKGSLPLIGEADCLHEKYGGLNKSKPYYTGEHAKAIGNCPIWVKTPLKLA
NGTKYRPPGGGWEGMIAGWHGYTSHGAHGVAVAADLKSTQEAINKITKNLNSLSELEVKNLQRLSGAMDEL
HNEILELDEKVDDLRADTISSQIELAVLLSNEGIINSEDEHLLALERKLKKMLGPSAVDIGNGCFETKHKC
NQTCLDRIAAGTFNAGEFSLPTFDSLNITAASLNDDGLDNHTILLYYSTAASSLAVTLMLAIFIVYMVSRD
NVSCSICL*

Schematic representation of construct number 2072 (2X35S/CPMV HT)

Schematic representation of construct number 2050 (2X35S/CPMV HT*(-Mprot))

Figure 17: 2X35S/CPMV HT (construct no 2074) and HT*(-Mprot) (construct no 2060) for PDISP/HA B Massachussetts (PrL-)+H1 California TMCT

Figure 17A (SEQ ID NO : 53) Nucleotide sequence of PDISP/HA B Massachussetts (PrL-)+H1 California TMCT.

ATGGCGAAAAACGTTGCGATTTTCGGCTTATTGTTTTCTCTTCTTGTGTTGGTTCCTTCTCAGATCTTCGC
CGATCGAATCTGCACTGGGATAACATCTTCAAACTCACCTCATGTGGTCAAAACAGCTACTCAAGGGGAGG
TCAATGTGACTGGTGTGATACCACTAACAACAACACCAACAAAATCTTATTTTGCAAATCTCAAAGGAACA
AAGACCAGAGGGAAACTATGCCCAGACTGTCTCAACTGTACAGATCTGGATGTGGCCCTGGGCAGGCCAAT
GTGTGTGGGAACTACACCTTCTGCGAAAGCTTCAATACTTCACGAAGTCAGACCTGTTACATCCGGGTGCT
TCCCTATAATGCACGACAGAACAAAAATCAGGCAACTAGCCAATCTTCTCAGAGGATATGAAAATATCAGG
TTATCAACCCAAAACGTTATCGATGCAGAAAAGGCACCAGGAGGACCCTACAGACTTGGAACCTCAGGATC
TTGCCCTAACGCTACCAGTAAAAGCGGATTTTTCGCAACAATGGCTTGGGCTGTCCCAAAGGACAACAACA
AAAATGCAACGAACCCATTAACAGTAGAAGTACCATACATTTGTGCAGAAGGGGAAGACCAAATTACTGTT
TGGGGGTTCCATTCAGATAACAAAACCCAAATGAAGAACCTCTATGGAGACTCAAATCCTCAAAAGTTCAC
CTCATCTGCTAATGGAGTAACCACACATTATGTTTCTCAGATTGGCGGCTTCCCAGATCAAACAGAAGACG
GAGGACTACCACAAAGCGGCAGAATTGTCGTTGATTACATGATGCAAAAACCTGGGAAAACAGGAACAATT
GTCTATCAAAGAGGTGTTTTGTTGCCTCAAAAGGTGTGGTGCGCGAGTGGCAGGAGCAAAGTAATAAAAGG
GTCCTTGCCTTTAATTGGTGAAGCAGATTGCCTTCATGAAAAATACGGTGGATTAAACAAAAGCAAGCCTT
ACTACACAGGAGAACATGCAAAAGCCATAGGAAATTGCCCAATATGGGTGAAAACACCTTTGAAGCTTGCC
AATGGAACCAAATATAGACCTCCTGGTGGAGGATGGGAAGGAATGATTGCAGGTTGGCACGGATACACATC
TCACGGAGCACATGGAGTGGCAGTTGCTGCAGACCTTAAGAGCACACAAGAAGCTATAAACAAGATAACAA
AAAATCTCAACTCTTTGAGTGAGCTAGAAGTAAAGAATCTTCAAAGGCTAAGTGGTGCCATGGATGAACTC
CACAACGAAATACTCGAGCTGGATGAGAAAGTGGATGACCTCAGAGCTGACACTATAAGTTCACAAATAGA
ACTTGCAGTCTTGCTTTCCAACGAAGGAATAATAAACAGTGAAGACGAGCATCTATTGGCACTTGAGAGAA
AACTAAAGAAAATGCTGGGTCCCTCTGCTGTAGACATAGGAAATGGATGCTTCGAAACCAAACACAAATGC
AACCAGACCTGCTTAGACAGGATAGCTGCTGGCACCTTTAATGCAGGAGAGTTTTCTCTCCCCACTTTTGA
TTCATTGAACATTACTGCTGCATCTTTAAATGATGATGGATTGGATAACTACCAGATTTTGGCGATCTATT
CAACTGTCGCCAGTTCATTGGTACTGGTAGTCTCCCTGGGGGCAATCAGTTTCTGGATGTGCTCTAATGGG
TCTCTACAGTGTAGAATATGTATTTAA

Figure 17B (SEQ ID NO :54) Amino acid sequence of PDISP/HA B Massachussetts (PrL-)+H1 California TMCT.

MAKNVAIFGLLFSLLVLVPSQIFADRICTGITSSNSPHVVKTATQGEVNVTGVIPLTTTPTKSYFANLKGT
KTRGKLCPDCLNCTDLDVALGRPMCVGTTPSAKASILHEVRPVTSGCFPIMHDRTKIRQLANLLRGYENIR
LSTQNVIDAEKAPGGPYRLGTSGSCPNATSKSGFFATMAWAVPKDNNKNATNPLTVEVPYICAEGEDQITV
WGFHSDNKTQMKNLYGDSNPQKFTSSANGVTTHYVSQIGGFPDQTEDGGLPQSGRIVVDYMMQKPGKTGTI
VYQRGVLLPQKVWCASGRSKVIKGSLPLIGEADCLHEKYGGLNKSKPYYTGEHAKAIGNCPIWVKTPLKLA
NGTKYRPPGGGWEGMIAGWHGYTSHGAHGVAVAADLKSTQEAINKITKNLNSLSELEVKNLQRLSGAMDEL
HNEILELDEKVDDLRADTISSQIELAVLLSNEGIINSEDEHLLALERKLKKMLGPSAVDIGNGCFETKHKC
NQTCLDRIAAGTFNAGEFSLPTFDSLNITAASLNDDGLDNYQILAIYSTVASSLVLVVSLGAISFWMCSNG
SLQCRICI*

Schematic representation of construct number 2074 (2X35S/CPMV HT)

Schematic representation of construct number 2060 (2X35S/CPMV HT*(-Mprot))

Figure 18: 2X35S/CPMV HT (construct no 1445), HT*(-Mprot) (construct no 1820) and HT(fl5'UTR) (construct no 1975) for HA B Wisconsin (PrL-)

Figure 18A ( SEQ ID NO : 55) Nucleotide sequence of HA B Wisconsin (PrL-).

ATGAAGGCAATAATTGTACTACTCATGGTAGTAACATCCAATGCAGATCGAATCTGCACTGGGATAACATC
TTCAAACTCACCTCATGTGGTCAAAACAGCTACTCAAGGGGAGGTCAATGTGACTGGCGTGATACCACTGA
CAACAACACCAACAAAATCTTATTTTGCAAATCTCAAAGGAACAAGGACCAGAGGGAAACTATGCCCGGAC
TGTCTCAACTGTACAGATCTGGATGTGGCCTTGGGCAGGCCAATGTGTGTGGGGACCACACCTTCTGCTAA
AGCTTCAATACTCCACGAGGTCAGACCTGTTACATCCGGGTGCTTTCCTATAATGCACGACAGAACAAAAA
TCAGGCAACTACCCAATCTTCTCAGAGGATATGAAAATATCAGGTTATCAACCCAAAACGTTATCGATGCA
GAAAAAGCACCAGGAGGACCCTACAGACTTGGAACCTCAGGATCTTGCCCTAACGCTACCAGTAAAATCGG
ATTTTTTGCAACAATGGCTTGGGCTGTCCCAAAGGACAACTACAAAAATGCAACGAACCCACTAACAGTAG
AAGTACCATACATTTGTACAGAAGGGGAAGACCAAATTACTGTTTGGGGGTTCCATTCAGATAACAAAACC
CAAATGAAGAGCCTCTATGGAGACTCAAATCCTCAAAAGTTCACCTCATCTGCTAATGGAGTAACCACACA
TTATGTTTCTCAGATTGGCGACTTCCCAGATCAAACAGAAGACGGAGGACTACCACAAAGCGGCAGAATTG
TTGTTGATTACATGATGCAAAAACCTGGGAAAACAGGAACAATTGTCTATCAAAGAGGTGTTTTGTTGCCT
CAAAAGGTGTGGTGCGCGAGTGGCAGGAGCAAAGTAATAAAAGGGTCATTGCCTTTAATTGGTGAAGCAGA
TTGCCTTCATGAAAAATACGGTGGATTAAACAAAAGCAAGCCTTACTACACAGGAGAACATGCAAAAGCCA
TAGGAAATTGCCCAATATGGGTAAAAACACCTTTGAAGCTTGCCAATGGAACCAAATATAGACCTCCTGGT
GGAGGATGGGAAGGAATGATTGCAGGTTGGCACGGATACACATCTCACGGAGCACATGGAGTGGCAGTGGC
GGCAGACCTTAAGAGTACACAAGAAGCTATAAATAAGATAACAAAAAATCTCAATTCTTTGAGTGAGCTAG
AAGTAAAGAACCTTCAAAGACTAAGTGGTGCCATGGATGAACTCCACAACGAAATACTCGAGCTGGATGAG
AAAGTGGATGATCTCAGAGCTGACACTATAAGCTCACAAATAGAACTTGCAGTCTTGCTTTCCAACGAAGG
AATAATAAACAGTGAAGACGAGCATCTATTGGCACTTGAGAGAAAACTAAAGAAAATGCTGGGTCCCTCTG
CTGTAGACATAGGAAACGGATGCTTCGAAACCAAACACAAATGCAACCAGACCTGCTTAGACAGGATAGCT
GCTGGCACCTTTAATGCAGGAGAATTTTCTCTCCCCACTTTTGATTCATTGAACATTACTGCTGCATCTTT
AAATGATGATGGATTGGATAACCATACTATACTGCTCTATTACTCAACTGCTGCTTCTAGTTTGGCTGTAA
CATTAATGCTAGCTATTTTTATTGTTTATATGGTCTCCAGAGACAACGTTTCATGCTCCATCTGTCTATAA

Figure 18B, (SEQ ID NO : 56) Amino acid sequence of HA B Wisconsin (PrL-).

MKAIIVLLMVVTSNADRICTGITSSNSPHVVKTATQGEVNVTGVIPLTTTPTKSYFANLKGTRTRGKLCPD
CLNCTDLDVALGRPMCVGTTPSAKASILHEVRPVTSGCFPIMHDRTKIRQLPNLLRGYENIRLSTQNVIDA
EKAPGGPYRLGTSGSCPNATSKIGFFATMAWAVPKDNYKNATNPLTVEVPYICTEGEDQITVWGFHSDNKT
QMKSLYGDSNPQKFTSSANGVTTHYVSQIGDFPDQTEDGGLPQSGRIVVDYMMQKPGKTGTIVYQRGVLLP
QKVWCASGRSKVIKGSLPLIGEADCLHEKYGGLNKSKPYYTGEHAKAIGNCPIWVKTPLKLANGTKYRPPG
GGWEGMIAGWHGYTSHGAHGVAVAADLKSTQEAINKITKNLNSLSELEVKNLQRLSGAMDELHNEILELDE
KVDDLRADTISSQIELAVLLSNEGIINSEDEHLLALERKLKKMLGPSAVDIGNGCFETKHKCNQTCLDRIA
AGTFNAGEFSLPTFDSLNITAASLNDDGLDNHTILLYYSTAASSLAVTLMLAIFIVYMVSRDNVSCSICL*

Schematic representation of construct number 1445 (2X35S/CPMV HT)

Schematic representation of construct number 1820 (2X35S/CPMV HT*(-Mprot))

Schematic representation of construct number 1975 (2X35S/CPMV HT*(fl5'UTR))

Figure 19: 2X35S/CPMV HT (construct no 1454) and HT*(-Mprot) (construct no 1893) for HA B Wisconsin (PrL-)+H1 California TMCT

Figure 19A (SEQ ID NO : 57) Nucleotide sequence of HA B Wisconsin (PrL-)+H1 California TMCT ATGAAGGCAATAATTGTACTACTCATGGTAGTAACATCCAATGCAGATCGAATCTGCACTGGGATAACATC
TTCAAACTCACCTCATGTGGTCAAAACAGCTACTCAAGGGGAGGTCAATGTGACTGGCGTGATACCACTGA
CAACAACACCAACAAAATCTTATTTTGCAAATCTCAAAGGAACAAGGACCAGAGGGAAACTATGCCCGGAC
TGTCTCAACTGTACAGATCTGGATGTGGCCTTGGGCAGGCCAATGTGTGTGGGGACCACACCTTCTGCTAA
AGCTTCAATACTCCACGAGGTCAGACCTGTTACATCCGGGTGCTTTCCTATAATGCACGACAGAACAAAAA
TCAGGCAACTACCCAATCTTCTCAGAGGATATGAAAATATCAGGTTATCAACCCAAAACGTTATCGATGCA
GAAAAAGCACCAGGAGGACCCTACAGACTTGGAACCTCAGGATCTTGCCCTAACGCTACCAGTAAAATCGG
ATTTTTTGCAACAATGGCTTGGGCTGTCCCAAAGGACAACTACAAAAATGCAACGAACCCACTAACAGTAG
AAGTACCATACATTTGTACAGAAGGGGAAGACCAAATTACTGTTTGGGGGTTCCATTCAGATAACAAAACC
CAAATGAAGAGCCTCTATGGAGACTCAAATCCTCAAAAGTTCACCTCATCTGCTAATGGAGTAACCACACA
TTATGTTTCTCAGATTGGCGACTTCCCAGATCAAACAGAAGACGGAGGACTACCACAAAGCGGCAGAATTG
TTGTTGATTACATGATGCAAAAACCTGGGAAAACAGGAACAATTGTCTATCAAAGAGGTGTTTTGTTGCCT
CAAAAGGTGTGGTGCGCGAGTGGCAGGAGCAAAGTAATAAAAGGGTCATTGCCTTTAATTGGTGAAGCAGA
TTGCCTTCATGAAAAATACGGTGGATTAAACAAAAGCAAGCCTTACTACACAGGAGAACATGCAAAAGCCA
TAGGAAATTGCCCAATATGGGTAAAAACACCTTTGAAGCTTGCCAATGGAACCAAATATAGACCTCCTGGT
GGAGGATGGGAAGGAATGATTGCAGGTTGGCACGGATACACATCTCACGGAGCACATGGAGTGGCAGTGGC
GGCAGACCTTAAGAGTACACAAGAAGCTATAAATAAGATAACAAAAAATCTCAATTCTTTGAGTGAGCTAG
AAGTAAAGAACCTTCAAAGACTAAGTGGTGCCATGGATGAACTCCACAACGAAATACTCGAGCTGGATGAG
AAAGTGGATGATCTCAGAGCTGACACTATAAGCTCACAAATAGAACTTGCAGTCTTGCTTTCCAACGAAGG
AATAATAAACAGTGAAGACGAGCATCTATTGGCACTTGAGAGAAAACTAAAGAAAATGCTGGGTCCCTCTG
CTGTAGACATAGGAAACGGATGCTTCGAAACCAAACACAAATGCAACCAGACCTGCTTAGACAGGATAGCT
GCTGGCACCTTTAATGCAGGAGAATTTTCTCTCCCCACTTTTGATTCATTGAACATTACTGCTGCATCTTT
AAATGATGATGGATTGGATAACTACCAGATTTTGGCGATCTATTCAACTGTCGCCAGTTCATTGGTACTGG
TAGTCTCCCTGGGGGCAATCAGTTTCTGGATGTGCTCTAATGGGTCTCTACAGTGTAGAATATGTATTTAA

Figure 19B (SEQ ID NO : 58) Amino acid sequence of HA B Wisconsin (PrL-)+H1 California TMC.

MKAIIVLLMVVTSNADRICTGITSSNSPHVVKTATQGEVNVTGVIPLTTTPTKSYFANLKGTRTRGKLCPD
CLNCTDLDVALGRPMCVGTTPSAKASILHEVRPVTSGCFPIMHDRTKIRQLPNLLRGYENIRLSTQNVIDA
EKAPGGPYRLGTSGSCPNATSKIGFFATMAWAVPKDNYKNATNPLTVEVPYICTEGEDQITVWGFHSDNKT
QMKSLYGDSNPQKFTSSANGVTTHYVSQIGDFPDQTEDGGLPQSGRIVVDYMMQKPGKTGTIVYQRGVLLP
QKVWCASGRSKVIKGSLPLIGEADCLHEKYGGLNKSKPYYTGEHAKAIGNCPIWVKTPLKLANGTKYRPPG
GGWEGMIAGWHGYTSHGAHGVAVAADLKSTQEAINKITKNLNSLSELEVKNLQRLSGAMDELHNEILELDE
KVDDLRADTISSQIELAVLLSNEGIINSEDEHLLALERKLKKMLGPSAVDIGNGCFETKHKCNQTCLDRIA
AGTFNAGEFSLPTFDSLNITAASLNDDGLDNYQILAIYSTVASSLVLVVSLGAISFWMCSNGSLQCRICI*

Schematic representation of construct number 1454 (2X35S/CPMV HT)

Schematic representation of construct number 1893 (2X35S/CPMV HT*(-Mprot))

Figure 20: 2X35S/CPMV HT (construct no 5001) and HT*(-Mprot) (construct no 2100) for HC Rituxan

Figure 20A (SEQ ID NO : 59) Nucleotide sequence of HC Rituxan.

ATGGGTTGGAGCCTCATCTTGCTCTTCCTTGTCGCTGTTGCTACGCGTGTCCTGTCCCAGGTACAACTGCA
GCAGCCTGGGGCTGAGCTGGTGAAGCCTGGGGCCTCAGTGAAGATGTCCTGCAAGGCTTCTGGCTACACAT
TTACCAGTTACAATATGCACTGGGTAAAACAGACACCTGGTCGGGGCCTGGAATGGATTGGAGCTATTTAT
CCCGGAAATGGTGATACTTCCTACAATCAGAAGTTCAAAGGCAAGGCCACATTGACTGCAGACAAATCCTC
CAGCACAGCCTACATGCAGCTCAGCAGCCTGACATCTGAGGACTCTGCGGTCTATTACTGTGCAAGATCGA
CTTACTACGGCGGTGACTGGTACTTCAATGTCTGGGGCGCAGGGACCACGGTCACCGTCTCTGCAGCTAGC
ACCAAGGGCCCATCGGTCTTCCCCCTGGCACCCTCCTCCAAGAGCACCTCTGGGGGCACAGCGGCCCTGGG
CTGCCTGGTCAAGGACTACTTCCCCGAACCGGTGACGGTGTCGTGGAACTCAGGCGCCCTGACCAGCGGCG
TGCACACCTTCCCGGCTGTCCTACAGTCCTCAGGACTCTACTCCCTCAGCAGCGTGGTGACCGTGCCCTCC
AGCAGCTTGGGCACCCAGACCTACATCTGCAACGTGAATCACAAGCCCAGCAACACCAAGGTGGACAAGAA
AGTTGAGCCCAAATCTTGTGACAAAACTCACACATGCCCACCGTGCCCAGCACCTGAACTCCTGGGGGGAC
CGTCAGTCTTCCTCTTCCCCCCAAAACCCAAGGACACCCTCATGATCTCCCGGACCCCTGAGGTCACATGC
GTGGTGGTGGACGTGAGCCACGAAGACCCTGAGGTCAAGTTCAACTGGTACGTGGACGGCGTGGAGGTGCA
TAATGCCAAGACAAAGCCGCGGGAGGAGCAGTACAACAGCACGTACCGTGTGGTCAGCGTCCTCACCGTCC
TGCACCAGGACTGGCTGAATGGCAAGGAGTACAAGTGCAAGGTCTCCAACAAAGCCCTCCCAGCCCCCATC
GAGAAAACCATCTCCAAAGCCAAAGGGCAGCCTAGGGAACCACAAGTGTACACTCTTCCACCATCTAGGGA
TGAGCTTACTAAGAACCAAGTTTCTCTTACTTGTCTTGTGAAGGGATTTTATCCATCTGACATCGCCGTGG
AATGGGAATCCAACGGACAACCAGAGAACAATTACAAGACTACTCCACCAGTTCTTGATTCTGATGGATCC
TTCTTTCTTTATTCCAAGCTTACTGTTGATAAGTCCAGATGGCAGCAAGGAAATGTGTTCTCTTGTTCTGT
TATGCACGAAGCTCTTCATAATCATTATACTCAAAAGTCCCTTTCTCTTTCTCCTGGAAAGTGA

Figure 20B (SEQ ID NO : 60) Amino acid sequence of HC Rituxan.

MGWSLILLFLVAVATRVLSQVQLQQPGAELVKPGASVKMSCKASGYTFTSYNMHWVKQTPGRGLEWIGAIY
PGNGDTSYNQKFKGKATLTADKSSSTAYMQLSSLTSEDSAVYYCARSTYYGGDWYFNVWGAGTTVTVSAAS
TKGPSVFPLAPSSKSTSGGTAALGCLVKDYFPEPVTVSWNSGALTSGVHTFPAVLQSSGLYSLSSVVTVPS
SSLGTQTYICNVNHKPSNTKVDKKVEPKSCDKTHTCPPCPAPELLGGPSVFLFPPKPKDTLMISRTPEVTC
VVVDVSHEDPEVKFNWYVDGVEVHNAKTKPREEQYNSTYRVVSVLTVLHQDWLNGKEYKCKVSNKALPAPI
EKTISKAKGQPREPQVYTLPPSRDELTKNQVSLTCLVKGFYPSDIAVEWESNGQPENNYKTTPPVLDSDGS
FFLYSKLTVDKSRWQQGNVFSCSVMHEALHNHYTQKSLSLSPGK*

Schematic representation of construct number 5001 (2X35S/CPMV HT)

Schematic representation of construct number 2100 (2X35S/CPMV HT*(-Mprot))

Figure 21: 2X35S/CPMV HT (construct no 5002) and HT*(-Mprot) (construct no 2109) for PDISP/HC Rituxan

Figure 21A, (SEQ ID NO : 61) Nucleotide sequence of PDISP/HC Rituxan.

ATGGCGAAAAACGTTGCGATTTTCGGCTTATTGTTTTCTCTTCTTGTGTTGGTTCCTTCTCAGATCTTCGC
CCAGGTACAACTGCAGCAGCCTGGGGCTGAGCTGGTGAAGCCTGGGGCCTCAGTGAAGATGTCCTGCAAGG
CTTCTGGCTACACATTTACCAGTTACAATATGCACTGGGTAAAACAGACACCTGGTCGGGGCCTGGAATGG
ATTGGAGCTATTTATCCCGGAAATGGTGATACTTCCTACAATCAGAAGTTCAAAGGCAAGGCCACATTGAC
TGCAGACAAATCCTCCAGCACAGCCTACATGCAGCTCAGCAGCCTGACATCTGAGGACTCTGCGGTCTATT
ACTGTGCAAGATCGACTTACTACGGCGGTGACTGGTACTTCAATGTCTGGGGCGCAGGGACCACGGTCACC
GTCTCTGCAGCTAGCACCAAGGGCCCATCGGTCTTCCCCCTGGCACCCTCCTCCAAGAGCACCTCTGGGGG
CACAGCGGCCCTGGGCTGCCTGGTCAAGGACTACTTCCCCGAACCGGTGACGGTGTCGTGGAACTCAGGCG
CCCTGACCAGCGGCGTGCACACCTTCCCGGCTGTCCTACAGTCCTCAGGACTCTACTCCCTCAGCAGCGTG
GTGACCGTGCCCTCCAGCAGCTTGGGCACCCAGACCTACATCTGCAACGTGAATCACAAGCCCAGCAACAC
CAAGGTGGACAAGAAAGTTGAGCCCAAATCTTGTGACAAAACTCACACATGCCCACCGTGCCCAGCACCTG
AACTCCTGGGGGGACCGTCAGTCTTCCTCTTCCCCCCAAAACCCAAGGACACCCTCATGATCTCCCGGACC
CCTGAGGTCACATGCGTGGTGGTGGACGTGAGCCACGAAGACCCTGAGGTCAAGTTCAACTGGTACGTGGA
CGGCGTGGAGGTGCATAATGCCAAGACAAAGCCGCGGGAGGAGCAGTACAACAGCACGTACCGTGTGGTCA
GCGTCCTCACCGTCCTGCACCAGGACTGGCTGAATGGCAAGGAGTACAAGTGCAAGGTCTCCAACAAAGCC
CTCCCAGCCCCCATCGAGAAAACCATCTCCAAAGCCAAAGGGCAGCCTAGGGAACCACAAGTGTACACTCT
TCCACCATCTAGGGATGAGCTTACTAAGAACCAAGTTTCTCTTACTTGTCTTGTGAAGGGATTTTATCCAT
CTGACATCGCCGTGGAATGGGAATCCAACGGACAACCAGAGAACAATTACAAGACTACTCCACCAGTTCTT
GATTCTGATGGATCCTTCTTTCTTTATTCCAAGCTTACTGTTGATAAGTCCAGATGGCAGCAAGGAAATGT
GTTCTCTTGTTCTGTTATGCACGAAGCTCTTCATAATCATTATACTCAAAAGTCCCTTTCTCTTTCTCCTG
GAAAGTGA

Figure 21B (SEQ ID NO : 62) Amino acid sequence of PDISP/HC Rituxan.

MAKNVAIFGLLFSLLVLVPSQIFAQVQLQQPGAELVKPGASVKMSCKASGYTFTSYNMHWVKQTPGRGLEW
IGAIYPGNGDTSYNQKFKGKATLTADKSSSTAYMQLSSLTSEDSAVYYCARSTYYGGDWYFNVWGAGTTVT
VSAASTKGPSVFPLAPSSKSTSGGTAALGCLVKDYFPEPVTVSWNSGALTSGVHTFPAVLQSSGLYSLSSV
VTVPSSSLGTQTYICNVNHKPSNTKVDKKVEPKSCDKTHTCPPCPAPELLGGPSVFLFPPKPKDTLMISRT
PEVTCVVVDVSHEDPEVKFNWYVDGVEVHNAKTKPREEQYNSTYRVVSVLTVLHQDWLNGKEYKCKVSNKA
LPAPIEKTISKAKGQPREPQVYTLPPSRDELTKNQVSLTCLVKGFYPSDIAVEWESNGQPENNYKTTPPVL
DSDGSFFLYSKLTVDKSRWQQGNVFSCSVMHEALHNHYTQKSLSLSPGK*

Schematic representation of construct number 5002 (2X35S/CPMV HT)

Schematic representation of construct number 2109 (2X35S/CPMV HT*(-Mprot))

Figure 22: 2X35S/CPMV HT (construct no 5021) and HT*(-Mprot) (construct no 2120) for LC Rituxan

Figure 22A (SEQ ID NO : 63) Nucleotide sequence of LC Rituxan.

ATGGATTTTCAGGTGCAGATTATCAGCTTCCTGCTAATCAGTGCTTCAGTCATAATGTCCAGAGGACAAAT
TGTTCTCTCCCAGTCTCCAGCAATCCTGTCTGCATCTCCAGGGGAGAAGGTCACAATGACTTGCAGGGCCA
GCTCAAGTGTAAGTTACATCCACTGGTTCCAGCAGAAGCCAGGATCCTCCCCCAAACCCTGGATTTATGCC
ACATCCAACCTGGCTTCTGGAGTCCCTGTTCGCTTCAGTGGCAGTGGGTCTGGGACTTCTTACTCTCTCAC
AATCAGCAGAGTGGAGGCTGAAGATGCTGCCACTTATTACTGCCAGCAGTGGACTAGTAACCCACCCACGT
TCGGAGGGGGGACCAAGCTGGAAATCAAACGTACGGTGGCTGCACCATCTGTCTTCATCTTCCCGCCATCT
GATGAGCAGTTGAAATCTGGAACTGCCTCTGTTGTGTGCCTGCTGAATAACTTCTATCCCAGAGAGGCCAA
AGTACAGTGGAAGGTGGATAACGCCCTCCAATCGGGTAACTCCCAGGAGAGTGTCACAGAGCAGGACAGCA
AGGACAGCACCTACAGCCTCAGCAGCACCCTGACGCTGAGCAAAGCAGACTACGAGAAACACAAAGTCTAC
GCCTGCGAAGTCACCCATCAGGGCCTGAGCTCGCCCGTCACAAAGAGCTTCAACAGGGGAGAGTGTTGA

Figure 22B (SEQ ID NO : 64) Amino acid sequence of LC Rituxan.

MDFQVQIISFLLISASVIMSRGQIVLSQSPAILSASPGEKVTMTCRASSSVSYIHWFQQKPGSSPKPWIYA
TSNLASGVPVRFSGSGSGTSYSLTISRVEAEDAATYYCQQWTSNPPTFGGGTKLEIKRTVAAPSVFIFPPS
DEQLKSGTASVVCLLNNFYPREAKVQWKVDNALQSGNSQESVTEQDSKDSTYSLSSTLTLSKADYEKHKVY
ACEVTHQGLSSPVTKSFNRGEC*

Schematic representation of construct number 5021 (2X35S/CPMV HT)

Schematic representation of construct number 2120 (2X35S/CPMV HT*(-Mprot))

Figure 23: 2X35S/CPMV HT (construct no 5022) and HT*(-Mprot) (construct no 2129) for PDISP/LC Rituxan

Figure 23A (SEQ ID NO : 65) Nucleotide sequence of PDISP/LC Rituxan.

ATGGCGAAAAACGTTGCGATTTTCGGCTTATTGTTTTCTCTTCTTGTGTTGGTTCCTTCTCAGATCTTCGC
CCAAATTGTTCTCTCCCAGTCTCCAGCAATCCTGTCTGCATCTCCAGGGGAGAAGGTCACAATGACTTGCA
GGGCCAGCTCAAGTGTAAGTTACATCCACTGGTTCCAGCAGAAGCCAGGATCCTCCCCCAAACCCTGGATT
TATGCCACATCCAACCTGGCTTCTGGAGTCCCTGTTCGCTTCAGTGGCAGTGGGTCTGGGACTTCTTACTC
TCTCACAATCAGCAGAGTGGAGGCTGAAGATGCTGCCACTTATTACTGCCAGCAGTGGACTAGTAACCCAC
CCACGTTCGGAGGGGGGACCAAGCTGGAAATCAAACGTACGGTGGCTGCACCATCTGTCTTCATCTTCCCG
CCATCTGATGAGCAGTTGAAATCTGGAACTGCCTCTGTTGTGTGCCTGCTGAATAACTTCTATCCCAGAGA
GGCCAAAGTACAGTGGAAGGTGGATAACGCCCTCCAATCGGGTAACTCCCAGGAGAGTGTCACAGAGCAGG
ACAGCAAGGACAGCACCTACAGCCTCAGCAGCACCCTGACGCTGAGCAAAGCAGACTACGAGAAACACAAA
GTCTACGCCTGCGAAGTCACCCATCAGGGCCTGAGCTCGCCCGTCACAAAGAGCTTCAACAGGGGAGAGTG
TTGA

Figure 23B (SEQ ID NO : 66) Amino acid sequence of PDISP/LC Rituxan.

MAKNVAIFGLLFSLLVLVPSQIFAQIVLSQSPAILSASPGEKVTMTCRASSSVSYIHWFQQKPGSSPKPWI
YATSNLASGVPVRFSGSGSGTSYSLTISRVEAEDAATYYCQQWTSNPPTFGGGTKLEIKRTVAAPSVFIFP
PSDEQLKSGTASVVCLLNNFYPREAKVQWKVDNALQSGNSQESVTEQDSKDSTYSLSSTLTLSKADYEKHK
VYACEVTHQGLSSPVTKSFNRGEC*

Schematic representation of construct number 5022 (2X35S/CPMV HT)

Schematic representation of construct number 2129 (2X35S/CPMV HT*(-Mprot))

SEQUENCE LISTING

<160> NUMBER OF SEQ ID NOS: 80

<210> SEQ ID NO 1
<211> LENGTH: 160
<212> TYPE: DNA
<213> ORGANISM: Artificial Sequence
<220> FEATURE:
<223> OTHER INFORMATION: CPMV160

<400> SEQUENCE: 1
tattaaaatc ttaataggtt ttgataaaag cgaacgtggg gaaacccgaa ccaaaccttc 60
ttctaaactc tctctcatct ctcttaaagc aaacttctct cttgtctttc ttgcgtgagc 120
gatcttcaac gttgtcagat cgtgcttcgg caccagtaca 160

-continued

<210> SEQ ID NO 2
<211> LENGTH: 181
<212> TYPE: DNA
<213> ORGANISM: Artificial Sequence
<220> FEATURE:
<223> OTHER INFORMATION: CPMV160+

<400> SEQUENCE: 2
tattaaaatc ttaataggtt ttgataaaag cgaacgtggg gaaacccgaa ccaaaccttc 60
ttctaaactc tctctcatct ctcttaaagc aaacttctct cttgtctttc ttgcgtgagc 120
gatcttcaac gttgtcagat cgtgcttcgg caccagtaca gggcccaata ccgcggagaa 180
a 181

<210> SEQ ID NO 3
<211> LENGTH: 6
<212> TYPE: DNA
<213> ORGANISM: Artificial Sequence
<220> FEATURE:
<223> OTHER INFORMATION: Consensus kozak sequence
<220> FEATURE:
<221> NAME/KEY: misc_feature
<222> LOCATION: (1)..(1)
<223> OTHER INFORMATION: a or absent
<220> FEATURE:
<221> NAME/KEY: misc_feature
<222> LOCATION: (3)..(4)
<223> OTHER INFORMATION: a or g
<220> FEATURE:
<221> NAME/KEY: misc_feature
<222> LOCATION: (5)..(5)
<223> OTHER INFORMATION: a or c

<400> SEQUENCE: 3 nannna 6

<210> SEQ ID NO 4
<211> LENGTH: 517
<212> TYPE: DNA
<213> ORGANISM: Artificial Sequence
<220> FEATURE:
<223> OTHER INFORMATION: CPMV HT (prior art 5'UTR)

<400> SEQUENCE: 4
tattaaaatc ttaataggtt ttgataaaag cgaacgtggg gaaacccgaa ccaaaccttc 60
ttctaaactc tctctcatct ctcttaaagc aaacttctct cttgtctttc ttgcgtgagc 120
gatcttcaac gttgtcagat cgtgcttcgg caccagtaca acgttttctt tcactgaagc 180
gaaatcaaag atctctttgt ggacacgtag tgcggcgcca ttaaataacg tgtacttgtc 240
ctattcttgt cggtgtggtc ttgggaaaag aaagcttgct ggaggctgct gttcagcccc 300
atacattact tgttacgatt ctgctgactt tcggcgggtg caatatctct acttctgctt 360
gacgaggtat tgttgcctgt acttctttct tcttcttctt gctgattggt tctataagaa 420
atctagtatt ttctttgaaa cagagttttc ccgtggtttt cgaacttgga gaaagattgt 480
taagcttctg tatattctgc ccaaatttgt cgggccc 517

<210> SEQ ID NO 5
<211> LENGTH: 5
<212> TYPE: DNA
<213> ORGANISM: Artificial Sequence
<220> FEATURE:
<223> OTHER INFORMATION: Consensus plant kingdom kozak sequence
<220> FEATURE:
<221> NAME/KEY: misc_feature
<222> LOCATION: (4)..(4)

<223> OTHER INFORMATION: a or c

<400> SEQUENCE: 5 caana 5

<210> SEQ ID NO 6
<211> LENGTH: 5
<212> TYPE: DNA
<213> ORGANISM: Artificial Sequence
<220> FEATURE:
<223> OTHER INFORMATION: Consensus dicot kozak sequence
<220> FEATURE:
<221> NAME/KEY: misc_feature
<222> LOCATION: (4)..(4)
<223> OTHER INFORMATION: a or c

<400> SEQUENCE: 6 aaana 5

<210> SEQ ID NO 7
<211> LENGTH: 5
<212> TYPE: DNA
<213> ORGANISM: Artificial Sequence
<220> FEATURE:
<223> OTHER INFORMATION: Consensus Arabidopsis kozak sequence
<220> FEATURE:
<221> NAME/KEY: misc_feature
<222> LOCATION: (3)..(3)
<223> OTHER INFORMATION: a or g
<220> FEATURE:
<221> NAME/KEY: misc_feature
<222> LOCATION: (4)..(4)
<223> OTHER INFORMATION: a or c

<400> SEQUENCE: 7 aanna 5

<210> SEQ ID NO 8
<211> LENGTH: 5
<212> TYPE: DNA
<213> ORGANISM: Artificial Sequence
<220> FEATURE:
<223> OTHER INFORMATION: kozak sequence AGAAA

<400> SEQUENCE: 8 agaaa 5

<210> SEQ ID NO 9
<211> LENGTH: 5
<212> TYPE: DNA
<213> ORGANISM: Artificial Sequence
<220> FEATURE:
<223> OTHER INFORMATION: kozak sequence AGACA

<400> SEQUENCE: 9 agaca 5

<210> SEQ ID NO 10
<211> LENGTH: 5
<212> TYPE: DNA
<213> ORGANISM: Artificial Sequence
<220> FEATURE:
<223> OTHER INFORMATION: kozak sequence AGGAA

<400> SEQUENCE: 10 aggaa 5

<210> SEQ ID NO 11
<211> LENGTH: 5
<212> TYPE: DNA
<213> ORGANISM: Artificial Sequence
<220> FEATURE:
<223> OTHER INFORMATION: kozak sequence AAAAA

<400> SEQUENCE: 11 aaaaa 5

<210> SEQ ID NO 12
<211> LENGTH: 5
<212> TYPE: DNA
<213> ORGANISM: Artificial Sequence
<220> FEATURE:
<223> OTHER INFORMATION: kozak sequence AAACA

<400> SEQUENCE: 12 aaaca 5

<210> SEQ ID NO 13
<211> LENGTH: 5
<212> TYPE: DNA
<213> ORGANISM: Artificial Sequence
<220> FEATURE:
<223> OTHER INFORMATION: kozak sequence AAGCA

<400> SEQUENCE: 13 aagca 5

<210> SEQ ID NO 14
<211> LENGTH: 5
<212> TYPE: DNA
<213> ORGANISM: Artificial Sequence
<220> FEATURE:
<223> OTHER INFORMATION: kozak sequence AAGAA

<400> SEQUENCE: 14 aagaa 5

<210> SEQ ID NO 15
<211> LENGTH: 6
<212> TYPE: DNA
<213> ORGANISM: Artificial Sequence
<220> FEATURE:
<223> OTHER INFORMATION: kozak sequence AAAGAA

<400> SEQUENCE: 15 aaagaa 6

<210> SEQ ID NO 16
<211> LENGTH: 6
<212> TYPE: DNA
<213> ORGANISM: Artificial Sequence
<220> FEATURE:
<223> OTHER INFORMATION: kozak sequence AAAAGAA

<400> SEQUENCE: 16 aaagaa 6

<210> SEQ ID NO 17
<211> LENGTH: 51
<212> TYPE: DNA
<213> ORGANISM: Artificial Sequence
<220> FEATURE:
<223> OTHER INFORMATION: IF-H3V36111.s1-4r

<400> SEQUENCE: 17
actaaagaaa ataggccttc aaatgcaaat gttgcaccta atgttgccct t 51

<210> SEQ ID NO 18
<211> LENGTH: 1725
<212> TYPE: DNA
<213> ORGANISM: Artificial Sequence
<220> FEATURE:
<223> OTHER INFORMATION: Nucleotide sequence of PDISP/H3 Victoria.

<400> SEQUENCE: 18
atggcgaaaa acgttgcgat tttcggctta ttgttttctc ttcttgtgtt ggttccttct 60
cagatcttcg cccaaaaact tcctggaaat gacaacagca cggcaacgct gtgccttggg 120
caccatgcag taccaaacgg aacgatagtg aaaacaatca cgaatgacca aattgaagtt 180
actaatgcta ctgagctggt tcagaattcc tcaataggtg aaatatgcga cagtcctcat 240
cagatccttg atggagaaaa ctgcacacta atagatgctc tattgggaga ccctcagtgt 300
gatggcttcc aaaataagaa atgggacctt tttgttgaac gaagcaaagc ctacagcaac 360
tgttaccctt atgatgtgcc ggattatgcc tcccttaggt cactagttgc ctcatccggc 420
acactggagt ttaacaatga aagcttcaat tggactggag tcactcaaaa cggaacaagt 480
tctgcttgca taaggagatc taataatagt ttctttagta gattaaattg gttgacccac 540
ttaaacttca aatacccagc attgaacgtg actatgccaa acaatgaaca atttgacaaa 600
ttgtacattt ggggggttca ccacccgggt acggacaagg accaaatctt cctgtatgct 660
caatcatcag gaagaatcac agtatctacc aaaagaagcc aacaagctgt aatcccgaat 720
atcggatcta gacccagaat aaggaatatc cctagcagaa taagcatcta ttggacaata 780
gtaaaaccgg gagacatact tttgattaac agcacaggga atctaattgc tcctaggggt 840
tacttcaaaa tacgaagtgg gaaaagctca ataatgagat cagatgcacc cattggcaaa 900
tgcaattctg aatgcatcac tccaaatgga agcattccca atgacaaacc attccaaaat 960
gtaaacagga tcacatacgg ggcctgtccc agatatgtta agcaaagcac tctgaaattg 1020
gcaacaggaa tgcgaaatgt accagagaaa caaactagag gcatatttgg cgcaatagcg 1080
ggtttcatag aaaatggttg ggagggaatg gtggatggtt ggtacggttt caggcatcaa 1140
aattctgagg gaagaggaca agcagcagat ctcaaaagca ctcaagcagc aatcgatcaa 1200
atcaatggga agctgaatcg attgatcggg aaaaccaacg agaaattcca tcagattgaa 1260
aaagaattct cagaagtcga agggagaatt caggaccttg agaaatatgt tgaggacact 1320
aaaatagatc tctggtcata caacgcggag cttcttgttg ccctggagaa ccaacataca 1380
attgatctaa ctgactcaga aatgaacaaa ctgtttgaaa aaacaaagaa gcaactaagg 1440
gaaaatgctg aggatatggg caatggttgt ttcaaaatat accacaaatg tgacaatgcc 1500
tgcataggat caatcagaaa tggaacttat gaccacgatg tatacagaga tgaagcatta 1560
aacaaccggt tccagatcaa gggagttgag ctgaagtcag ggtacaaaga ttggatccta 1620
tggatttcct ttgccatatc atgttttttg ctttgtgttg ctttgttggg gttcatcatg 1680
tgggcctgcc aaaagggcaa cattaggtgc aacatttgca tttga 1725

<210> SEQ ID NO 19
<211> LENGTH: 4903
<212> TYPE: DNA
<213> ORGANISM: Artificial Sequence
<220> FEATURE:
<223> OTHER INFORMATION: Nucleotide sequence of construct 1191

<400> SEQUENCE: 19
tggcaggata tattgtggtg taaacaaatt gacgcttaga caacttaata acacattgcg 60
gacgttttta atgtactgaa ttaacgccga atcccgggct ggtatattta tatgttgtca 120
aataactcaa aaaccataaa agtttaagtt agcaagtgtg tacattttta cttgaacaaa 180
aatattcacc tactactgtt ataaatcatt attaaacatt agagtaaaga aatatggatg 240
ataagaacaa gagtagtgat attttgacaa caattttgtt gcaacatttg agaaaatttt 300
gttgttctct cttttcattg gtcaaaaaca atagagagag aaaaaggaag agggagaata 360
aaaacataat gtgagtatga gagagaaagt tgtacaaaag ttgtaccaaa atagttgtac 420
aaatatcatt gaggaatttg acaaaagcta cacaaataag ggttaattgc tgtaaataaa 480
taaggatgac gcattagaga gatgtaccat tagagaattt ttggcaagtc attaaaaaga 540
aagaataaat tatttttaaa attaaaagtt gagtcatttg attaaacatg tgattattta 600
atgaattgat gaaagagttg gattaaagtt gtattagtaa ttagaatttg gtgtcaaatt 660
taatttgaca tttgatcttt tcctatatat tgccccatag agtcagttaa ctcattttta 720
tatttcatag atcaaataag agaaataacg gtatattaat ccctccaaaa aaaaaaaacg 780
gtatatttac taaaaaatct aagccacgta ggaggataac aggatccccg taggaggata 840
acatccaatc caaccaatca caacaatcct gatgagataa cccactttaa gcccacgcat 900
ctgtggcaca tctacattat ctaaatcaca cattcttcca cacatctgag ccacacaaaa 960
accaatccac atctttatca cccattctat aaaaaatcac actttgtgag tctacacttt 1020
gattcccttc aaacacatac aaagagaaga gactaattaa ttaattaatc atcttgagag 1080
aaaatggaac gagctataca aggaaacgac gctagggaac aagctaacag tgaacgttgg 1140
gatggaggat caggaggtac cacttctccc ttcaaacttc ctgacgaaag tccgagttgg 1200
actgagtggc ggctacataa cgatgagacg aattcgaatc aagataatcc ccttggtttc 1260
aaggaaagct ggggtttcgg gaaagttgta tttaagagat atctcagata cgacaggacg 1320
gaagcttcac tgcacagagt ccttggatct tggacgggag attcggttaa ctatgcagca 1380
tctcgatttt tcggtttcga ccagatcgga tgtacctata gtattcggtt tcgaggagtt 1440
agtatcaccg tttctggagg gtcgcgaact cttcagcatc tctgtgagat ggcaattcgg 1500
tctaagcaag aactgctaca gcttgcccca atcgaagtgg aaagtaatgt atcaagagga 1560
tgccctgaag gtactcaaac cttcgaaaaa gaaagcgagt aagttaaaat gcttcttcgt 1620
ctcctattta taatatggtt tgttattgtt aattttgttc ttgtagaaga gcttaattaa 1680
tcgttgttgt tatgaaatac tatttgtatg agatgaactg gtgtaatgta attcatttac 1740
ataagtggag tcagaatcag aatgtttcct ccataactaa ctagacatga agacctgccg 1800
cgtacaattg tcttatattt gaacaactaa aattgaacat cttttgccac aactttataa 1860
gtggttaata tagctcaaat atatggtcaa gttcaataga ttaataatgg aaatatcagt 1920
tatcgaaatt cattaacaat caacttaacg ttattaacta ctaattttat atcatcccct 1980
ttgataaatg atagtacacc aattaggaag gagcatgctc gcctaggaga ttgtcgtttc 2040
ccgccttcag tttgcaagct gctctagccg tgtagccaat acgcaaaccg cctctccccg 2100
cgcgttggga attactagcg cgtgtcgaca agcttgcatg ccggtcaaca tggtggagca 2160
cgacacactt gtctactcca aaaatatcaa agatacagtc tcagaagacc aaagggcaat 2220
tgagactttt caacaaaggg taatatccgg aaacctcctc ggattccatt gcccagctat 2280

-continued

```
ctgtcacttt attgtgaaga tagtggaaaa ggaaggtggc tcctacaaat gccatcattg   2340
cgataaagga aaggccatcg ttgaagatgc ctctgccgac agtggtccca aagatggacc   2400
cccacccacg aggagcatcg tggaaaaaga agacgttcca accacgtctt caaagcaagt   2460
ggattgatgt gataacatgg tggagcacga cacacttgtc tactccaaaa atatcaaaga   2520
tacagtctca gaagaccaaa gggcaattga gacttttcaa caaagggtaa tatccggaaa   2580
cctcctcgga ttccattgcc cagctatctg tcactttatt gtgaagatag tggaaaagga   2640
aggtggctcc tacaaatgcc atcattgcga taaaggaaag gccatcgttg aagatgcctc   2700
tgccgacagt ggtcccaaag atggaccccc acccacgagg agcatcgtgg aaaaagaaga   2760
cgttccaacc acgtcttcaa agcaagtgga ttgatgtgat atctccactg acgtaaggga   2820
tgacgcacaa tcccactatc cttcgcaaga cccttcctct atataaggaa gttcatttca   2880
tttggagagg tattaaaatc ttaataggtt ttgataaaag cgaacgtggg gaaacccgaa   2940
ccaaaccttc ttctaaactc tctctcatct ctcttaaagc aaacttctct cttgtctttc   3000
ttgcgtgagc gatcttcaac gttgtcagat cgtgcttcgg caccagtaca acgttttctt   3060
tcactgaagc gaaatcaaag atctctttgt ggacacgtag tgcggcgcca ttaaataacg   3120
tgtacttgtc ctattcttgt cggtgtggtc ttgggaaaag aaagcttgct ggaggctgct   3180
gttcagcccc atacattact tgttacgatt ctgctgactt tcggcgggtg caatatctct   3240
acttctgctt gacgaggtat tgttgcctgt acttctttct tcttcttctt gctgattggt   3300
tctataagaa atctagtatt ttctttgaaa cagagttttc ccgtggtttt cgaacttgga   3360
gaaagattgt taagcttctg tatattctgc ccaaatttgt cgggcccgcg gatggcgaaa   3420
aacgttgcga ttttcggctt attgttttct cttcttgtgt tggttccttc tcagatcttc   3480
gcctgcaggc tcctcagcca aaacgacacc cccatctgtc tatccactgg cccctggatc   3540
tgctgcccaa actaactcca tggtgaccct gggatgcctg gtcaagggct atttccctga   3600
gccagtgaca gtgacctgga actctggatc cctgtccagc ggtgtgcaca ccttcccagc   3660
tgtcctgcag tctgacctct acactctgag cagctcagtg actgtcccct ccagcacctg   3720
gcccagcgag accgtcacct gcaacgttgc ccacccggcc agcagcacca aggtggacaa   3780
gaaaattgtg cccagggatt gtggttgtaa gccttgcata tgtacagtcc cagaagtatc   3840
atctgtcttc atcttccccc caaagcccaa ggatgtgctc accattactc tgactcctaa   3900
ggtcacgtgt gttgtggtag acatcagcaa ggatgatccc gaggtccagt tcagctggtt   3960
tgtagatgat gtggaggtgc acacagctca gacgcaaccc cgggaggagc agttcaacag   4020
cactttccgc tcagtcagtg aacttcccat catgcaccag gactggctca atggcaagga   4080
gcgatcgctc accatcacca tcaccatcac catcaccatt aaaggcctat tttctttagt   4140
ttgaatttac tgttattcgg tgtgcatttc tatgtttggt gagcggtttt ctgtgctcag   4200
agtgtgttta ttttatgtaa tttaatttct ttgtgagctc ctgtttagca ggtcgtccct   4260
tcagcaagga cacaaaaaga ttttaatttt attaaaaaaa aaaaaaaaaa agaccgggaa   4320
ttcgatatca agcttatcga cctgcagatc gttcaaacat ttggcaataa agtttcttaa   4380
gattgaatcc tgttgccggt cttgcgatga ttatcatata atttctgttg aattacgtta   4440
agcatgtaat aattaacatg taatgcatga cgttatttat gagatgggtt tttatgatta   4500
gagtcccgca attatacatt taatacgcga tagaaaacaa aatatagcgc gcaaactagg   4560
ataaattatc gcgcgcggtg tcatctatgt tactagatct ctagagtctc aagcttggcg   4620
cgcccacgtg actagtggca ctggccgtcg ttttacaacg tcgtgactgg gaaaaccctg   4680
```

```
gcgttaccca acttaatcgc cttgcagcac atcccccttt cgccagctgg cgtaatagcg   4740

aagaggcccg caccgatcgc ccttcccaac agttgcgcag cctgaatggc gaatgctaga   4800

gcagcttgag cttggatcag attgtcgttt cccgccttca gtttaaacta tcagtgtttg   4860

acaggatata ttggcgggta aacctaagag aaaagagcgt tta                     4903
```

<210> SEQ ID NO 20
<211> LENGTH: 3465
<212> TYPE: DNA
<213> ORGANISM: Artificial Sequence
<220> FEATURE:
<223> OTHER INFORMATION: Nucleotide sequence of expression cassette number 1391

<400> SEQUENCE: 20

```
gtcaacatgg tggagcacga cacacttgtc tactccaaaa atatcaaaga tacagtctca     60

gaagaccaaa gggcaattga gacttttcaa caaagggtaa tatccggaaa cctcctcgga    120

ttccattgcc cagctatctg tcactttatt gtgaagatag tggaaaagga aggtggctcc    180

tacaaatgcc atcattgcga taaaggaaag gccatcgttg aagatgcctc tgccgacagt    240

ggtcccaaag atggaccccc acccacgagg agcatcgtgg aaaaagaaga cgttccaacc    300

acgtcttcaa agcaagtgga ttgatgtgat aacatggtgg agcacgacac acttgtctac    360

tccaaaaata tcaaagatac agtctcagaa gaccaaaggg caattgagac ttttcaacaa    420

agggtaatat ccggaaacct cctcggattc cattgcccag ctatctgtca ctttattgtg    480

aagatagtgg aaaaggaagg tggctcctac aaatgccatc attgcgataa aggaaaggcc    540

atcgttgaag atgcctctgc cgacagtggt cccaaagatg gacccccacc cacgaggagc    600

atcgtggaaa aagaagacgt tccaaccacg tcttcaaagc aagtggattg atgtgatatc    660

tccactgacg taagggatga cgcacaatcc cactatcctt cgcaagaccc ttcctctata    720

taaggaagtt catttcattt ggagaggtat taaaatctta ataggttttg ataaaagcga    780

acgtggggaa acccgaacca aaccttcttc taaactctct ctcatctctc ttaaagcaaa    840

cttctctctt gtctttcttg cgtgagcgat cttcaacgtt gtcagatcgt gcttcggcac    900

cagtacaacg ttttctttca ctgaagcgaa atcaaagatc tctttgtgga cacgtagtgc    960

ggcgccatta aataacgtgt acttgtccta ttcttgtcgg tgtggtcttg ggaaaagaaa   1020

gcttgctgga ggctgctgtt cagccccata cattacttgt tacgattctg ctgactttcg   1080

gcgggtgcaa tatctctact tctgcttgac gaggtattgt tgcctgtact tctttcttct   1140

tcttcttgct gattggttct ataagaaatc tagtattttc tttgaaacag agttttcccg   1200

tggttttcga acttggagaa agattgttaa gcttctgtat attctgccca aatttgtcgg   1260

gcccatggcg aaaaacgttg cgattttcgg cttattgttt tctcttcttg tgttggttcc   1320

ttctcagatc ttcgcccaaa aacttcctgg aaatgacaac agcacggcaa cgctgtgcct   1380

tgggcaccat gcagtaccaa acggaacgat agtgaaaaca atcacgaatg accaaattga   1440

agttactaat gctactgagc tggttcagaa ttcctcaata ggtgaaatat gcgacagtcc   1500

tcatcagatc cttgatggag aaaactgcac actaatagat gctctattgg gagaccctca   1560

gtgtgatggc ttccaaaata agaaatggga cctttttgtt gaacgaagca aagcctacag   1620

caactgttac ccttatgatg tgccggatta tgcctccctt aggtcactag ttgcctcatc   1680

cggcacactg gagtttaaca atgaaagctt caattggact ggagtcactc aaaacggaac   1740

aagttctgct tgcataagga gatctaataa tagtttcttt agtagattaa attggttgac   1800
```

```
ccacttaaac ttcaaatacc cagcattgaa cgtgactatg ccaaacaatg aacaatttga   1860

caaattgtac atttgggggg ttcaccaccc gggtacggac aaggaccaaa tcttcctgta   1920

tgctcaatca tcaggaagaa tcacagtatc taccaaaaga agccaacaag ctgtaatccc   1980

gaatatcgga tctagaccca gaataaggaa tatccctagc agaataagca tctattggac   2040

aatagtaaaa ccgggagaca tacttttgat taacagcaca gggaatctaa ttgctcctag   2100

gggttacttc aaaatacgaa gtgggaaaag ctcaataatg agatcagatg cacccattgg   2160

caaatgcaat tctgaatgca tcactccaaa tggaagcatt cccaatgaca aaccattcca   2220

aaatgtaaac aggatcacat acggggcctg tcccagatat gttaagcaaa gcactctgaa   2280

attggcaaca ggaatgcgaa atgtaccaga gaaacaaact agaggcatat ttggcgcaat   2340

agcgggtttc atagaaaatg gttgggaggg aatggtggat ggttggtacg gtttcaggca   2400

tcaaaattct gagggaagag gacaagcagc agatctcaaa agcactcaag cagcaatcga   2460

tcaaatcaat gggaagctga atcgattgat cgggaaaacc aacgagaaat tccatcagat   2520

tgaaaaagaa ttctcagaag tcgaagggag aattcaggac cttgagaaat atgttgagga   2580

cactaaaata gatctctggt catacaacgc ggagcttctt gttgccctgg agaaccaaca   2640

tacaattgat ctaactgact cagaaatgaa caaactgttt gaaaaaacaa agaagcaact   2700

aagggaaaat gctgaggata tgggcaatgg ttgtttcaaa atataccaca aatgtgacaa   2760

tgcctgcata ggatcaatca gaaatggaac ttatgaccac gatgtataca gagatgaagc   2820

attaaacaac cggttccaga tcaagggagt tgagctgaag tcagggtaca aagattggat   2880

cctatggatt tcctttgcca tatcatgttt tttgctttgt gttgctttgt tggggttcat   2940

catgtgggcc tgccaaaagg gcaacattag gtgcaacatt tgcatttgaa ggcctatttt   3000

ctttagtttg aatttactgt tattcggtgt gcatttctat gtttggtgag cggttttctg   3060

tgctcagagt gtgtttattt tatgtaattt aatttctttg tgagctcctg tttagcaggt   3120

cgtcccttca gcaaggacac aaaaagattt taattttatt aaaaaaaaaa aaaaaaaaga   3180

ccgggaattc gatatcaagc ttatcgacct gcagatcgtt caaacatttg gcaataaagt   3240

ttcttaagat tgaatcctgt tgccggtctt gcgatgatta tcatataatt tctgttgaat   3300

tacgttaagc atgtaataat taacatgtaa tgcatgacgt tatttatgag atgggttttt   3360

atgattagag tcccgcaatt atacatttaa tacgcgatag aaaacaaaat atagcgcgca   3420

aactaggata aattatcgcg cgcggtgtca tctatgttac tagat                   3465
```

<210> SEQ ID NO 21
<211> LENGTH: 574
<212> TYPE: PRT
<213> ORGANISM: Artificial Sequence
<220> FEATURE:
<223> OTHER INFORMATION: Amino acid sequence of PDISP/H3 Victoria

<400> SEQUENCE: 21

```
Met Ala Lys Asn Val Ala Ile Phe Gly Leu Leu Phe Ser Leu Leu Val
1               5                   10                  15

Leu Val Pro Ser Gln Ile Phe Ala Gln Lys Leu Pro Gly Asn Asp Asn
            20                  25                  30

Ser Thr Ala Thr Leu Cys Leu Gly His His Ala Val Pro Asn Gly Thr
        35                  40                  45

Ile Val Lys Thr Ile Thr Asn Asp Gln Ile Glu Val Thr Asn Ala Thr
    50                  55                  60
```

-continued

```
Glu Leu Val Gln Asn Ser Ser Ile Gly Glu Ile Cys Asp Ser Pro His
65                  70                  75                  80

Gln Ile Leu Asp Gly Glu Asn Cys Thr Leu Ile Asp Ala Leu Leu Gly
                85                  90                  95

Asp Pro Gln Cys Asp Gly Phe Gln Asn Lys Lys Trp Asp Leu Phe Val
            100                 105                 110

Glu Arg Ser Lys Ala Tyr Ser Asn Cys Tyr Pro Tyr Asp Val Pro Asp
        115                 120                 125

Tyr Ala Ser Leu Arg Ser Leu Val Ala Ser Ser Gly Thr Leu Glu Phe
    130                 135                 140

Asn Asn Glu Ser Phe Asn Trp Thr Gly Val Thr Gln Asn Gly Thr Ser
145                 150                 155                 160

Ser Ala Cys Ile Arg Arg Ser Asn Asn Ser Phe Phe Ser Arg Leu Asn
                165                 170                 175

Trp Leu Thr His Leu Asn Phe Lys Tyr Pro Ala Leu Asn Val Thr Met
            180                 185                 190

Pro Asn Asn Glu Gln Phe Asp Lys Leu Tyr Ile Trp Gly Val His His
        195                 200                 205

Pro Gly Thr Asp Lys Asp Gln Ile Phe Leu Tyr Ala Gln Ser Ser Gly
    210                 215                 220

Arg Ile Thr Val Ser Thr Lys Arg Ser Gln Gln Ala Val Ile Pro Asn
225                 230                 235                 240

Ile Gly Ser Arg Pro Arg Ile Arg Asn Ile Pro Ser Arg Ile Ser Ile
                245                 250                 255

Tyr Trp Thr Ile Val Lys Pro Gly Asp Ile Leu Leu Ile Asn Ser Thr
            260                 265                 270

Gly Asn Leu Ile Ala Pro Arg Gly Tyr Phe Lys Ile Arg Ser Gly Lys
        275                 280                 285

Ser Ser Ile Met Arg Ser Asp Ala Pro Ile Gly Lys Cys Asn Ser Glu
    290                 295                 300

Cys Ile Thr Pro Asn Gly Ser Ile Pro Asn Asp Lys Pro Phe Gln Asn
305                 310                 315                 320

Val Asn Arg Ile Thr Tyr Gly Ala Cys Pro Arg Tyr Val Lys Gln Ser
                325                 330                 335

Thr Leu Lys Leu Ala Thr Gly Met Arg Asn Val Pro Glu Lys Gln Thr
            340                 345                 350

Arg Gly Ile Phe Gly Ala Ile Ala Gly Phe Ile Glu Asn Gly Trp Glu
        355                 360                 365

Gly Met Val Asp Gly Trp Tyr Gly Phe Arg His Gln Asn Ser Glu Gly
    370                 375                 380

Arg Gly Gln Ala Ala Asp Leu Lys Ser Thr Gln Ala Ala Ile Asp Gln
385                 390                 395                 400

Ile Asn Gly Lys Leu Asn Arg Leu Ile Gly Lys Thr Asn Glu Lys Phe
                405                 410                 415

His Gln Ile Glu Lys Glu Phe Ser Glu Val Glu Gly Arg Ile Gln Asp
            420                 425                 430

Leu Glu Lys Tyr Val Glu Asp Thr Lys Ile Asp Leu Trp Ser Tyr Asn
        435                 440                 445

Ala Glu Leu Leu Val Ala Leu Glu Asn Gln His Thr Ile Asp Leu Thr
    450                 455                 460

Asp Ser Glu Met Asn Lys Leu Phe Glu Lys Thr Lys Lys Gln Leu Arg
465                 470                 475                 480

Glu Asn Ala Glu Asp Met Gly Asn Gly Cys Phe Lys Ile Tyr His Lys
```

```
            485                 490                 495

Cys Asp Asn Ala Cys Ile Gly Ser Ile Arg Asn Gly Thr Tyr Asp His
        500                 505                 510

Asp Val Tyr Arg Asp Glu Ala Leu Asn Asn Arg Phe Gln Ile Lys Gly
    515                 520                 525

Val Glu Leu Lys Ser Gly Tyr Lys Asp Trp Ile Leu Trp Ile Ser Phe
530                 535                 540

Ala Ile Ser Cys Phe Leu Leu Cys Val Ala Leu Leu Gly Phe Ile Met
545                 550                 555                 560

Trp Ala Cys Gln Lys Gly Asn Ile Arg Cys Asn Ile Cys Ile
            565                 570


<210> SEQ ID NO 22
<211> LENGTH: 52
<212> TYPE: DNA
<213> ORGANISM: Artificial Sequence
<220> FEATURE:
<223> OTHER INFORMATION: IF**(SacII)-PDI.s1+4c

<400> SEQUENCE: 22

acagggccca ataccgcgga gaaaatggcg aaaaacgttg cgattttcgg ct             52


<210> SEQ ID NO 23
<211> LENGTH: 51
<212> TYPE: DNA
<213> ORGANISM: Artificial Sequence
<220> FEATURE:
<223> OTHER INFORMATION: IF-H3V36111.s1-4r

<400> SEQUENCE: 23

actaaagaaa ataggccttc aaatgcaaat gttgcaccta atgttgccct t              51


<210> SEQ ID NO 24
<211> LENGTH: 155
<212> TYPE: DNA
<213> ORGANISM: Artificial Sequence
<220> FEATURE:
<223> OTHER INFORMATION: CPMV155

<400> SEQUENCE: 24

tattaaaatc ttaataggtt ttgataaaag cgaacgtggg gaaacccgaa ccaaaccttc      60

ttctaaactc tctctcatct ctcttaaagc aaacttctct cttgtctttc ttgcgtgagc     120

gatcttcaac gttgtcagat cgtgcttcgg cacca                               155


<210> SEQ ID NO 25
<211> LENGTH: 4644
<212> TYPE: DNA
<213> ORGANISM: Artificial Sequence
<220> FEATURE:
<223> OTHER INFORMATION: Nucleotide sequence of construct 2171

<400> SEQUENCE: 25

tggcaggata tattgtggtg taaacaaatt gacgcttaga caacttaata acacattgcg      60

gacgttttta atgtactgaa ttaacgccga atcccgggct ggtatattta tatgttgtca     120

aataactcaa aaaccataaa agtttaagtt agcaagtgtg tacattttta cttgaacaaa     180

aatattcacc tactactgtt ataaatcatt attaaacatt agagtaaaga aatatggatg     240

ataagaacaa gagtagtgat attttgacaa caattttgtt gcaacatttg agaaaatttt     300

gttgttctct cttttcattg gtcaaaaaca atagagagag aaaaaggaag agggagaata     360
```

-continued

```
aaaacataat gtgagtatga gagagaaagt tgtacaaaag ttgtaccaaa atagttgtac    420
aaatatcatt gaggaatttg acaaaagcta cacaaataag ggttaattgc tgtaaataaa    480
taaggatgac gcattagaga gatgtaccat tagagaattt ttggcaagtc attaaaaaga    540
aagaataaat tatttttaaa attaaaagtt gagtcatttg attaaacatg tgattattta    600
atgaattgat gaaagagttg gattaaagtt gtattagtaa ttagaatttg gtgtcaaatt    660
taatttgaca tttgatcttt tcctatatat tgccccatag agtcagttaa ctcattttta    720
tatttcatag atcaaataag agaaataacg gtatattaat ccctccaaaa aaaaaaaacg    780
gtatatttac taaaaaatct aagccacgta ggaggataac aggatccccg taggaggata    840
acatccaatc caaccaatca caacaatcct gatgagataa cccactttaa gcccacgcat    900
ctgtggcaca tctacattat ctaaatcaca cattcttcca cacatctgag ccacacaaaa    960
accaatccac atctttatca cccattctat aaaaaatcac actttgtgag tctacacttt   1020
gattcccttc aaacacatac aaagagaaga gactaattaa ttaattaatc atcttgagag   1080
aaaatggaac gagctataca aggaaacgac gctagggaac aagctaacag tgaacgttgg   1140
gatggaggat caggaggtac cacttctccc ttcaaacttc ctgacgaaag tccgagttgg   1200
actgagtggc ggctacataa cgatgagacg aattcgaatc aagataatcc ccttggtttc   1260
aaggaaagct ggggtttcgg gaaagttgta tttaagagat atctcagata cgacaggacg   1320
gaagcttcac tgcacagagt ccttggatct tggacgggag attcggttaa ctatgcagca   1380
tctcgatttt tcggtttcga ccagatcgga tgtacctata gtattcggtt tcgaggagtt   1440
agtatcaccg tttctggagg gtcgcgaact cttcagcatc tctgtgagat ggcaattcgg   1500
tctaagcaag aactgctaca gcttgcccca atcgaagtgg aaagtaatgt atcaagagga   1560
tgccctgaag gtactcaaac cttcgaaaaa gaaagcgagt aagttaaaat gcttcttcgt   1620
ctcctattta taatatggtt tgttattgtt aattttgttc ttgtagaaga gcttaattaa   1680
tcgttgttgt tatgaaatac tatttgtatg agatgaactg gtgtaatgta attcatttac   1740
ataagtggag tcagaatcag aatgtttcct ccataactaa ctagacatga agacctgccg   1800
cgtacaattg tcttatattt gaacaactaa aattgaacat cttttgccac aactttataa   1860
gtggttaata tagctcaaat atatggtcaa gttcaataga ttaataatgg aaatatcagt   1920
tatcgaaatt cattaacaat caacttaacg ttattaacta ctaattttat atcatcccct   1980
ttgataaatg atagtacacc aattaggaag gagcatgctc gcctaggaga ttgtcgtttc   2040
ccgccttcag tttgcaagct gctctagccg tgtagccaat acgcaaaccg cctctccccg   2100
cgcgttggga attactagcg cgtgtcgaca agcttgcatg ccggtcaaca tggtggagca   2160
cgacacactt gtctactcca aaaatatcaa agatacagtc tcagaagacc aaagggcaat   2220
tgagactttt caacaaaggg taatatccgg aaacctcctc ggattccatt gcccagctat   2280
ctgtcacttt attgtgaaga tagtggaaaa ggaaggtggc tcctacaaat gccatcattg   2340
cgataaagga aaggccatcg ttgaagatgc ctctgccgac agtggtccca aagatggacc   2400
cccacccacg aggagcatcg tggaaaaaga agacgttcca accacgtctt caaagcaagt   2460
ggattgatgt gataacatgg tggagcacga cacacttgtc tactccaaaa atatcaaaga   2520
tacagtctca gaagaccaaa gggcaattga gacttttcaa caaagggtaa tatccggaaa   2580
cctcctcgga ttccattgcc cagctatctg tcactttatt gtgaagatag tggaaaagga   2640
aggtggctcc tacaaatgcc atcattgcga taaaggaaag gccatcgttg aagatgcctc   2700
tgccgacagt ggtcccaaag atggaccccc acccacgagg agcatcgtgg aaaaagaaga   2760
```

```
cgttccaacc acgtcttcaa agcaagtgga ttgatgtgat atctccactg acgtaaggga   2820
tgacgcacaa tcccactatc cttcgcaaga cccttcctct atataaggaa gttcatttca   2880
tttggagagg tattaaaatc ttaataggtt ttgataaaag cgaacgtggg gaaacccgaa   2940
ccaaaccttc ttctaaactc tctctcatct ctcttaaagc aaacttctct cttgtctttc   3000
ttgcgtgagc gatcttcaac gttgtcagat cgtgcttcgg caccagtaca gggcccaata   3060
ccgcggagaa aatggcgaaa aacgttgcga ttttcggctt attgttttct cttcttgtgt   3120
tggttccttc tcagatcttc gcgacgtcac tcctcagcca aaacgacacc cccatctgtc   3180
tatccactgg cccctggatc tgctgcccaa actaactcca tggtgaccct gggatgcctg   3240
gtcaagggct atttccctga gccagtgaca gtgacctgga actctggatc cctgtccagc   3300
ggtgtgcaca ccttcccagc tgtcctgcag tctgacctct acactctgag cagctcagtg   3360
actgtcccct ccagcacctg gcccagcgag accgtcacct gcaacgttgc ccacccggcc   3420
agcagcacca aggtggacaa gaaaattgtg cccagggatt gtggttgtaa gccttgcata   3480
tgtacagtcc cagaagtatc atctgtcttc atcttccccc caaagcccaa ggatgtgctc   3540
accattactc tgactcctaa ggtcacgtgt gttgtggtag acatcagcaa ggatgatccc   3600
gaggtccagt tcagctggtt tgtagatgat gtggaggtgc acacagctca gacgcaaccc   3660
cgggaggagc agttcaacag cactttccgc tcagtcagtg aacttcccat catgcaccag   3720
gactggctca atggcaagga gacgtccaga ttttggcgat ctattcaact gtcgccagtt   3780
cattggtact ggtagtctcc ctgggggcaa tcagtttctg gatgtgctct aatgggtctc   3840
tacagtgtag aatatgtatt taaaggccta ttttctttag tttgaattta ctgttattcg   3900
gtgtgcattt ctatgtttgg tgagcggttt tctgtgctca gagtgtgttt attttatgta   3960
atttaatttc tttgtgagct cctgtttagc aggtcgtccc ttcagcaagg acacaaaaag   4020
attttaattt tattaaaaaa aaaaaaaaaa aagaccggga attcgatatc aagcttatcg   4080
acctgcagat cgttcaaaca tttggcaata aagtttctta agattgaatc ctgttgccgg   4140
tcttgcgatg attatcatat aatttctgtt gaattacgtt aagcatgtaa taattaacat   4200
gtaatgcatg acgttattta tgagatgggt ttttatgatt agagtcccgc aattatacat   4260
ttaatacgcg atagaaaaca aaatatagcg cgcaaactag gataaattat cgcgcgcggt   4320
gtcatctatg ttactagatc tctagagtct caagcttggc gcgcccacgt gactagtggc   4380
actggccgtc gttttacaac gtcgtgactg ggaaaaccct ggcgttaccc aacttaatcg   4440
ccttgcagca catcccccttt tcgccagctg gcgtaatagc gaagaggccc gcaccgatcg   4500
cccttcccaa cagttgcgca gcctgaatgg cgaatgctag agcagcttga gcttggatca   4560
gattgtcgtt tcccgccttc agtttaaact atcagtgttt gacaggatat attggcgggt   4620
aaacctaaga gaaaagagcg ttta                                          4644
```

<210> SEQ ID NO 26
<211> LENGTH: 3129
<212> TYPE: DNA
<213> ORGANISM: Artificial Sequence
<220> FEATURE:
<223> OTHER INFORMATION: Nucleotide sequence of expression cassette number 1800 from 2X35S promoter to NOS terminator

<400> SEQUENCE: 26

```
gtcaacatgg tggagcacga cacacttgtc tactccaaaa atatcaaaga tacagtctca     60
gaagaccaaa gggcaattga gacttttcaa caaagggtaa tatccggaaa cctcctcgga    120
```

ttccattgcc cagctatctg tcactttatt gtgaagatag tggaaaagga aggtggctcc 180
tacaaatgcc atcattgcga taaaggaaag gccatcgttg aagatgcctc tgccgacagt 240
ggtcccaaag atggaccccc acccacgagg agcatcgtgg aaaaagaaga cgttccaacc 300
acgtcttcaa agcaagtgga ttgatgtgat aacatggtgg agcacgacac acttgtctac 360
tccaaaaata tcaaagatac agtctcagaa gaccaaaggg caattgagac ttttcaacaa 420
agggtaatat ccggaaacct cctcggattc cattgcccag ctatctgtca ctttattgtg 480
aagatagtgg aaaaggaagg tggctcctac aaatgccatc attgcgataa aggaaaggcc 540
atcgttgaag atgcctctgc cgacagtggt cccaaagatg gacccccacc cacgaggagc 600
atcgtggaaa aagaagacgt tccaaccacg tcttcaaagc aagtggattg atgtgatatc 660
tccactgacg taagggatga cgcacaatcc cactatcctt cgcaagaccc ttcctctata 720
taaggaagtt catttcattt ggagaggtat taaaatctta ataggttttg ataaaagcga 780
acgtggggaa acccgaacca aaccttcttc taaactctct ctcatctctc ttaaagcaaa 840
cttctctctt gtctttcttg cgtgagcgat cttcaacgtt gtcagatcgt gcttcggcac 900
cagtacaggg cccaataccg cggagaaaat ggcgaaaaac gttgcgattt tcggcttatt 960
gttttctctt cttgtgttgg ttccttctca gatcttcgcc caaaaacttc ctggaaatga 1020
caacagcacg gcaacgctgt gccttgggca ccatgcagta ccaaacggaa cgatagtgaa 1080
aacaatcacg aatgaccaaa ttgaagttac taatgctact gagctggttc agaattcctc 1140
aataggtgaa atatgcgaca gtcctcatca gatccttgat ggagaaaact gcacactaat 1200
agatgctcta ttgggagacc ctcagtgtga tggcttccaa aataagaaat gggacctttt 1260
tgttgaacga agcaaagcct acagcaactg ttacccttat gatgtgccgg attatgcctc 1320
ccttaggtca ctagttgcct catccggcac actggagttt aacaatgaaa gcttcaattg 1380
gactggagtc actcaaaacg gaacaagttc tgcttgcata aggagatcta ataatagttt 1440
ctttagtaga ttaaattggt tgacccactt aaacttcaaa tacccagcat tgaacgtgac 1500
tatgccaaac aatgaacaat ttgacaaatt gtacatttgg ggggttcacc acccgggtac 1560
ggacaaggac caaatcttcc tgtatgctca atcatcagga agaatcacag tatctaccaa 1620
aagaagccaa caagctgtaa tcccgaatat cggatctaga cccagaataa ggaatatccc 1680
tagcagaata agcatctatt ggacaatagt aaaaccggga gacatacttt tgattaacag 1740
cacagggaat ctaattgctc ctaggggtta cttcaaaata cgaagtggga aaagctcaat 1800
aatgagatca gatgcaccca ttggcaaatg caattctgaa tgcatcactc caaatggaag 1860
cattcccaat gacaaaccat tccaaaatgt aaacaggatc acatacgggg cctgtcccag 1920
atatgttaag caaagcactc tgaaattggc aacaggaatg cgaaatgtac cagagaaaca 1980
aactagaggc atatttggcg caatagcggg tttcatagaa aatggttggg agggaatggt 2040
ggatggttgg tacggtttca ggcatcaaaa ttctgaggga agaggacaag cagcagatct 2100
caaaagcact caagcagcaa tcgatcaaat caatgggaag ctgaatcgat tgatcgggaa 2160
aaccaacgag aaattccatc agattgaaaa agaattctca gaagtcgaag ggagaattca 2220
ggaccttgag aaatatgttg aggacactaa aatagatctc tggtcataca acgcggagct 2280
tcttgttgcc ctggagaacc aacatacaat tgatctaact gactcagaaa tgaacaaact 2340
gtttgaaaaa acaaagaagc aactaaggga aaatgctgag gatatgggca atggttgttt 2400
caaaatatac cacaaatgtg acaatgcctg cataggatca atcagaaatg gaacttatga 2460

```
ccacgatgta tacagagatg aagcattaaa caaccggttc cagatcaagg gagttgagct   2520

gaagtcaggg tacaaagatt ggatcctatg gatttccttt gccatatcat gttttttgct   2580

ttgtgttgct ttgttggggt tcatcatgtg ggcctgccaa aagggcaaca ttaggtgcaa   2640

catttgcatt tgaaggccta ttttctttag tttgaattta ctgttattcg gtgtgcattt   2700

ctatgtttgg tgagcggttt tctgtgctca gagtgtgttt attttatgta atttaatttc   2760

tttgtgagct cctgtttagc aggtcgtccc ttcagcaagg acacaaaaag attttaattt   2820

tattaaaaaa aaaaaaaaaa aagaccggga attcgatatc aagcttatcg acctgcagat   2880

cgttcaaaca tttggcaata aagtttctta agattgaatc ctgttgccgg tcttgcgatg   2940

attatcatat aatttctgtt gaattacgtt aagcatgtaa taattaacat gtaatgcatg   3000

acgttattta tgagatgggt ttttatgatt agagtcccgc aattatacat ttaatacgcg   3060

atagaaaaca aaatatagcg cgcaaactag gataaattat cgcgcgcggt gtcatctatg   3120

ttactagat                                                            3129
```

<210> SEQ ID NO 27
<211> LENGTH: 150
<212> TYPE: DNA
<213> ORGANISM: Artificial Sequence
<220> FEATURE:
<223> OTHER INFORMATION: CPMV150

<400> SEQUENCE: 27

```
tattaaaatc ttaataggtt ttgataaaag cgaacgtggg gaaacccgaa ccaaaccttc     60

ttctaaactc tctctcatct ctcttaaagc aaacttctct cttgtctttc ttgcgtgagc    120

gatcttcaac gttgtcagat cgtgcttcgg                                     150
```

<210> SEQ ID NO 28
<211> LENGTH: 49
<212> TYPE: DNA
<213> ORGANISM: Artificial Sequence
<220> FEATURE:
<223> OTHER INFORMATION: IF-CPMV(fl5'UTR)_SpPDI.c

<400> SEQUENCE: 28

```
tcgtgcttcg gcaccagtac aatggcgaaa aacgttgcga ttttcggct                 49
```

<210> SEQ ID NO 29
<211> LENGTH: 4540
<212> TYPE: DNA
<213> ORGANISM: Artificial Sequence
<220> FEATURE:
<223> OTHER INFORMATION: Nucleotide sequence of construct 1190

<400> SEQUENCE: 29

```
tggcaggata tattgtggtg taaacaaatt gacgcttaga caacttaata acacattgcg     60

gacgttttta atgtactgaa ttaacgccga atcccgggct ggtatattta tatgttgtca    120

aataactcaa aaaccataaa agtttaagtt agcaagtgtg tacattttta cttgaacaaa    180

aatattcacc tactactgtt ataaatcatt attaaacatt agagtaaaga aatatggatg    240

ataagaacaa gagtagtgat attttgacaa caattttgtt gcaacatttg agaaaatttt    300

gttgttctct cttttcattg gtcaaaaaca atagagagag aaaaaggaag agggagaata    360

aaaacataat gtgagtatga gagagaaagt tgtacaaaag ttgtaccaaa atagttgtac    420

aaatatcatt gaggaatttg acaaaagcta cacaaataag ggttaattgc tgtaaataaa    480

taaggatgac gcattagaga gatgtaccat tagagaattt ttggcaagtc attaaaaaga    540
```

```
aagaataaat tatttttaaa attaaaagtt gagtcatttg attaaacatg tgattattta    600
atgaattgat gaaagagttg gattaaagtt gtattagtaa ttagaatttg gtgtcaaatt    660
taatttgaca tttgatcttt tcctatatat tgccccatag agtcagttaa ctcattttta    720
tatttcatag atcaaataag agaaataacg gtatattaat ccctccaaaa aaaaaaaacg    780
gtatatttac taaaaaatct aagccacgta ggaggataac aggatccccg taggaggata    840
acatccaatc caaccaatca caacaatcct gatgagataa cccactttaa gcccacgcat    900
ctgtggcaca tctacattat ctaaatcaca cattcttcca cacatctgag ccacacaaaa    960
accaatccac atctttatca cccattctat aaaaaatcac actttgtgag tctacacttt   1020
gattcccttc aaacacatac aaagagaaga gactaattaa ttaattaatc atcttgagag   1080
aaaatggaac gagctataca aggaaacgac gctagggaac aagctaacag tgaacgttgg   1140
gatggaggat caggaggtac cacttctccc ttcaaacttc ctgacgaaag tccgagttgg   1200
actgagtggc ggctacataa cgatgagacg aattcgaatc aagataatcc ccttggtttc   1260
aaggaaagct ggggtttcgg gaaagttgta tttaagagat atctcagata cgacaggacg   1320
gaagcttcac tgcacagagt ccttggatct tggacgggag attcggttaa ctatgcagca   1380
tctcgatttt tcggtttcga ccagatcgga tgtacctata gtattcggtt tcgaggagtt   1440
agtatcaccg tttctggagg gtcgcgaact cttcagcatc tctgtgagat ggcaattcgg   1500
tctaagcaag aactgctaca gcttgcccca atcgaagtgg aaagtaatgt atcaagagga   1560
tgccctgaag gtactcaaac cttcgaaaaa gaaagcgagt aagttaaaat gcttcttcgt   1620
ctcctattta taatatggtt tgttattgtt aattttgttc ttgtagaaga gcttaattaa   1680
tcgttgttgt tatgaaatac tatttgtatg agatgaactg gtgtaatgta attcatttac   1740
ataagtggag tcagaatcag aatgtttcct ccataactaa ctagacatga agacctgccg   1800
cgtacaattg tcttatattt gaacaactaa aattgaacat cttttgccac aactttataa   1860
gtggttaata tagctcaaat atatggtcaa gttcaataga ttaataatgg aaatatcagt   1920
tatcgaaatt cattaacaat caacttaacg ttattaacta ctaattttat atcatcccct   1980
ttgataaatg atagtacacc aattaggaag gagcatgctc gcctaggaga ttgtcgtttc   2040
ccgccttcag tttgcaagct gctctagccg tgtagccaat acgcaaaccg cctctccccg   2100
cgcgttggga attactagcg cgtgtcgaca agcttgcatg ccggtcaaca tggtggagca   2160
cgacacactt gtctactcca aaaatatcaa agatacagtc tcagaagacc aaagggcaat   2220
tgagactttt caacaaaggg taatatccgg aaacctcctc ggattccatt gcccagctat   2280
ctgtcacttt attgtgaaga tagtggaaaa ggaaggtggc tcctacaaat gccatcattg   2340
cgataaagga aaggccatcg ttgaagatgc ctctgccgac agtggtccca aagatggacc   2400
cccacccacg aggagcatcg tggaaaaaga agacgttcca accacgtctt caaagcaagt   2460
ggattgatgt gataacatgg tggagcacga cacacttgtc tactccaaaa atatcaaaga   2520
tacagtctca gaagaccaaa gggcaattga gacttttcaa caaagggtaa tatccggaaa   2580
cctcctcgga ttccattgcc cagctatctg tcactttatt gtgaagatag tggaaaagga   2640
aggtggctcc tacaaatgcc atcattgcga taaaggaaag gccatcgttg aagatgcctc   2700
tgccgacagt ggtcccaaag atggaccccc acccacgagg agcatcgtgg aaaaagaaga   2760
cgttccaacc acgtcttcaa agcaagtgga ttgatgtgat atctccactg acgtaaggga   2820
tgacgcacaa tcccactatc cttcgcaaga cccttcctct atataaggaa gttcatttca   2880
```

-continued

```
tttggagagg tattaaaatc ttaataggtt ttgataaaag cgaacgtggg gaaacccgaa   2940
ccaaaccttc ttctaaactc tctctcatct ctcttaaagc aaacttctct cttgtctttc   3000
ttgcgtgagc gatcttcaac gttgtcagat cgtgcttcgg caccgcggat ggcgaaaaac   3060
gttgcgattt tcggcttatt gttttctctt cttgtgttgg ttccttctca gatcttcgcc   3120
tgcaggctcc tcagccaaaa cgacaccccc atctgtctat ccactggccc ctggatctgc   3180
tgcccaaact aactccatgg tgaccctggg atgcctggtc aagggctatt tccctgagcc   3240
agtgacagtg acctggaact ctggatccct gtccagcggt gtgcacacct tcccagctgt   3300
cctgcagtct gacctctaca ctctgagcag ctcagtgact gtcccctcca gcacctggcc   3360
cagcgagacc gtcacctgca acgttgccca cccggccagc agcaccaagg tggacaagaa   3420
aattgtgccc agggattgtg gttgtaagcc ttgcatatgt acagtcccag aagtatcatc   3480
tgtcttcatc ttccccccaa agcccaagga tgtgctcacc attactctga ctcctaaggt   3540
cacgtgtgtt gtggtagaca tcagcaagga tgatcccgag gtccagttca gctggtttgt   3600
agatgatgtg gaggtgcaca cagctcagac gcaaccccgg gaggagcagt tcaacagcac   3660
tttccgctca gtcagtgaac ttcccatcat gcaccaggac tggctcaatg gcaaggagcg   3720
atcgctcacc atcaccatca ccatcaccat caccattaaa ggcctatttt ctttagtttg   3780
aatttactgt tattcggtgt gcatttctat gtttggtgag cggttttctg tgctcagagt   3840
gtgtttattt tatgtaattt aatttctttg tgagctcctg tttagcaggt cgtcccttca   3900
gcaaggacac aaaaagattt taattttatt aaaaaaaaaa aaaaaaaaga ccgggaattc   3960
gatatcaagc ttatcgacct gcagatcgtt caaacatttg gcaataaagt ttcttaagat   4020
tgaatcctgt tgccggtctt gcgatgatta tcatataatt tctgttgaat tacgttaagc   4080
atgtaataat taacatgtaa tgcatgacgt tatttatgag atgggttttt atgattagag   4140
tcccgcaatt atacatttaa tacgcgatag aaaacaaaat atagcgcgca aactaggata   4200
aattatcgcg cgcggtgtca tctatgttac tagatctcta gagtctcaag cttggcgcgc   4260
ccacgtgact agtggcactg gccgtcgttt tacaacgtcg tgactgggaa aaccctggcg   4320
ttacccaact taatcgcctt gcagcacatc ccccttttcgc cagctggcgt aatagcgaag   4380
aggcccgcac cgatcgccct tcccaacagt tgcgcagcct gaatggcgaa tgctagagca   4440
gcttgagctt ggatcagatt gtcgtttccc gccttcagtt taaactatca gtgtttgaca   4500
ggatatattg gcgggtaaac ctaagagaaa agagcgttta                         4540
```

<210> SEQ ID NO 30
<211> LENGTH: 3108
<212> TYPE: DNA
<213> ORGANISM: Artificial Sequence
<220> FEATURE:
<223> OTHER INFORMATION: Nucleotide sequence of expression cassette number 1935 from 2X35S promoter to NOS terminator

<400> SEQUENCE: 30

```
gtcaacatgg tggagcacga cacacttgtc tactccaaaa atatcaaaga tacagtctca     60
gaagaccaaa gggcaattga gacttttcaa caaagggtaa tatccggaaa cctcctcgga    120
ttccattgcc cagctatctg tcactttatt gtgaagatag tggaaaagga aggtggctcc    180
tacaaatgcc atcattgcga taaaggaaag gccatcgttg aagatgcctc tgccgacagt    240
ggtcccaaag atggaccccc acccacgagg agcatcgtgg aaaaagaaga cgttccaacc    300
acgtcttcaa agcaagtgga ttgatgtgat aacatggtgg agcacgacac acttgtctac    360
```

-continued

```
tccaaaaata tcaaagatac agtctcagaa gaccaaaggg caattgagac ttttcaacaa     420
agggtaatat ccggaaacct cctcggattc cattgcccag ctatctgtca ctttattgtg     480
aagatagtgg aaaaggaagg tggctcctac aaatgccatc attgcgataa aggaaaggcc     540
atcgttgaag atgcctctgc cgacagtggt cccaaagatg gacccccacc cacgaggagc     600
atcgtggaaa aagaagacgt tccaaccacg tcttcaaagc aagtggattg atgtgatatc     660
tccactgacg taagggatga cgcacaatcc cactatcctt cgcaagaccc ttcctctata     720
taaggaagtt catttcattt ggagaggtat taaaatctta ataggttttg ataaaagcga     780
acgtggggaa acccgaacca aaccttcttc taaactctct ctcatctctc ttaaagcaaa     840
cttctctctt gtctttcttg cgtgagcgat cttcaacgtt gtcagatcgt gcttcggcac     900
cagtacaatg gcgaaaaacg ttgcgatttt cggcttattg ttttctcttc ttgtgttggt     960
tccttctcag atcttcgccc aaaaacttcc tggaaatgac aacagcacgg caacgctgtg    1020
ccttgggcac catgcagtac caaacggaac gatagtgaaa acaatcacga atgaccaaat    1080
tgaagttact aatgctactg agctggttca gaattcctca ataggtgaaa tatgcgacag    1140
tcctcatcag atccttgatg gagaaaactg cacactaata gatgctctat tgggagaccc    1200
tcagtgtgat ggcttccaaa ataagaaatg ggaccttttt gttgaacgaa gcaaagccta    1260
cagcaactgt taccctttatg atgtgccgga ttatgcctcc cttaggtcac tagttgcctc    1320
atccggcaca ctggagttta acaatgaaag cttcaattgg actggagtca ctcaaaacgg    1380
aacaagttct gcttgcataa ggagatctaa taatagtttc tttagtagat taaattggtt    1440
gacccactta aacttcaaat acccagcatt gaacgtgact atgccaaaca atgaacaatt    1500
tgacaaattg tacatttggg gggttcacca cccgggtacg gacaaggacc aaatcttcct    1560
gtatgctcaa tcatcaggaa gaatcacagt atctaccaaa agaagccaac aagctgtaat    1620
cccgaatatc ggatctagac ccagaataag gaatatccct agcagaataa gcatctattg    1680
gacaatagta aaaccgggag acatactttt gattaacagc acagggaatc taattgctcc    1740
taggggttac ttcaaaatac gaagtgggaa aagctcaata atgagatcag atgcacccat    1800
tggcaaatgc aattctgaat gcatcactcc aaatggaagc attcccaatg acaaaccatt    1860
ccaaaatgta aacaggatca catacggggc ctgtcccaga tatgttaagc aaagcactct    1920
gaaattggca acaggaatgc gaaatgtacc agagaaacaa actagaggca tatttggcgc    1980
aatagcgggt ttcatagaaa atggttggga gggaatggtg gatggttggt acggtttcag    2040
gcatcaaaat tctgagggaa gaggacaagc agcagatctc aaaagcactc aagcagcaat    2100
cgatcaaatc aatgggaagc tgaatcgatt gatcgggaaa accaacgaga aattccatca    2160
gattgaaaaa gaattctcag aagtcgaagg gagaattcag gaccttgaga aatatgttga    2220
ggacactaaa atagatctct ggtcatacaa cgcggagctt cttgttgccc tggagaacca    2280
acatacaatt gatctaactg actcagaaat gaacaaactg tttgaaaaaa caaagaagca    2340
actaagggaa aatgctgagg atatgggcaa tggttgtttc aaaatatacc acaaatgtga    2400
caatgcctgc ataggatcaa tcagaaatgg aacttatgac cacgatgtat acagagatga    2460
agcattaaac aaccggttcc agatcaaggg agttgagctg aagtcagggt acaaagattg    2520
gatcctatgg atttcctttg ccatatcatg ttttttgctt tgtgttgctt tgttggggtt    2580
catcatgtgg gcctgccaaa agggcaacat taggtgcaac atttgcattt gaaggcctat    2640
tttctttagt ttgaatttac tgttattcgg tgtgcatttc tatgtttggt gagcggtttt    2700
ctgtgctcag agtgtgttta ttttatgtaa tttaatttct ttgtgagctc ctgtttagca    2760
```

ggtcgtccct tcagcaagga cacaaaaaga ttttaatttt attaaaaaaa aaaaaaaaaa 2820
agaccgggaa ttcgatatca agcttatcga cctgcagatc gttcaaacat ttggcaataa 2880
agtttcttaa gattgaatcc tgttgccggt cttgcgatga ttatcatata atttctgttg 2940
aattacgtta agcatgtaat aattaacatg taatgcatga cgttatttat gagatgggtt 3000
tttatgatta gagtcccgca attatacatt taatacgcga tagaaaacaa aatatagcgc 3060
gcaaactagg ataaattatc gcgcgcggtg tcatctatgt tactagat 3108

<210> SEQ ID NO 31
<211> LENGTH: 52
<212> TYPE: DNA
<213> ORGANISM: Artificial Sequence
<220> FEATURE:
<223> OTHER INFORMATION: IF-HT1*(-Mprot)-PDI.c

<400> SEQUENCE: 31
acagggccca ataccgcgga gacaatggcg aaaaacgttg cgattttcgg ct 52

<210> SEQ ID NO 32
<211> LENGTH: 52
<212> TYPE: DNA
<213> ORGANISM: Artificial Sequence
<220> FEATURE:
<223> OTHER INFORMATION: IF-HT2*(-Mprot)-PDI.c

<400> SEQUENCE: 32
acagggccca ataccgcgga ggaaatggcg aaaaacgttg cgattttcgg ct 52

<210> SEQ ID NO 33
<211> LENGTH: 52
<212> TYPE: DNA
<213> ORGANISM: Artificial Sequence
<220> FEATURE:
<223> OTHER INFORMATION: IF-HT3*(-Mprot)-PDI.c

<400> SEQUENCE: 33
acagggccca ataccgcgga aaaaatggcg aaaaacgttg cgattttcgg ct 52

<210> SEQ ID NO 34
<211> LENGTH: 52
<212> TYPE: DNA
<213> ORGANISM: Artificial Sequence
<220> FEATURE:
<223> OTHER INFORMATION: IF-HT4*(-Mprot)-PDI.c

<400> SEQUENCE: 34
acagggccca ataccgcgga aacaatggcg aaaaacgttg cgattttcgg ct 52

<210> SEQ ID NO 35
<211> LENGTH: 52
<212> TYPE: DNA
<213> ORGANISM: Artificial Sequence
<220> FEATURE:
<223> OTHER INFORMATION: IF-HT5*(-Mprot)-PDI.c

<400> SEQUENCE: 35
acagggccca ataccgcgga agcaatggcg aaaaacgttg cgattttcgg ct 52

<210> SEQ ID NO 36
<211> LENGTH: 52
<212> TYPE: DNA
<213> ORGANISM: Artificial Sequence
<220> FEATURE:

-continued

<223> OTHER INFORMATION: IF-HT6*(-Mprot)-PDI.c

<400> SEQUENCE: 36
acagggccca ataccgcgga agaaatggcg aaaaacgttg cgattttcgg ct 52

<210> SEQ ID NO 37
<211> LENGTH: 53
<212> TYPE: DNA
<213> ORGANISM: Artificial Sequence
<220> FEATURE:
<223> OTHER INFORMATION: IF-HT7*(-Mprot)-PDI.c

<400> SEQUENCE: 37
acagggccca ataccgcgga aagaaatggc gaaaaacgtt gcgattttcg gct 53

<210> SEQ ID NO 38
<211> LENGTH: 54
<212> TYPE: DNA
<213> ORGANISM: Artificial Sequence
<220> FEATURE:
<223> OTHER INFORMATION: IF-HT8*(-Mprot)-PDI.c

<400> SEQUENCE: 38
acagggccca ataccgcgga aaagaaatgg cgaaaaacgt tgcgattttc ggct 54

<210> SEQ ID NO 39
<211> LENGTH: 1722
<212> TYPE: DNA
<213> ORGANISM: Artificial Sequence
<220> FEATURE:
<223> OTHER INFORMATION: Nucleotide sequence of PDISP/H1 California

<400> SEQUENCE: 39
atggcgaaaa acgttgcgat tttcggctta ttgttttctc ttcttgtgtt ggttccttct 60
cagatcttcg ctgacacatt atgtataggt tatcatgcga acaattcaac agacactgta 120
gacacagtac tagaaaagaa tgtaacagta acacactctg ttaaccttct agaagacaag 180
cataacggga aactatgcaa actaagaggg gtagccccat tgcatttggg taaatgtaac 240
attgctggct ggatcctggg aaatccagag tgtgaatcac tctccacagc aagctcatgg 300
tcctacattg tggaaacacc tagttcagac aatggaacgt gttacccagg agatttcatc 360
gattatgagg agctaagaga gcaattgagc tcagtgtcat catttgaaag gtttgagata 420
ttccccaaga caagttcatg gcccaatcat gactcgaaca aaggtgtaac ggcagcatgt 480
cctcatgctg gagcaaaaag cttctacaaa aatttaatat ggctagttaa aaaaggaaat 540
tcatacccaa agctcagcaa atcctacatt aatgataaag ggaaagaagt cctcgtgcta 600
tggggcattc accatccatc tactagtgct gaccaacaaa gtctctatca gaatgcagat 660
gcatatgttt ttgtggggtc atcaagatac agcaagaagt tcaagccgga aatagcaata 720
agacccaaag tgagggatca agaagggaga atgaactatt actggacact agtagagccg 780
ggagacaaaa taacattcga agcaactgga aatctagtgg taccgagata tgcattcgca 840
atggaaagaa atgctggatc tggtattatc atttcagata caccagtcca cgattgcaat 900
acaacttgtc aaacacccaa gggtgctata aacaccagcc tcccatttca gaatatacat 960
ccgatcacaa ttggaaaatg tccaaaatat gtaaaaagca caaaattgag actggccaca 1020
ggattgagga atatcccgtc tattcaatct agaggactat ttggggccat tgccggtttc 1080
attgaagggg ggtggacagg gatggtagat ggatggtacg gttatcacca tcaaaatgag 1140
caggggtcag gatatgcagc cgacctgaag agcacacaga atgccattga cgagattact 1200

```
aacaaagtaa attctgttat tgaaaagatg aatacacagt tcacagcagt aggtaaagag   1260

ttcaaccacc tggaaaaaag aatagagaat ttaaataaaa aagttgatga tggtttcctg   1320

gacatttgga cttacaatgc cgaactgttg gttctattgg aaaatgaaag aactttggac   1380

taccacgatt caaatgtgaa gaacttatat gaaaaggtaa gaagccagct aaaaaacaat   1440

gccaaggaaa ttggaaacgg ctgctttgaa ttttaccaca aatgcgataa cacgtgcatg   1500

gaaagtgtca aaaatgggac ttatgactac ccaaaatact cagaggaagc aaaattaaac   1560

agagaagaaa tagatggggt aaagctggaa tcaacaagga tttaccagat tttggcgatc   1620

tattcaactg tcgccagttc attggtactg gtagtctccc tgggggcaat cagtttctgg   1680

atgtgctcta atgggtctct acagtgtaga atatgtattt aa                      1722
```

<210> SEQ ID NO 40
<211> LENGTH: 573
<212> TYPE: PRT
<213> ORGANISM: Artificial Sequence
<220> FEATURE:
<223> OTHER INFORMATION: Amino acid sequence of PDISP/H1 California

<400> SEQUENCE: 40

```
Met Ala Lys Asn Val Ala Ile Phe Gly Leu Leu Phe Ser Leu Leu Val
1               5                   10                  15

Leu Val Pro Ser Gln Ile Phe Ala Asp Thr Leu Cys Ile Gly Tyr His
            20                  25                  30

Ala Asn Asn Ser Thr Asp Thr Val Asp Thr Val Leu Glu Lys Asn Val
        35                  40                  45

Thr Val Thr His Ser Val Asn Leu Leu Glu Asp Lys His Asn Gly Lys
    50                  55                  60

Leu Cys Lys Leu Arg Gly Val Ala Pro Leu His Leu Gly Lys Cys Asn
65                  70                  75                  80

Ile Ala Gly Trp Ile Leu Gly Asn Pro Glu Cys Glu Ser Leu Ser Thr
                85                  90                  95

Ala Ser Ser Trp Ser Tyr Ile Val Glu Thr Pro Ser Ser Asp Asn Gly
            100                 105                 110

Thr Cys Tyr Pro Gly Asp Phe Ile Asp Tyr Glu Glu Leu Arg Glu Gln
        115                 120                 125

Leu Ser Ser Val Ser Ser Phe Glu Arg Phe Glu Ile Phe Pro Lys Thr
    130                 135                 140

Ser Ser Trp Pro Asn His Asp Ser Asn Lys Gly Val Thr Ala Ala Cys
145                 150                 155                 160

Pro His Ala Gly Ala Lys Ser Phe Tyr Lys Asn Leu Ile Trp Leu Val
                165                 170                 175

Lys Lys Gly Asn Ser Tyr Pro Lys Leu Ser Lys Ser Tyr Ile Asn Asp
            180                 185                 190

Lys Gly Lys Glu Val Leu Val Leu Trp Gly Ile His His Pro Ser Thr
        195                 200                 205

Ser Ala Asp Gln Gln Ser Leu Tyr Gln Asn Ala Asp Ala Tyr Val Phe
    210                 215                 220

Val Gly Ser Ser Arg Tyr Ser Lys Lys Phe Lys Pro Glu Ile Ala Ile
225                 230                 235                 240

Arg Pro Lys Val Arg Asp Gln Glu Gly Arg Met Asn Tyr Tyr Trp Thr
                245                 250                 255

Leu Val Glu Pro Gly Asp Lys Ile Thr Phe Glu Ala Thr Gly Asn Leu
            260                 265                 270
```

```
Val Val Pro Arg Tyr Ala Phe Ala Met Glu Arg Asn Ala Gly Ser Gly
        275                 280                 285

Ile Ile Ile Ser Asp Thr Pro Val His Asp Cys Asn Thr Thr Cys Gln
    290                 295                 300

Thr Pro Lys Gly Ala Ile Asn Thr Ser Leu Pro Phe Gln Asn Ile His
305                 310                 315                 320

Pro Ile Thr Ile Gly Lys Cys Pro Lys Tyr Val Lys Ser Thr Lys Leu
                325                 330                 335

Arg Leu Ala Thr Gly Leu Arg Asn Ile Pro Ser Ile Gln Ser Arg Gly
            340                 345                 350

Leu Phe Gly Ala Ile Ala Gly Phe Ile Glu Gly Gly Trp Thr Gly Met
        355                 360                 365

Val Asp Gly Trp Tyr Gly Tyr His His Gln Asn Glu Gln Gly Ser Gly
    370                 375                 380

Tyr Ala Ala Asp Leu Lys Ser Thr Gln Asn Ala Ile Asp Glu Ile Thr
385                 390                 395                 400

Asn Lys Val Asn Ser Val Ile Glu Lys Met Asn Thr Gln Phe Thr Ala
                405                 410                 415

Val Gly Lys Glu Phe Asn His Leu Glu Lys Arg Ile Glu Asn Leu Asn
            420                 425                 430

Lys Lys Val Asp Asp Gly Phe Leu Asp Ile Trp Thr Tyr Asn Ala Glu
        435                 440                 445

Leu Leu Val Leu Leu Glu Asn Glu Arg Thr Leu Asp Tyr His Asp Ser
    450                 455                 460

Asn Val Lys Asn Leu Tyr Glu Lys Val Arg Ser Gln Leu Lys Asn Asn
465                 470                 475                 480

Ala Lys Glu Ile Gly Asn Gly Cys Phe Glu Phe Tyr His Lys Cys Asp
                485                 490                 495

Asn Thr Cys Met Glu Ser Val Lys Asn Gly Thr Tyr Asp Tyr Pro Lys
            500                 505                 510

Tyr Ser Glu Glu Ala Lys Leu Asn Arg Glu Glu Ile Asp Gly Val Lys
        515                 520                 525

Leu Glu Ser Thr Arg Ile Tyr Gln Ile Leu Ala Ile Tyr Ser Thr Val
    530                 535                 540

Ala Ser Ser Leu Val Leu Val Val Ser Leu Gly Ala Ile Ser Phe Trp
545                 550                 555                 560

Met Cys Ser Asn Gly Ser Leu Gln Cys Arg Ile Cys Ile
                565                 570


<210> SEQ ID NO 41
<211> LENGTH: 1707
<212> TYPE: DNA
<213> ORGANISM: Influenza Virus H5 Indonesia

<400> SEQUENCE: 41

atggagaaaa tagtgcttct tcttgcaata gtcagtcttg ttaaaagtga tcagatttgc      60

attggttacc atgcaaacaa ttcaacagag caggttgaca caatcatgga aaagaacgtt     120

actgttacac atgcccaaga catactggaa aagacacaca acgggaagct ctgcgatcta     180

gatggagtga agcctctaat tttaagagat tgtagtgtag ctggatggct cctcgggaac     240

ccaatgtgtg acgaattcat caatgtaccg gaatggtctt acatagtgga gaaggccaat     300

ccaaccaatg acctctgtta cccagggagt ttcaacgact atgaagaact gaaacaccta     360

ttgagcagaa taaaccattt tgagaaaatt caaatcatcc ccaaaagttc ttggtccgat     420
```

```
catgaagcct catcaggagt tagctcagca tgtccatacc tgggaagtcc ctcctttttt    480

agaaatgtgg tatggcttat caaaaagaac agtacatacc caacaataaa gaaaagctac    540

aataatacca accaagagga tcttttggta ctgtggggaa ttcaccatcc taatgatgcg    600

gcagagcaga caaggctata tcaaaaccca accacctata tttccattgg gacatcaaca    660

ctaaaccaga gattggtacc aaaaatagct actagatcca aagtaaacgg gcaaagtgga    720

aggatggagt tcttctggac aattttaaaa cctaatgatg caatcaactt cgagagtaat    780

ggaaatttca ttgctccaga atatgcatac aaaattgtca agaaagggga ctcagcaatt    840

atgaaaagtg aattggaata tggtaactgc aacaccaagt gtcaaactcc aatggggggcg   900

ataaactcta gtatgccatt ccacaacata caccctctca ccatcgggga atgccccaaa    960

tatgtgaaat caaacagatt agtccttgca acagggctca gaaatagccc tcaaagagag   1020

agcagaagaa aaaagagagg actatttgga gctatagcag gttttataga gggaggatgg   1080

cagggaatgg tagatggttg gtatgggtac caccatagca atgagcaggg gagtgggtac   1140

gctgcagaca aagaatccac tcaaaaggca atagatggag tcaccaataa ggtcaactca   1200

atcattgaca aaatgaacac tcagtttgag gccgttggaa gggaatttaa taacttagaa   1260

aggagaatag agaatttaaa caagaagatg gaagacgggt ttctagatgt ctggacttat   1320

aatgccgaac ttctggttct catggaaaat gagagaactc tagactttca tgactcaaat   1380

gttaagaacc tctacgacaa ggtccgacta cagcttaggg ataatgcaaa ggagctgggt   1440

aacggttgtt tcgagttcta tcacaaatgt gataatgaat gtatggaaag tataagaaac   1500

ggaacgtaca actatccgca gtattcagaa gaagcaagat taaaaagaga ggaaataagt   1560

ggggtaaaat tggaatcaat aggaacttac caaatactgt caatttattc aacagtggcg   1620

agttccctag cactggcaat catgatggct ggtctatctt tatggatgtg ctccaatgga   1680

tcgttacaat gcagaatttg catttaa                                        1707
```

```
<210> SEQ ID NO 42
<211> LENGTH: 568
<212> TYPE: PRT
<213> ORGANISM: Influenza virus H5 Indonesia

<400> SEQUENCE: 42

Met Glu Lys Ile Val Leu Leu Leu Ala Ile Val Ser Leu Val Lys Ser
1               5                   10                  15

Asp Gln Ile Cys Ile Gly Tyr His Ala Asn Asn Ser Thr Glu Gln Val
            20                  25                  30

Asp Thr Ile Met Glu Lys Asn Val Thr Val Thr His Ala Gln Asp Ile
        35                  40                  45

Leu Glu Lys Thr His Asn Gly Lys Leu Cys Asp Leu Asp Gly Val Lys
    50                  55                  60

Pro Leu Ile Leu Arg Asp Cys Ser Val Ala Gly Trp Leu Leu Gly Asn
65                  70                  75                  80

Pro Met Cys Asp Glu Phe Ile Asn Val Pro Glu Trp Ser Tyr Ile Val
                85                  90                  95

Glu Lys Ala Asn Pro Thr Asn Asp Leu Cys Tyr Pro Gly Ser Phe Asn
            100                 105                 110

Asp Tyr Glu Glu Leu Lys His Leu Leu Ser Arg Ile Asn His Phe Glu
        115                 120                 125

Lys Ile Gln Ile Ile Pro Lys Ser Ser Trp Ser Asp His Glu Ala Ser
    130                 135                 140
```

-continued

```
Ser Gly Val Ser Ser Ala Cys Pro Tyr Leu Gly Ser Pro Ser Phe Phe
145                 150                 155                 160

Arg Asn Val Val Trp Leu Ile Lys Lys Asn Ser Thr Tyr Pro Thr Ile
                165                 170                 175

Lys Lys Ser Tyr Asn Asn Thr Asn Gln Glu Asp Leu Leu Val Leu Trp
            180                 185                 190

Gly Ile His His Pro Asn Asp Ala Ala Glu Gln Thr Arg Leu Tyr Gln
        195                 200                 205

Asn Pro Thr Thr Tyr Ile Ser Ile Gly Thr Ser Thr Leu Asn Gln Arg
    210                 215                 220

Leu Val Pro Lys Ile Ala Thr Arg Ser Lys Val Asn Gly Gln Ser Gly
225                 230                 235                 240

Arg Met Glu Phe Phe Trp Thr Ile Leu Lys Pro Asn Asp Ala Ile Asn
                245                 250                 255

Phe Glu Ser Asn Gly Asn Phe Ile Ala Pro Glu Tyr Ala Tyr Lys Ile
            260                 265                 270

Val Lys Lys Gly Asp Ser Ala Ile Met Lys Ser Glu Leu Glu Tyr Gly
        275                 280                 285

Asn Cys Asn Thr Lys Cys Gln Thr Pro Met Gly Ala Ile Asn Ser Ser
    290                 295                 300

Met Pro Phe His Asn Ile His Pro Leu Thr Ile Gly Glu Cys Pro Lys
305                 310                 315                 320

Tyr Val Lys Ser Asn Arg Leu Val Leu Ala Thr Gly Leu Arg Asn Ser
                325                 330                 335

Pro Gln Arg Glu Ser Arg Arg Lys Lys Arg Gly Leu Phe Gly Ala Ile
            340                 345                 350

Ala Gly Phe Ile Glu Gly Gly Trp Gln Gly Met Val Asp Gly Trp Tyr
        355                 360                 365

Gly Tyr His His Ser Asn Glu Gln Gly Ser Gly Tyr Ala Ala Asp Lys
    370                 375                 380

Glu Ser Thr Gln Lys Ala Ile Asp Gly Val Thr Asn Lys Val Asn Ser
385                 390                 395                 400

Ile Ile Asp Lys Met Asn Thr Gln Phe Glu Ala Val Gly Arg Glu Phe
                405                 410                 415

Asn Asn Leu Glu Arg Arg Ile Glu Asn Leu Asn Lys Lys Met Glu Asp
            420                 425                 430

Gly Phe Leu Asp Val Trp Thr Tyr Asn Ala Glu Leu Leu Val Leu Met
        435                 440                 445

Glu Asn Glu Arg Thr Leu Asp Phe His Asp Ser Asn Val Lys Asn Leu
    450                 455                 460

Tyr Asp Lys Val Arg Leu Gln Leu Arg Asp Asn Ala Lys Glu Leu Gly
465                 470                 475                 480

Asn Gly Cys Phe Glu Phe Tyr His Lys Cys Asp Asn Glu Cys Met Glu
                485                 490                 495

Ser Ile Arg Asn Gly Thr Tyr Asn Tyr Pro Gln Tyr Ser Glu Glu Ala
            500                 505                 510

Arg Leu Lys Arg Glu Glu Ile Ser Gly Val Lys Leu Glu Ser Ile Gly
        515                 520                 525

Thr Tyr Gln Ile Leu Ser Ile Tyr Ser Thr Val Ala Ser Ser Leu Ala
    530                 535                 540

Leu Ala Ile Met Met Ala Gly Leu Ser Leu Trp Met Cys Ser Asn Gly
545                 550                 555                 560
```

Ser Leu Gln Cys Arg Ile Cys Ile
565

<210> SEQ ID NO 43
<211> LENGTH: 1701
<212> TYPE: DNA
<213> ORGANISM: Artificial Sequence
<220> FEATURE:
<223> OTHER INFORMATION: Nucleotide sequence of PDISP/H7 Hangzhou

<400> SEQUENCE: 43
atggcgaaaa acgttgcgat tttcggctta ttgttttctc ttcttgtgtt ggttccttct 60
cagatcttcg cggacaaaat ctgcctcgga catcatgccg tgtcaaacgg aaccaaagta 120
aacacattaa ctgaaagagg agtggaagtc gtcaatgcaa ctgaaacagt ggaacgaaca 180
aacatcccca ggatctgctc aaaagggaaa aggacagttg acctcggtca atgtggactc 240
ctggggacaa tcactggacc acctcaatgt gaccaattcc tagaattttc agccgattta 300
attattgaga ggcgagaagg aagtgatgtc tgttatcctg ggaaattcgt gaatgaagaa 360
gctctgaggc aaattctcag agaatcaggc ggaattgaca aggaagcaat gggattcaca 420
tacagtggaa taagaactaa tggagcaacc agtgcatgta ggagatcagg atcttcattc 480
tatgcagaaa tgaaatggct cctgtcaaac acagataatg ctgcattccc gcagatgact 540
aagtcatata aaaatacaag aaaaagccca gctctaatag tatgggggat ccatcattcc 600
gtatcaactg cagagcaaac caagctatat gggagtggaa acaaactggt gacagttggg 660
agttctaatt atcaacaatc ttttgtaccg agtccaggag cgagaccaca agttaatggt 720
atatctggaa gaattgactt tcattggcta atgctaaatc ccaatgatac agtcactttc 780
agtttcaatg gggctttcat agctccagac cgtgcaagct tcctgagagg aaaatctatg 840
ggaatccaga gtggagtaca ggttgatgcc aattgtgaag gggactgcta tcatagtgga 900
gggacaataa taagtaactt gccatttcag aacatagata gcagggcagt tggaaaatgt 960
ccgagatatg ttaagcaaag gagtctgctg ctagcaacag ggatgaagaa tgttcctgag 1020
attccaaagg gaagaggcct atttggtgct atagcgggtt tcattgaaaa tggatgggaa 1080
ggcctaattg atggttggta tggtttcaga caccagaatg cacagggaga gggaactgct 1140
gcagattaca aaagcactca atcggcaatt gatcaaataa caggaaaatt aaaccggctt 1200
atagaaaaaa ccaaccaaca atttgagttg atcgacaatg aattcaatga ggtagagaag 1260
caaatcggta atgtgataaa ttggaccaga gattctataa cagaagtgtg gtcatacaat 1320
gctgaactct tggtagcaat ggagaaccag catacaattg atctggctga ttcagaaatg 1380
gacaaactgt acgaacgagt gaaaagacag ctgagagaga atgctgaaga agatggcact 1440
ggttgctttg aaatatttca caagtgtgat gatgactgta tggccagtat tagaaataac 1500
acctatgatc acagcaaata cagggaagag gcaatgcaaa atagaataca gattgaccca 1560
gtcaaactaa gcagcggcta caaagatgtg atactttggt ttagcttcgg ggcatcatgt 1620
ttcatacttc tagccattgt aatgggcctt gtcttcatat gtgtaaagaa tggaaacatg 1680
cggtgcacta tttgtatata a 1701

<210> SEQ ID NO 44
<211> LENGTH: 566
<212> TYPE: PRT
<213> ORGANISM: Artificial Sequence
<220> FEATURE:
<223> OTHER INFORMATION: Amino acid sequence of PDISP/H7 Hangzhou

<400> SEQUENCE: 44

Met Ala Lys Asn Val Ala Ile Phe Gly Leu Leu Phe Ser Leu Leu Val
1 5 10 15

Leu Val Pro Ser Gln Ile Phe Ala Asp Lys Ile Cys Leu Gly His His
20 25 30

Ala Val Ser Asn Gly Thr Lys Val Asn Thr Leu Thr Glu Arg Gly Val
35 40 45

Glu Val Val Asn Ala Thr Glu Thr Val Glu Arg Thr Asn Ile Pro Arg
50 55 60

Ile Cys Ser Lys Gly Lys Arg Thr Val Asp Leu Gly Gln Cys Gly Leu
65 70 75 80

Leu Gly Thr Ile Thr Gly Pro Pro Gln Cys Asp Gln Phe Leu Glu Phe
85 90 95

Ser Ala Asp Leu Ile Ile Glu Arg Arg Glu Gly Ser Asp Val Cys Tyr
100 105 110

Pro Gly Lys Phe Val Asn Glu Glu Ala Leu Arg Gln Ile Leu Arg Glu
115 120 125

Ser Gly Gly Ile Asp Lys Glu Ala Met Gly Phe Thr Tyr Ser Gly Ile
130 135 140

Arg Thr Asn Gly Ala Thr Ser Ala Cys Arg Arg Ser Gly Ser Ser Phe
145 150 155 160

Tyr Ala Glu Met Lys Trp Leu Leu Ser Asn Thr Asp Asn Ala Ala Phe
165 170 175

Pro Gln Met Thr Lys Ser Tyr Lys Asn Thr Arg Lys Ser Pro Ala Leu
180 185 190

Ile Val Trp Gly Ile His His Ser Val Ser Thr Ala Glu Gln Thr Lys
195 200 205

Leu Tyr Gly Ser Gly Asn Lys Leu Val Thr Val Gly Ser Ser Asn Tyr
210 215 220

Gln Gln Ser Phe Val Pro Ser Pro Gly Ala Arg Pro Gln Val Asn Gly
225 230 235 240

Ile Ser Gly Arg Ile Asp Phe His Trp Leu Met Leu Asn Pro Asn Asp
245 250 255

Thr Val Thr Phe Ser Phe Asn Gly Ala Phe Ile Ala Pro Asp Arg Ala
260 265 270

Ser Phe Leu Arg Gly Lys Ser Met Gly Ile Gln Ser Gly Val Gln Val
275 280 285

Asp Ala Asn Cys Glu Gly Asp Cys Tyr His Ser Gly Gly Thr Ile Ile
290 295 300

Ser Asn Leu Pro Phe Gln Asn Ile Asp Ser Arg Ala Val Gly Lys Cys
305 310 315 320

Pro Arg Tyr Val Lys Gln Arg Ser Leu Leu Leu Ala Thr Gly Met Lys
325 330 335

Asn Val Pro Glu Ile Pro Lys Gly Arg Gly Leu Phe Gly Ala Ile Ala
340 345 350

Gly Phe Ile Glu Asn Gly Trp Glu Gly Leu Ile Asp Gly Trp Tyr Gly
355 360 365

Phe Arg His Gln Asn Ala Gln Gly Glu Gly Thr Ala Ala Asp Tyr Lys
370 375 380

Ser Thr Gln Ser Ala Ile Asp Gln Ile Thr Gly Lys Leu Asn Arg Leu
385 390 395 400

Ile Glu Lys Thr Asn Gln Gln Phe Glu Leu Ile Asp Asn Glu Phe Asn
405 410 415

```
Glu Val Glu Lys Gln Ile Gly Asn Val Ile Asn Trp Thr Arg Asp Ser
            420                 425                 430

Ile Thr Glu Val Trp Ser Tyr Asn Ala Glu Leu Leu Val Ala Met Glu
        435                 440                 445

Asn Gln His Thr Ile Asp Leu Ala Asp Ser Glu Met Asp Lys Leu Tyr
    450                 455                 460

Glu Arg Val Lys Arg Gln Leu Arg Glu Asn Ala Glu Glu Asp Gly Thr
465                 470                 475                 480

Gly Cys Phe Glu Ile Phe His Lys Cys Asp Asp Asp Cys Met Ala Ser
                485                 490                 495

Ile Arg Asn Asn Thr Tyr Asp His Ser Lys Tyr Arg Glu Glu Ala Met
            500                 505                 510

Gln Asn Arg Ile Gln Ile Asp Pro Val Lys Leu Ser Ser Gly Tyr Lys
        515                 520                 525

Asp Val Ile Leu Trp Phe Ser Phe Gly Ala Ser Cys Phe Ile Leu Leu
    530                 535                 540

Ala Ile Val Met Gly Leu Val Phe Ile Cys Val Lys Asn Gly Asn Met
545                 550                 555                 560

Arg Cys Thr Ile Cys Ile
                565


<210> SEQ ID NO 45
<211> LENGTH: 1698
<212> TYPE: DNA
<213> ORGANISM: Artificial Sequence
<220> FEATURE:
<223> OTHER INFORMATION: Nucleotide sequence of PDISP/H7 Hangzhou+H5
      Indonesia TMCT

<400> SEQUENCE: 45

atggcgaaaa acgttgcgat tttcggctta ttgttttctc ttcttgtgtt ggttccttct     60

cagatcttcg cggacaaaat ctgcctcgga catcatgccg tgtcaaacgg aaccaaagta    120

aacacattaa ctgaaagagg agtggaagtc gtcaatgcaa ctgaaacagt ggaacgaaca    180

aacatcccca ggatctgctc aaaagggaaa aggacagttg acctcggtca atgtggactc    240

ctggggacaa tcactggacc acctcaatgt gaccaattcc tagaattttc agccgattta    300

attattgaga ggcgagaagg aagtgatgtc tgttatcctg ggaaattcgt gaatgaagaa    360

gctctgaggc aaattctcag agaatcaggc ggaattgaca aggaagcaat gggattcaca    420

tacagtggaa taagaactaa tggagcaacc agtgcatgta ggagatcagg atcttcattc    480

tatgcagaaa tgaaatggct cctgtcaaac acagataatg ctgcattccc gcagatgact    540

aagtcatata aaaatacaag aaaaagccca gctctaatag tatgggggat ccatcattcc    600

gtatcaactg cagagcaaac caagctatat gggagtggaa acaaactggt gacagttggg    660

agttctaatt atcaacaatc ttttgtaccg agtccaggag cgagaccaca agttaatggt    720

atatctggaa gaattgactt tcattggcta atgctaaatc ccaatgatac agtcactttc    780

agtttcaatg ggctttcat agctccagac cgtgcaagct tcctgagagg aaaatctatg    840

ggaatccaga gtggagtaca ggttgatgcc aattgtgaag gggactgcta tcatagtgga    900

gggacaataa taagtaactt gccatttcag aacatagata gcagggcagt tggaaaatgt    960

ccgagatatg ttaagcaaag gagtctgctg ctagcaacag ggatgaagaa tgttcctgag   1020

attccaaagg gaagaggcct atttggtgct atagcgggtt tcattgaaaa tggatgggaa   1080

ggcctaattg atggttggta tggtttcaga caccagaatg cacagggaga gggaactgct   1140
```

```
gcagattaca aaagcactca atcggcaatt gatcaaataa caggaaaatt aaaccggctt   1200

atagaaaaaa ccaaccaaca atttgagttg atcgacaatg aattcaatga ggtagagaag   1260

caaatcggta atgtgataaa ttggaccaga gattctataa cagaagtgtg gtcatacaat   1320

gctgaactct tggtagcaat ggagaaccag catacaattg atctggctga ttcagaaatg   1380

gacaaactgt acgaacgagt gaaaagacag ctgagagaga atgctgaaga agatggcact   1440

ggttgctttg aaatatttca caagtgtgat gatgactgta tggccagtat tagaaataac   1500

acctatgatc acagcaaata cagggaagag gcaatgcaaa atagaataca gattgaccca   1560

gtcaaactaa gcagcggcta ccaaatactg tcaatttatt caacagtggc gagttcccta   1620

gcactggcaa tcatgatggc tggtctatct ttatggatgt gctccaatgg atcgttacaa   1680

tgcagaattt gcatttaa                                                 1698


<210> SEQ ID NO 46
<211> LENGTH: 565
<212> TYPE: PRT
<213> ORGANISM: Artificial Sequence
<220> FEATURE:
<223> OTHER INFORMATION: Amino acid sequence of PDISP/H7 Hangzhou+H5
      Indonesia TMCT

<400> SEQUENCE: 46

Met Ala Lys Asn Val Ala Ile Phe Gly Leu Leu Phe Ser Leu Leu Val
1               5                   10                  15

Leu Val Pro Ser Gln Ile Phe Ala Asp Lys Ile Cys Leu Gly His His
            20                  25                  30

Ala Val Ser Asn Gly Thr Lys Val Asn Thr Leu Thr Glu Arg Gly Val
        35                  40                  45

Glu Val Val Asn Ala Thr Glu Thr Val Glu Arg Thr Asn Ile Pro Arg
    50                  55                  60

Ile Cys Ser Lys Gly Lys Arg Thr Val Asp Leu Gly Gln Cys Gly Leu
65                  70                  75                  80

Leu Gly Thr Ile Thr Gly Pro Pro Gln Cys Asp Gln Phe Leu Glu Phe
                85                  90                  95

Ser Ala Asp Leu Ile Ile Glu Arg Arg Glu Gly Ser Asp Val Cys Tyr
            100                 105                 110

Pro Gly Lys Phe Val Asn Glu Glu Ala Leu Arg Gln Ile Leu Arg Glu
        115                 120                 125

Ser Gly Gly Ile Asp Lys Glu Ala Met Gly Phe Thr Tyr Ser Gly Ile
    130                 135                 140

Arg Thr Asn Gly Ala Thr Ser Ala Cys Arg Arg Ser Gly Ser Ser Phe
145                 150                 155                 160

Tyr Ala Glu Met Lys Trp Leu Leu Ser Asn Thr Asp Asn Ala Ala Phe
                165                 170                 175

Pro Gln Met Thr Lys Ser Tyr Lys Asn Thr Arg Lys Ser Pro Ala Leu
            180                 185                 190

Ile Val Trp Gly Ile His His Ser Val Ser Thr Ala Glu Gln Thr Lys
        195                 200                 205

Leu Tyr Gly Ser Gly Asn Lys Leu Val Thr Val Gly Ser Ser Asn Tyr
    210                 215                 220

Gln Gln Ser Phe Val Pro Ser Pro Gly Ala Arg Pro Gln Val Asn Gly
225                 230                 235                 240

Ile Ser Gly Arg Ile Asp Phe His Trp Leu Met Leu Asn Pro Asn Asp
                245                 250                 255
```

```
Thr Val Thr Phe Ser Phe Asn Gly Ala Phe Ile Ala Pro Asp Arg Ala
            260                 265                 270

Ser Phe Leu Arg Gly Lys Ser Met Gly Ile Gln Ser Gly Val Gln Val
        275                 280                 285

Asp Ala Asn Cys Glu Gly Asp Cys Tyr His Ser Gly Gly Thr Ile Ile
    290                 295                 300

Ser Asn Leu Pro Phe Gln Asn Ile Asp Ser Arg Ala Val Gly Lys Cys
305                 310                 315                 320

Pro Arg Tyr Val Lys Gln Arg Ser Leu Leu Leu Ala Thr Gly Met Lys
                325                 330                 335

Asn Val Pro Glu Ile Pro Lys Gly Arg Gly Leu Phe Gly Ala Ile Ala
            340                 345                 350

Gly Phe Ile Glu Asn Gly Trp Glu Gly Leu Ile Asp Gly Trp Tyr Gly
        355                 360                 365

Phe Arg His Gln Asn Ala Gln Gly Glu Gly Thr Ala Ala Asp Tyr Lys
    370                 375                 380

Ser Thr Gln Ser Ala Ile Asp Gln Ile Thr Gly Lys Leu Asn Arg Leu
385                 390                 395                 400

Ile Glu Lys Thr Asn Gln Gln Phe Glu Leu Ile Asp Asn Glu Phe Asn
                405                 410                 415

Glu Val Glu Lys Gln Ile Gly Asn Val Ile Asn Trp Thr Arg Asp Ser
            420                 425                 430

Ile Thr Glu Val Trp Ser Tyr Asn Ala Glu Leu Leu Val Ala Met Glu
        435                 440                 445

Asn Gln His Thr Ile Asp Leu Ala Asp Ser Glu Met Asp Lys Leu Tyr
    450                 455                 460

Glu Arg Val Lys Arg Gln Leu Arg Glu Asn Ala Glu Glu Asp Gly Thr
465                 470                 475                 480

Gly Cys Phe Glu Ile Phe His Lys Cys Asp Asp Asp Cys Met Ala Ser
                485                 490                 495

Ile Arg Asn Asn Thr Tyr Asp His Ser Lys Tyr Arg Glu Glu Ala Met
            500                 505                 510

Gln Asn Arg Ile Gln Ile Asp Pro Val Lys Leu Ser Ser Gly Tyr Gln
        515                 520                 525

Ile Leu Ser Ile Tyr Ser Thr Val Ala Ser Ser Leu Ala Leu Ala Ile
    530                 535                 540

Met Met Ala Gly Leu Ser Leu Trp Met Cys Ser Asn Gly Ser Leu Gln
545                 550                 555                 560

Cys Arg Ile Cys Ile
                565


<210> SEQ ID NO 47
<211> LENGTH: 1734
<212> TYPE: DNA
<213> ORGANISM: Artificial Sequence
<220> FEATURE:
<223> OTHER INFORMATION: Nucleotide sequence of PDISP/HA B Brisbane
      (PrL-)

<400> SEQUENCE: 47

atggcgaaaa acgttgcgat tttcggctta ttgttttctc ttcttgtgtt ggttccttct      60

cagatcttcg ccgatcgaat ctgcactgga ataacatcgt caaactcacc acatgtcgtc     120

aaaactgcta ctcaagggga ggtcaatgtg actggtgtaa taccactgac aacaacaccc     180

accaaatctc attttgcaaa tctcaaagga acagaaacca gggggaaact atgcccaaaa     240
```

```
tgcctcaact gcacagatct ggacgtagcc ttgggcagac caaaatgcac ggggaaaata    300
ccctcggcaa gagtttcaat actccatgaa gtcagacctg ttacatctgg gtgctttcct    360
ataatgcacg acagaacaaa aattagacag ctgcctaacc ttctccgagg atacgaacat    420
atcaggttat caacccataa cgttatcaat gcagaaaatg caccaggagg accctacaaa    480
attggaacct cagggtcttg ccctaacatt accaatggaa acggattttt cgcaacaatg    540
gcttgggccg tcccaaaaaa cgacaaaaac aaaacagcaa caaatccatt aacaatagaa    600
gtaccataca tttgtacaga aggagaagac caaattaccg tttgggggtt ccactctgac    660
aacgagaccc aaatggcaaa gctctatggg gactcaaagc cccagaagtt cacctcatct    720
gccaacggag tgaccacaca ttacgtttca cagattggtg gcttcccaaa tcaaacagaa    780
gacggaggac taccacaaag tggtagaatt gttgttgatt acatggtgca aaaatctggg    840
aaaacaggaa caattaccta tcaaaggggt attttattgc ctcaaaaggt gtggtgcgca    900
agtggcagga gcaaggtaat aaaaggatcc ttgcctttaa ttggagaagc agattgcctc    960
cacgaaaaat acggtggatt aaacaaaagc aagccttact acacagggga acatgcaaag   1020
gccataggaa attgcccaat atgggtgaaa acacccttga agctggccaa tggaaccaaa   1080
tatagacctc ctggtggagg atgggaagga atgattgcag gttggcacgg atacacatcc   1140
catggggcac atggagtagc ggtggcagca gaccttaaga gcactcaaga ggccataaac   1200
aagataacaa aaaatctcaa ctctttgagt gagctggaag taaagaatct tcaaagacta   1260
agcggtgcca tggatgaact ccacaacgaa atactagaac tagatgagaa agtggatgat   1320
ctcagagctg atacaataag ctcacaaata gaactcgcag tcctgctttc caatgaagga   1380
ataataaaca gtgaagatga acatctcttg gcgcttgaaa gaaagctgaa gaaaatgctg   1440
ggcccctctg ctgtagagat agggaatgga tgctttgaaa ccaaacacaa gtgcaaccag   1500
acctgtctcg acagaatagc tgctggtacc tttgatgcag gagaattttc tctccccacc   1560
tttgattcac tgaatattac tgctgcatct ttaaatgacg atggattgga taatcatact   1620
atactgcttt actactcaac tgctgcctcc agtttggctg taacactgat gatagctatc   1680
tttgttgttt atatggtctc cagagacaat gtttcttgct ccatctgtct ataa         1734
```

<210> SEQ ID NO 48
<211> LENGTH: 577
<212> TYPE: PRT
<213> ORGANISM: Artificial Sequence
<220> FEATURE:
<223> OTHER INFORMATION: Amino acid sequence of PDISP/HA B Brisbane (PrL-)

<400> SEQUENCE: 48

```
Met Ala Lys Asn Val Ala Ile Phe Gly Leu Leu Phe Ser Leu Leu Val
1               5                   10                  15

Leu Val Pro Ser Gln Ile Phe Ala Asp Arg Ile Cys Thr Gly Ile Thr
            20                  25                  30

Ser Ser Asn Ser Pro His Val Val Lys Thr Ala Thr Gln Gly Glu Val
        35                  40                  45

Asn Val Thr Gly Val Ile Pro Leu Thr Thr Thr Pro Thr Lys Ser His
    50                  55                  60

Phe Ala Asn Leu Lys Gly Thr Glu Thr Arg Gly Lys Leu Cys Pro Lys
65                  70                  75                  80

Cys Leu Asn Cys Thr Asp Leu Asp Val Ala Leu Gly Arg Pro Lys Cys
                85                  90                  95
```

```
Thr Gly Lys Ile Pro Ser Ala Arg Val Ser Ile Leu His Glu Val Arg
            100                 105                 110

Pro Val Thr Ser Gly Cys Phe Pro Ile Met His Asp Arg Thr Lys Ile
        115                 120                 125

Arg Gln Leu Pro Asn Leu Leu Arg Gly Tyr Glu His Ile Arg Leu Ser
    130                 135                 140

Thr His Asn Val Ile Asn Ala Glu Asn Ala Pro Gly Gly Pro Tyr Lys
145                 150                 155                 160

Ile Gly Thr Ser Gly Ser Cys Pro Asn Ile Thr Asn Gly Asn Gly Phe
                165                 170                 175

Phe Ala Thr Met Ala Trp Ala Val Pro Lys Asn Asp Lys Asn Lys Thr
            180                 185                 190

Ala Thr Asn Pro Leu Thr Ile Glu Val Pro Tyr Ile Cys Thr Glu Gly
        195                 200                 205

Glu Asp Gln Ile Thr Val Trp Gly Phe His Ser Asp Asn Glu Thr Gln
    210                 215                 220

Met Ala Lys Leu Tyr Gly Asp Ser Lys Pro Gln Lys Phe Thr Ser Ser
225                 230                 235                 240

Ala Asn Gly Val Thr Thr His Tyr Val Ser Gln Ile Gly Gly Phe Pro
                245                 250                 255

Asn Gln Thr Glu Asp Gly Gly Leu Pro Gln Ser Gly Arg Ile Val Val
            260                 265                 270

Asp Tyr Met Val Gln Lys Ser Gly Lys Thr Gly Thr Ile Thr Tyr Gln
        275                 280                 285

Arg Gly Ile Leu Leu Pro Gln Lys Val Trp Cys Ala Ser Gly Arg Ser
    290                 295                 300

Lys Val Ile Lys Gly Ser Leu Pro Leu Ile Gly Glu Ala Asp Cys Leu
305                 310                 315                 320

His Glu Lys Tyr Gly Gly Leu Asn Lys Ser Lys Pro Tyr Tyr Thr Gly
                325                 330                 335

Glu His Ala Lys Ala Ile Gly Asn Cys Pro Ile Trp Val Lys Thr Pro
            340                 345                 350

Leu Lys Leu Ala Asn Gly Thr Lys Tyr Arg Pro Pro Gly Gly Gly Trp
        355                 360                 365

Glu Gly Met Ile Ala Gly Trp His Gly Tyr Thr Ser His Gly Ala His
    370                 375                 380

Gly Val Ala Val Ala Ala Asp Leu Lys Ser Thr Gln Glu Ala Ile Asn
385                 390                 395                 400

Lys Ile Thr Lys Asn Leu Asn Ser Leu Ser Glu Leu Glu Val Lys Asn
                405                 410                 415

Leu Gln Arg Leu Ser Gly Ala Met Asp Glu Leu His Asn Glu Ile Leu
            420                 425                 430

Glu Leu Asp Glu Lys Val Asp Asp Leu Arg Ala Asp Thr Ile Ser Ser
        435                 440                 445

Gln Ile Glu Leu Ala Val Leu Leu Ser Asn Glu Gly Ile Ile Asn Ser
    450                 455                 460

Glu Asp Glu His Leu Leu Ala Leu Glu Arg Lys Leu Lys Lys Met Leu
465                 470                 475                 480

Gly Pro Ser Ala Val Glu Ile Gly Asn Gly Cys Phe Glu Thr Lys His
                485                 490                 495

Lys Cys Asn Gln Thr Cys Leu Asp Arg Ile Ala Ala Gly Thr Phe Asp
            500                 505                 510
```

-continued

```
Ala Gly Glu Phe Ser Leu Pro Thr Phe Asp Ser Leu Asn Ile Thr Ala
        515                 520                 525

Ala Ser Leu Asn Asp Asp Gly Leu Asp Asn His Thr Ile Leu Leu Tyr
    530                 535                 540

Tyr Ser Thr Ala Ala Ser Ser Leu Ala Val Thr Leu Met Ile Ala Ile
545                 550                 555                 560

Phe Val Val Tyr Met Val Ser Arg Asp Asn Val Ser Cys Ser Ile Cys
                565                 570                 575

Leu


<210> SEQ ID NO 49
<211> LENGTH: 1734
<212> TYPE: DNA
<213> ORGANISM: Artificial Sequence
<220> FEATURE:
<223> OTHER INFORMATION: Nucleotide sequence of PDISP/HA B Brisbane
      (PrL-)+H1 California TMCT

<400> SEQUENCE: 49

atggcgaaaa acgttgcgat tttcggctta ttgttttctc ttcttgtgtt ggttccttct      60

cagatcttcg ccgatcgaat ctgcactgga ataacatcgt caaactcacc acatgtcgtc     120

aaaactgcta ctcaagggga ggtcaatgtg actggtgtaa taccactgac aacaacaccc     180

accaaatctc attttgcaaa tctcaaagga acagaaacca gggggaaact atgcccaaaa     240

tgcctcaact gcacagatct ggacgtagcc ttgggcagac caaaatgcac ggggaaaata     300

ccctcggcaa gagtttcaat actccatgaa gtcagacctg ttacatctgg gtgctttcct     360

ataatgcacg acagaacaaa aattagacag ctgcctaacc ttctccgagg atacgaacat     420

atcaggttat caacccataa cgttatcaat gcagaaaatg caccaggagg accctacaaa     480

attggaacct cagggtcttg ccctaacatt accaatggaa acggattttt cgcaacaatg     540

gcttgggccg tcccaaaaaa cgacaaaaac aaaacagcaa caaatccatt aacaatagaa     600

gtaccataca tttgtacaga aggagaagac caaattaccg tttgggggtt ccactctgac     660

aacgagaccc aaatggcaaa gctctatggg gactcaaagc cccagaagtt cacctcatct     720

gccaacggag tgaccacaca ttacgtttca cagattggtg gcttcccaaa tcaaacagaa     780

gacggaggac taccacaaag tggtagaatt gttgttgatt acatggtgca aaaatctggg     840

aaaacaggaa caattaccta tcaaaggggt attttattgc ctcaaaaggt gtggtgcgca     900

agtggcagga gcaaggtaat aaaaggatcc ttgcctttaa ttggagaagc agattgcctc     960

cacgaaaaat acggtggatt aaacaaaagc aagccttact acacagggga acatgcaaag    1020

gccataggaa attgcccaat atgggtgaaa acacccttga agctggccaa tggaaccaaa    1080

tatagacctc ctggtggagg atgggaagga atgattgcag gttggcacgg atacacatcc    1140

catggggcac atggagtagc ggtggcagca gaccttaaga gcactcaaga ggccataaac    1200

aagataacaa aaaatctcaa ctctttgagt gagctggaag taaagaatct tcaaagacta    1260

agcggtgcca tggatgaact ccacaacgaa atactagaac tagatgagaa agtggatgat    1320

ctcagagctg atacaataag ctcacaaata gaactcgcag tcctgctttc caatgaagga    1380

ataataaaca gtgaagatga acatctcttg gcgcttgaaa gaaagctgaa gaaaatgctg    1440

ggcccctctg ctgtagagat agggaatgga tgctttgaaa ccaaacacaa gtgcaaccag    1500

acctgtctcg acagaatagc tgctggtacc tttgatgcag gagaattttc tctccccacc    1560

tttgattcac tgaatattac tgctgcatct ttaaatgacg atggattgga taattaccag    1620
```

```
atttggcga tctattcaac tgtcgccagt tcattggtac tggtagtctc cctgggggca   1680

atcagtttct ggatgtgctc taatgggtct ctacagtgta gaatatgtat ttaa         1734


<210> SEQ ID NO 50
<211> LENGTH: 577
<212> TYPE: PRT
<213> ORGANISM: Artificial Sequence
<220> FEATURE:
<223> OTHER INFORMATION: Amino acid sequence of PDISP/HA B Brisbane
      (PrL-)+H1 California TMCT

<400> SEQUENCE: 50

Met Ala Lys Asn Val Ala Ile Phe Gly Leu Leu Phe Ser Leu Leu Val
1               5                   10                  15

Leu Val Pro Ser Gln Ile Phe Ala Asp Arg Ile Cys Thr Gly Ile Thr
            20                  25                  30

Ser Ser Asn Ser Pro His Val Val Lys Thr Ala Thr Gln Gly Glu Val
        35                  40                  45

Asn Val Thr Gly Val Ile Pro Leu Thr Thr Thr Pro Thr Lys Ser His
    50                  55                  60

Phe Ala Asn Leu Lys Gly Thr Glu Thr Arg Gly Lys Leu Cys Pro Lys
65                  70                  75                  80

Cys Leu Asn Cys Thr Asp Leu Asp Val Ala Leu Gly Arg Pro Lys Cys
                85                  90                  95

Thr Gly Lys Ile Pro Ser Ala Arg Val Ser Ile Leu His Glu Val Arg
            100                 105                 110

Pro Val Thr Ser Gly Cys Phe Pro Ile Met His Asp Arg Thr Lys Ile
        115                 120                 125

Arg Gln Leu Pro Asn Leu Leu Arg Gly Tyr Glu His Ile Arg Leu Ser
    130                 135                 140

Thr His Asn Val Ile Asn Ala Glu Asn Ala Pro Gly Gly Pro Tyr Lys
145                 150                 155                 160

Ile Gly Thr Ser Gly Ser Cys Pro Asn Ile Thr Asn Gly Asn Gly Phe
                165                 170                 175

Phe Ala Thr Met Ala Trp Ala Val Pro Lys Asn Asp Lys Asn Lys Thr
            180                 185                 190

Ala Thr Asn Pro Leu Thr Ile Glu Val Pro Tyr Ile Cys Thr Glu Gly
        195                 200                 205

Glu Asp Gln Ile Thr Val Trp Gly Phe His Ser Asp Asn Glu Thr Gln
    210                 215                 220

Met Ala Lys Leu Tyr Gly Asp Ser Lys Pro Gln Lys Phe Thr Ser Ser
225                 230                 235                 240

Ala Asn Gly Val Thr Thr His Tyr Val Ser Gln Ile Gly Gly Phe Pro
                245                 250                 255

Asn Gln Thr Glu Asp Gly Gly Leu Pro Gln Ser Gly Arg Ile Val Val
            260                 265                 270

Asp Tyr Met Val Gln Lys Ser Gly Lys Thr Gly Thr Ile Thr Tyr Gln
        275                 280                 285

Arg Gly Ile Leu Leu Pro Gln Lys Val Trp Cys Ala Ser Gly Arg Ser
    290                 295                 300

Lys Val Ile Lys Gly Ser Leu Pro Leu Ile Gly Glu Ala Asp Cys Leu
305                 310                 315                 320

His Glu Lys Tyr Gly Gly Leu Asn Lys Ser Lys Pro Tyr Tyr Thr Gly
                325                 330                 335

Glu His Ala Lys Ala Ile Gly Asn Cys Pro Ile Trp Val Lys Thr Pro
```

```
            340                 345                 350

Leu Lys Leu Ala Asn Gly Thr Lys Tyr Arg Pro Pro Gly Gly Gly Trp
        355                 360                 365

Glu Gly Met Ile Ala Gly Trp His Gly Tyr Thr Ser His Gly Ala His
    370                 375                 380

Gly Val Ala Val Ala Ala Asp Leu Lys Ser Thr Gln Glu Ala Ile Asn
385                 390                 395                 400

Lys Ile Thr Lys Asn Leu Asn Ser Leu Ser Glu Leu Glu Val Lys Asn
                405                 410                 415

Leu Gln Arg Leu Ser Gly Ala Met Asp Glu Leu His Asn Glu Ile Leu
            420                 425                 430

Glu Leu Asp Glu Lys Val Asp Asp Leu Arg Ala Asp Thr Ile Ser Ser
        435                 440                 445

Gln Ile Glu Leu Ala Val Leu Leu Ser Asn Glu Gly Ile Ile Asn Ser
    450                 455                 460

Glu Asp Glu His Leu Leu Ala Leu Glu Arg Lys Leu Lys Lys Met Leu
465                 470                 475                 480

Gly Pro Ser Ala Val Glu Ile Gly Asn Gly Cys Phe Glu Thr Lys His
                485                 490                 495

Lys Cys Asn Gln Thr Cys Leu Asp Arg Ile Ala Ala Gly Thr Phe Asp
            500                 505                 510

Ala Gly Glu Phe Ser Leu Pro Thr Phe Asp Ser Leu Asn Ile Thr Ala
        515                 520                 525

Ala Ser Leu Asn Asp Asp Gly Leu Asp Asn Tyr Gln Ile Leu Ala Ile
    530                 535                 540

Tyr Ser Thr Val Ala Ser Ser Leu Val Leu Val Val Ser Leu Gly Ala
545                 550                 555                 560

Ile Ser Phe Trp Met Cys Ser Asn Gly Ser Leu Gln Cys Arg Ile Cys
                565                 570                 575

Ile


<210> SEQ ID NO 51
<211> LENGTH: 1731
<212> TYPE: DNA
<213> ORGANISM: Artificial sequence
<220> FEATURE:
<223> OTHER INFORMATION: Nucleotide sequence of PDISP/HA B
      Massachussetts (PrL-)

<400> SEQUENCE: 51

atggcgaaaa acgttgcgat ttcggcttta ttgttttctc ttcttgtgtt ggttccttct      60

cagatcttcg ccgatcgaat ctgcactggg ataacatctt caaactcacc tcatgtggtc     120

aaaacagcta ctcaagggga ggtcaatgtg actggtgtga taccactaac aacaacacca     180

acaaaatctt attttgcaaa tctcaaagga acaaagacca gagggaaact atgcccagac     240

tgtctcaact gtacagatct ggatgtggcc ctgggcaggc caatgtgtgt gggaactaca     300

ccttctgcga aagcttcaat acttcacgaa gtcagacctg ttacatccgg gtgcttccct     360

ataatgcacg acagaacaaa aatcaggcaa ctagccaatc ttctcagagg atatgaaaat     420

atcaggttat caacccaaaa cgttatcgat gcagaaaagg caccaggagg accctacaga     480

cttggaacct caggatcttg ccctaacgct accagtaaaa gcggattttt cgcaacaatg     540

gcttgggctg tcccaaagga caacaacaaa aatgcaacga acccattaac agtagaagta     600

ccatacattt gtgcagaagg ggaagaccaa attactgttt gggggttcca ttcagataac     660
```

```
aaaacccaaa tgaagaacct ctatggagac tcaaatcctc aaaagttcac ctcatctgct    720

aatggagtaa ccacacatta tgtttctcag attggcggct tcccagatca aacagaagac    780

ggaggactac cacaaagcgg cagaattgtc gttgattaca tgatgcaaaa acctgggaaa    840

acaggaacaa ttgtctatca aagaggtgtt ttgttgcctc aaaaggtgtg gtgcgcgagt    900

ggcaggagca aagtaataaa agggtccttg cctttaattg gtgaagcaga ttgccttcat    960

gaaaaatacg gtggattaaa caaaagcaag ccttactaca caggagaaca tgcaaaagcc   1020

ataggaaatt gcccaatatg ggtgaaaaca cctttgaagc ttgccaatgg aaccaaatat   1080

agacctcctg gtggaggatg ggaaggaatg attgcaggtt ggcacggata cacatctcac   1140

ggagcacatg gagtggcagt tgctgcagac cttaagagca cacaagaagc tataaacaag   1200

ataacaaaaa atctcaactc tttgagtgag ctagaagtaa agaatcttca aaggctaagt   1260

ggtgccatgg atgaactcca caacgaaata ctcgagctgg atgagaaagt ggatgacctc   1320

agagctgaca ctataagttc acaaatagaa cttgcagtct tgctttccaa cgaaggaata   1380

ataaacagtg aagacgagca tctattggca cttgagagaa aactaaagaa aatgctgggt   1440

ccctctgctg tagacatagg aaatggatgc ttcgaaacca aacacaaatg caaccagacc   1500

tgcttagaca ggatagctgc tggcaccttt aatgcaggag agttttctct ccccactttt   1560

gattcattga acattactgc tgcatcttta aatgatgatg gattggataa ccatactata   1620

ctgctctatt actcaactgc tgcttctagt ttggctgtaa cattgatgct agctattttt   1680

attgtttata tggtctccag agacaacgtt tcatgctcca tctgtctata a            1731
```

```
<210> SEQ ID NO 52
<211> LENGTH: 576
<212> TYPE: PRT
<213> ORGANISM: Artificial Sequence
<220> FEATURE:
<223> OTHER INFORMATION: Amino acid sequence of PDISP/HA B
      Massachussetts (PrL-)

<400> SEQUENCE: 52

Met Ala Lys Asn Val Ala Ile Phe Gly Leu Leu Phe Ser Leu Leu Val
1               5                   10                  15

Leu Val Pro Ser Gln Ile Phe Ala Asp Arg Ile Cys Thr Gly Ile Thr
            20                  25                  30

Ser Ser Asn Ser Pro His Val Val Lys Thr Ala Thr Gln Gly Glu Val
        35                  40                  45

Asn Val Thr Gly Val Ile Pro Leu Thr Thr Thr Pro Thr Lys Ser Tyr
    50                  55                  60

Phe Ala Asn Leu Lys Gly Thr Lys Thr Arg Gly Lys Leu Cys Pro Asp
65                  70                  75                  80

Cys Leu Asn Cys Thr Asp Leu Asp Val Ala Leu Gly Arg Pro Met Cys
                85                  90                  95

Val Gly Thr Thr Pro Ser Ala Lys Ala Ser Ile Leu His Glu Val Arg
            100                 105                 110

Pro Val Thr Ser Gly Cys Phe Pro Ile Met His Asp Arg Thr Lys Ile
        115                 120                 125

Arg Gln Leu Ala Asn Leu Leu Arg Gly Tyr Glu Asn Ile Arg Leu Ser
    130                 135                 140

Thr Gln Asn Val Ile Asp Ala Glu Lys Ala Pro Gly Gly Pro Tyr Arg
145                 150                 155                 160

Leu Gly Thr Ser Gly Ser Cys Pro Asn Ala Thr Ser Lys Ser Gly Phe
                165                 170                 175
```

```
Phe Ala Thr Met Ala Trp Ala Val Pro Lys Asp Asn Asn Lys Asn Ala
            180                 185                 190

Thr Asn Pro Leu Thr Val Glu Val Pro Tyr Ile Cys Ala Glu Gly Glu
        195                 200                 205

Asp Gln Ile Thr Val Trp Gly Phe His Ser Asp Asn Lys Thr Gln Met
    210                 215                 220

Lys Asn Leu Tyr Gly Asp Ser Asn Pro Gln Lys Phe Thr Ser Ser Ala
225                 230                 235                 240

Asn Gly Val Thr Thr His Tyr Val Ser Gln Ile Gly Gly Phe Pro Asp
                245                 250                 255

Gln Thr Glu Asp Gly Gly Leu Pro Gln Ser Gly Arg Ile Val Val Asp
            260                 265                 270

Tyr Met Met Gln Lys Pro Gly Lys Thr Gly Thr Ile Val Tyr Gln Arg
        275                 280                 285

Gly Val Leu Leu Pro Gln Lys Val Trp Cys Ala Ser Gly Arg Ser Lys
    290                 295                 300

Val Ile Lys Gly Ser Leu Pro Leu Ile Gly Glu Ala Asp Cys Leu His
305                 310                 315                 320

Glu Lys Tyr Gly Gly Leu Asn Lys Ser Lys Pro Tyr Tyr Thr Gly Glu
                325                 330                 335

His Ala Lys Ala Ile Gly Asn Cys Pro Ile Trp Val Lys Thr Pro Leu
            340                 345                 350

Lys Leu Ala Asn Gly Thr Lys Tyr Arg Pro Pro Gly Gly Gly Trp Glu
        355                 360                 365

Gly Met Ile Ala Gly Trp His Gly Tyr Thr Ser His Gly Ala His Gly
    370                 375                 380

Val Ala Val Ala Ala Asp Leu Lys Ser Thr Gln Glu Ala Ile Asn Lys
385                 390                 395                 400

Ile Thr Lys Asn Leu Asn Ser Leu Ser Glu Leu Glu Val Lys Asn Leu
                405                 410                 415

Gln Arg Leu Ser Gly Ala Met Asp Glu Leu His Asn Glu Ile Leu Glu
            420                 425                 430

Leu Asp Glu Lys Val Asp Asp Leu Arg Ala Asp Thr Ile Ser Ser Gln
        435                 440                 445

Ile Glu Leu Ala Val Leu Leu Ser Asn Glu Gly Ile Ile Asn Ser Glu
    450                 455                 460

Asp Glu His Leu Leu Ala Leu Glu Arg Lys Leu Lys Lys Met Leu Gly
465                 470                 475                 480

Pro Ser Ala Val Asp Ile Gly Asn Gly Cys Phe Glu Thr Lys His Lys
                485                 490                 495

Cys Asn Gln Thr Cys Leu Asp Arg Ile Ala Ala Gly Thr Phe Asn Ala
            500                 505                 510

Gly Glu Phe Ser Leu Pro Thr Phe Asp Ser Leu Asn Ile Thr Ala Ala
        515                 520                 525

Ser Leu Asn Asp Asp Gly Leu Asp Asn His Thr Ile Leu Leu Tyr Tyr
    530                 535                 540

Ser Thr Ala Ala Ser Ser Leu Ala Val Thr Leu Met Leu Ala Ile Phe
545                 550                 555                 560

Ile Val Tyr Met Val Ser Arg Asp Asn Val Ser Cys Ser Ile Cys Leu
                565                 570                 575
```

<210> SEQ ID NO 53
<211> LENGTH: 1731

<212> TYPE: DNA
<213> ORGANISM: Artificial Sequence
<220> FEATURE:
<223> OTHER INFORMATION: Nucleotide sequence of PDISP/HA B Massachussetts (PrL-)+H1 California TMCT

<400> SEQUENCE: 53

```
atggcgaaaa acgttgcgat tttcggctta ttgttttctc ttcttgtgtt ggttccttct     60
cagatcttcg ccgatcgaat ctgcactggg ataacatctt caaactcacc tcatgtggtc    120
aaaacagcta ctcaagggga ggtcaatgtg actggtgtga taccactaac aacaacacca    180
acaaaatctt attttgcaaa tctcaaagga acaaagacca gagggaaact atgcccagac    240
tgtctcaact gtacagatct ggatgtggcc ctgggcaggc caatgtgtgt gggaactaca    300
ccttctgcga aagcttcaat acttcacgaa gtcagacctg ttacatccgg gtgcttccct    360
ataatgcacg acagaacaaa aatcaggcaa ctagccaatc ttctcagagg atatgaaaat    420
atcaggttat caacccaaaa cgttatcgat gcagaaaagg caccaggagg accctacaga    480
cttggaacct caggatcttg ccctaacgct accagtaaaa gcggattttt cgcaacaatg    540
gcttgggctg tcccaaagga caacaacaaa aatgcaacga acccattaac agtagaagta    600
ccatacattt gtgcagaagg ggaagaccaa attactgttt gggggttcca ttcagataac    660
aaaacccaaa tgaagaacct ctatggagac tcaaatcctc aaaagttcac ctcatctgct    720
aatggagtaa ccacacatta tgtttctcag attggcggct tcccagatca aacagaagac    780
ggaggactac cacaaagcgg cagaattgtc gttgattaca tgatgcaaaa acctgggaaa    840
acaggaacaa ttgtctatca aagaggtgtt ttgttgcctc aaaaggtgtg gtgcgcgagt    900
ggcaggagca aagtaataaa agggtccttg cctttaattg gtgaagcaga ttgccttcat    960
gaaaaatacg gtggattaaa caaaagcaag ccttactaca caggagaaca tgcaaaagcc   1020
ataggaaatt gcccaatatg ggtgaaaaca ccttttgaagc ttgccaatgg aaccaaatat   1080
agacctcctg gtggaggatg ggaaggaatg attgcaggtt ggcacggata cacatctcac   1140
ggagcacatg gagtggcagt tgctgcagac cttaagagca cacaagaagc tataaacaag   1200
ataacaaaaa atctcaactc tttgagtgag ctagaagtaa agaatcttca aaggctaagt   1260
ggtgccatgg atgaactcca caacgaaata ctcgagctgg atgagaaagt ggatgacctc   1320
agagctgaca ctataagttc acaaatagaa cttgcagtct tgctttccaa cgaaggaata   1380
ataaacagtg aagacgagca tctattggca cttgagagaa aactaaagaa aatgctgggt   1440
ccctctgctg tagacatagg aaatggatgc ttcgaaacca aacacaaatg caaccagacc   1500
tgcttagaca ggatagctgc tggcaccttt aatgcaggag agttttctct ccccactttt   1560
gattcattga acattactgc tgcatcttta aatgatgatg gattggataa ctaccagatt   1620
ttggcgatct attcaactgt cgccagttca ttggtactgg tagtctccct gggggcaatc   1680
agtttctgga tgtgctctaa tgggtctcta cagtgtagaa tatgtattta a            1731
```

<210> SEQ ID NO 54
<211> LENGTH: 576
<212> TYPE: PRT
<213> ORGANISM: Artificial Sequence
<220> FEATURE:
<223> OTHER INFORMATION: Amino acid sequence of PDISP/HA B Massachussetts (PrL-)+H1 California TMCT

<400> SEQUENCE: 54

```
Met Ala Lys Asn Val Ala Ile Phe Gly Leu Leu Phe Ser Leu Leu Val
1               5                   10                  15
```

-continued

```
Leu Val Pro Ser Gln Ile Phe Ala Asp Arg Ile Cys Thr Gly Ile Thr
            20                  25                  30

Ser Ser Asn Ser Pro His Val Val Lys Thr Ala Thr Gln Gly Glu Val
        35                  40                  45

Asn Val Thr Gly Val Ile Pro Leu Thr Thr Thr Pro Thr Lys Ser Tyr
    50                  55                  60

Phe Ala Asn Leu Lys Gly Thr Lys Thr Arg Gly Lys Leu Cys Pro Asp
65                  70                  75                  80

Cys Leu Asn Cys Thr Asp Leu Asp Val Ala Leu Gly Arg Pro Met Cys
                85                  90                  95

Val Gly Thr Thr Pro Ser Ala Lys Ala Ser Ile Leu His Glu Val Arg
            100                 105                 110

Pro Val Thr Ser Gly Cys Phe Pro Ile Met His Asp Arg Thr Lys Ile
        115                 120                 125

Arg Gln Leu Ala Asn Leu Leu Arg Gly Tyr Glu Asn Ile Arg Leu Ser
    130                 135                 140

Thr Gln Asn Val Ile Asp Ala Glu Lys Ala Pro Gly Gly Pro Tyr Arg
145                 150                 155                 160

Leu Gly Thr Ser Gly Ser Cys Pro Asn Ala Thr Ser Lys Ser Gly Phe
                165                 170                 175

Phe Ala Thr Met Ala Trp Ala Val Pro Lys Asp Asn Asn Lys Asn Ala
            180                 185                 190

Thr Asn Pro Leu Thr Val Glu Val Pro Tyr Ile Cys Ala Glu Gly Glu
        195                 200                 205

Asp Gln Ile Thr Val Trp Gly Phe His Ser Asp Asn Lys Thr Gln Met
    210                 215                 220

Lys Asn Leu Tyr Gly Asp Ser Asn Pro Gln Lys Phe Thr Ser Ser Ala
225                 230                 235                 240

Asn Gly Val Thr Thr His Tyr Val Ser Gln Ile Gly Gly Phe Pro Asp
                245                 250                 255

Gln Thr Glu Asp Gly Gly Leu Pro Gln Ser Gly Arg Ile Val Val Asp
            260                 265                 270

Tyr Met Met Gln Lys Pro Gly Lys Thr Gly Thr Ile Val Tyr Gln Arg
        275                 280                 285

Gly Val Leu Leu Pro Gln Lys Val Trp Cys Ala Ser Gly Arg Ser Lys
    290                 295                 300

Val Ile Lys Gly Ser Leu Pro Leu Ile Gly Glu Ala Asp Cys Leu His
305                 310                 315                 320

Glu Lys Tyr Gly Gly Leu Asn Lys Ser Lys Pro Tyr Tyr Thr Gly Glu
                325                 330                 335

His Ala Lys Ala Ile Gly Asn Cys Pro Ile Trp Val Lys Thr Pro Leu
            340                 345                 350

Lys Leu Ala Asn Gly Thr Lys Tyr Arg Pro Pro Gly Gly Gly Trp Glu
        355                 360                 365

Gly Met Ile Ala Gly Trp His Gly Tyr Thr Ser His Gly Ala His Gly
    370                 375                 380

Val Ala Val Ala Ala Asp Leu Lys Ser Thr Gln Glu Ala Ile Asn Lys
385                 390                 395                 400

Ile Thr Lys Asn Leu Asn Ser Leu Ser Glu Leu Glu Val Lys Asn Leu
                405                 410                 415

Gln Arg Leu Ser Gly Ala Met Asp Glu Leu His Asn Glu Ile Leu Glu
            420                 425                 430
```

```
Leu Asp Glu Lys Val Asp Asp Leu Arg Ala Asp Thr Ile Ser Ser Gln
        435                 440                 445

Ile Glu Leu Ala Val Leu Leu Ser Asn Glu Gly Ile Ile Asn Ser Glu
    450                 455                 460

Asp Glu His Leu Leu Ala Leu Glu Arg Lys Leu Lys Lys Met Leu Gly
465                 470                 475                 480

Pro Ser Ala Val Asp Ile Gly Asn Gly Cys Phe Glu Thr Lys His Lys
                485                 490                 495

Cys Asn Gln Thr Cys Leu Asp Arg Ile Ala Ala Gly Thr Phe Asn Ala
            500                 505                 510

Gly Glu Phe Ser Leu Pro Thr Phe Asp Ser Leu Asn Ile Thr Ala Ala
        515                 520                 525

Ser Leu Asn Asp Asp Gly Leu Asp Asn Tyr Gln Ile Leu Ala Ile Tyr
    530                 535                 540

Ser Thr Val Ala Ser Ser Leu Val Leu Val Val Ser Leu Gly Ala Ile
545                 550                 555                 560

Ser Phe Trp Met Cys Ser Asn Gly Ser Leu Gln Cys Arg Ile Cys Ile
                565                 570                 575


<210> SEQ ID NO 55
<211> LENGTH: 1704
<212> TYPE: DNA
<213> ORGANISM: Artificial Sequence
<220> FEATURE:
<223> OTHER INFORMATION: Nucleotide sequence of HA B Wisconsin (PrL-)

<400> SEQUENCE: 55

atgaaggcaa taattgtact actcatggta gtaacatcca atgcagatcg aatctgcact      60

gggataacat cttcaaactc acctcatgtg gtcaaaacag ctactcaagg ggaggtcaat     120

gtgactggcg tgataccact gacaacaaca ccaacaaaat cttattttgc aaatctcaaa     180

ggaacaagga ccagagggaa actatgcccg gactgtctca actgtacaga tctggatgtg     240

gccttgggca ggccaatgtg tgtggggacc acaccttctg ctaaagcttc aatactccac     300

gaggtcagac ctgttacatc cgggtgcttt cctataatgc acgacagaac aaaaatcagg     360

caactaccca atcttctcag aggatatgaa aatatcaggt tatcaaccca aaacgttatc     420

gatgcagaaa aagcaccagg aggaccctac agacttggaa cctcaggatc ttgccctaac     480

gctaccagta aaatcggatt ttttgcaaca atggcttggg ctgtcccaaa ggacaactac     540

aaaaatgcaa cgaacccact aacagtagaa gtaccataca tttgtacaga aggggaagac     600

caaattactg tttgggggtt ccattcagat aacaaaaccc aaatgaagag cctctatgga     660

gactcaaatc ctcaaaagtt cacctcatct gctaatggag taaccacaca ttatgtttct     720

cagattggcg acttcccaga tcaaacagaa gacggaggac taccacaaag cggcagaatt     780

gttgttgatt acatgatgca aaaacctggg aaaacaggaa caattgtcta tcaaagaggt     840

gttttgttgc ctcaaaaggt gtggtgcgcg agtggcagga gcaaagtaat aaaagggtca     900

ttgcctttaa ttggtgaagc agattgcctt catgaaaaat acggtggatt aaacaaaagc     960

aagccttact acacaggaga acatgcaaaa gccataggaa attgcccaat atgggtaaaa    1020

acacctttga agcttgccaa tggaaccaaa tatagacctc ctggtggagg atgggaagga    1080

atgattgcag gttggcacgg atacacatct cacggagcac atggagtggc agtggcggca    1140

gaccttaaga gtacacaaga agctataaat aagataacaa aaaatctcaa ttctttgagt    1200

gagctagaag taaagaacct tcaaagacta agtggtgcca tggatgaact ccacaacgaa    1260
```

-continued

```
atactcgagc tggatgagaa agtggatgat ctcagagctg acactataag ctcacaaata   1320

gaacttgcag tcttgctttc caacgaagga ataataaaca gtgaagacga gcatctattg   1380

gcacttgaga gaaaactaaa gaaaatgctg ggtccctctg ctgtagacat aggaaacgga   1440

tgcttcgaaa ccaaacacaa atgcaaccag acctgcttag acaggatagc tgctggcacc   1500

tttaatgcag gagaattttc tctccccact tttgattcat tgaacattac tgctgcatct   1560

ttaaatgatg atggattgga taaccatact atactgctct attactcaac tgctgcttct   1620

agtttggctg taacattaat gctagctatt tttattgttt atatggtctc cagagacaac   1680

gtttcatgct ccatctgtct ataa                                          1704
```

<210> SEQ ID NO 56
<211> LENGTH: 567
<212> TYPE: PRT
<213> ORGANISM: Artificial Sequence
<220> FEATURE:
<223> OTHER INFORMATION: Amino acid sequence of HA B Wisconsin (PrL-)

<400> SEQUENCE: 56

```
Met Lys Ala Ile Ile Val Leu Leu Met Val Val Thr Ser Asn Ala Asp
1               5                   10                  15

Arg Ile Cys Thr Gly Ile Thr Ser Ser Asn Ser Pro His Val Val Lys
            20                  25                  30

Thr Ala Thr Gln Gly Glu Val Asn Val Thr Gly Val Ile Pro Leu Thr
        35                  40                  45

Thr Thr Pro Thr Lys Ser Tyr Phe Ala Asn Leu Lys Gly Thr Arg Thr
    50                  55                  60

Arg Gly Lys Leu Cys Pro Asp Cys Leu Asn Cys Thr Asp Leu Asp Val
65                  70                  75                  80

Ala Leu Gly Arg Pro Met Cys Val Gly Thr Thr Pro Ser Ala Lys Ala
                85                  90                  95

Ser Ile Leu His Glu Val Arg Pro Val Thr Ser Gly Cys Phe Pro Ile
            100                 105                 110

Met His Asp Arg Thr Lys Ile Arg Gln Leu Pro Asn Leu Leu Arg Gly
        115                 120                 125

Tyr Glu Asn Ile Arg Leu Ser Thr Gln Asn Val Ile Asp Ala Glu Lys
    130                 135                 140

Ala Pro Gly Gly Pro Tyr Arg Leu Gly Thr Ser Gly Ser Cys Pro Asn
145                 150                 155                 160

Ala Thr Ser Lys Ile Gly Phe Phe Ala Thr Met Ala Trp Ala Val Pro
                165                 170                 175

Lys Asp Asn Tyr Lys Asn Ala Thr Asn Pro Leu Thr Val Glu Val Pro
            180                 185                 190

Tyr Ile Cys Thr Glu Gly Glu Asp Gln Ile Thr Val Trp Gly Phe His
        195                 200                 205

Ser Asp Asn Lys Thr Gln Met Lys Ser Leu Tyr Gly Asp Ser Asn Pro
    210                 215                 220

Gln Lys Phe Thr Ser Ser Ala Asn Gly Val Thr Thr His Tyr Val Ser
225                 230                 235                 240

Gln Ile Gly Asp Phe Pro Asp Gln Thr Glu Asp Gly Gly Leu Pro Gln
                245                 250                 255

Ser Gly Arg Ile Val Val Asp Tyr Met Met Gln Lys Pro Gly Lys Thr
            260                 265                 270

Gly Thr Ile Val Tyr Gln Arg Gly Val Leu Leu Pro Gln Lys Val Trp
        275                 280                 285
```

```
Cys Ala Ser Gly Arg Ser Lys Val Ile Lys Gly Ser Leu Pro Leu Ile
    290                 295                 300

Gly Glu Ala Asp Cys Leu His Glu Lys Tyr Gly Gly Leu Asn Lys Ser
305                 310                 315                 320

Lys Pro Tyr Tyr Thr Gly Glu His Ala Lys Ala Ile Gly Asn Cys Pro
                325                 330                 335

Ile Trp Val Lys Thr Pro Leu Lys Leu Ala Asn Gly Thr Lys Tyr Arg
            340                 345                 350

Pro Pro Gly Gly Gly Trp Glu Gly Met Ile Ala Gly Trp His Gly Tyr
        355                 360                 365

Thr Ser His Gly Ala His Gly Val Ala Val Ala Ala Asp Leu Lys Ser
    370                 375                 380

Thr Gln Glu Ala Ile Asn Lys Ile Thr Lys Asn Leu Asn Ser Leu Ser
385                 390                 395                 400

Glu Leu Glu Val Lys Asn Leu Gln Arg Leu Ser Gly Ala Met Asp Glu
                405                 410                 415

Leu His Asn Glu Ile Leu Glu Leu Asp Glu Lys Val Asp Asp Leu Arg
            420                 425                 430

Ala Asp Thr Ile Ser Ser Gln Ile Glu Leu Ala Val Leu Leu Ser Asn
        435                 440                 445

Glu Gly Ile Ile Asn Ser Glu Asp Glu His Leu Leu Ala Leu Glu Arg
    450                 455                 460

Lys Leu Lys Lys Met Leu Gly Pro Ser Ala Val Asp Ile Gly Asn Gly
465                 470                 475                 480

Cys Phe Glu Thr Lys His Lys Cys Asn Gln Thr Cys Leu Asp Arg Ile
                485                 490                 495

Ala Ala Gly Thr Phe Asn Ala Gly Glu Phe Ser Leu Pro Thr Phe Asp
            500                 505                 510

Ser Leu Asn Ile Thr Ala Ala Ser Leu Asn Asp Asp Gly Leu Asp Asn
        515                 520                 525

His Thr Ile Leu Leu Tyr Tyr Ser Thr Ala Ala Ser Ser Leu Ala Val
    530                 535                 540

Thr Leu Met Leu Ala Ile Phe Ile Val Tyr Met Val Ser Arg Asp Asn
545                 550                 555                 560

Val Ser Cys Ser Ile Cys Leu
                565


<210> SEQ ID NO 57
<211> LENGTH: 1704
<212> TYPE: DNA
<213> ORGANISM: Artificial Sequence
<220> FEATURE:
<223> OTHER INFORMATION: Nucleotide sequence of HA B Wisconsin (PrL-)+H1
      California TMCT

<400> SEQUENCE: 57

atgaaggcaa taattgtact actcatggta gtaacatcca atgcagatcg aatctgcact      60

gggataacat cttcaaactc acctcatgtg gtcaaaacag ctactcaagg ggaggtcaat     120

gtgactggcg tgataccact gacaacaaca ccaacaaaat cttattttgc aaatctcaaa     180

ggaacaagga ccagagggaa actatgcccg gactgtctca actgtacaga tctggatgtg     240

gccttgggca ggccaatgtg tgtggggacc acaccttctg ctaaagcttc aatactccac     300

gaggtcagac ctgttacatc cgggtgcttt cctataatgc acgacagaac aaaaatcagg     360

caactaccca atcttctcag aggatatgaa aatatcaggt tatcaaccca aaacgttatc     420
```

```
gatgcagaaa aagcaccagg aggaccctac agacttggaa cctcaggatc ttgccctaac    480

gctaccagta aaatcggatt ttttgcaaca atggcttggg ctgtcccaaa ggacaactac    540

aaaaatgcaa cgaacccact aacagtagaa gtaccataca tttgtacaga aggggaagac    600

caaattactg tttgggggtt ccattcagat aacaaaaccc aaatgaagag cctctatgga    660

gactcaaatc ctcaaaagtt cacctcatct gctaatggag taaccacaca ttatgtttct    720

cagattggcg acttcccaga tcaaacagaa gacggaggac taccacaaag cggcagaatt    780

gttgttgatt acatgatgca aaaacctggg aaaacaggaa caattgtcta tcaaagaggt    840

gttttgttgc ctcaaaaggt gtggtgcgcg agtggcagga gcaaagtaat aaaagggtca    900

ttgcctttaa ttggtgaagc agattgcctt catgaaaaat acggtggatt aaacaaaagc    960

aagccttact acacaggaga acatgcaaaa gccataggaa attgcccaat atgggtaaaa   1020

acacctttga agcttgccaa tggaaccaaa tatagacctc ctggtggagg atgggaagga   1080

atgattgcag gttggcacgg atacacatct cacggagcac atggagtggc agtggcggca   1140

gaccttaaga gtacacaaga agctataaat aagataacaa aaatctcaa ttctttgagt   1200

gagctagaag taaagaacct tcaaagacta agtggtgcca tggatgaact ccacaacgaa   1260

atactcgagc tggatgagaa agtggatgat ctcagagctg acactataag ctcacaaata   1320

gaacttgcag tcttgctttc caacgaagga ataataaaca gtgaagacga gcatctattg   1380

gcacttgaga gaaaactaaa gaaaatgctg ggtccctctg ctgtagacat aggaaacgga   1440

tgcttcgaaa ccaaacacaa atgcaaccag acctgcttag acaggatagc tgctggcacc   1500

tttaatgcag gagaattttc tctccccact tttgattcat tgaacattac tgctgcatct   1560

ttaaatgatg atggattgga taactaccag attttggcga tctattcaac tgtcgccagt   1620

tcattggtac tggtagtctc cctgggggca atcagtttct ggatgtgctc taatgggtct   1680

ctacagtgta gaatatgtat ttaa                                          1704
```

<210> SEQ ID NO 58
<211> LENGTH: 567
<212> TYPE: PRT
<213> ORGANISM: Artificial Sequence
<220> FEATURE:
<223> OTHER INFORMATION: Amino acid sequence of HA B Wisconsin (PrL-)+H1 California TMC

<400> SEQUENCE: 58

```
Met Lys Ala Ile Ile Val Leu Leu Met Val Val Thr Ser Asn Ala Asp
1               5                   10                  15

Arg Ile Cys Thr Gly Ile Thr Ser Ser Asn Ser Pro His Val Val Lys
            20                  25                  30

Thr Ala Thr Gln Gly Glu Val Asn Val Thr Gly Val Ile Pro Leu Thr
        35                  40                  45

Thr Thr Pro Thr Lys Ser Tyr Phe Ala Asn Leu Lys Gly Thr Arg Thr
    50                  55                  60

Arg Gly Lys Leu Cys Pro Asp Cys Leu Asn Cys Thr Asp Leu Asp Val
65                  70                  75                  80

Ala Leu Gly Arg Pro Met Cys Val Gly Thr Thr Pro Ser Ala Lys Ala
                85                  90                  95

Ser Ile Leu His Glu Val Arg Pro Val Thr Ser Gly Cys Phe Pro Ile
            100                 105                 110

Met His Asp Arg Thr Lys Ile Arg Gln Leu Pro Asn Leu Leu Arg Gly
        115                 120                 125
```

```
Tyr Glu Asn Ile Arg Leu Ser Thr Gln Asn Val Ile Asp Ala Glu Lys
    130                 135                 140

Ala Pro Gly Gly Pro Tyr Arg Leu Gly Thr Ser Gly Ser Cys Pro Asn
145                 150                 155                 160

Ala Thr Ser Lys Ile Gly Phe Phe Ala Thr Met Ala Trp Ala Val Pro
                165                 170                 175

Lys Asp Asn Tyr Lys Asn Ala Thr Asn Pro Leu Thr Val Glu Val Pro
            180                 185                 190

Tyr Ile Cys Thr Glu Gly Glu Asp Gln Ile Thr Val Trp Gly Phe His
        195                 200                 205

Ser Asp Asn Lys Thr Gln Met Lys Ser Leu Tyr Gly Asp Ser Asn Pro
    210                 215                 220

Gln Lys Phe Thr Ser Ser Ala Asn Gly Val Thr Thr His Tyr Val Ser
225                 230                 235                 240

Gln Ile Gly Asp Phe Pro Asp Gln Thr Glu Asp Gly Gly Leu Pro Gln
                245                 250                 255

Ser Gly Arg Ile Val Val Asp Tyr Met Met Gln Lys Pro Gly Lys Thr
            260                 265                 270

Gly Thr Ile Val Tyr Gln Arg Gly Val Leu Leu Pro Gln Lys Val Trp
        275                 280                 285

Cys Ala Ser Gly Arg Ser Lys Val Ile Lys Gly Ser Leu Pro Leu Ile
    290                 295                 300

Gly Glu Ala Asp Cys Leu His Glu Lys Tyr Gly Gly Leu Asn Lys Ser
305                 310                 315                 320

Lys Pro Tyr Tyr Thr Gly Glu His Ala Lys Ala Ile Gly Asn Cys Pro
                325                 330                 335

Ile Trp Val Lys Thr Pro Leu Lys Leu Ala Asn Gly Thr Lys Tyr Arg
            340                 345                 350

Pro Pro Gly Gly Gly Trp Glu Gly Met Ile Ala Gly Trp His Gly Tyr
        355                 360                 365

Thr Ser His Gly Ala His Gly Val Ala Val Ala Ala Asp Leu Lys Ser
    370                 375                 380

Thr Gln Glu Ala Ile Asn Lys Ile Thr Lys Asn Leu Asn Ser Leu Ser
385                 390                 395                 400

Glu Leu Glu Val Lys Asn Leu Gln Arg Leu Ser Gly Ala Met Asp Glu
                405                 410                 415

Leu His Asn Glu Ile Leu Glu Leu Asp Glu Lys Val Asp Asp Leu Arg
            420                 425                 430

Ala Asp Thr Ile Ser Ser Gln Ile Glu Leu Ala Val Leu Leu Ser Asn
        435                 440                 445

Glu Gly Ile Ile Asn Ser Glu Asp Glu His Leu Leu Ala Leu Glu Arg
    450                 455                 460

Lys Leu Lys Lys Met Leu Gly Pro Ser Ala Val Asp Ile Gly Asn Gly
465                 470                 475                 480

Cys Phe Glu Thr Lys His Lys Cys Asn Gln Thr Cys Leu Asp Arg Ile
                485                 490                 495

Ala Ala Gly Thr Phe Asn Ala Gly Glu Phe Ser Leu Pro Thr Phe Asp
            500                 505                 510

Ser Leu Asn Ile Thr Ala Ala Ser Leu Asn Asp Asp Gly Leu Asp Asn
        515                 520                 525

Tyr Gln Ile Leu Ala Ile Tyr Ser Thr Val Ala Ser Ser Leu Val Leu
    530                 535                 540
```

-continued

```
Val Val Ser Leu Gly Ala Ile Ser Phe Trp Met Cys Ser Asn Gly Ser
545                 550                 555                 560

Leu Gln Cys Arg Ile Cys Ile
                565


<210> SEQ ID NO 59
<211> LENGTH: 1413
<212> TYPE: DNA
<213> ORGANISM: Artificial Sequence
<220> FEATURE:
<223> OTHER INFORMATION: Nucleotide sequence of HC Rituxan

<400> SEQUENCE: 59

atgggttgga gcctcatctt gctcttcctt gtcgctgttg ctacgcgtgt cctgtcccag     60

gtacaactgc agcagcctgg ggctgagctg gtgaagcctg gggcctcagt gaagatgtcc    120

tgcaaggctt ctggctacac atttaccagt tacaatatgc actgggtaaa acagacacct    180

ggtcggggcc tggaatggat tggagctatt tatcccggaa atggtgatac ttcctacaat    240

cagaagttca aaggcaaggc cacattgact gcagacaaat cctccagcac agcctacatg    300

cagctcagca gcctgacatc tgaggactct gcggtctatt actgtgcaag atcgacttac    360

tacggcggtg actggtactt caatgtctgg ggcgcaggga ccacggtcac cgtctctgca    420

gctagcacca agggcccatc ggtcttcccc ctggcaccct cctccaagag cacctctggg    480

ggcacagcgg ccctgggctg cctggtcaag gactacttcc ccgaaccggt gacggtgtcg    540

tggaactcag gcgccctgac cagcggcgtg cacaccttcc cggctgtcct acagtcctca    600

ggactctact ccctcagcag cgtggtgacc gtgccctcca gcagcttggg cacccagacc    660

tacatctgca acgtgaatca caagcccagc aacaccaagg tggacaagaa agttgagccc    720

aaatcttgtg acaaaactca cacatgccca ccgtgcccag cacctgaact cctgggggga    780

ccgtcagtct tcctcttccc cccaaaaccc aaggacaccc tcatgatctc ccggacccct    840

gaggtcacat gcgtggtggt ggacgtgagc cacgaagacc ctgaggtcaa gttcaactgg    900

tacgtggacg gcgtggaggt gcataatgcc aagacaaagc cgcgggagga gcagtacaac    960

agcacgtacc gtgtggtcag cgtcctcacc gtcctgcacc aggactggct gaatggcaag   1020

gagtacaagt gcaaggtctc caacaaagcc ctcccagccc ccatcgagaa aaccatctcc   1080

aaagccaaag ggcagcctag ggaaccacaa gtgtacactc ttccaccatc tagggatgag   1140

cttactaaga accaagtttc tcttacttgt cttgtgaagg gattttatcc atctgacatc   1200

gccgtggaat gggaatccaa cggacaacca gagaacaatt acaagactac tccaccagtt   1260

cttgattctg atggatcctt ctttctttat tccaagctta ctgttgataa gtccagatgg   1320

cagcaaggaa atgtgttctc ttgttctgtt atgcacgaag ctcttcataa tcattatact   1380

caaaagtccc tttctctttc tcctggaaag tga                                1413


<210> SEQ ID NO 60
<211> LENGTH: 470
<212> TYPE: PRT
<213> ORGANISM: Artificial Sequence
<220> FEATURE:
<223> OTHER INFORMATION: Amino acid sequence of HC Rituxan

<400> SEQUENCE: 60

Met Gly Trp Ser Leu Ile Leu Leu Phe Leu Val Ala Val Ala Thr Arg
1               5                   10                  15

Val Leu Ser Gln Val Gln Leu Gln Gln Pro Gly Ala Glu Leu Val Lys
            20                  25                  30
```

-continued

```
Pro Gly Ala Ser Val Lys Met Ser Cys Lys Ala Ser Gly Tyr Thr Phe
        35                  40                  45

Thr Ser Tyr Asn Met His Trp Val Lys Gln Thr Pro Gly Arg Gly Leu
    50                  55                  60

Glu Trp Ile Gly Ala Ile Tyr Pro Gly Asn Gly Asp Thr Ser Tyr Asn
65                  70                  75                  80

Gln Lys Phe Lys Gly Lys Ala Thr Leu Thr Ala Asp Lys Ser Ser Ser
                85                  90                  95

Thr Ala Tyr Met Gln Leu Ser Ser Leu Thr Ser Glu Asp Ser Ala Val
            100                 105                 110

Tyr Tyr Cys Ala Arg Ser Thr Tyr Tyr Gly Gly Asp Trp Tyr Phe Asn
        115                 120                 125

Val Trp Gly Ala Gly Thr Thr Val Thr Val Ser Ala Ala Ser Thr Lys
    130                 135                 140

Gly Pro Ser Val Phe Pro Leu Ala Pro Ser Ser Lys Ser Thr Ser Gly
145                 150                 155                 160

Gly Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
        195                 200                 205

Val Thr Val Pro Ser Ser Ser Leu Gly Thr Gln Thr Tyr Ile Cys Asn
    210                 215                 220

Val Asn His Lys Pro Ser Asn Thr Lys Val Asp Lys Lys Val Glu Pro
225                 230                 235                 240

Lys Ser Cys Asp Lys Thr His Thr Cys Pro Pro Cys Pro Ala Pro Glu
                245                 250                 255

Leu Leu Gly Gly Pro Ser Val Phe Leu Phe Pro Pro Lys Pro Lys Asp
            260                 265                 270

Thr Leu Met Ile Ser Arg Thr Pro Glu Val Thr Cys Val Val Val Asp
        275                 280                 285

Val Ser His Glu Asp Pro Glu Val Lys Phe Asn Trp Tyr Val Asp Gly
    290                 295                 300

Val Glu Val His Asn Ala Lys Thr Lys Pro Arg Glu Glu Gln Tyr Asn
305                 310                 315                 320

Ser Thr Tyr Arg Val Val Ser Val Leu Thr Val Leu His Gln Asp Trp
                325                 330                 335

Leu Asn Gly Lys Glu Tyr Lys Cys Lys Val Ser Asn Lys Ala Leu Pro
            340                 345                 350

Ala Pro Ile Glu Lys Thr Ile Ser Lys Ala Lys Gly Gln Pro Arg Glu
        355                 360                 365

Pro Gln Val Tyr Thr Leu Pro Pro Ser Arg Asp Glu Leu Thr Lys Asn
    370                 375                 380

Gln Val Ser Leu Thr Cys Leu Val Lys Gly Phe Tyr Pro Ser Asp Ile
385                 390                 395                 400

Ala Val Glu Trp Glu Ser Asn Gly Gln Pro Glu Asn Asn Tyr Lys Thr
                405                 410                 415

Thr Pro Pro Val Leu Asp Ser Asp Gly Ser Phe Phe Leu Tyr Ser Lys
            420                 425                 430

Leu Thr Val Asp Lys Ser Arg Trp Gln Gln Gly Asn Val Phe Ser Cys
        435                 440                 445
```

-continued

Ser Val Met His Glu Ala Leu His Asn His Tyr Thr Gln Lys Ser Leu
    450                 455                 460

Ser Leu Ser Pro Gly Lys
465                 470

<210> SEQ ID NO 61
<211> LENGTH: 1428
<212> TYPE: DNA
<213> ORGANISM: Artificial Sequence
<220> FEATURE:
<223> OTHER INFORMATION: Nucleotide sequence of PDISP/HC Rituxan

<400> SEQUENCE: 61
atggcgaaaa acgttgcgat tttcggctta ttgttttctc ttcttgtgtt ggttccttct 60
cagatcttcg cccaggtaca actgcagcag cctggggctg agctggtgaa gcctggggcc 120
tcagtgaaga tgtcctgcaa ggcttctggc tacacattta ccagttacaa tatgcactgg 180
gtaaaacaga cacctggtcg gggcctggaa tggattggag ctatttatcc cggaaatggt 240
gatacttcct acaatcagaa gttcaaaggc aaggccacat tgactgcaga caaatcctcc 300
agcacagcct acatgcagct cagcagcctg acatctgagg actctgcggt ctattactgt 360
gcaagatcga cttactacgg cggtgactgg tacttcaatg tctggggcgc agggaccacg 420
gtcaccgtct ctgcagctag caccaagggc ccatcggtct tccccctggc accctcctcc 480
aagagcacct ctgggggcac agcggccctg ggctgcctgg tcaaggacta cttccccgaa 540
ccggtgacgg tgtcgtggaa ctcaggcgcc ctgaccagcg gcgtgcacac cttcccggct 600
gtcctacagt cctcaggact ctactccctc agcagcgtgg tgaccgtgcc ctccagcagc 660
ttgggcaccc agacctacat ctgcaacgtg aatcacaagc ccagcaacac caaggtggac 720
aagaaagttg agcccaaatc ttgtgacaaa actcacacat gcccaccgtg cccagcacct 780
gaactcctgg ggggaccgtc agtcttcctc ttccccccaa aacccaagga caccctcatg 840
atctcccgga cccctgaggt cacatgcgtg gtggtggacg tgagccacga agaccctgag 900
gtcaagttca actggtacgt ggacggcgtg gaggtgcata atgccaagac aaagccgcgg 960
gaggagcagt acaacagcac gtaccgtgtg gtcagcgtcc tcaccgtcct gcaccaggac 1020
tggctgaatg gcaaggagta caagtgcaag gtctccaaca aagccctccc agcccccatc 1080
gagaaaacca tctccaaagc caaagggcag cctagggaac cacaagtgta cactcttcca 1140
ccatctaggg atgagcttac taagaaccaa gtttctctta cttgtcttgt gaagggattt 1200
tatccatctg acatcgccgt ggaatgggaa tccaacggac aaccagagaa caattacaag 1260
actactccac cagttcttga ttctgatgga tccttctttc tttattccaa gcttactgtt 1320
gataagtcca gatggcagca aggaaatgtg ttctcttgtt ctgttatgca cgaagctctt 1380
cataatcatt atactcaaaa gtccctttct ctttctcctg gaaagtga 1428

<210> SEQ ID NO 62
<211> LENGTH: 475
<212> TYPE: PRT
<213> ORGANISM: Artificial Sequence
<220> FEATURE:
<223> OTHER INFORMATION: Amino acid sequence of PDISP/HC Rituxan

<400> SEQUENCE: 62

Met Ala Lys Asn Val Ala Ile Phe Gly Leu Leu Phe Ser Leu Leu Val
1               5                   10                  15

Leu Val Pro Ser Gln Ile Phe Ala Gln Val Gln Leu Gln Gln Pro Gly
            20                  25                  30

```
Ala Glu Leu Val Lys Pro Gly Ala Ser Val Lys Met Ser Cys Lys Ala
        35                  40                  45

Ser Gly Tyr Thr Phe Thr Ser Tyr Asn Met His Trp Val Lys Gln Thr
    50                  55                  60

Pro Gly Arg Gly Leu Glu Trp Ile Gly Ala Ile Tyr Pro Gly Asn Gly
65                  70                  75                  80

Asp Thr Ser Tyr Asn Gln Lys Phe Lys Gly Lys Ala Thr Leu Thr Ala
                85                  90                  95

Asp Lys Ser Ser Ser Thr Ala Tyr Met Gln Leu Ser Ser Leu Thr Ser
            100                 105                 110

Glu Asp Ser Ala Val Tyr Tyr Cys Ala Arg Ser Thr Tyr Tyr Gly Gly
        115                 120                 125

Asp Trp Tyr Phe Asn Val Trp Gly Ala Gly Thr Thr Val Thr Val Ser
    130                 135                 140

Ala Ala Ser Thr Lys Gly Pro Ser Val Phe Pro Leu Ala Pro Ser Ser
145                 150                 155                 160

Lys Ser Thr Ser Gly Gly Thr Ala Ala Leu Gly Cys Leu Val Lys Asp
                165                 170                 175

Tyr Phe Pro Glu Pro Val Thr Val Ser Trp Asn Ser Gly Ala Leu Thr
            180                 185                 190

Ser Gly Val His Thr Phe Pro Ala Val Leu Gln Ser Ser Gly Leu Tyr
        195                 200                 205

Ser Leu Ser Ser Val Val Thr Val Pro Ser Ser Ser Leu Gly Thr Gln
    210                 215                 220

Thr Tyr Ile Cys Asn Val Asn His Lys Pro Ser Asn Thr Lys Val Asp
225                 230                 235                 240

Lys Lys Val Glu Pro Lys Ser Cys Asp Lys Thr His Thr Cys Pro Pro
                245                 250                 255

Cys Pro Ala Pro Glu Leu Leu Gly Gly Pro Ser Val Phe Leu Phe Pro
            260                 265                 270

Pro Lys Pro Lys Asp Thr Leu Met Ile Ser Arg Thr Pro Glu Val Thr
        275                 280                 285

Cys Val Val Val Asp Val Ser His Glu Asp Pro Glu Val Lys Phe Asn
    290                 295                 300

Trp Tyr Val Asp Gly Val Glu Val His Asn Ala Lys Thr Lys Pro Arg
305                 310                 315                 320

Glu Glu Gln Tyr Asn Ser Thr Tyr Arg Val Val Ser Val Leu Thr Val
                325                 330                 335

Leu His Gln Asp Trp Leu Asn Gly Lys Glu Tyr Lys Cys Lys Val Ser
            340                 345                 350

Asn Lys Ala Leu Pro Ala Pro Ile Glu Lys Thr Ile Ser Lys Ala Lys
        355                 360                 365

Gly Gln Pro Arg Glu Pro Gln Val Tyr Thr Leu Pro Pro Ser Arg Asp
    370                 375                 380

Glu Leu Thr Lys Asn Gln Val Ser Leu Thr Cys Leu Val Lys Gly Phe
385                 390                 395                 400

Tyr Pro Ser Asp Ile Ala Val Glu Trp Glu Ser Asn Gly Gln Pro Glu
                405                 410                 415

Asn Asn Tyr Lys Thr Thr Pro Pro Val Leu Asp Ser Asp Gly Ser Phe
            420                 425                 430

Phe Leu Tyr Ser Lys Leu Thr Val Asp Lys Ser Arg Trp Gln Gln Gly
        435                 440                 445
```

```
Asn Val Phe Ser Cys Ser Val Met His Glu Ala Leu His Asn His Tyr
    450                 455                 460

Thr Gln Lys Ser Leu Ser Leu Ser Pro Gly Lys
465                 470                 475
```

<210> SEQ ID NO 63
<211> LENGTH: 708
<212> TYPE: DNA
<213> ORGANISM: Artificial Sequence
<220> FEATURE:
<223> OTHER INFORMATION: Nucleotide sequence of LC Rituxan

<400> SEQUENCE: 63

```
atggattttc aggtgcagat tatcagcttc ctgctaatca gtgcttcagt cataatgtcc     60

agaggacaaa ttgttctctc ccagtctcca gcaatcctgt ctgcatctcc aggggagaag    120

gtcacaatga cttgcagggc cagctcaagt gtaagttaca tccactggtt ccagcagaag    180

ccaggatcct cccccaaacc ctggatttat gccacatcca acctggcttc tggagtccct    240

gttcgcttca gtggcagtgg gtctgggact tcttactctc tcacaatcag cagagtggag    300

gctgaagatg ctgccactta ttactgccag cagtggacta gtaacccacc cacgttcgga    360

ggggggacca agctggaaat caaacgtacg gtggctgcac catctgtctt catcttcccg    420

ccatctgatg agcagttgaa atctggaact gcctctgttg tgtgcctgct gaataacttc    480

tatcccagag aggccaaagt acagtggaag gtggataacg ccctccaatc gggtaactcc    540

caggagagtg tcacagagca ggacagcaag gacagcacct acagcctcag cagcaccctg    600

acgctgagca aagcagacta cgagaaacac aaagtctacg cctgcgaagt cacccatcag    660

ggcctgagct cgcccgtcac aaagagcttc aacaggggag agtgttga                 708
```

<210> SEQ ID NO 64
<211> LENGTH: 235
<212> TYPE: PRT
<213> ORGANISM: Artificial Sequence
<220> FEATURE:
<223> OTHER INFORMATION: Amino acid sequence of LC Rituxan

<400> SEQUENCE: 64

```
Met Asp Phe Gln Val Gln Ile Ile Ser Phe Leu Leu Ile Ser Ala Ser
1               5                   10                  15

Val Ile Met Ser Arg Gly Gln Ile Val Leu Ser Gln Ser Pro Ala Ile
            20                  25                  30

Leu Ser Ala Ser Pro Gly Glu Lys Val Thr Met Thr Cys Arg Ala Ser
        35                  40                  45

Ser Ser Val Ser Tyr Ile His Trp Phe Gln Gln Lys Pro Gly Ser Ser
    50                  55                  60

Pro Lys Pro Trp Ile Tyr Ala Thr Ser Asn Leu Ala Ser Gly Val Pro
65                  70                  75                  80

Val Arg Phe Ser Gly Ser Gly Ser Gly Thr Ser Tyr Ser Leu Thr Ile
                85                  90                  95

Ser Arg Val Glu Ala Glu Asp Ala Ala Thr Tyr Tyr Cys Gln Gln Trp
            100                 105                 110

Thr Ser Asn Pro Pro Thr Phe Gly Gly Gly Thr Lys Leu Glu Ile Lys
        115                 120                 125

Arg Thr Val Ala Ala Pro Ser Val Phe Ile Phe Pro Pro Ser Asp Glu
    130                 135                 140

Gln Leu Lys Ser Gly Thr Ala Ser Val Val Cys Leu Leu Asn Asn Phe
145                 150                 155                 160
```

```
Tyr Pro Arg Glu Ala Lys Val Gln Trp Lys Val Asp Asn Ala Leu Gln
                165                 170                 175

Ser Gly Asn Ser Gln Glu Ser Val Thr Glu Gln Asp Ser Lys Asp Ser
            180                 185                 190

Thr Tyr Ser Leu Ser Ser Thr Leu Thr Leu Ser Lys Ala Asp Tyr Glu
        195                 200                 205

Lys His Lys Val Tyr Ala Cys Glu Val Thr His Gln Gly Leu Ser Ser
    210                 215                 220

Pro Val Thr Lys Ser Phe Asn Arg Gly Glu Cys
225                 230                 235
```

<210> SEQ ID NO 65
<211> LENGTH: 714
<212> TYPE: DNA
<213> ORGANISM: Artificial Sequence
<220> FEATURE:
<223> OTHER INFORMATION: Nucleotide sequence of PDISP/LC Rituxan

<400> SEQUENCE: 65

```
atggcgaaaa acgttgcgat tttcggctta ttgttttctc ttcttgtgtt ggttccttct      60

cagatcttcg cccaaattgt tctctcccag tctccagcaa tcctgtctgc atctccaggg     120

gagaaggtca caatgacttg cagggccagc tcaagtgtaa gttacatcca ctggttccag     180

cagaagccag gatcctcccc caaaccctgg atttatgcca catccaacct ggcttctgga     240

gtccctgttc gcttcagtgg cagtgggtct gggacttctt actctctcac aatcagcaga     300

gtggaggctg aagatgctgc cacttattac tgccagcagt ggactagtaa cccacccacg     360

ttcggagggg ggaccaagct ggaaatcaaa cgtacggtgg ctgcaccatc tgtcttcatc     420

ttcccgccat ctgatgagca gttgaaatct ggaactgcct ctgttgtgtg cctgctgaat     480

aacttctatc ccagagaggc caaagtacag tggaaggtgg ataacgccct ccaatcgggt     540

aactcccagg agagtgtcac agagcaggac agcaaggaca gcacctacag cctcagcagc     600

accctgacgc tgagcaaagc agactacgag aaacacaaag tctacgcctg cgaagtcacc     660

catcagggcc tgagctcgcc cgtcacaaag agcttcaaca ggggagagtg ttga           714
```

<210> SEQ ID NO 66
<211> LENGTH: 237
<212> TYPE: PRT
<213> ORGANISM: Artificial Sequence
<220> FEATURE:
<223> OTHER INFORMATION: Amino acid sequence of PDISP/LC Rituxan.

<400> SEQUENCE: 66

```
Met Ala Lys Asn Val Ala Ile Phe Gly Leu Leu Phe Ser Leu Leu Val
1               5                   10                  15

Leu Val Pro Ser Gln Ile Phe Ala Gln Ile Val Leu Ser Gln Ser Pro
            20                  25                  30

Ala Ile Leu Ser Ala Ser Pro Gly Glu Lys Val Thr Met Thr Cys Arg
        35                  40                  45

Ala Ser Ser Ser Val Ser Tyr Ile His Trp Phe Gln Gln Lys Pro Gly
    50                  55                  60

Ser Ser Pro Lys Pro Trp Ile Tyr Ala Thr Ser Asn Leu Ala Ser Gly
65                  70                  75                  80

Val Pro Val Arg Phe Ser Gly Ser Gly Ser Gly Thr Ser Tyr Ser Leu
                85                  90                  95

Thr Ile Ser Arg Val Glu Ala Glu Asp Ala Ala Thr Tyr Tyr Cys Gln
```

```
            100                 105                 110

Gln Trp Thr Ser Asn Pro Pro Thr Phe Gly Gly Gly Thr Lys Leu Glu
        115                 120                 125

Ile Lys Arg Thr Val Ala Ala Pro Ser Val Phe Ile Phe Pro Pro Ser
    130                 135                 140

Asp Glu Gln Leu Lys Ser Gly Thr Ala Ser Val Val Cys Leu Leu Asn
145                 150                 155                 160

Asn Phe Tyr Pro Arg Glu Ala Lys Val Gln Trp Lys Val Asp Asn Ala
                165                 170                 175

Leu Gln Ser Gly Asn Ser Gln Glu Ser Val Thr Glu Gln Asp Ser Lys
            180                 185                 190

Asp Ser Thr Tyr Ser Leu Ser Ser Thr Leu Thr Leu Ser Lys Ala Asp
        195                 200                 205

Tyr Glu Lys His Lys Val Tyr Ala Cys Glu Val Thr His Gln Gly Leu
    210                 215                 220

Ser Ser Pro Val Thr Lys Ser Phe Asn Arg Gly Glu Cys
225                 230                 235


<210> SEQ ID NO 67
<211> LENGTH: 48
<212> TYPE: DNA
<213> ORGANISM: Artificial Sequence
<220> FEATURE:
<223> OTHER INFORMATION: IF-PDI.S1+3c

<400> SEQUENCE: 67

aaatttgtcg ggcccatggc gaaaaacgtt gcgattttcg gcttattg                  48


<210> SEQ ID NO 68
<211> LENGTH: 114
<212> TYPE: DNA
<213> ORGANISM: Artificial Sequence
<220> FEATURE:
<223> OTHER INFORMATION: CPMV114

<400> SEQUENCE: 68

tattaaaatc ttaataggtt ttgataaaag cgaacgtggg gaaacccgaa ccaaaccttc      60

ttctaaactc tctctcatct ctcttaaagc aaacttctct cttgtctttc ttgc           114


<210> SEQ ID NO 69
<211> LENGTH: 160
<212> TYPE: DNA
<213> ORGANISM: Artificial Sequence
<220> FEATURE:
<223> OTHER INFORMATION: CPMV160, 115A

<400> SEQUENCE: 69

tattaaaatc ttaataggtt ttgataaaag cgaacgtggg gaaacccgaa ccaaaccttc      60

ttctaaactc tctctcatct ctcttaaagc aaacttctct cttgtctttc ttgcatgagc     120

gatcttcaac gttgtcagat cgtgcttcgg caccagtaca                           160


<210> SEQ ID NO 70
<211> LENGTH: 155
<212> TYPE: DNA
<213> ORGANISM: Artificial Sequence
<220> FEATURE:
<223> OTHER INFORMATION: CPMV155, 115A

<400> SEQUENCE: 70

tattaaaatc ttaataggtt ttgataaaag cgaacgtggg gaaacccgaa ccaaaccttc      60
```

ttctaaactc tctctcatct ctcttaaagc aaacttctct cttgtctttc ttgcatgagc 120
gatcttcaac gttgtcagat cgtgcttcgg cacca 155

<210> SEQ ID NO 71
<211> LENGTH: 150
<212> TYPE: DNA
<213> ORGANISM: Artificial Sequence
<220> FEATURE:
<223> OTHER INFORMATION: CPMV150,115A

<400> SEQUENCE: 71
tattaaaatc ttaataggtt ttgataaaag cgaacgtggg gaaacccgaa ccaaaccttc 60
ttctaaactc tctctcatct ctcttaaagc aaacttctct cttgtctttc ttgcatgagc 120
gatcttcaac gttgtcagat cgtgcttcgg 150

<210> SEQ ID NO 72
<211> LENGTH: 176
<212> TYPE: DNA
<213> ORGANISM: Artificial Sequence
<220> FEATURE:
<223> OTHER INFORMATION: CPMV155+

<400> SEQUENCE: 72
tattaaaatc ttaataggtt ttgataaaag cgaacgtggg gaaacccgaa ccaaaccttc 60
ttctaaactc tctctcatct ctcttaaagc aaacttctct cttgtctttc ttgcgtgagc 120
gatcttcaac gttgtcagat cgtgcttcgg caccagggcc caataccgcg gagaaa 176

<210> SEQ ID NO 73
<211> LENGTH: 171
<212> TYPE: DNA
<213> ORGANISM: Artificial Sequence
<220> FEATURE:
<223> OTHER INFORMATION: CPMV150+

<400> SEQUENCE: 73
tattaaaatc ttaataggtt ttgataaaag cgaacgtggg gaaacccgaa ccaaaccttc 60
ttctaaactc tctctcatct ctcttaaagc aaacttctct cttgtctttc ttgcgtgagc 120
gatcttcaac gttgtcagat cgtgcttcgg gggcccaata ccgcggagaa a 171

<210> SEQ ID NO 74
<211> LENGTH: 135
<212> TYPE: DNA
<213> ORGANISM: Artificial Sequence
<220> FEATURE:
<223> OTHER INFORMATION: CPMV114+

<400> SEQUENCE: 74
tattaaaatc ttaataggtt ttgataaaag cgaacgtggg gaaacccgaa ccaaaccttc 60
ttctaaactc tctctcatct ctcttaaagc aaacttctct cttgtctttc ttgcgggccc 120
aataccgcgg agaaa 135

<210> SEQ ID NO 75
<211> LENGTH: 181
<212> TYPE: DNA
<213> ORGANISM: Artificial Sequence
<220> FEATURE:
<223> OTHER INFORMATION: CPMV160+, 115A

<400> SEQUENCE: 75
tattaaaatc ttaataggtt ttgataaaag cgaacgtggg gaaacccgaa ccaaaccttc 60
ttctaaactc tctctcatct ctcttaaagc aaacttctct cttgtctttc ttgcatgagc 120
gatcttcaac gttgtcagat cgtgcttcgg caccagtaca gggcccaata ccgcggagaa 180
a 181

<210> SEQ ID NO 76
<211> LENGTH: 176
<212> TYPE: DNA
<213> ORGANISM: Artificial Sequence
<220> FEATURE:
<223> OTHER INFORMATION: CPMV155+, 115A

<400> SEQUENCE: 76
tattaaaatc ttaataggtt ttgataaaag cgaacgtggg gaaacccgaa ccaaaccttc 60
ttctaaactc tctctcatct ctcttaaagc aaacttctct cttgtctttc ttgcatgagc 120
gatcttcaac gttgtcagat cgtgcttcgg caccagggcc caataccgcg gagaaa 176

<210> SEQ ID NO 77
<211> LENGTH: 171
<212> TYPE: DNA
<213> ORGANISM: Artificial Sequence
<220> FEATURE:
<223> OTHER INFORMATION: CPMV150+, 115A

<400> SEQUENCE: 77
tattaaaatc ttaataggtt ttgataaaag cgaacgtggg gaaacccgaa ccaaaccttc 60
ttctaaactc tctctcatct ctcttaaagc aaacttctct cttgtctttc ttgcatgagc 120
gatcttcaac gttgtcagat cgtgcttcgg gggcccaata ccgcggagaa a 171

<210> SEQ ID NO 78
<211> LENGTH: 29
<212> TYPE: PRT
<213> ORGANISM: Artificial Sequence
<220> FEATURE:
<223> OTHER INFORMATION: Transmembrane domain consensus amino acid
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (15)..(15)
<223> OTHER INFORMATION: Xaa can be any naturally occurring amino acid
<220> FEATURE:
<221> NAME/KEY: misc_feature
<222> LOCATION: (17)..(18)
<223> OTHER INFORMATION: Xaa can be any naturally occurring amino acid
<220> FEATURE:
<221> NAME/KEY: misc_feature
<222> LOCATION: (23)..(23)
<223> OTHER INFORMATION: Xaa can be any naturally occurring amino acid
<220> FEATURE:
<221> NAME/KEY: misc_feature
<222> LOCATION: (25)..(25)
<223> OTHER INFORMATION: Xaa can be any naturally occurring amino acid

<400> SEQUENCE: 78

Ile Leu Xaa Ile Tyr Tyr Ser Thr Val Ala Ile Ser Ser Leu Xaa Leu
1 5 10 15

Xaa Xaa Met Leu Ala Gly Xaa Ser Xaa Trp Met Cys Ser
20 25

<210> SEQ ID NO 79
<211> LENGTH: 69

-continued

```
<212> TYPE: DNA
<213> ORGANISM: Artificial Sequence
<220> FEATURE:
<223> OTHER INFORMATION: Patatin signal peptide; nucleic acid sequence

<400> SEQUENCE: 79

atggcaacta ctaaaacttt tttaatttta ttttttatga tattagcaac tactagttca     60

acatgtgct                                                             69


<210> SEQ ID NO 80
<211> LENGTH: 23
<212> TYPE: PRT
<213> ORGANISM: Artificial Sequence
<220> FEATURE:
<223> OTHER INFORMATION: Patatin signal peptide; amino acid sequence

<400> SEQUENCE: 80

Met Ala Thr Thr Lys Thr Phe Leu Ile Leu Phe Phe Met Ile Leu Ala
1               5                   10                  15

Thr Thr Ser Ser Thr Cys Ala
            20
```

CPMV ENHANCER ELEMENTS

CROSS-REFERENCE TO RELATED APPLICATIONS

This application is a national stage application of PCT/CA2015/050009, filed Jan. 8, 2015. PCT/CA2015/050009 is a Continuation-In-Part of and claims priority from PCT Application No. PCT/CA2014/050326, filed Mar. 28, 2014. PCT/CA2015/050009 also claims priority from U.S. Provisional Application No. 61/925,852, filed Jan. 10, 2014. The content of each of these applications is hereby incorporated by reference.

REFERENCE TO SEQUENCE LISTING

The content of the following text file, which provides a computer-readable form (CRF) of the Sequence Listing for this application, is incorporated herein by reference in its entirety:

file name: pctca2015050009-seql.txt; created: Jul. 8, 2016; size: 140 KB.

FIELD OF INVENTION

The present invention relates to the expression of proteins of interest in plants. The present invention also provides methods and compositions for the production of proteins of interest in plants.

BACKGROUND OF THE INVENTION

Plants offer great potential as production systems for recombinant proteins. One approach to producing foreign proteins in plants is to generate stable transgenic plant lines. However this is a time consuming and labor intensive process. An alternative to transgenic plants is the use of plant virus-based expression vectors. Plant virus-based vectors allow for the rapid, high level, transient expression of proteins in plants.

One method to achieve high level transient expression of foreign proteins in plants involves the use of vectors based on RNA plant viruses, including comoviruses, such as Cowpea mosaic virus (CPMV; see, for example, WO2007/135480; WO2009/087391; US 2010/0287670, Sainsbury F. et al., 2008, *Plant Physiology;* 148: 121-1218; Sainsbury F. et al., 2008, *Plant Biotechnology Journal;* 6: 82-92; Sainsbury F. et al., 2009, *Plant Biotechnology Journal;* 7: 682-693; Sainsbury F. et al. 2009, *Methods in Molecular Biology, Recombinant Proteins From Plants*, vol. 483: 25-39).

Comoviruses are RNA viruses with a bipartite genome. The segments of the comoviral RNA genome are referred to as RNA-1 and RNA-2. RNA-1 encodes the VPg, replicase and protease proteins. The replicase is required by the virus for replication of the viral genome. The RNA-2 of the comovirus cowpea mosaic virus (CPMV) produces a polyprotein of 105 kDa or 95 kDa processed into 4 functional peptides.

The 5' region of CPMV RNA-2 comprises start codons (AUGs) at positions 115, 161, 512 and 524. The start codons at positions 161 and 512 are in the same triplet reading frame. Initiation at the start codon at position 161 results in the synthesis of the 105K polyprotein while initiation at the start codon at position 512 directs the synthesis of the 95K polyprotein. Initiation of translation at the start codon at position 512 in CPMV is more efficient than initiation at position 161, resulting in the production of more 95K polyprotein than 105K polyprotein. The start codon at position 115 is not essential for virus replication (Wellink et al., 1993 Biochimie. 75(8):741-7).

Maintenance of the frame between the initiation sites at positions 161 and 512 in CPMV RNA-2 is required for efficient replication of RNA-2 by the RNA-1-encoded replicase (Holness et al., 1989; Virology 172, 311-320; van Bokhoven et al. 1993, Virology 195, 377-386; Rohll et al., 1993 Virology 193, 672-679; Wellink et al., 1993, Biochimie. 75(8):741-7). This requirement impacts the length of sequences which can be inserted upstream of the 512 start codon in replicative forms of CPMV RNA-2 expression vectors. Furthermore, the use of polylinkers must be used with caution as they may shift the codon reading frame (ORF) between these initiation sites.

CPMV has served as the basis for the development of vector systems suitable for the production of heterologous polypeptides in plants (Liu et al., 2005 Vaccine 23, 1788-1792; Sainsbury et al., 2007 Virus Expression Vectors (Hefferon, K. ed), pp. 339-555). These systems are based on the modification of RNA-2 but differ in whether full-length or deleted versions are used. Replication of the modified RNA-2 is achieved by co-inoculation with RNA-1. Foreign proteins are fused to the C-terminus of the RNA-2-derived polyproteins. Release of the N-terminal polypeptide is mediated by the action of the 2A catalytic peptide sequence from foot-and-mouth-disease virus (Gopinath et al., 2000, Virology 267: 159-173). The resulting RNA-2 molecules are capable of spreading both within and between plants. This strategy has been used to express a number of recombinant proteins, such as the Hepatitis B core antigen (HBcAg) and Small Immune Proteins (SIPs), in cowpea plants (Mechtcheriakova et al. J. Virol. Methods 131, 10-15; 2006; Monger et al., 2006, Plant Biotechnol. J. 4,623-631; Alamillo et al., 2006, Biotechnol. J. 1, 1103-1111). Though successful, the use of a full-length viral vector limits the size of inserted sequences, and movement between plants raises concerns about biocontainment of the virus.

To address the issue of biocontainment and insert size, Canizares et al. (2006 Plant Biotechnol, J 4:183-193) replaced the majority of the coding region of RNA-2 with a sequence of interest to produce a disabled version of CPMV RNA-2 (deIRNA-2). The sequence to be expressed was fused to the AUG at position 512 of RNA-2, immediately upstream of the 3' untranslated region (UTR) to create a molecule that mimics RNA-2. Such constructs were capable of replication when introduced into plants in the presence of RNA-1 and a suppressor of silencing, and directed the synthesis of substantial levels of heterologous proteins (Sainsbury et al., 2008 Plant Biotechnol J 6:82-92).

Mutation of the start codon at position 161 in a CPMV RNA-2 vector (U162C; HT) increases the levels of expression of a protein encoded by a sequence inserted after the start codon at position 512. This permits the production of high levels of foreign proteins without the need for viral replication and was termed the CPMV-HT system (WO2009/087391; Sainsbury and Lomonossoff, 2008, Plant Physiol. 148, 1212-1218). In pEAQ expression plasmids (Sainsbury et al., 2009, Plant Biotechnology Journal, 7, pp 682-693; US 2010/0287670), the sequence to be expressed is positioned between the 5'UTR and the 3' UTR. The 5'UTR in the pEAQ series carries the U162C (HT) mutation.

SUMMARY OF THE INVENTION

The present invention relates to the expression of proteins of interest in plants. The present invention also provides methods and compositions for the production of proteins of interest in plants.

As described herein, there is provided an expression enhancer comprising a CPMV 5'UTR nucleotide sequence consisting of X nucleotides (CMPVX), where X=160, 155, 150, or 114 of SEQ ID NO:1, or consisting of a nucleotide sequence comprising from about 80% to 100% sequence similarity with CMPVX, where X=160, 155, 150, or 114 of SEQ ID NO:1. The expression enhancer may comprise a nucleotide sequence selected from the group of SEQ ID NO: 24, 27, 68, 69, 70 and 71.

The present invention also provides the expression enhancer as defined above, where the expression enhancer furthers comprises a stuffer sequence (CPMVX+, where X=160, 155, 150, 114 of SEQ ID NO:1). The stuffer sequence may comprise a length from 0 to about 100 nucleotides, or any length therein between, one or more plant kozak sequences, a multiple cloning site, one or more linker sequences, one or more recombination sites, or a combination thereof. The present invention also provides the expression enhancer as defined above, where the kozak sequence is selected from the group of sequences as shown in SEQ ID NO's: 5-17. The expression enhancer as just defined (CPMVX+, where X=160, 155, 150, or 114 of SEQ ID NO:1) may comprise a nucleotide sequence selected from the group of SEQ ID NO: 2, 72, 73, 74, 75, 76 and 77.

Also provided is a plant expression system comprising a nucleic acid sequence comprising a regulatory region, operatively linked with the expression enhancer CPMVX, CPMVX+, as defined above, the expression enhancer operatively linked with a nucleotide sequence of interest. The plant expression system may further comprise a comovirus 3' UTR. The plant expression system may further comprise a second nucleic acid sequence encoding a suppressor of silencing, for example HcPro or p19.

The nucleotide sequence of interest of the plant expression system as defined above may encode a viral protein or an antibody. For example, the viral protein may be an influenza hemagglutinin and may be selected from the group of H1, H2, H3, H4, H5, H6, H7, H8, H9, H10, H11, H12, H13, H14, H15, H16, and an influenza type B hemagglutinin. The nucleotide sequence encoding the viral protein or the antibody may comprise a native signal peptide sequence, or a non-native signal peptide, for example the non-native signal peptide may be obtained from Protein disulfide isomerase (PDI).

As described herein there is provided a method of producing a protein of interest in a plant or in a portion of a plant comprising, introducing into the plant or in the portion of a plant the plant expression system comprising CPMVX or CPMVX+, as defined above, and incubating the plant or the portion of a plant under conditions that permit expression of the nucleotide sequence encoding the protein of interest.

The present invention also provides a plant or portion of a plant transiently transfected or stably transformed with the plant expression system as described above.

Plant-based expression systems as described herein result in increasing or enhancing expression of a nucleotide sequence encoding a heterologous open reading frame that is operatively linked to the expression enhancer, either CPMVX, or CPMVX+ as defined herein. The increase in expression may be determined by comparing the level of expression obtained using the CPMVX based, or CPMVX+ based expression enhancers with the level of expression of the same nucleotide sequence encoding the heterologous open reading frame operatively linked to the prior art enhancer sequence (CPMV HT) comprising an incomplete M protein (as described in Sainsbury F., and Lomonossoff G. P., 2008, Plant Physiol. 148: pp. 1212-1218; which is incorporated herein by reference). An example of a prior art CPMV HT sequence is provided in SEQ ID NO:4.

The plant based expression systems as described herein may also have a number of properties such as, for example, containing convenient cloning sites for genes or nucleotide sequences of interest, may easily infect plants in a cost-effective manner, may cause efficient local or systemic infection of inoculated plants. In addition, the infection should provide a good yield of useful protein material.

This summary of the invention does not necessarily describe all features of the invention.

BRIEF DESCRIPTION OF THE DRAWINGS

These and other features of the invention will become more apparent from the following description in which reference is made to the appended drawings wherein:

FIG. 1B shows examples of several variants of constructs comprising enhancer sequences, as described herein (CPMV160, complete sequence provided as SEQ ID NO:1; CPMV155, complete sequence provided as SEQ ID NO:24; CPMV150, complete sequence provided as SEQ ID NO:27; and CPMV114, complete sequence provided as SEQ ID NO:68), operatively linked to plant regulatory region (in these non-limiting examples 2X35S) at their 5' ends, and at their 3' ends, a nucleotide sequence of interest, or "GOT", which includes a plant kozak sequence adjacent to the ATG initiation site (elements shown within the square brackets are include for context, and they are not part of the CPMVX or CPMVX+ enhancer sequences). FIG. 1C shows examples of several variants of constructs comprising enhancer sequences, as described herein (CPMV160+, complete sequence provided as SEQ ID NO:2; CPMV155+, complete sequence provided as SEQ ID NO:72; CPMV150+, complete sequence provided as SEQ ID NO:73; and CPMV114+, complete sequence provided as SEQ ID NO:74), operatively linked to plant regulatory region (in these non-limiting examples 2X35S) at their 5' ends, and at their 3' ends, a stuffer fragment (in these non-limiting examples, comprising a multiple cloning site and plant kozak sequence), a nucleotide sequence of interest, "GOT" comprising an ATG initiation site (elements shown within the square brackets are include for context, and they are not part of the CPMVX or CPMVX+ enhancer sequences).

CPMV HT; and construct number 1800, 5'UTR: CMPV160+; see Examples 1 and 2, respectively), H5 from Influenza A/Indonesia/5/2005 with a native signal peptide (WtSp-H5 Indo; construct number 489, 5'UTR: CMPV HT; and construct number 1880, 5'UTR: CMPV160+; see Example 6), and B/Wisconsin/1/2010 with deleted proteolytic loop and with a native signal peptide (WtSp-B WisPrL; construct number 1445, 5'UTR: CMPV HT; and construct number 1975, 5'UTR: CMPV160+, see Example 13) are shown. PDI: Protein disulfide isomerase signal peptide; PrL-: deleted proteolytic loop.

Figure 3:
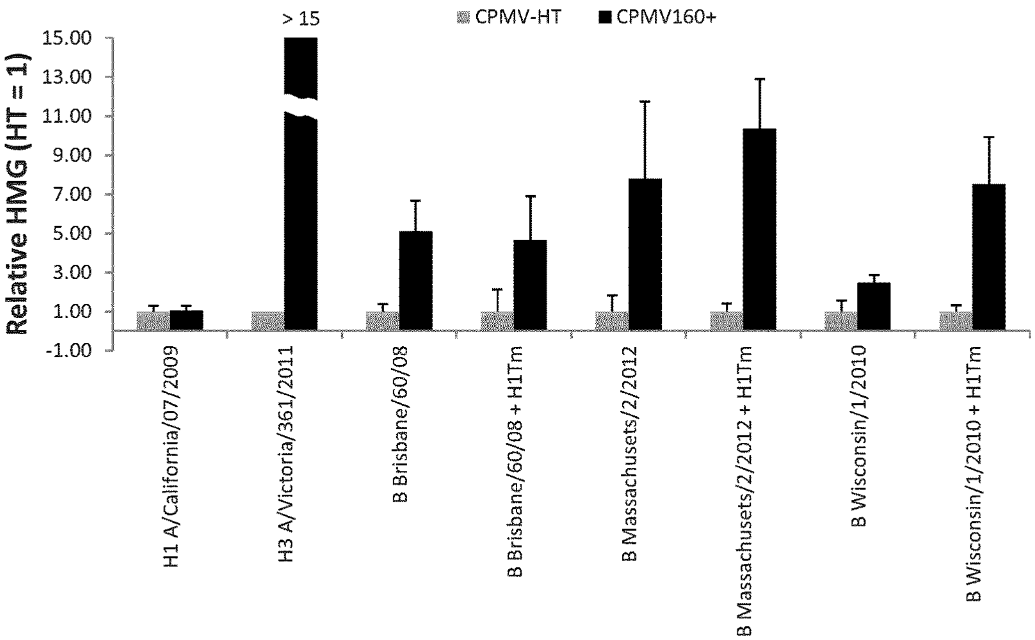

FIG. 3 shows the relative hemagglutination titres (HMG) in crude protein extracts of proteins produced in plants comprising CPMV-HT (prior art) expression constructs, and CPMV160+ based expression constructs. Data for the expression of HA from H1 A/California/07/2009 with a PDI signal peptide (construct number 484, 5'UTR: CMPV HT; and construct number 1897 5'UTR: CMPV160+, see Example 5), H3 A/Victoria/361/2011 with a PDI signal peptide (construct number 1391, 5'UTR: CMPV HT; and construct number 1800 5'UTR: CMPV160+, see Examples 1 and 2, respectively), B Brisbane/60/08 with deleted proteolytic loop and with a PDI signal peptide (construct number 1039, 5'UTR: CMPV HT; and construct number 1937, 5'UTR: CMPV160+; see Example 9), B Brisbane/60/08+H1Tm, with deleted proteolytic loop, with transmembrane domain and cytoplasmic tail replaced by those of H1 A/California/07/2009, and with a PDI signal peptide (construct number 1067, 5'UTR: CMPV HT; and construct number 1977, 5'UTR: CMPV160+; see Example 10), B Massachusetts/2/2012 2012 with deleted proteolytic loop and with a PDI signal peptide (construct number 2072, 5'UTR: CMPV HT; and construct number 2050, 5'UTR: CMPV160+; see Example 11), B Massachusetts/2/2012+H1Tm with deleted proteolytic loop, with transmembrane domain and cytoplasmic tail replaced by those of H1 A/California/07/2009 and with a PDI signal peptide (construct number 2074, 5'UTR: CMPV HT; and construct number 2060, 5'UTR: CMPV160+; see Example 12), B Wisconsin/1/2010 with deleted proteolytic loop and with the native signal peptide (construct number 1445, 5'UTR: CMPV HT; and construct number 1975, 5'UTR: CMPV160+; see Example 13), and B Wisconsin/1/2010+H1Tm with deleted proteolytic loop, with transmembrane domain and cytoplasmic tail replaced by those of H1 A/California/07/2009 and with the native signal peptide (construct number 1454, 5'UTR: CMPV HT; and construct number 1893, 5'UTR: CMPV160+; see Example 14), are shown.

Figure 4A:
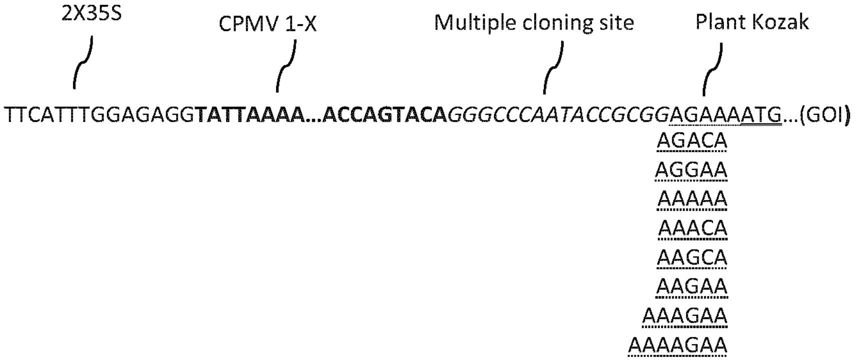
Figure 4B:
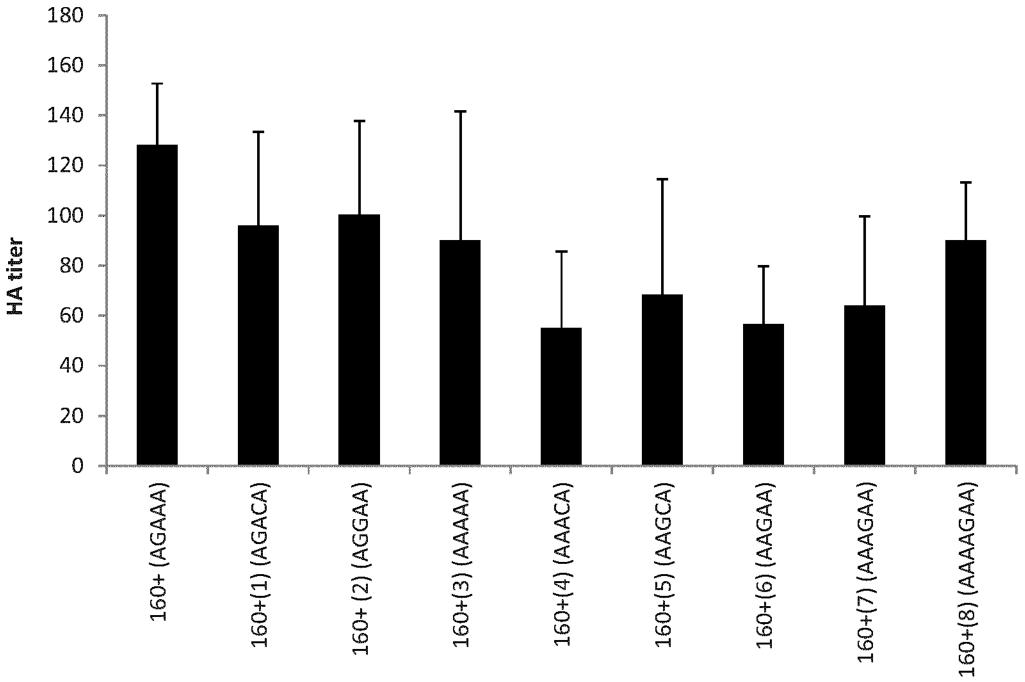

FIG. 4A shows examples of variants of plant Kozak sequences tested. Constructs showing a partial sequence of the CPMVX+, a plant regulatory region, a stuffer fragment, and a nucleotide sequence of interest (GOI). In this non-limiting example, the construct comprises a 2X35S regulatory region, CPMV160+, a stuffer fragment comprising a multiple cloning site and a plant kozak sequence (the 5' end of a nucleotide sequence of interest is also indicated: "ATG. GOI"; where the GOT is H3 A/Victoria/361). The construct sequence in FIG. 4A shows bases 734-931 of SEQ ID NO:26 (expression cassette number 1800, FIG. 7E), with an internal portion omitted for brevity. Variants of plant kozak sequences are also shown below the sequence (also see FIG. 9). Each variant plant Kozak sequence was fused to the 3' end of the stuffer fragment, and to the 5'-ATG site of the nucleotide sequence of interest (in these non-limiting examples, H3 A/Victoria/361). The other elements of the constructs remained the same). FIG. 4B shows HA titers of a nucleotide sequence of interest produced in plants comprising CMPV160+ expression construct and a variant plant Kozak sequence as indicated.

Figure 5:
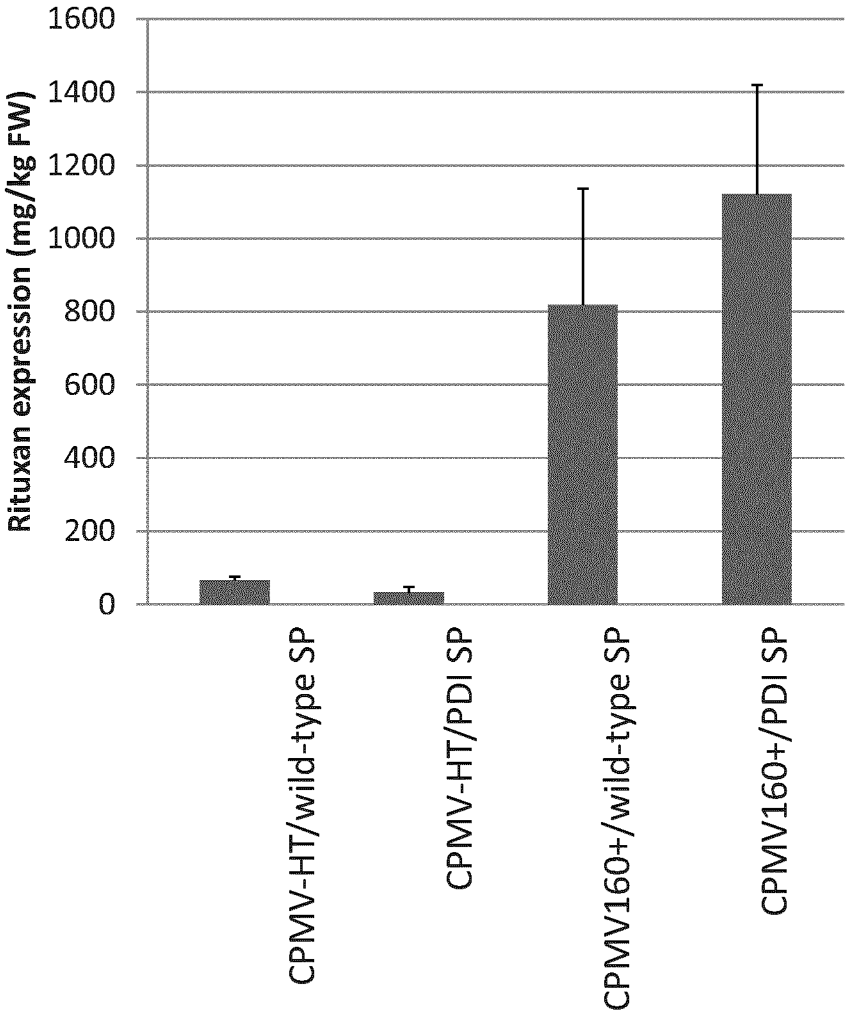

FIG. 5 shows the expression of the antibody rituximab (Rituxan) under the control of CPMV-HT (construct numbers 5001 and 5002, see examples 15 and 16) or CPMV160 (construct numbers 2100 and 2109, see example 15 and 16) and with either its native signal peptide or the native signal peptide replaced with the signal peptide of Protein disulfide isomerase (PDI).

FIG. 6 shows the sequence components used to prepare construct number 1391(A-2X35S CPMV-HT PDISP H3Victoria NOS; see example 1). Construct number 1391 incorporates a prior art CPMV-HT sequence (CMPV 5'UTR with mutated start codon at position 161 fused to a sequence encoding an incomplete M protein and does not comprise a heterologous kozak sequence between the 5'UTR and the nucleotide sequence of interest (PDISP/H3 Victoria)). PDISP: protein disulfide isomerase signal peptide. NOS: nopaline synthase terminator. FIG. 6A shows primer sequence IF-PDI.S1=3c (SEQ ID NO:67). FIG. 6B shows primer sequence IF-H3V36111.s1-4r (SEQ ID NO:17). FIG. 6C shows the sequence of PDISP/H3 Victoria (SEQ ID NO:18). FIG. 6D shows a schematic representation of construct 1191. FIG. 6E shows construct 1191; from left to right t-DNA borders (underlined), 2X35S CPMV-HT NOS, with Plastocyanine-P19-Plastocyanine silencing inhibitor expression cassette (SEQ ID NO:19). FIG. 6F shows expression cassette number 1391 from 2X35S promoter to NOS terminator. The PDISP/H3 Victoria nucleotide sequence is underlined; CPMV 5'UTR in bold; incomplete M-protein in italics (SEQ ID NO:20). FIG. 6G shows the amino acid sequence of PDISP/H3 Victoria (SEQ ID NO:21). FIG. 6H shows a schematic representation of construct number 1391 (a reference construct).

FIG. 7 shows the sequence components used to prepare construct number 1800 (A-2X35S CPMV160+ PDISP H3Victoria NOS; see example 2). Construct number 1800 includes a CPMV 5'UTR comprising 160 nucleotides, a stuffer fragment (multiple cloning site), and a plant kozak sequence (this construct does not comprise a sequence encoding an incomplete M protein) and is an example of a CPMV160+(CPMVX+, where X=160) based construct. PDISP: protein disulfide isomerase signal peptide. NOS: nopaline synthase terminator. FIG. 7A shows primer sequence IF(SacII)-PDI.s1+4c (SEQ ID NO:22). FIG. 7B shows primer sequence IF-H3V36111.s1-4r (SEQ ID NO:23). The sequence of PDISP/H3 Victoria is shown in FIG. 6C (SEQ ID NO:18). FIG. 7C shows a schematic representation of construct 2171 (SacII and StuI restriction enzyme sites used for plasmid linearization are indicated). FIG. 7D shows construct 2171 from left to right t-DNA borders (underlined), 2X35S/CPMV160+/NOS with Plastocyanine-P19-Plastocyanine silencing inhibitor expression cassette, an H1 California transmembrane cytoplasmic tail, and the CPMV3'UTR (SEQ ID NO:25). FIG. 7E shows expression cassette number 1800 from 2X35S promoter to NOS terminator. PDISP/H3 Victoria nucleotide sequence is underlined; 5'UTR is shown in bold; plant kozak sequence double underline; a stuffer fragment (multiple cloning site) of 16 base pairs is positioned between the 5'UTR and plant kozak sequence (SEQ ID NO:26). The amino acid sequence of PDISP/H3 Victoria is shown in FIG. 6G (SEQ ID NO:27). FIG. 7**F shows a schematic representation of construct number 1800 (a CPMVX+ based construct, where X=160).

Figure 8B:
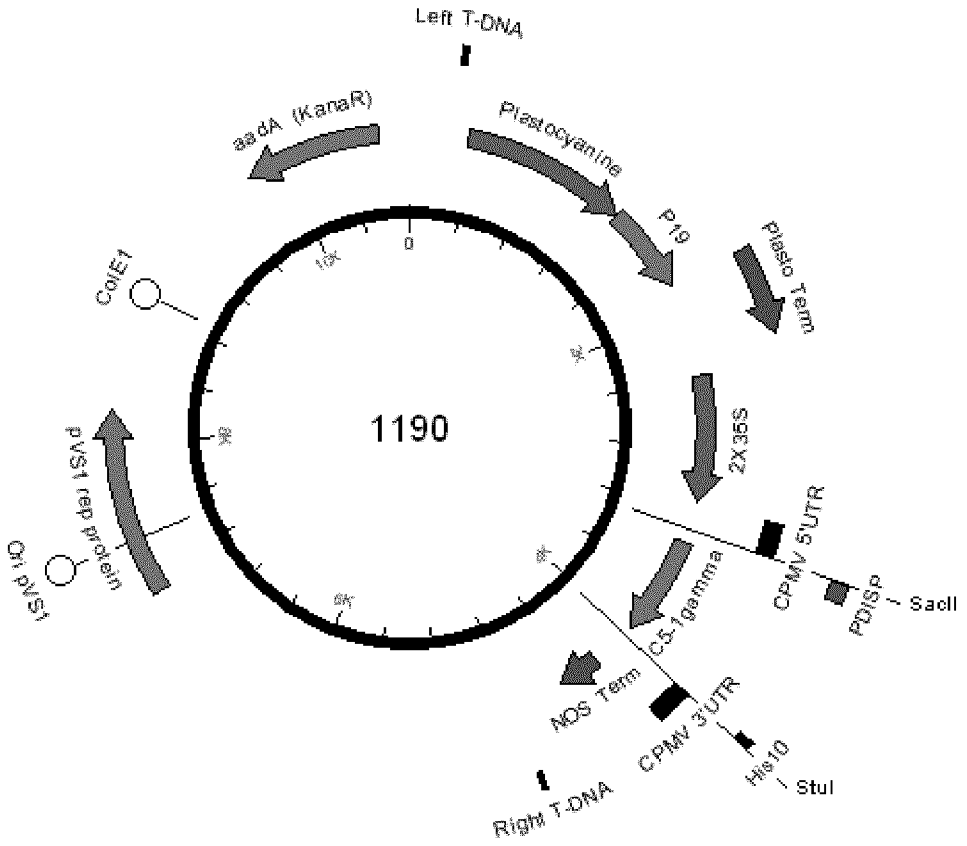
Figure 8E:
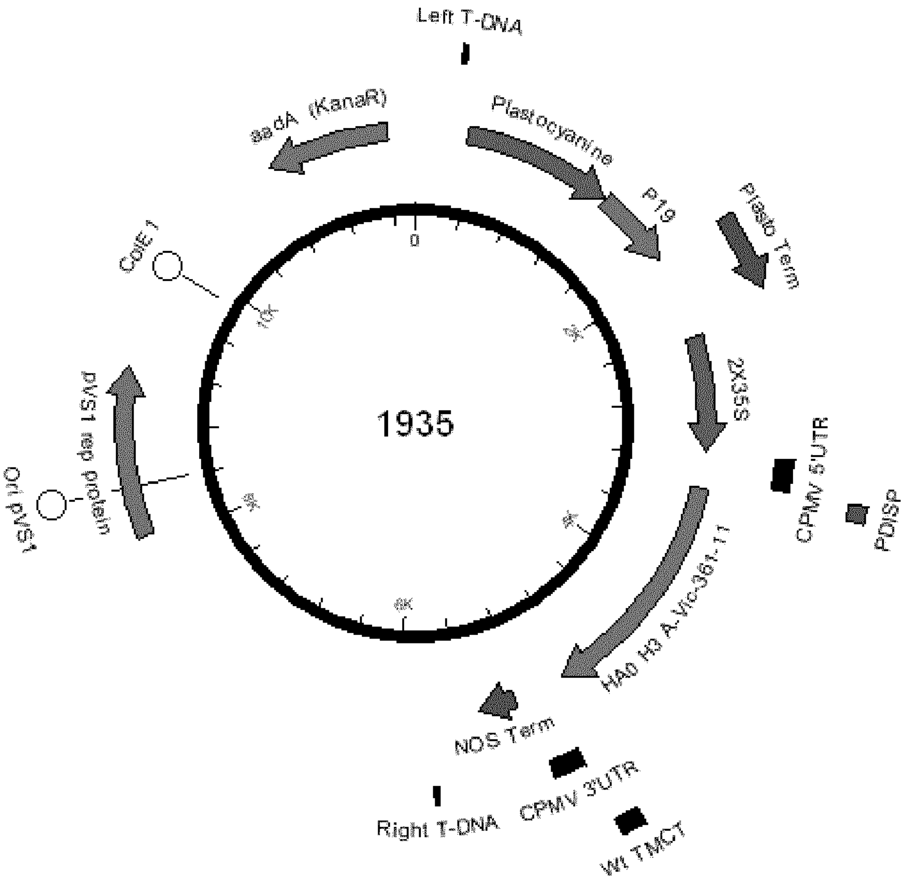

FIG. 8 shows the sequence components used to prepare construct number 1935 (2X35S/CPMV160/PDISP/H3 Victoria/NOS; see example 3). Construct number 1935 includes a CPMV 5'UTR comprising 160 nucleotides, and does not include a stuffer fragment (multiple cloning site), or a plant kozak sequence (this construct also does not comprise a sequence encoding an incomplete M protein) and is an example of a CPMV160 (CPMVX, where X=160) based construct. PDISP: protein disulfide isomerase signal peptide. NOS: nopaline synthase terminator. FIG. 8A shows primer sequence IF-CPMV(fl5'UTR)_SpPDI.c (SEQ ID NO:28). FIG. 8B shows a schematic representation of construct 1190. FIG. 8C shows the nucleic acid sequence of construct 1190 from left to right t-DNA borders (underlined), 2X35S/CPMV160/NOS with Plastocyanine-P19-Plastocyanine silencing inhibitor expression cassette, and a CPMV3'UTR (SEQ ID NO:29). FIG. 8D shows expression cassette number 1935 from 2X35S promoter to NOS terminator. PDISP/H3 Victoria nucleotide sequence is underlined, 5'UTR is shown in bold (SEQ ID NO:30). This cassette does not include a plant kozak sequence or a stuffer fragment (multiple cloning site). FIG. 8E shows a schematic representation of construct number 1935 (a CPMVX based construct, where X=160).

Figure 9I:
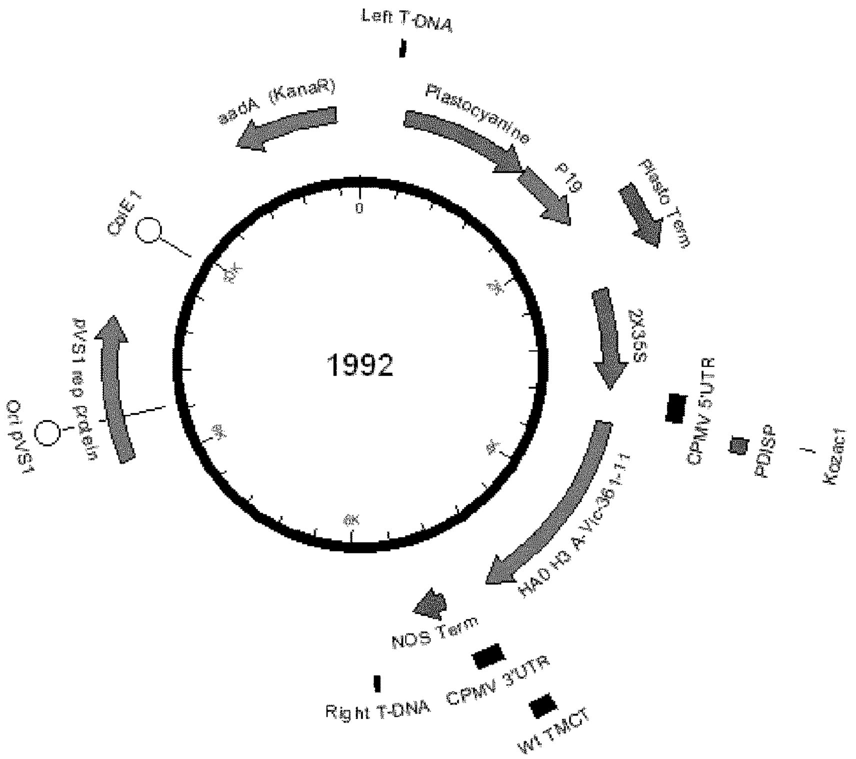

FIG. 9 shows sequences comprising variations in a plant kozak sequence used to prepare a selection of "CPMV160+" based constructs (constructs number 1992 to 1999). Variation of sequence between SacII restriction site and ATG of PDISP/H3 Victoria in 2X35S/CPMV160+/NOS expression system, comprising variations in a plant kozak sequence are shown (the sequences are shown as variations from the corresponding sequence from construct 1800; see Example 4). The variant plant kozak sequence are underlined. PDISP: protein disulfide isomerase signal peptide. FIG. 9A shows the nucleotide sequence of IF-HT1*(-Mprot)-PDI.c (SEQ ID NO: 31; used to prepare construct number 1992). FIG. 9B shows the nucleotide sequence of IF-HT2*(-Mprot)-PDI.c (SEQ ID NO:32; used to prepare construct number 1993). FIG. 9C shows the nucleotide sequence of IF-HT3*(-Mprot)-PDI.c (SEQ ID NO:33; used to prepare construct number 1994). FIG. 9D shows the nucleotide sequence of IF-HT4*(-Mprot)-PDI.c (SEQ ID NO:34; used to prepare construct number 1995). FIG. 9E shows the nucleotide sequence of IF-HT5*(-Mprot)-PDI.c (SEQ ID NO:35; used to prepare construct number 1996). FIG. 9F shows the nucleotide sequence of IF-HT6*(-Mprot)-PDI.c (SEQ ID NO:36 used to prepare construct number 1997). FIG. 9G shows the nucleotide sequence of IF-HT7*(-Mprot)-PDI.c (SEQ ID NO:37; used to prepare construct number 1998). FIG. 9H shows the nucleotide sequence of IF-HT8*(-Mprot)-PDI.c (SEQ ID NO:38; used to prepare construct number 1999). FIG. 9I shows a schematic representation of construct number 1992 comprising a plant kozak sequence (Kozak1) using SEQ ID NO:31 (FIG. 9A). Constructs 1993-1999 comprise the same features as construct 1992, except that each construct (1993-1999) comprises a modified plant Kozak sequence (Kozak1) as shown in FIGS. 9B to 9H (SEQ ID NOs: 32 to 38), respectively.

Figure 10C:
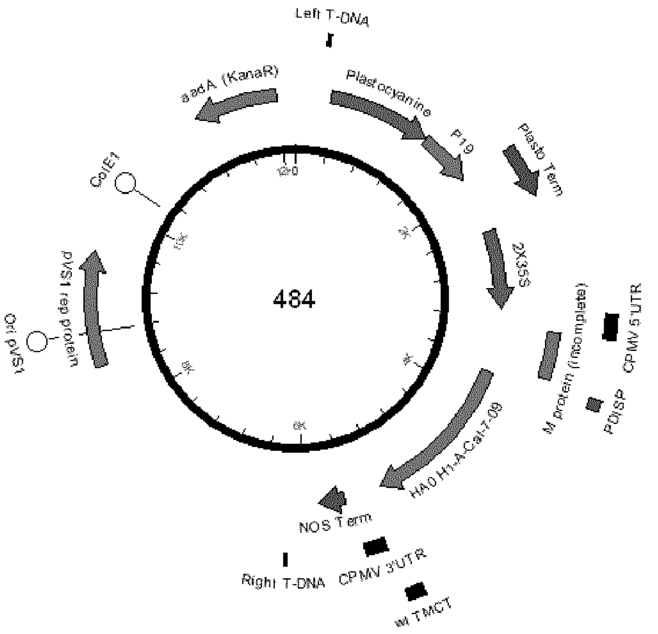
Figure 10D:
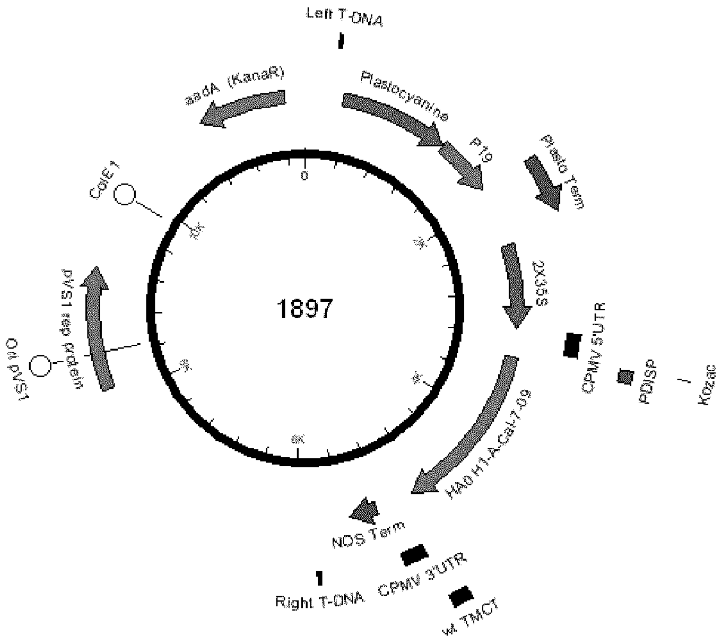

FIG. 10 shows sequence components used to prepare construct numbers 484 and 1897 (2X35S/CPMV HT PDISP/H1 California NOS and 2X35S/CPMV160+ PDISP/H1 California NOS, respectively; see Example 5). Construct number 484 incorporates a prior art CPMV-HT sequence (CMPV 5'UTR with mutated start codon at position 161 fused to a sequence encoding an incomplete M protein) and does not comprise a heterologous kozak sequence between the 5'UTR and the nucleotide sequence of interest (PDISP/H1 California). Construct number 1897 includes a CPMV 5'UTR comprising 160 nucleotides, a stuffer fragment (multiple cloning site), and a plant kozak sequence (this construct does not comprise a sequence encoding an incomplete M protein) and is an example of a CPMV160+(CPMVX+, where X=160) based construct. PDISP: protein disulfide isomerase signal peptide. NOS: nopaline synthase terminator. FIG. 10A shows the nucleotide sequence of PDISP/H1 California (SEQ ID NO: 39). FIG. 10B shows the amino acid sequence of PDISP/H1 California (SEQ ID NO: 40). FIG. 10C shows a schematic representation of construct number 484 (2X35S/CPMV HT; reference construct). FIG. 10D shows a schematic representation of construct number 1897 (2X35S/CPMV160+; a CPMVX+ based construct, where X=160).

Figure 11C:
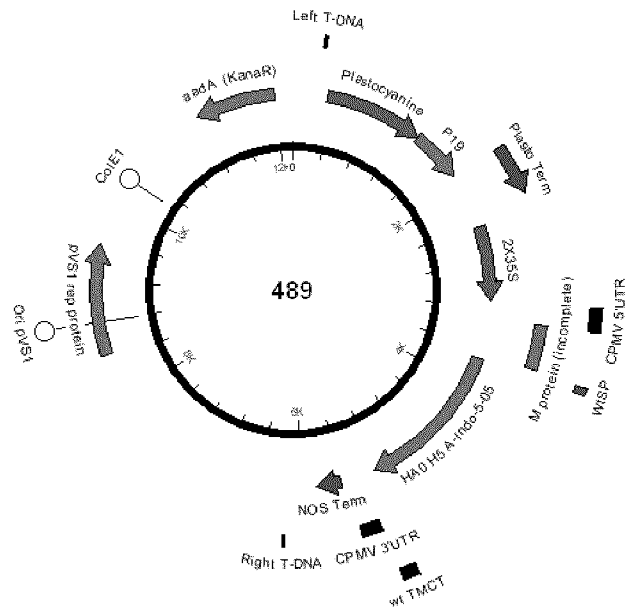
Figure 11D:
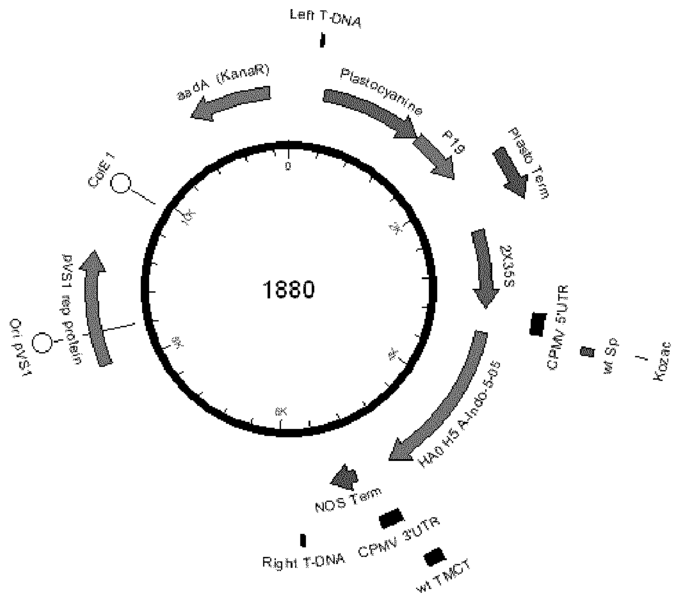
Figure 11E:
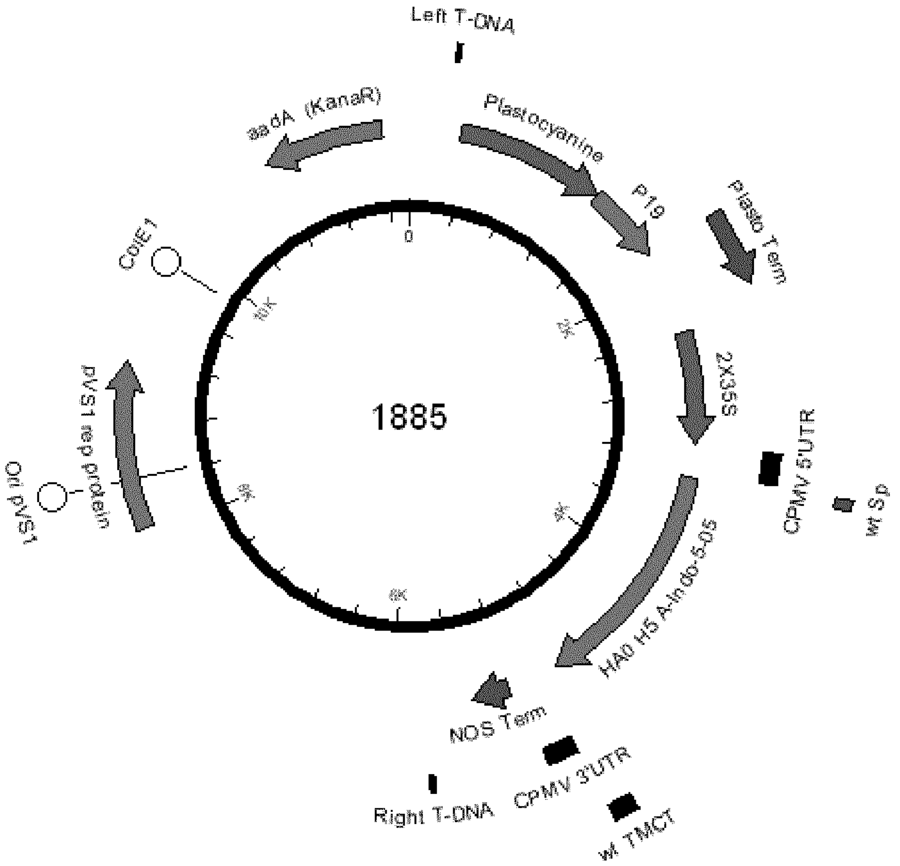

FIG. 11 shows sequence components used to prepare construct numbers 489, 1880 and 1885 (2X35S/CPMV HT H5 Indonesia NOS; CPMV160+H5 Indonesia NOS, and CPMV160 H5 Indonesia NOS, respectively; see Example 6). Construct number 489 incorporates a prior art CPMV-HT sequence (CMPV 5'UTR with mutated start codon at position 161 fused to a sequence encoding an incomplete M protein) and does not comprise a heterologous kozak sequence between the 5'UTR and the nucleotide sequence of interest (PDISP/H1 California). Construct number 1880 includes a CPMV 5'UTR comprising 160 nucleotides, a stuffer fragment (multiple cloning site), and a plant kozak sequence (this construct does not comprise a sequence encoding an incomplete M protein) and is an example of a CPMV160+(CPMVX+, where X=160) based construct. Construct number 1885 includes a CPMV 5'UTR comprising 160 nucleotides, and does not include a stuffer fragment (multiple cloning site), or a plant kozak sequence (this construct also does not comprise a sequence encoding an incomplete M protein) and is an example of a CPMV160 (CPMVX, where X=160) based construct. NOS: nopaline synthase terminator. FIG. 11A shows the nucleotide sequence of native H5 Indonesia (SEQ ID NO: 41). FIG. 11B shows the amino acid sequence of native H5 Indonesia (SEQ ID NO: 42). FIG. 11C shows a schematic representation of construct number 489 (2X35S/CPMV HT; reference construct). FIG. 11D shows a schematic representation of construct number 1880 (2X35S/CPMV160+; a CPMVX+ based construct, where X=160). FIG. 11E shows a schematic representation of construct number 1885 (2X35S/CPMV160, a CPMVX based construct, where X=160).

Figure 12C:
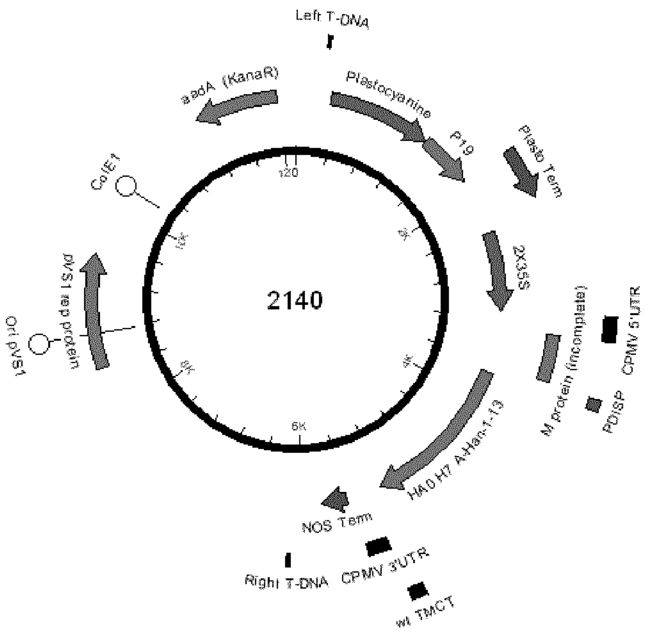
Figure 12D:
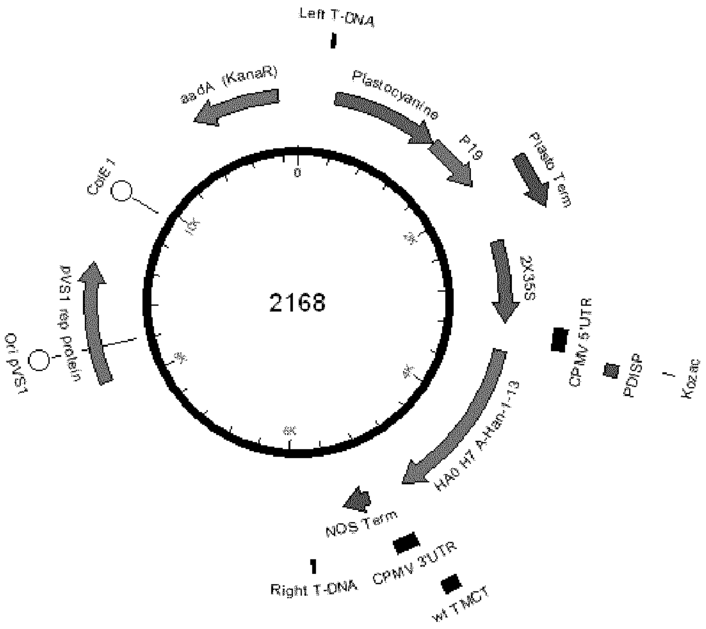

FIG. 12 shows sequence components used to prepare construct numbers 1240 and 2168 (2X35S/CPMV HT PDISP/H7 Hangzhou NOS and 2X35S/CPMV160+ PDISP/H7 Hangzhou NOS, respectively; see Example 7). Construct number 1240 incorporates a prior art CPMV-HT sequence (CMPV 5'UTR with mutated start codon at position 161 fused to a sequence encoding an incomplete M protein) and does not comprise a heterologous kozak sequence between the 5'UTR and the nucleotide sequence of interest (PDISP/H7 Hangzhou). Construct number 1897 includes a CPMV 5'UTR comprising 160 nucleotides, a stuffer fragment (multiple cloning site), and a plant kozak sequence (this construct does not comprise a sequence encoding an incomplete M protein) and is an example of a CPMV160+(CPMVX+, where X=160) based construct. PDISP: protein disulfide isomerase signal peptide. NOS: nopaline synthase terminator. FIG. 12A shows the nucleotide sequence of PDISP/H7 Hangzhou (SEQ ID NO: 43). FIG. 12B shows the amino acid sequence of PDISP/H7 Hangzhou (SEQ ID NO: 44). FIG. 12C shows a schematic representation of construct number 2140 (2X35S/CPMV HT; reference construct). FIG. 12D shows a schematic representation of construct number 2168 (2X35S/CPMV160+; a CPMVX+ based construct, where X=160).

Figure 13C:
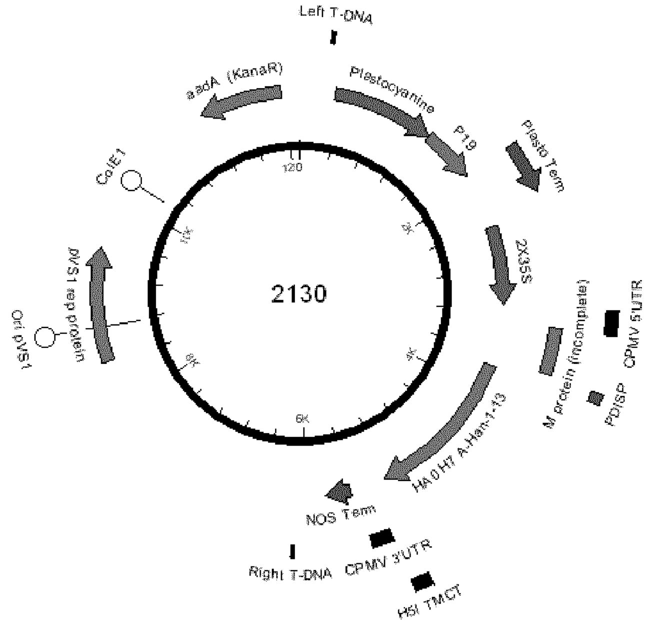
Figure 13D:
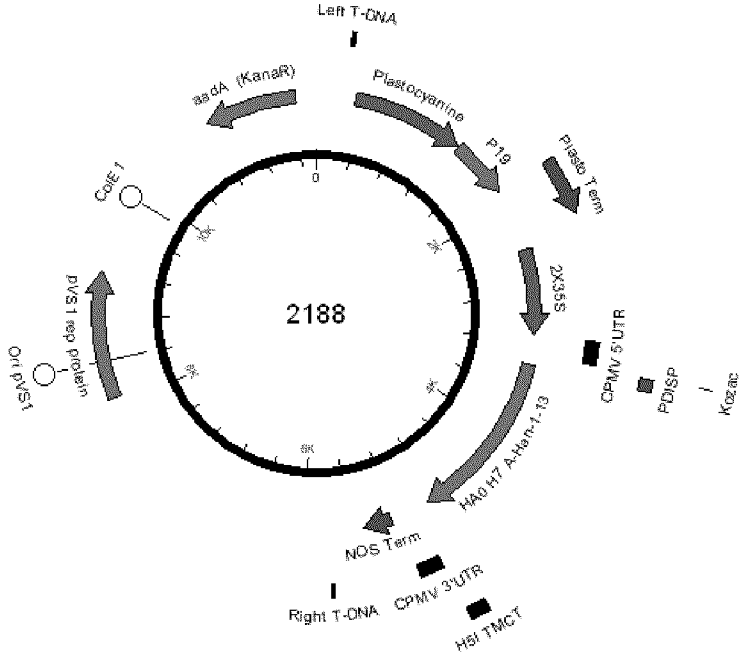

FIG. 13 shows sequence components used to prepare construct numbers 2130 and 2188 (2X35S/CPMV HT PDISP/H7 Hangzhou+H5 Indonesia TMCT NOS and 2X35S/CPMV160+ PDISP/H7 Hangzhou+H5 Indonesia TMCT NOS, respectively; see Example 8). Construct number 2130 incorporates a prior art CPMV-HT sequence (CMPV 5'UTR with mutated start codon at position 161 fused to a sequence encoding an incomplete M protein) and does not comprise a heterologous kozak sequence between the 5'UTR and the nucleotide sequence of interest (PDISP/H7 Hangzhou+H5 Indonesia TMCT). Construct number 1897 includes a CPMV 5'UTR comprising 160 nucleotides, a stuffer fragment (multiple cloning site), and a plant kozak sequence (this construct does not comprise a sequence encoding an incomplete M protein) and is an example of a CPMV160+(CPMVX+, where X=160) based construct. PDISP: protein disulfide isomerase signal peptide; NOS: nopaline synthase terminator; TMCT: transmembrane domain cytoplasmic tail. FIG. 13A shows the nucleotide sequence of PDISP/H7 Hangzhou+H5 Indonesia TMCT (SEQ ID NO: 45). FIG. 13B shows the amino acid sequence of PDISP/H7 Hangzhou+H5 Indonesia TMCT (SEQ ID NO: 46). FIG. 13C shows a schematic representation of construct number 2130 (2X35S/CPMV HT; reference construct). FIG. 13D shows a schematic representation of construct number 2188 (2X35S/CPMV160+; a CPMVX+ based construct, where X=160).

Figure 14C:
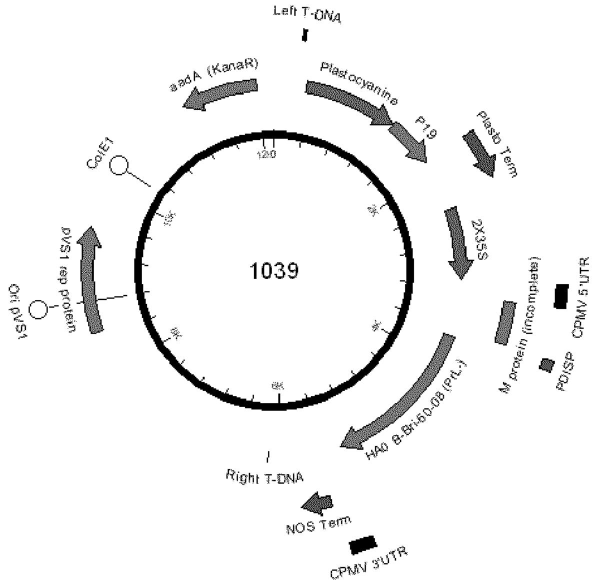
Figure 14D:
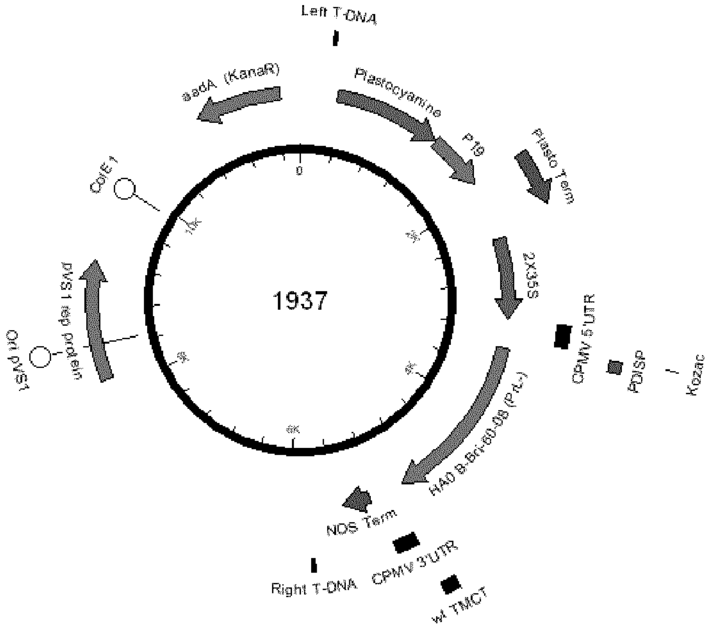

FIG. 14 shows sequence components used to prepare construct numbers 1039 and 1937 (2X35S/CPMV HT PDISP/HA B Brisbane (PrL-) NOS and 2X35S/CPMV160+ PDISP/HA B Brisbane (PrL-) NOS, respectively; see Example 9). Construct number 1039 incorporates a prior art CPMV-HT sequence (CMPV 5'UTR with mutated start codon at position 161 fused to a sequence encoding an incomplete M protein) and does not comprise a heterologous kozak sequence between the 5'UTR and the nucleotide sequence of interest (PDISP/HA B Brisbane (PrL-)). Construct number 1937 includes a CPMV 5'UTR comprising 160 nucleotides, a stuffer fragment (multiple cloning site), and a plant kozak sequence (this construct does not comprise a sequence encoding an incomplete M protein) and is an example of a CPMV160+(CPMVX+, where X=160) based construct. PDISP: protein disulfide isomerase signal peptide; NOS: nopaline synthase terminator; PrL-: deleted proteolytic loop. FIG. 14A shows the nucleotide sequence of PDISP/HA B Brisbane (PrL-) (SEQ ID NO: 47). FIG. 14B shows the amino acid sequence of PDISP/HA B Brisbane (PrL-) (SEQ ID NO: 48). FIG. 14C shows a schematic representation of construct number 1039 (2X35S/CPMV HT; reference construct). FIG. 14D shows a schematic representation of construct number 1937 (2X35S/CPMV160+; a CPMVX+ based construct, where X=160).

Figure 15C:
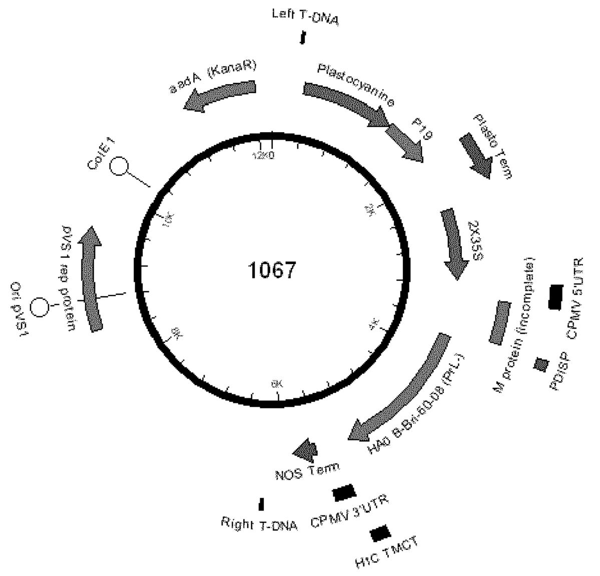
Figure 15D:
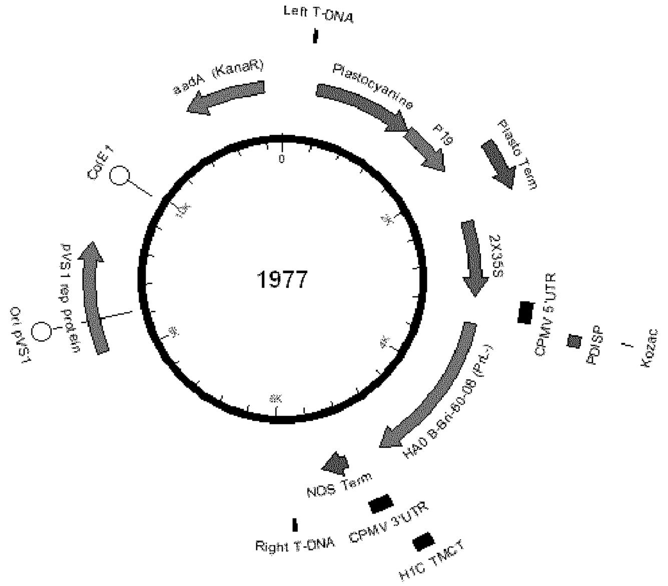

FIG. 15 shows sequence components used to prepare construct numbers 1067 and 1977 (2X35S/CPMV HT PDISP/HA B Brisbane (Prl-)+H1 California TMCT NOS and 2X35S/CPMV160+ PDISP/HA B Brisbane (PrL-)+H1 California TMCT NOS, respectively; see Example 10). Construct number 1067 incorporates a prior art CPMV-HT sequence (CMPV 5'UTR with mutated start codon at position 161 fused to a sequence encoding an incomplete M protein) and does not comprise a heterologous kozak sequence between the 5'UTR and the nucleotide sequence of interest (PDISP/HA B Brisbane (PrL-)+H1 California TMCT). Construct number 1977 includes a CPMV 5'UTR comprising 160 nucleotides, a stuffer fragment (multiple cloning site), and a plant kozak sequence (this construct does not comprise a sequence encoding an incomplete M protein) and is an example of a CPMV160+(CPMVX+, where X=160) based construct. PDISP: protein disulfide isomerase signal peptide; NOS: nopaline synthase terminator; PrL-: deleted proteolytic loop; TMCT: transmembrane domain cytoplasmic tail. FIG. 15A shows the nucleotide sequence of PDISP/HA B Brisbane (PrL-)+H1 California TMCT (SEQ ID NO: 49). FIG. 15B shows the amino acid sequence of PDISP/HA B Brisbane (PrL-)+H1 California TMCT (SEQ ID NO: 50). FIG. 15C shows a schematic representation of construct number 1067 (2X35S/CPMV HT; reference construct). FIG. 15D shows a schematic representation of construct number 1977 (2X35S/CPMV160+; a CPMVX+ based construct, where X=160).

Figure 16C:
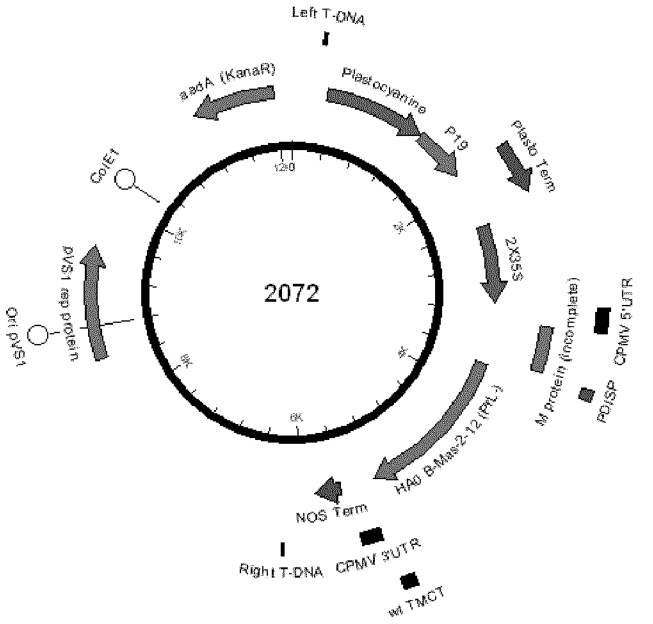
Figure 16D:
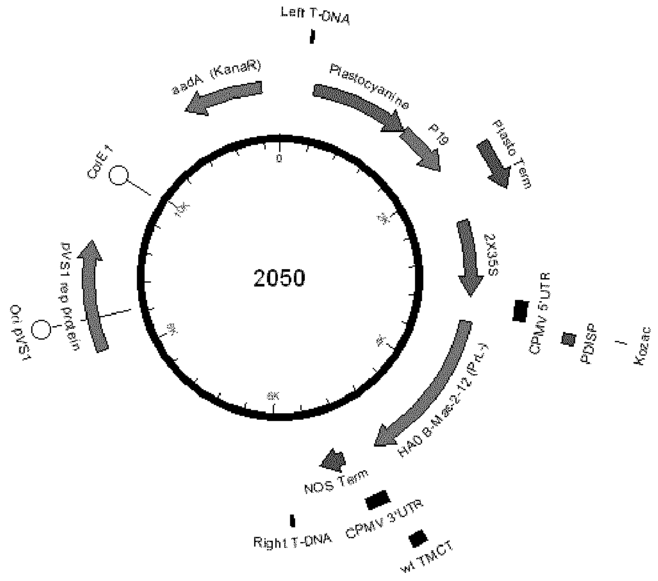

FIG. 16 shows sequence components used to prepare construct numbers 2072 and 2050 (2X35S/CPMV HT PDISP/HA B Massachusetts (PrL-) NOS and 2X35S/CPMV160+ PDISP/HA B Massachusetts (PrL-) NOS, respectively; see Example 11). Construct number 2072 incorporates a prior art CPMV-HT sequence (CMPV 5'UTR with mutated start codon at position 161 fused to a sequence encoding an incomplete M protein) and does not comprise a heterologous kozak sequence between the 5'UTR and the nucleotide sequence of interest (PDISP/HA B Massachusetts (PrL-)). Construct number 2050 includes a CPMV 5'UTR comprising 160 nucleotides, a stuffer fragment (multiple cloning site), and a plant kozak sequence (this construct does not comprise a sequence encoding an incomplete M protein) and is an example of a CPMV160+(CPMVX+, where X=160) based construct. PDISP: protein disulfide isomerase signal peptide; NOS: nopaline synthase terminator; PrL-: deleted proteolytic loop. FIG. 16A shows the nucleotide sequence of PDISP/HA B Massachusetts (PrL-) (SEQ ID NO: 51). FIG. 16B shows the amino acid sequence of PDISP/HA B Massachusetts (PrL-) (SEQ ID NO: 52). FIG. 16C shows a schematic representation of construct number 2072 (2X35S/CPMV HT; reference construct). FIG. 16D shows a schematic representation of construct number 2050 (2X35S/CPMV160+; a CPMVX+ based construct, where X=160).

Figure 17C:
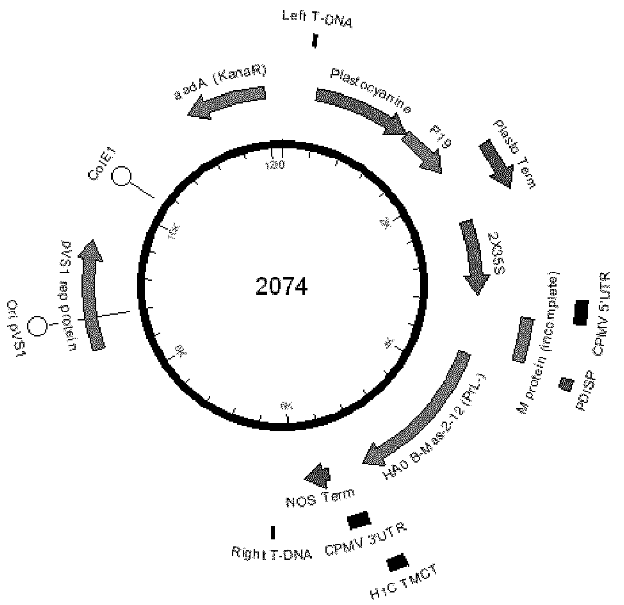
Figure 17D:
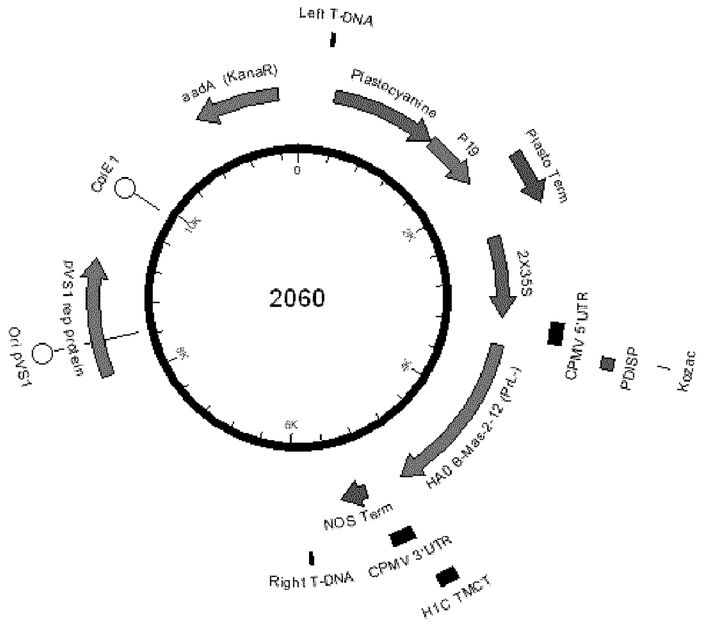

FIG. 17 shows sequence components used to prepare construct numbers 2074 and 2060 (2X35S/CPMV HT PDISP/HA B Massachusetts (PrL-)+H1 California TMCT NOS and 2X35S/CPMV160+ PDISP/HA B Massachusetts (PrL-)+H1 California TMCT NOS, respectively; see Example 12). Construct number 2074 incorporates a prior art CPMV-HT sequence (CMPV 5'UTR with mutated start codon at position 161 fused to a sequence encoding an incomplete M protein) and does not comprise a heterologous kozak sequence between the 5'UTR and the nucleotide sequence of interest (PDISP/HA B Massachusetts (PrL-)+H1 California TMCT). Construct number 2060 includes a CPMV 5'UTR comprising 160 nucleotides, a staffer fragment (multiple cloning site), and a plant kozak sequence (this construct does not comprise a sequence encoding an incomplete M protein) and is an example of a CPMV160+(CPMVX+, where X=160) based construct. PDISP: protein disulfide isomerase signal peptide; NOS: nopaline synthase terminator; PrL-: deleted proteolytic loop; TMCT: transmembrane domain cytoplasmic tail. FIG. 17A shows the nucleotide sequence of PDISP/HA B Massachusetts (PrL-)+H1 California TMCT (SEQ ID NO: 53). FIG. 17B shows the amino acid sequence of PDISP/HA B Massachusetts (PrL-)+H1 California TMCT (SEQ ID NO: 54). FIG. 17C shows a schematic representation of construct number 2074 (2X35S/CPMV HT; reference construct). FIG. 17D shows a schematic representation of construct number 2060 (2X35S/CPMV160+; a CPMVX+ based construct, where X=160).

Figure 18C:
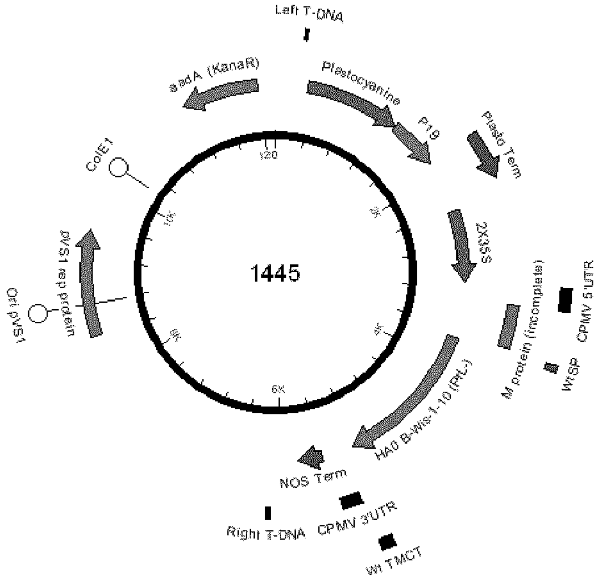
Figure 18D:
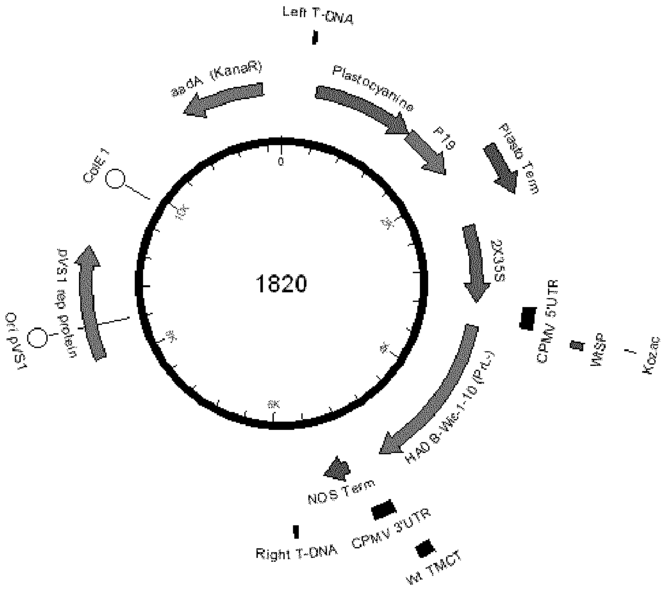
Figure 18E:
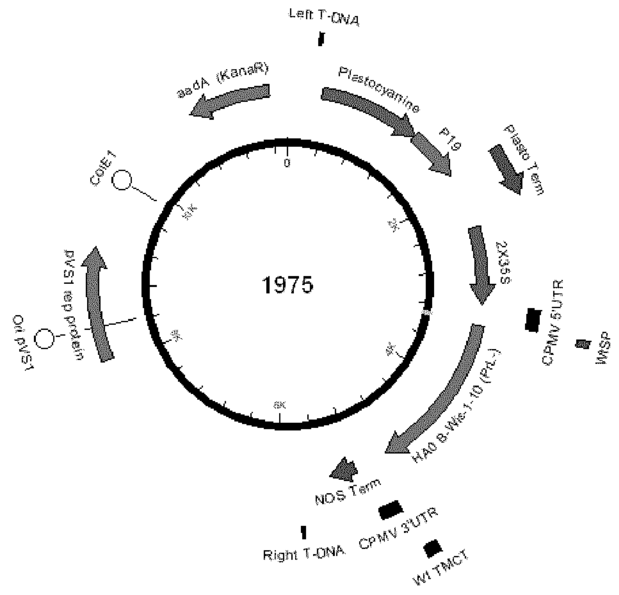

FIG. 18 shows sequence components used to prepare construct numbers 1445, 1820 and 1975 (2X35S/CPMV HT HA B Wisconsin (PrL-) NOS, 2X35S/CPMV160+HA B Wisconsin (PrL-) NOS and 2X35S/CPMV160 HA B Wisconsin (PrL-) NOS, respectively; see Example 13). Construct number 1445 incorporates a prior art CPMV-HT sequence (CMPV 5'UTR with mutated start codon at position 161 fused to a sequence encoding an incomplete M protein) and does not comprise a heterologous kozak sequence between the 5'UTR and the nucleotide sequence of interest (HA B Wisconsin (PrL-)). Construct number 1820 includes a CPMV 5'UTR comprising 160 nucleotides, a stuffer fragment (multiple cloning site), and a plant kozak sequence (this construct does not comprise a sequence encoding an incomplete M protein) and is an example of a CPMV160+(CPMVX+, where X=160) based construct. Construct number 1975 includes a CPMV 5'UTR comprising 160 nucleotides, and does not include a stuffer fragment (multiple cloning site), or a plant kozak sequence (this construct also does not comprise a sequence encoding an incomplete M protein) and is an example of a "CPMV160" (CPMVX) based construct. PrL-: deleted proteolytic loop; NOS: nopaline synthase terminator. FIG. 18A shows the nucleotide sequence of HA B Wisconsin (PrL-) (SEQ ID NO: 55). FIG. 18B shows the amino acid sequence of HA B Wisconsin (PrL-) (SEQ ID NO: 56). FIG. 18C shows a schematic representation of construct number 1445 (2X35S/CPMV HT; reference construct). FIG. 18D shows a schematic representation of construct number 1820 (2X35S/CPMV160+; a CPMVX+ based construct). FIG. 18E shows a schematic representation of construct number 1975 (2X35S/CPMV160; a CPMVX based construct, where X=160).

Figure 19C:
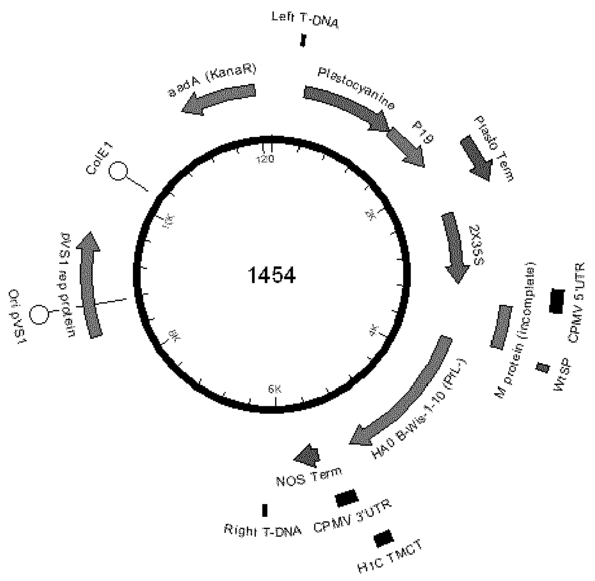
Figure 19D:
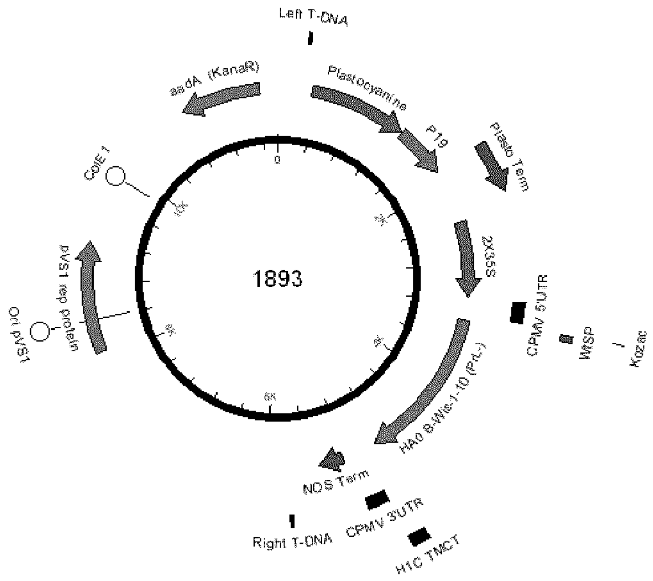

FIG. 19 shows sequence components used to prepare construct numbers 1454 and 1893 (2X35S/CPMV HT HA B Wisconsin (PrL-)+H1 California TMCT NOS and 2X35S/CPMV160+HA B Wisconsin (PrL-)+H1 California TMCT NOS, respectively; see Example 14). Construct number 1454 incorporates a prior art CPMV-HT sequence (CMPV 5'UTR with mutated start codon at position 161 fused to a sequence encoding an incomplete M protein) and does not comprise a heterologous kozak sequence between the 5'UTR and the nucleotide sequence of interest (HA B Wisconsin (PrL-)+H1 California TMCT). Construct number 1893 includes a CPMV 5'UTR comprising 160 nucleotides, a stuffer fragment (multiple cloning site), and a plant kozak sequence (this construct does not comprise a sequence encoding an incomplete M protein) and is an example of a CPMV160+(CPMVX+, where X=160) based construct. NOS: nopaline synthase terminator; PrL-: deleted proteolytic loop; TMCT: transmembrane domain cytoplasmic tail. FIG. 19A shows the nucleotide sequence of HA B Wisconsin (PrL-)+H1 California TMCT (SEQ ID NO: 57). FIG. 19B shows the amino acid sequence of PDISP/HA B Wisconsin (PrL-)+H1 California TMCT (SEQ ID NO: 58). FIG. 19C shows a schematic representation of construct number 1454 (2X35S/CPMV HT; reference construct). FIG. 19D shows a schematic representation of construct number 1893 (2X35S/CPMV160+; a CPMVX+ based construct, where X=160).

Figure 20C:
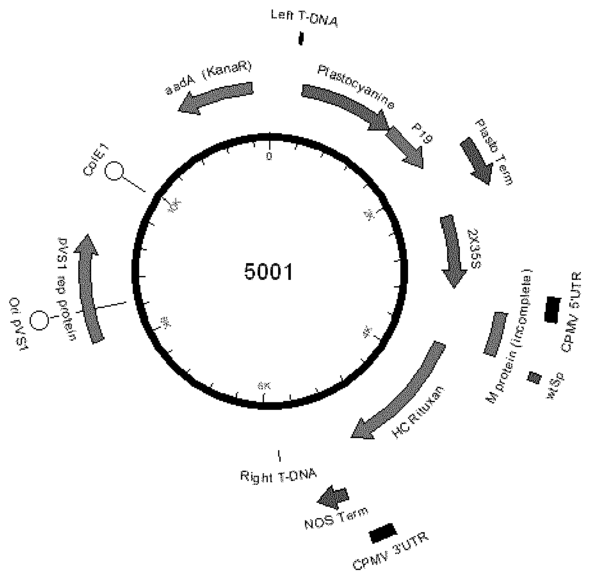
Figure 20D:
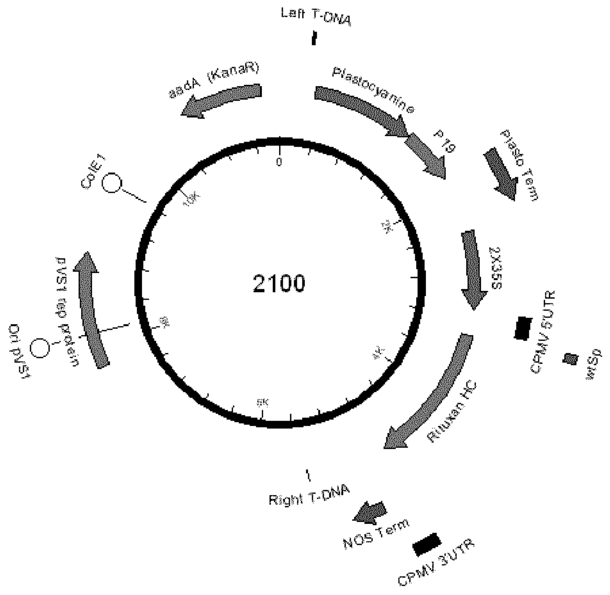

FIG. 20 shows sequence components used to prepare construct numbers 5001 and 2100 (2X35S/CPMV HT HC rituximab (Rituxan) NOS and 2X35S/CPMV160+HC rituximab (Rituxan) NOS, respectively; see Example 15). Construct number 5001 incorporates a prior art CPMV-HT sequence (CMPV 5'UTR with mutated start codon at position 161 fused to a sequence encoding an incomplete M protein) and does not comprise a heterologous kozak sequence between the 5'UTR and the nucleotide sequence of interest (HC rituximab (Rituxan)). Construct number 2100 includes a CPMV 5'UTR comprising 160 nucleotides, a stuffer fragment (multiple cloning site), and a plant kozak sequence (this construct does not comprise a sequence encoding an incomplete M protein) and is an example of a CPMV160+(CPMVX+, where X=160) based construct. HC: heavy chain; NOS: nopaline synthase terminator. FIG. 20A shows the nucleotide sequence of HC rituximab (Rituxan; SEQ ID NO: 59). FIG. 20B shows the amino acid sequence of HC rituximab (Rituxan; SEQ ID NO: 60). FIG. 20C shows a schematic representation of construct number 5001 (2X35S/CPMV HT; reference construct). FIG. 20D shows a schematic representation of construct number 2100 (2X35S/CPMV160+; a CPMVX+ based construct, where X=160).

Figure 21C:
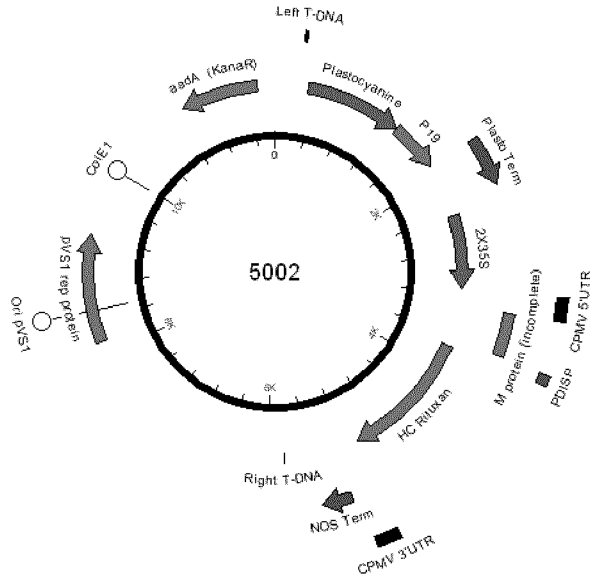
Figure 21D:
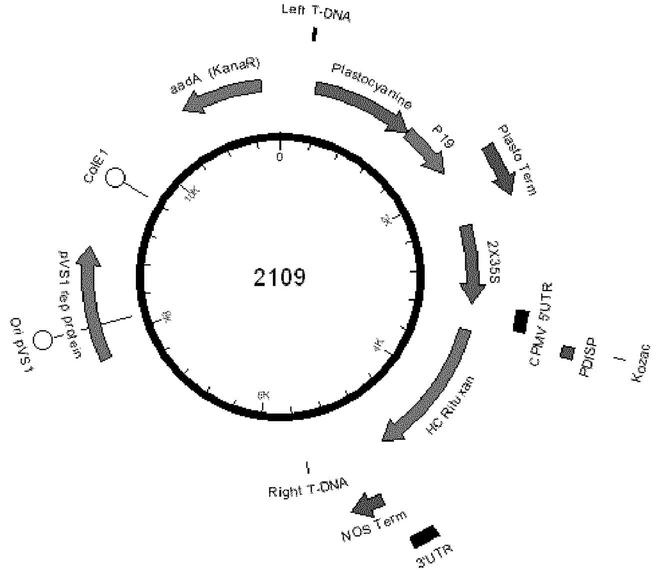

FIG. 21 shows sequence components used to prepare construct numbers 5002 and 2109 (2X35S/CPMV HT PDISP/HC rituximab (Rituxan) NOS and 2X35S/CPMV160+ PDISP/HC rituximab (Rituxan) NOS, respectively; see Example 16). Construct number 5001 incorporates a prior art CPMV-HT sequence (CMPV 5'UTR with mutated start codon at position 161 fused to a sequence encoding an incomplete M protein) and does not comprise a heterologous kozak sequence between the 5'UTR and the nucleotide sequence of interest (PDISP/HC Rituzan). Construct number 2100 includes a CPMV 5'UTR comprising 160 nucleotides, a stuffer fragment (multiple cloning site), and a plant kozak sequence (this construct does not comprise a sequence encoding an incomplete M protein) and is an example of a CPMV160+(CPMVX+, where X=160) based construct. PDISP: protein disulfide isomerase signal peptide; HC: heavy chain; NOS: nopaline synthase terminator. FIG. 21A shows the nucleotide sequence of PDISP/HC rituximab (Rituxan; SEQ ID NO: 61). FIG. 21B shows the amino acid sequence of PSISP/HC rituximab (Rituxan; SEQ ID NO: 62). FIG. 21C shows a schematic representation of construct number 5002 (2X35S/CPMV HT; reference construct). FIG. 21D shows a schematic representation of construct number 2109 (2X35S/CPMV160+; a CPMVX+ based construct, where X=160).

Figure 22C:
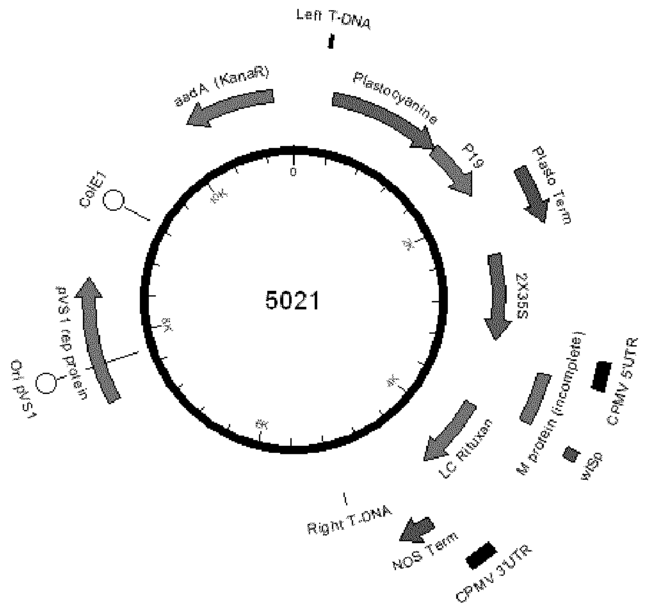
Figure 22D:
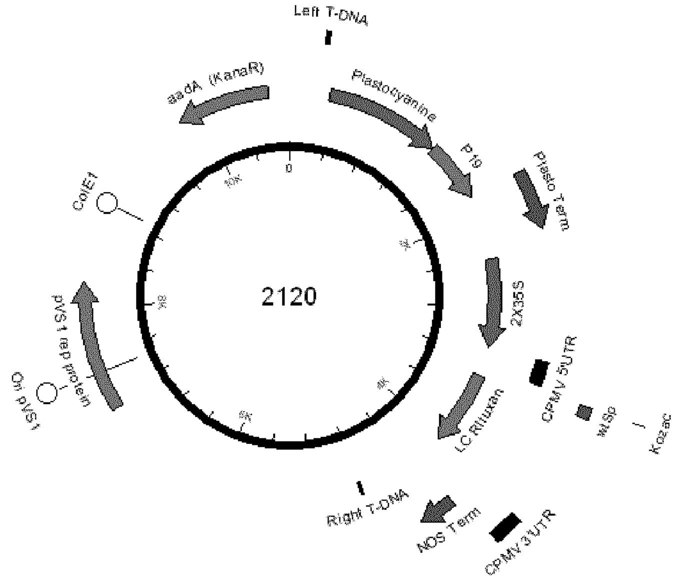

FIG. 22 shows sequence components used to prepare construct numbers 5021 and 2120 (2X35S/CPMV HT LC rituximab (Rituxan) NOS and 2X35S/CPMV160+ LC rituximab (Rituxan) NOS, respectively; see Example 17). Construct number 5021 incorporates a prior art CPMV-HT sequence (CMPV 5'UTR with mutated start codon at position 161 fused to a sequence encoding an incomplete M protein) and does not comprise a heterologous kozak sequence between the 5'UTR and the nucleotide sequence of interest (LC rituximab (Rituxan)). Construct number 2120 includes a CPMV 5'UTR comprising 160 nucleotides, a stuffer fragment (multiple cloning site), and a plant kozak sequence (this construct does not comprise a sequence encoding an incomplete M protein) and is an example of a CPMV160+ (CPMVX+, where X=160) based construct. LC: light chain; NOS: nopaline synthase terminator. FIG. 22A shows the nucleotide sequence of LC rituximab (Rituxan; SEQ ID NO: 63). FIG. 22B shows the amino acid sequence of LC rituximab (Rituxan; SEQ ID NO: 64). FIG. 22C shows a schematic representation of construct number 5021 (2X35S/CPMV HT; reference construct). FIG. 22D shows a schematic representation of construct number 2120 (2X35S/CPMV160+; a CPMVX+ based construct, where X=160).

Figure 23C:
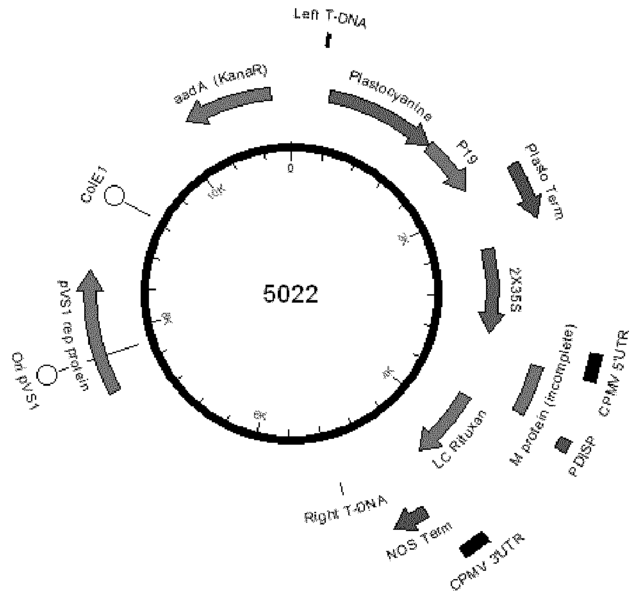
Figure 23D:
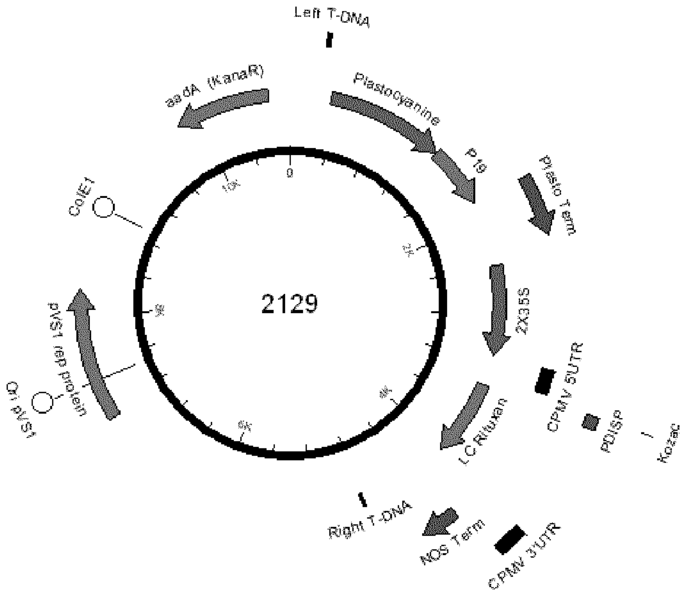

FIG. 23 shows sequence components used to prepare construct numbers 5022 and 2129 (2X35S/CPMV HT PDISP/LC rituximab (Rituxan) NOS and 2X35S/CPMV160+ PDISP/LC rituximab (Rituxan) NOS, respectively; see Example 18). Construct number 5001 incorporates a prior art CPMV-HT sequence (CMPV 5'UTR with mutated start codon at position 161 fused to a sequence encoding an incomplete M protein) and does not comprise a heterologous kozak sequence between the 5'UTR and the nucleotide sequence of interest (PDISP/LC rituximab (Rituxan)). Construct number 2100 includes a CPMV 5'UTR comprising 160 nucleotides, a stuffer fragment (multiple cloning site), and a plant kozak sequence (this construct does not comprise a sequence encoding an incomplete M protein) and is an example of a CPMV160+ (CPMVX+, where X=160) based construct. PDISP: protein disulfide isomerase signal peptide; HC: heavy chain; NOS: nopaline synthase terminator. FIG. 23A shows the nucleotide sequence of PDISP/LC rituximab (Rituxan; SEQ ID NO: 65). FIG. 23B shows the amino acid sequence of PSISP/LC rituximab (Rituxan; SEQ ID NO: 66). FIG. 23C shows a schematic representation of construct number 5022 (2X35S/CPMV HT; reference construct). FIG. 23D shows a schematic representation of construct number 2129 (2X35S/CPMV160+; a CPMVX+ based construct, where X=160).

DETAILED DESCRIPTION

The present invention relates to the expression of proteins of interest in plants. The present invention also provides methods and compositions for the production of proteins of interest in plants.

In the description that follows, a number of terms are used extensively, the following definitions are provided to facilitate understanding of various aspects of the invention. Use of examples in the specification, including examples of terms, is for illustrative purposes only and is not intended to limit the scope and meaning of the embodiments of the invention herein.

As used herein, the use of the word "a" or "an" when used herein in conjunction with the term "comprising" may mean "one," but it is also consistent with the meaning of "one or more," "at least one" and "one or more than one". The term "about" refers to an approximately +1-10% variation from a given value. The term "plurality", means more than one, for example, two or more, three or more, four or more, and the like.

The present invention provides an expression enhancer comprising a CPMV 5' untranslated region (UTR), "CPMVX", comprising X nucleotides of SEQ ID NO:1, where X=160, 155, 150, or 114 of SEQ ID NO:1, or a sequence that comprises between 80% to 100% sequence similarity with CPMVX, where X=160, 155, 150, or 114 of SEQ ID NO:1. This expression enhancer is generally referred to as CPMVX (see FIG. 1A).

The CPMVX enhancer sequence may further be fused to a stuffer sequence, wherein the CMPVX comprises X nucleotides of SEQ ID NO:1, where X=160, 155, 150, or 114 of SEQ ID NO:1, or a sequence that comprises between 80 to 100% sequence similarity with CPMVX, where X=160, 155, 150, or 114 of SEQ ID NO:1, and the stuffer sequence comprises from 1-100 nucleotides fused to the 3' end of the CMPVX sequence. For example, the stuffer sequence may comprise from about 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, or 100 nucleotides, or any number of nucleotides therebetween.

If the CMPVX sequence comprises a stuffer fragment, then this expression enhancer may be referred to as CPMVX+ (see FIG. 1A), where X=160, 155, 150, 114 of SEQ ID NO:1, it may also be referred to as CMPVX comprising a stuffer sequence, or it may be referred to as CPMV160+; CPMV155+; CPMV150+; CPMV114+, when X-160, 155, 150, or 114, respectively. Constructs comprising CPMVX that do not comprise a stuffer sequence may be termed CPMVX+, where X=160, 155, 150, 114 of SEQ ID NO:1, and where the stuffer sequence is of 0 nucleotides in length.

The stuffer sequence may be modified by truncation, deletion, or replacement of the native CMPV5'UTR sequence that is located 3' to nucleotide 160. The modified stuffer sequence may be removed, replaced, truncated or shortened when compared to the initial or unmodified (i.e. native) stuffer sequence associated with the 5'UTR (as described in Sainsbury F., and Lomonossoff G. P., 2008, Plant Physiol. 148: pp. 1212-1218). The stuffer sequence may comprise a one or more restriction sites (polylinker, multiple cloning site, one or more cloning sites), one or more plant kozak sequences, one or more linker sequences, one or more recombination sites, or a combination thereof. For example, which is not to be considered limiting, a stuffer sequence may comprise in series, a multiple cloning site of a desired length fused to a plant kozak sequence. The stuffer sequence does not comprise a nucleotide sequence from the native 5'UTR sequence that is positioned 3' to nucleotide 160 of the native CPMV 5'UTR, for example nucleotides 161 to 512 as shown in FIG. 1 of Sainsbury F., and Lomonossoff G. P. (2008, Plant Physiol. 148: pp. 1212-1218; which is incorporated herein by reference), or nucleotides 161-509 of SEQ ID NO:4. That is, the incomplete M protein present in the prior art CPMV HT sequence (FIG. 1; of Sainsbury F., and Lomonossoff G. P., 2008) is removed from the 5'UTR in the present invention.

The expression enhancer CPMVX, or CPMVX+, may be operatively linked at the 5' end of the enhancer sequence with a regulatory region that is active in a plant, and operatively linked to a nucleotide sequence of interest at the 3' end of the expression enhancer (FIG. 1A), in order to drive expression of the nucleotide sequence of interest within a plant host.

Expression systems to produce one or more proteins of interest in a plant using either CMPVX or CPMVX+ are also provided. The expression systems described herein comprise an expression cassette comprising CPMVX, or a sequence that comprises 80% sequence similarity with CPMVX, and optionally, a stuffer sequence fused to CMPVX (CPMVX+). The expression cassette comprising CMPVX or CMPVX+, may further comprise a regulatory region that is active in a plant that is operatively linked to the 5' end of the expression enhancer. A nucleotide sequence of interest may be operatively linked to the 3' end of the expression cassette so that when introduced within a plant, expression of the nucleotide sequence of interest within a plant host is achieved.

Plant cells, plant tissues, whole plants, inoculum, nucleic acids, constructs comprising nucleotide sequences of interest encoding proteins of interest, expression cassettes or expression systems comprising CPMVX or CPMVX+ as described herein, and methods of expressing a protein of interest in plants are also provided.

Figure 1A:
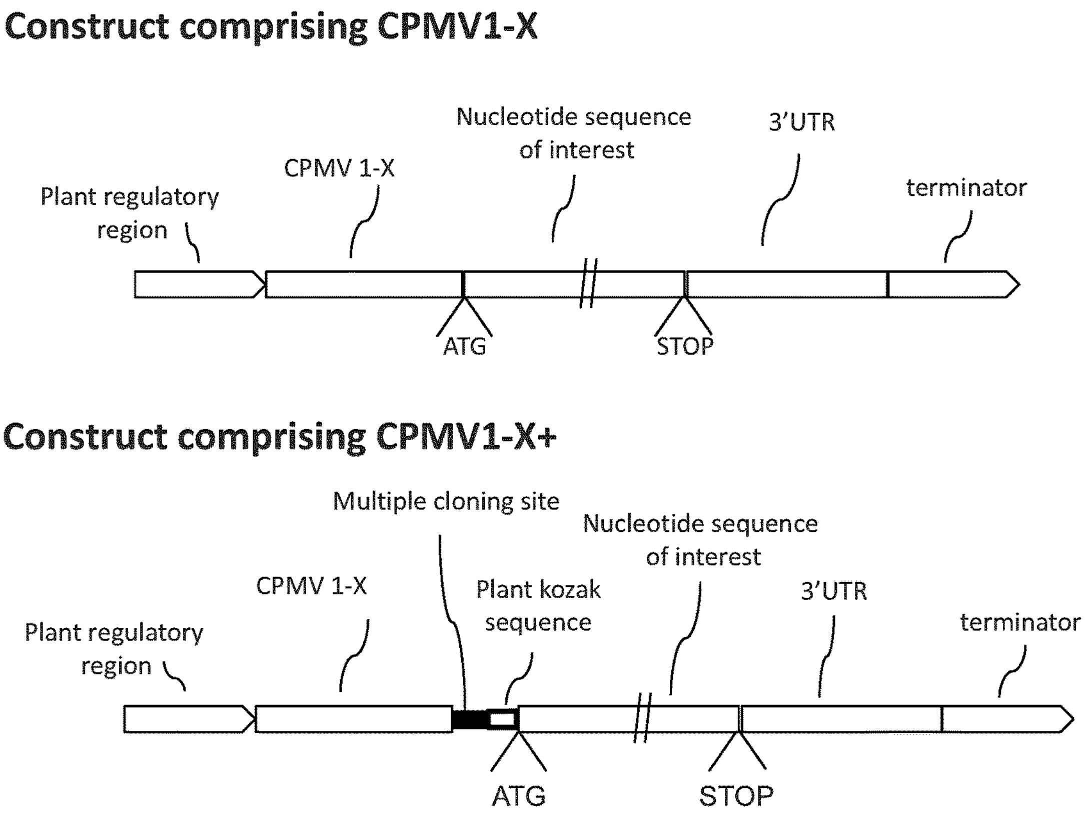
FIG. 1A shows a general schematic of an example of several enhancer sequences, CPMVX, and CPMVX+ (comprising CPMVX, and a stuffer fragment, which in this non-limiting example, comprises a multiple cloning site and plant kozak sequence), as described herein. CPMCX and CPMVX+ are each shown as operatively linked to plant regulatory region at their 5' ends, and at their 3' ends, in series, a nucleotide sequence of interest (including an ATG initiation site and STOP site), a 3'UTR, and a terminator sequence. An example of construct CPMVX as described herein, is CPMV160. An example of construct CPMVX+ as described herein, is CPMV160+.
Figure 2:
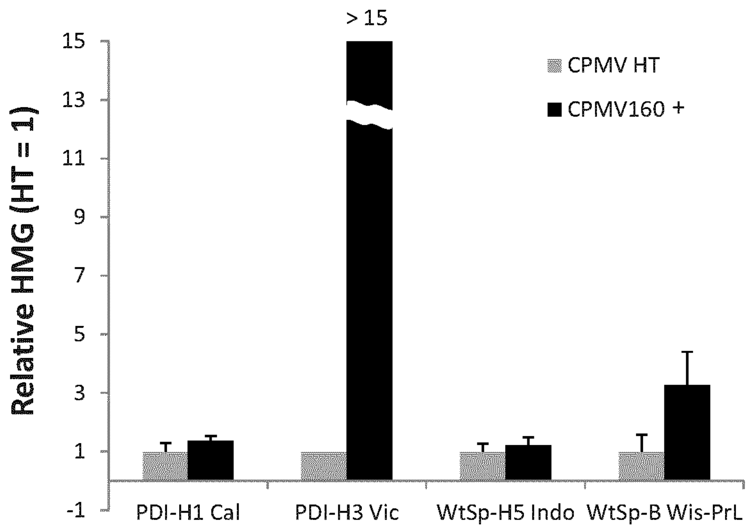
FIG. 2 shows the relative hemagglutination titre (HMG) in crude protein extracts of proteins produced in plants comprising CPMV-HT (prior art) expression constructs, and CPMV160+ based expression constructs, operatively linked with a nucleotide sequence of interest. Data for the expression of HA from H1 A/California/07/2009 with a PDI signal peptide (PDI-H1 Cal; construct number 484 5' UTR: CPMV HT; and construct number 1897, 5'UTR: CPMV160+; see Example 5), H3 A/Victoria/361/2011 with a PDI signal peptide (PDI-H3 Vic; construct number 1391, 5'UTR.

With reference to FIGS. 1A, 1B and 1C, non-limiting examples of an expression enhancer comprising a CPMV 5' UTR (CPMVX) sequence comprising nucleotides from X of SEQ ID NO:1, where X=160, 155, 150, or 114 of SEQ ID NO:1 are provided. The expression enhancer CMPVX may also be referred to as CPMV160; CPMV155; CPMV150; CPMV114, when X-160, 155, 150, or 114, respectively.

The nucleotide sequence of interest may be fused (operatively linked) to the enhancer sequence comprising a plant regulatory region, using a variety of approaches. For example, which are not to be considered limiting:

1) A nucleotide sequence of interest encoding a protein of interest may be fused to the 3' end of the expression enhancer immediately after the 5'UTR sequence, for example CPMVX, where X=160, 155, 150, 114 nucleotides of SEQ ID NO: 1. In this example, the nucleotide sequence of interest is fused to the 5'UTR without a multiple cloning site, and the nucleotide sequence of interest may include at its 5' end a plant kozak sequence immediately upstream from an ATG initiation site of the nucleotide sequence of interest (see FIG. 1B). If X=160 (i.e. CPMV160), then a nucleotide sequence of interest that is operatively linked to CPMV160 may not require a plant kozak sequence fused to its 5' end, as nucleotides 150-160, or 155-160, of SEQ ID NO:1 comprise a kozak-like sequence. However, a plant kozak sequence may be included in constructs comprising CPMV160 if desired (see FIG. 1B: "+/− plant kozak"). If X-155, 150, or 114, then including a plant kozak sequence that is fused to the 5' end of the nucleotide sequence of interest in constructs comprising CPMV155, CPMV150, or CPMV114 is recommended for optimal expression of the nucleotide sequence of interest.

2) The nucleotide sequence of interest, may be fused to a CMPVX+ expression enhancer (where X=160, 155, 150, 114 of SEQ ID NO:1) that comprises a plant kozak sequence at the 3' end of the expression enhancer, so that the nucleotide sequence of interest is positioned immediately after the plank kozak sequence. In this example, the nucleotide sequence of interest that is fused to CPMVX+ would not include a multiple cloning site or plant kozak sequence (the resulting construct would. be analogous to those as presented in FIG. 1B).

3) The nucleotide sequence of interest may be fused to a CPMVX+ expression enhancer (where X=160, 155, 150, 114 of SEQ ID NO:1), comprising a multiple cloning site (MCS) at the 3' end of the expression enhancer, using the multiple cloning site. In this example, the nucleotide sequence of interest may include at its 5' end a corresponding sequence to permit fusion with the multiple cloning sire of the expression enhancer, and a plant kozak sequence immediately upstream from the ATG initiation site of the nucleotide sequence of interest (see FIG. 1C).

The overall result using any of the above methods, is a construct (or expression cassette) comprising a plant regulatory region in operative association (operatively linked) with a CPMV 5'UTR sequence comprising nucleotides X, where X=160, 155, 150, 114 of SEQ ID NO:1 (or an enhancer sequence that comprises 80% sequence similarity with CPMV 5'UTR sequence), the 3' end of the CPMV 5'UTR sequence is fused to the 5' end of a plant kozak sequence, the 3' end of the plant kozak sequence fused and adjacent to the 5' end of the nucleotide sequence of interest comprising an ATG initiation sequence. The construct may, or may not, comprise a multiple cloning site located between the 5'UTR and the plant kozak sequence. The construct may further comprise a 3' untranslated region (UTR) sequence, for example, a comovirus 3'UTR, or a plastocyanin 3' UTR, and a terminator sequence, for example a NOS terminator, operatively linked to the 3' end of the nucleotide sequence of interest (see FIG. 1A).

A plant expression system comprising a nucleic acid comprising a regulatory region, operatively linked with one or more than one expression enhancer as described herein (e.g. CPMVX), and a nucleotide sequence of interest. is also provided. Furthermore, a nucleic acid comprising a promoter (regulatory region) sequence, operatively linked with an expression enhancer comprising a CPMV 5'UTR and a modified or deleted stuffer sequence (e.g. CPMVX+) and a nucleotide sequence of interest is described. The nucleic acid may further comprise a sequence encoding a 3'UTR, for example a comovirus 3' UTR, or a plastocyanin 3' UTR, and a terminator sequence, for example a NOS terminator, so that the nucleotide sequence of interest is inserted upstream from the 3'UTR.

By "operatively linked" it is meant that the particular sequences interact either directly or indirectly to carry out an intended function, such as mediation or modulation of expression of a nucleic acid sequence. The interaction of operatively linked sequences may, for example, be mediated by proteins that interact with the operatively linked sequences.

"Expression enhancer(s)", "enhancer sequence(s)" or "enhancer element(s)", as referred to herein, include sequences derived from, or that share sequence similarity with, portions of the CPMV 5'UTR from the RNA-2 genome segment. An enhancer sequence can enhance expression of a downstream heterologous open reading frame (ORF) to which they are attached.

The term "5'UTR" or "5' untranslated region" or "5' leader sequence" refers to regions of an mRNA that are not translated. The 5'UTR typically begins at the transcription start site and ends just before the translation initiation site or start codon (usually AUG in an mRNA, ATG in a DNA sequence) of the coding region. The length of the 5'UTR may be modified by mutation for example substitution, deletion or insertion of the 5'UTR. The 5'UTR may be further modified by mutating a naturally occurring start codon or translation initiation site such that the codon no longer functions as start codon and translation may initiate at an alternate initiation site.

The 5'UTR from nucleotides 1-160 of the CPMV RNA-2 sequence (SEQ ID NO: 1), starts at the transcription start site to the first in frame initiation start codon (at position 161), which serve as the initiation site for the production of the longer of two carboxy coterminal proteins encoded by a wild-type comovirus genome segment. Furthermore a 'third' initiation site at (or corresponding to) position 115 in the CPMV RNA-2 genomic sequence may also be mutated, deleted or otherwise altered. It has been shown that removal of AUG 115 in addition to the removal of AUG 161 enhances expression when combined with an incomplete M protein (Sainsbury and Lomonossoff, 2008*, Plant Physiology;* 148: 1212-1218; WO 2009/087391; which are incorporated herein by reference).

The expression enhancer may comprise a CPMV 5' untranslated region (UTR) comprising nucleotides from X of SEQ ID NO:1, where X=160, 155, 150, or 114 of SEQ ID NO:1 (CPMVX), or a sequence that comprises 80% sequence similarity with CPMVX (where X=160, 155, 150, or 114 of SEQ ID NO:1; see FIGS. 1A and 1B) and exhibits the property of enhancing expression of a nucleotide sequence encoding a heterologous open reading frame that is operatively linked to the expression enhancer, when compared to the expression of the same nucleotide sequence encoding a heterologous open reading frame operatively linked to the prior art CPMV HT enhancer sequence comprising an incomplete M protein (as described in Sainsbury F., and Lomonossoff G. P., 2008, Plant Physiol. 148: pp. 1212-1218; which is incorporated herein by reference).

The CPMVX enhancer sequence may also be fused to a stuffer sequence, for example a multiple cloning site (MCS), or an MCS linked to a plant kozak sequence, wherein the CMPVX comprises nucleotides from X of SEQ ID NO:1, where X=160, 155, 150, or 114 of SEQ ID NO:1, or a sequence that comprises 80% sequence similarity with CPMVX (where X=160, 155, 150, or 114 of SEQ ID NO:1), and exhibits the property of enhancing the expression of nucleotide sequence encoding a heterologous open reading frame operatively linked to the expression enhancer, when compared to the expression of the same sequence encoding a heterologous open reading frame operatively linked to the prior art CPMV HT enhancer sequence comprising an incomplete M protein (as described in Sainsbury F., and Lomonossoff G. P., 2008, Plant Physiol. 148: pp. 1212-1218; which is incorporated herein by reference). The stuffer sequence comprises from 0-500 nucleotides fused to the 3' end of the CMPVX sequence. Preferably, the stuffer sequence comprises an multiple cloning site (MCS), or an MCS linked to a plant kozak sequence, and does not include an M protein. If the CMPVX sequence comprises a stuffer fragment (without an M protein), then this expression enhancer may be referred to as "CPMVX+" (see FIGS. 1A and 1C), as "CMPVX comprising a stuffer sequence and a plant kozak sequence", or as "CMPVX comprising an MCS along with a plant kozak sequence".

The expression enhancer CPMVX, where X=160, consists of nucleotides 1-160 of SEQ ID NO: 1:

(SEQ ID NO: 1)
```
  1  tattaaaatc ttaataggtt ttgataaaag cgaacgtggg gaaacccgaa ccaaaccttc

 61  ttctaaactc tctctcatct ctcttaaagc aaacttctct cttgtctttc ttgcgtgagc

121  gatcttcaac gttgtcagat cgtgcttcgg caccagtaca
```

If the expression enhancer consists of nucleotide 1-160 of SEQ ID NO:1 (CPMV160), then a nucleotide sequence of interest with or without a 5' plant kozak sequence located at the 5' end adjacent to an initiation sequence (ATG), may be fused to the 3' end of the 5'UTR (after nucleotide 160 of SEQ ID NO:1), so that the overall construct resembles that as shown in FIG. 1B (CPMV160). The construct comprising CPMV160 may further comprise a regulatory region operatively linked to the 5' end of the expression enhancer, and a sequence encoding a 3'UTR, for example a comovirus 3' untranslated region (UTR) or a plastocyanin 3' UTR, and a terminator sequence, for example a NOS terminator, fused to the 3' end of the nucleotide sequence of interest. Without wishing to be bound by theory, CPMV160 may not require the addition of a plant kozak sequence to the 5' end of the nucleotide sequence of interest, since the sequence at positions 150-155, 155-160, or 150-160 of SEQ ID NO:1 may function as an active (native) kozak sequence in a plant. Construct number 1935 (see Example 3) and construct number 1885 (see Example 6) are examples of CPMV160 (CPMVX, where X=160) based constructs.

The expression enhancer may comprise CPMVX+, where X=160. A non-limiting example of such an enhancer is CPMV160+(see FIG. 1C) comprising the sequence of SEQ ID NO:2 (5'UTR: nucleotide 1-160; multiple cloning site in italics nucleotides 161-176; plant kozak sequence in caps and bold, nucleotides 177-181):

(SEQ ID NO: 2)

1 tattaaaatc ttaataggtt ttgataaaag cgaacgtggg gaaacccgaa ccaaaccttc 61 ttctaaactc tctctcatct ctcttaaagc aaacttctct cttgtctttc ttgcgtgagc 121 gatcttcaac gttgtcagat cgtgcttcgg caccagtaca *gggcccaata ccgcgg*A*GAA*

181 *A*

Examples of constructs using SEQ ID NO:2 as an expression enhancer include constructs 1800, 1897, 1880, 2168, 2188, 1937, 1977, 2050, 2060, 1975, 1893, 2100, 2109, 2120, 2129 (see Examples 3, and 5-18, respectively).

As would be evident to one of skill in the art, any multiple cloning site (MCS), or an MCS of different length (either shorter or longer) may used in place of the sequence at nucleotides 161-176 of SEQ ID NO:2. Furthermore, the plant kozak sequence of SEQ ID NO:2 (shown at nucleotides 177-181) may be any plant kozak sequence, including but not limited, one of the sequences selected from SEQ ID NO's:5-17 (also see FIG. 4A; the construct of FIG. 4 includes SEQ ID NO:2, with variations of the plant kozak sequence as indicated, and comprises a plant regulatory region attached to the 5' end of the 5'UTR, and the transcription initiation site, ATG, of a nucleotide sequence of interest, located 3' to the plant kozak sequence).

The expression enhancer CPMVX, may include an "A" in position 115 (115A), so that CMPVX, 115A, where X=160, 155 or 150, comprises the sequence of the wild-type CPMV RNA2 genome (see WO 2009/087391, which is incorporated herein by reference, for the complete sequence of the wild type CPMV RNA-2 genome segment). An example of an expression enhancer CPMVX, 115A is "CPMV160, 115A", as defined by SEQ ID NO: 69 (the "A" is shown in bold and underline):

(SEQ ID NO: 69)

1 tattaaaatc ttaataggtt ttgataaaag cgaacgtggg gaaacccgaa ccaaaccttc 61 ttctaaactc tctctcatct ctcttaaagc aaacttctct cttgtctttc ttgc<u>a</u>tgagc 121 gatcttcaac gttgtcagat cgtgcttcgg caccagtaca The expression enhancer CPMVX+, may also include an "A" in position 115 (115A), so that CMPVX+, 115A, where X=160, 155 or 150, comprises the sequence of the wild-type CPMV RNA2 genome (WO 2009/087391, which is incorporated herein by reference). A non-limiting example of an expression enhancer CPMVX+, 115A is "CPMV160+, 115A", as defined by SEQ ID NO: 75 (the "A" is shown in bold and underline):

(SEQ ID NO: 75)

1 tattaaaatc ttaataggtt ttgataaaag cgaacgtggg gaaacccgaa ccaaaccttc 61 ttctaaactc tctctcatct ctcttaaagc aaacttctct cttgtctttc ttgcatgagc 121 gatcttcaac gttgtcagat cgtgcttcgg caccagtaca *gggcccaata ccgcgg*A*GAA*

181 *A*

As noted above for SEQ ID NO:2, any MCS, or an MCS of different length, may used in place of the MCS sequence of SEQ ID NO:75, and the plant kozak sequence may be any plant kozak sequence.

If the expression enhancer consists of nucleotide 1-155 of SEQ ID NO:1 (CPMV155):

(SEQ ID NO: 24)

1 tattaaaatc ttaataggtt ttgataaaag cgaacgtggg gaaacccgaa ccaaaccttc 61 ttctaaactc tctctcatct ctcttaaagc aaacttctct cttgtctttc ttgcgtgagc 121 gatcttcaac gttgtcagat cgtgcttcgg cacca, then a nucleotide sequence of interest with a plant kozak sequence located at the 5' end, adjacent an initiation sequence (ATG), may be fused to the 3' end of the 5'UTR (after nucleotide 155 of SEQ ID NO:1), so that the overall construct resembles that as shown in FIG. 1B (CPMV155). The construct comprising CPMV155 may further comprise a regulatory region operatively linked to the 5' end of the expression enhancer, and a sequence encoding a 3'UTR, for example a comovirus 3' untranslated region (UTR) or a plastocyanin 3' UTR, and a terminator sequence, for example a NOS terminator, fused to the 3' end of the nucleotide sequence of interest. In this example, the nucleotide sequence of interest comprises a plant kozak sequence at its 5' end, since the native kozak sequence or a portion of this sequence (nucleotides 155-160 of SEQ ID NO:1), is removed.

The expression enhancer may comprise CPMV155+, comprising the sequence of SEQ ID NO:72 (5'UTR: nucleotide 1-155; multiple cloning site in italics nucleotides 156-171; plant kozak sequence in caps and bold, nucleotides 172-176):

(SEQ ID NO: 72)

1 tattaaaatc ttaataggtt ttgataaaag cgaacgtggg gaaacccgaa ccaaaccttc 61 ttctaaactc tctctcatct ctcttaaagc aaacttctct cttgtctttc ttgcgtgagc 121 gatcttcaac gttgtcagat cgtgcttcgg cacca*gggcc caataccgcg g*AGAAA

As noted above for CPMV160+(SEQ ID NO:2), any MCS, including an MCS's of different length, may used in place of the MCS sequence of SEQ ID NO:72, and the plant kozak sequence may be any plant kozak sequence.

The expression enhancer CPMV155, may include an "A" in position 115 (115A), so that "CMPV155, 115A" comprises the sequence of the wild-type CPMV RNA2 genome (see WO 2009/087391, which is incorporated herein by reference), as defined by SEQ ID NO: 70 ("A" is bolded and underlined):

(SEQ ID NO: 70)
1 tattaaaatc ttaataggtt ttgataaaag cgaacgtggg gaaacccgaa ccaaaccttc 61 ttctaaactc tctctcatct ctcttaaagc aaacttctct cttgtctttc ttgcatgagc 121 gatcttcaac gttgtcagat cgtgcttcgg cacca The expression enhancer CPMV155+, may also include an "A" in position 115 (115A), so that "CMPV155+, 115a" comprises the sequence of the wild-type CPMV RNA2 genome (WO 2009/087391, which is incorporated herein by reference), as defined by SEQ ID NO: 76 (the "A" is shown in bold and underline):

(SEQ ID NO: 76)
1 tattaaaatc ttaataggtt ttgataaaag cgaacgtggg gaaacccgaa ccaaaccttc 61 ttctaaactc tctctcatct ctcttaaagc aaacttctct cttgtctttc ttgcatgagc 121 gatcttcaac gttgtcagat cgtgcttcgg cacca*gggcc caataccgcg g*A*GAA*

181 *A*

As noted above for SEQ ID NO:2, any MCS, or an MCS of different length, may used in place of the MCS sequence of SEQ ID NO:76, and the plant kozak sequence may be any plant kozak sequence.

If the expression enhancer consists of nucleotide 1-150 of SEQ ID NO:1 (CPMV150):

(SEQ ID NO: 27)
1 tattaaaatc ttaataggtt ttgataaaag cgaacgtggg gaaacccgaa ccaaaccttc 61 ttctaaactc tctctcatct ctcttaaagc aaacttctct cttgtctttc ttgcgtgagc 121 gatcttcaac gttgtcagat cgtgcttcgg, then a nucleotide sequence of interest with a plant kozak sequence located at the 5' end, adjacent an initiation sequence (ATG), may be fused to the 3' end of the 5'UTR (after nucleotide 150 of SEQ ID NO:1), so that the overall construct resembles that as shown in FIG. 1B (CPMV150). The construct comprising CPMV150 may further comprise a regulatory region operatively linked to the 5' end of the expression enhancer, and a sequence encoding a 3'UTR, for example a comovirus 3' untranslated region (UTR) or a plastocyanin 3' UTR, and a terminator sequence, for example a NOS terminator, fused to the 3' end of the nucleotide sequence of interest. In this example, the nucleotide sequence of interest comprises a plant kozak sequence at its 5' end, since the native kozak sequence at position 150-160 of SEQ ID NO:1, is removed.

The expression enhancer may comprise CPMV150+, comprising the sequence of SEQ ID NO:73 (5'UTR: nucleotide 1-150; multiple cloning site in italics nucleotides 156-166; plant kozak sequence in caps and bold, nucleotides 167-171):

(SEQ ID NO: 73)
1 tattaaaatc ttaataggtt ttgataaaag cgaacgtggg gaaacccgaa ccaaaccttc 61 ttctaaactc tctctcatct ctcttaaagc aaacttctct cttgtctttc ttgcgtgagc 121 gatcttcaac gttgtcagat cgtgcttcgg *gggcccaata ccgcgg*AGAA A

As noted above for CPMV160+(SEQ ID NO:2), any MCS, including an MCS's of different length, may used in place of the MCS sequence of SEQ ID NO:73, and the plant kozak sequence may be any plant kozak sequence.

The expression enhancer CPMV150, may include an "A" in position 115 (115A), so that "CMPV150, 115A" comprises the sequence of the wild-type CPMV RNA2 genome (see WO 2009/087391, which is incorporated herein by reference) as defined by SEQ ID NO: 71 (the "A" is shown in bold and underline):

(SEQ ID NO: 71)

1 tattaaaatc ttaataggtt ttgataaaag cgaacgtggg gaaacccgaa ccaaaccttc 61 ttctaaactc tctctcatct ctcttaaagc aaacttctct cttgtctttc ttgcatgagc 121 gatcttcaac gttgtcagat cgtgcttcgg The expression enhancer CPMV150+, may also include an "A" in position 115 (115A), so that "CMPV150+, 115A" comprises the sequence of the wild-type CPMV RNA2 genome (WO 2009/087391, which is incorporated herein by reference), as defined by SEQ ID NO: 77 (the "A" is shown in bold and underline):

(SEQ ID NO: 77)

1 tattaaaatc ttaataggtt ttgataaaag cgaacgtggg gaaacccgaa ccaaaccttc 61 ttctaaactc tctctcatct ctcttaaagc aaacttctct cttgtctttc ttgcatgagc 121 gatcttcaac gttgtcagat cgtgcttcgg *gggcccaata ccgcgg*A*GAA*

181 *A*

As noted above for SEQ ID NO:2, any MCS, or an MCS of different length, may used in place of the MCS sequence of SEQ ID NO:77, and the plant kozak sequence may be any plant kozak sequence.

If the expression enhancer consists of nucleotide 1-114 of SEQ ID NO:1:

(SEQ ID NO: 68)

1 tattaaaatc ttaataggtt ttgataaaag cgaacgtggg gaaacccgaa ccaaaccttc 61 ttctaaactc tctctcatct ctcttaaagc aaacttctct cttgtctttc ttgc then a nucleotide sequence of interest with a plant kozak sequence located at the 5' end, adjacent an initiation sequence (ATG), may be fused to the 3' end of the 5'UTR (after nucleotide 114 of SEQ ID NO:1), so that the overall construct resembles that as shown in FIG. 1B (CPMV114). The construct comprising CPMV1114 may further comprise a regulatory region operatively linked to the 5' end of the expression enhancer, and a sequence encoding a 3'UTR, for example a comovirus 3' untranslated region (UTR) or a plastocyanin 3' UTR, and a terminator sequence, for example a NOS terminator, fused to the 3' end of the nucleotide sequence of interest. In this example, the nucleotide sequence of interest comprises a plant kozak sequence at its 5' end, since there is kozak-like sequence 5' to nucleotide 114 of SEQ ID NO:1.

The expression enhancer may comprise CPMV114+, comprising the sequence of SEQ ID NO:74 (5'UTR: nucleotide 1-114; multiple cloning site in italics nucleotides 115-130; plant kozak sequence in caps and bold, nucleotides 131-135):

(SEQ ID NO: 74)

1 tattaaaatc ttaataggtt ttgataaaag cgaacgtggg gaaacccgaa ccaaaccttc 61 ttctaaactc tctctcatct ctcttaaagc aaacttctct cttgtctttc ttg*cgggccc*

121 *aataccgcgg* AGAAA

As noted above for CPMV160+(SEQ ID NO:2), any MCS, including an MCS's of different length, may used in place of the MCS sequence of SEQ ID NO:73, and the plant kozak sequence may be any plant kozak sequence.

The expression enhancer may also comprise nucleotides 1-160 of SEQ ID NO: 1, fused with a plant kozak sequence located downstream from position 160 of SEQ ID NO:1. The plant kozak sequence may be located immediately adjacent to nucleotide 160 of SEQ ID NO:1, or the expression enhancer may comprise a stuffer fragment of about 0 to about 500 nucleotides, or any amount therebetween, located immediately adjacent to nucleotide 160 of SEQ ID NO:1 (CPMVX+) and the plant kozak sequence linked to 3' end of the stuffer fragment. The stuffer fragment may comprise a multiple cloning site (MCS) of from about 4 to 100 nucleotides or any amount therebetween, and a nucleotide sequence of interest comprising a plant kozak sequence and a corresponding cloning site at its 5' end may be operatively linked to the CMPVX expression enhancer using the MCS, or the stuffer fragment may comprise a multiple cloning site of from about 4 to 100 nucleotides fused to a plant kozak sequence, and a nucleotide sequence of interest may be fused to the expression enhancer immediately downstream of the plant kozak sequence. Preferably, the stuffer fragment does not comprise a sequence encoding an M protein.

An example, which is not to be considered limiting, of a construct, comprising in series, a plant regulatory region fused to a CPMV 5'UTR consisting of nucleotides 1-160 of SEQ ID NO:1, that is fused to a stuffer fragment is CPMV160+ as shown in FIG. 1C (in FIG. 1C, the ATG start site of the nucleotide sequence of interest "GOT", is also shown for clarity). In this example, the stuffer fragment is fused to the 3' end of the CPMV 1-160 sequence and comprises, in series, a multiple cloning site fused to a plant kozak sequence (in this example which is not to be considered limiting, the plant kozak sequence is: AGAAA). The stuffer fragment does not comprise any sequence encoding an M protein If the CPMV160+ construct is fused to a nucleotide sequence of interest (as shown in FIG. 1C), then the plant kozak sequence is located 5' to the nucleotide sequence of interest, and adjacent to the ATG initiation site of the nucleotide sequence of interest. As would be appreciated by one of skill in the art, the multiple cloning site may comprise one or more than one suitable restriction sites, and the sequence of the multiple cloning site is not limited to the example shown in FIG. 1C. Furthermore, the plant kozak sequence may be any plant kozak sequence and not limited to the sequence shown in FIG. 1C. Construct numbers 1800, 1897, 1880, 2168, 2188, 1937, 1977, 2050, 2060, 1975, 1893, 2100, 2109, 2120, 2129 (see Examples 3, and 5-18, respectively) are examples of CPMV160+ (CPMVX+, where X=160) based constructs.

Also shown in FIG. 1C are example of expression enhancers CPMV155+, CPMV150+, and CPMV114+ each comprising nucleotides 1-155, 1-150, or 1-114 of SEQ ID NO:1, respectively, fused to a stuffer fragment in a similar manner as that described for CPMV160+, above. In FIG. 1C, the ATG start site of the nucleotide sequence of interest (GOT) is also shown for each of CPMV155+, CPMV150+, and CPMV114+. In these examples, the stuffer fragment is fused to the 3' end of the CPMV enhancer sequence comprises, in series, a multiple cloning site fused to a plant kozak sequence. The stuffer fragment does not comprise any sequence encoding an M protein. As would be appreciated by one of skill in the art, the multiple cloning site may comprise one or more than one suitable restriction sites, and the sequence of the multiple cloning site is not limited to the examples shown in FIG. 1C. Furthermore, the plant kozak sequence may be any plant kozak sequence and not limited to the sequence shown in FIG. 1C (AGAAA).

The expression enhancer may also comprise the expression enhancer CPMVX, where X=160, 155, 150, or 114 of SEQ ID NO: 1, in combination with a multiple cloning site (polylinker, restriction site; cloning site) fused to the 3' end of the 5'UTR sequence, and lacking a plant kozak sequence (i.e. CPMVX+, where X=160, 155, 150, or 114 of SEQ ID NO: 1). In these cases the nucleic acid sequence encoding a protein of interest (nucleotide sequence of interest) to be joined to the enhancer, will comprises, in series from the 5' end to the 3' end of the nucleotide sequence of interest, a multiple cloning site (complimentary with that of the stuffer fragment; the stuffer fragment does not comprise any sequence encoding an M protein.) fused to a plant kozak sequence located upstream from and adjacent to an ATG initiation site (transcriptional start site) of the nucleotide sequence of interest.

The expression enhancer may further comprise one or more "kozak consensus sequence" or "kozak sequence". Kozak sequences play a major role in the initiation of translation. The rate of translation can be optimized by ensuring that any mRNA instability sequences are eliminated from the transgene construct, and that the translational start site or initiation site matches the Kozak consensus for plants (Gutierrrez, R. A. et al., 1999, Trends Plant Sci. 4, 429-438; Kawaguchi, R. and Bailey-Serres, J., 2002, Curr. Opin. Plant Biol. 5, 460-465). The most highly conserved position in this motif is the purine (which is most often an A) three nucleotides upstream of the ATG codon, which indicates the start of translation (Kozak, M., 1987, J. Mol. Biol. 20:947-950, herein incorporated by reference). Plant Kozak consensus sequences are known in the art (see for example Rangan et al. Mol. Biotechnol., 2008, July 39(3), pp. 207-213). Both naturally occurring and synthetic Kozak sequences may be used in the expression enhancer or may be fused to the nucleotide sequence of interest as described herein.

The plant kozak sequence may be any known plant kozak sequences (see for example L. Rangan et al. Mol. Biotechnol., 2008, July 39(3), pp. 207-213), including, but not limited to the following plant consensus sequences:

```
caA(A/C)a        (SEQ ID NO: 5; plant kingdom)

aaA(A/C)a        (SEQ ID NO: 6; dicots)

aa(A/G)(A/C)a    (SEQ ID NO: 7; arabidopsis)
```

The plant kozak sequence may also be selected from the group of (see FIG. 4):

```
AGAAA                  (SEQ ID NO: 8)

AGACA                  (SEQ ID NO: 9)

AGGAA                  (SEQ ID NO: 10)

AAAAA                  (SEQ ID NO: 11)

AAACA                  (SEQ ID NO: 12)

AAGCA                  (SEQ ID NO: 13)

AAGAA                  (SEQ ID NO: 14)

AAAGAA                 (SEQ ID NO: 15)

AAAAGAA                (SEQ ID NO: 16)

(A/-)A(A/G)(A/G)(A/C)A.
(SEQ ID NO: 3; Consensus sequence)
```

The expression enhancer may further comprise one or more "restriction site(s)" or "restriction recognition site(s)", "multiple cloning site", "MCS", "cloning site(s)" "polylinker sequence" or "polylinker" to facilitate the insertion of the nucleotide of interest into the plant expression system. Restrictions sites are specific sequence motifs that are recognized by restriction enzymes as are well known in the art. The expression enhancer may comprise one or more restriction sites or cloning sites that are located downstream (3') of the 5'UTR. The one or more restriction sites or cloning sites may further be located up-stream (5') of one or more kozak sequences, and located between a 5' UTR and a kozak sequence. The polylinker sequence (multiple cloning site) may comprise any sequence of nucleic acids that are useful for adding and removing nucleic acid sequences, including a nucleotide sequence encoding a protein of interest, to the 3' end of the 5'UTR. A polylinker sequence may comprise from 4 to about 100 nucleic acids, or any amount therebetween.

The expression enhancer may also comprise the sequence of SEQ ID NO:1 in operative association with a plant regulatory region and a transcriptional start site (ATG) fused to a nucleotide sequence of interest (GOT), as shown in FIG. 1B (CPMVX; where X=160, 155, 150 or 114). CPMVX may also comprise any plant kozak sequence including but not limited to, one of the sequences of SEQ ID NO's:5-17.

The 5'UTR for use in the expression enhancer described herein (CPMVX or CPMVX+, where X=160, 155, 150 or 144), may be derived from a bipartite RNA virus, e.g. from the RNA-2 genome segment of a bipartite RNA virus such as a comovirus, provided that it exhibits 100%, 99%, 98%, 97%, 96%, 95%, 90%, 85% or 80% identity to the sequence as set forth in either SEQ ID NO's: 1 and 2. For example the enhancer sequence may have from about 80% to about 100% identity to the sequence of SEQ ID NO's: 1 and 2, or any amount therebetween, from about 90% to about 100% identity to the sequence of SEQ ID NO's: 1 and 2, or any amount therebetween, about 95% to about 100%, identity to the sequence of SEQ ID NO's: 1 and 2, or any amount therebetween, or about 98% to about 100%, identity to the sequence of SEQ ID NO's: 1 and 2, or any amount therebetween wherein the expression enhancer, when operatively linked to a plant regulatory region and a plant kozak sequence as described herein, increases the level of expression of a nucleotide sequence of interest that is operatively linked to the expression enhancer when compared to the level of expression of the nucleotide sequence of interest fused to the CMPV HT (SEQ ID NO:4; prior art enhancer sequence comprising an incomplete M protein as described in Sainsbury F., and Lomonossoff G. P., 2008, Plant Physiol. 148: pp. 1212-1218; which is incorporated herein by reference) using the same plant regulatory region.

SEQ ID NO:4 comprises a CPMV HT expression enhancer as known in the prior art (e.g. FIG. 1 of Sainsbury and Lomonossoff 2008, Plant Physiol. 148: pp. 1212-1218; which is incorporated herein by reference). "CPMV HT" includes the 5'UTR sequence from nucleotides 1-160 of SEQ ID NO:4 with modified nucleotides at positions 115 (cgt) and 162 (acg), and an incomplete M protein, and lacks a plant kozak sequence (5'UTR: nucleotides 1-160; incomplete M protein underlined, nucleotides 161-509). SEQ ID NO:4 also includes a multiple cloning site (italics, nucleotides 510-528) which is not present in the prior art CPMV HT sequence:

```
                                                             SEQ ID NO: 4
  1   tattaaaatc ttaataggtt ttgataaaag cgaacgtggg gaaacccgaa ccaaaccttc

 61   ttctaaactc tctctcatct ctcttaaagc aaacttctct cttgtctttc ttgcgtgagc

121   gatcttcaac gttgtcagat cgtgcttcgg caccagtaca acgttttctt tcactgaagc

181   gaaatcaaag atctctttgt ggacacgtag tgcggcgcca ttaaataacg tgtacttgtc

241   ctattcttgt cggtgtggtc ttgggaaaag aaagcttgct ggaggctgct gttcagcccc

301   atacattact tgttacgatt ctgctgactt toggcgggtg caatatctct acttctgctt

361   gacgaggtat tgttgcctgt acttctttct tcttcttctt gctgattggt tctataagaa

421   atctagtatt ttctttgaaa cagagttttc ccgtggtttt cgaacttgga gaaagattgt

481   taagcttctg tatattctgc ccaaatttgt cgggccc
```

Constructs comprising CPMV HT are used herein as reference constructs, so that the expression levels of a nucleotide sequence of interest, or a product encoded by the nucleotide sequence of interest produced using a construct comprising CPMVX or CPMVX+, may be compared. Constructs 1391, 484, 489, 2140, 2130, 1039, 1067, 2072, 2074, 1445, 1454, 5001, 5002, 5021 and 5022 (see Examples 1 and 5-18, respectively) comprise the reference construct CPMV HT.

As shown in FIGS. 2-5, the use of the expression enhancers as described herein resulted in an increase of expression of the nucleotide sequence of interest, when compared to the expression of the same nucleotide sequence of interest using the same promoter and 3'UTR and terminator sequences. For example, with reference to FIGS. 2, 3 and 5, there is shown a comparison of expression of proteins produced in plants comprising CPMV-HT (prior art) expression constructs and CPMV160+ based expression constructs, operatively linked with:

H1 A/California/07/2009 ("PDI-H1 Cal", or "H1 A/California/07/2009"): CPMV160+ based construct number 1897, CPMV HT based construct number 484 (see Example 5);

H3 A/Victoria/361/2011 ("PDI-H3 Vic", or "H3 A/Victoria/361/2011"): CPMV160+ based construct number 1800; CPMV HT based construct number 1391 (see Examples 1 and 2, respectively);

H5 from Influenza A/Indonesia/5/2005 with a native signal peptide (WtSp-H5 Indo): CPMV160+ based construct number 1880; CPMV HT based construct number 489 (see Example 6);

B/Wisconsin/1/2010 with deleted proteolytic loop and with a native signal peptide ("WtSp-B Wis-PrL", or "B/Wisconsin/1/2010"): CPMV160+ based construct number 1975; CPMV HT based construct number 1445 (see Example 13);

B Brisbane/60/08 with deleted proteolytic loop and with a PDI signal peptide ("B Brisbane/60/08"): CPMV160+ based construct number 1937; CMPV HT based construct number 1039 (see Example 9);

B Brisbane/60/08+H1Tm, with deleted proteolytic loop fused to the transmembrane domain and cytoplasmic tail and with a PDI signal peptide ("B Brisbane/60/08+H1Tm"): CPMV160+ based construct number 1977; CMPV HT based construct 1067 (see Example 10), B Massachusetts/2/2012 2012 with deleted proteolytic loop and with a PDI signal peptide ("B Massachusetts/2/2012 2012"): CPMV160+ based construct number 2050; CPMV HT based construct number 2072 (see Example 11), B Massachusetts/2/2012+H1Tm with deleted proteolytic loop fused to the transmembrane domain and cytoplasmic tail and with a PDI signal peptide ("B Massachusetts/2/2012+H1Tm"): CPMV160+ based construct number 2060; CPMV HT based construct 2074 (see Example 12), B Wisconsin/1/2010+H1Tm with deleted proteolytic loop fused to the transmembrane domain and cytoplasmic tail and with the native signal peptide ("B Wisconsin/1/2010+H1Tm"): CPMV160+ based construct number 1893; CPMV HT based construct 1454 (see Example 14);

Rituximab (Rituxan) under the control of CPMV-HT with a native or PDI signal peptide ("CPMV-HT/wild-type SP" and "CPMV-HT/PDISP"; construct numbers 5001 and 5002, respectively, see examples 15 and 16), or CPMV160+ ("CPMV160+/wile-typeSP" and "CPMV160+/PDISP"; construct numbers 2100 and 2109, respectively, see example 15 and 16).

In each case, the expression (determined as hemagglutination activity or rituximab (Rituxan) expression as the case may be) is increased in the CMPV160+ based construct when compared to that for the prior art CPMV based construct. Furthermore, several of the nucleotide sequences of interest encoded chimeric or modified proteins, for example comprising heterologous signal peptides (e.g. PDI), heterologous transmembrane domain cytoplasmic tail sequences (TDCT), and/or modified sequences including a deleted proteolytic loop (PrL-).

The increase in expression observed using CPMV160+ based constructs is also observed if the plant kozak sequence used in the CPMV160+ based constructs above is replaced with other plant kozak sequences for example, one of those plant kozak sequences defined in SEQ ID NO:8-16. For example, with reference to FIG. 4, there is shown a comparison of the expression of proteins produced in plants comprising CPMV160+ based expression constructs, operatively linked with a nucleotide sequence of interest (H3 A/Victoria/361) each fused to various plant kozak sequences. In each case, the expression (determined as hemagglutination titre) the CMPV160+ based construct demonstrates significant expression levels and greater than the prior art CMPV HT based construct.

The terms "percent similarity", or "percent identity" when referring to a particular sequence are used for example as set forth in the University of Wisconsin GCG software program, or by manual alignment and visual inspection (see, e.g., Current Protocols in Molecular Biology, Ausubel et al., eds. 1995 supplement). Methods of alignment of sequences for comparison are well-known in the art. Optimal alignment of sequences for comparison can be conducted, using for example the algorithm of Smith & Waterman, (1981, Adv. Appl. Math. 2:482), by the alignment algorithm of Needleman & Wunsch, (1970, J. Mol. Biol. 48:443), by the search for similarity method of Pearson & Lipman, (1988, Proc. Nat'l. Acad. Sci. USA 85:2444), by computerized implementations of these algorithms (for example: GAP, BESTFIT, FASTA, and TFASTA in the Wisconsin Genetics Software Package, Genetics Computer Group (GCG), 575 Science Dr., Madison, Wis.).

An example of an algorithm suitable for determining percent sequence identity and sequence similarity are the BLAST and BLAST 2.0 algorithms, which are described in Altschul et al., (1977, Nuc. Acids Res. 25:3389-3402) and Altschul et al., (1990, J. Mol. Biol. 215:403-410), respectively. BLAST and BLAST 2.0 are used, with the parameters described herein, to determine percent sequence identity for the nucleic acids and proteins of the invention. For example the BLASTN program (for nucleotide sequences) may use as defaults a wordlength (W) of 11, an expectation (E) of 10, M=5, N=−4 and a comparison of both strands. For amino acid sequences, the BLASTP program may use as defaults a wordlength of 3, and expectation (E) of 10, and the BLOSUM62 scoring matrix (see Henikoff & Henikoff, 1989, Proc. Natl. Acad. Sci. USA 89:10915) alignments (B) of 50, expectation (E) of 10, M=5, N=−4, and a comparison of both strands. Software for performing BLAST analyses is publicly available through the National Center for Biotechnology Information (see URL: ncbi.nlm.nih.gov/).

A nucleotide sequence interest that encodes a protein requires the presence of a "translation initiation site" or "initiation site" or "translation start site" or "start site" or "start codon" located upstream of the gene to be expressed. Such initiation sites may be provided either as part of an enhancer sequence or as part of a nucleotide sequence encoding the protein of interest.

"Expression cassette" refers to a nucleotide sequence comprising a nucleic acid of interest under the control of, and operably (or operatively) linked to, an appropriate promoter or other regulatory elements for transcription of the nucleic acid of interest in a host cell.

By "proteolytic loop" or "cleavage site" is meant the consensus sequence of the proteolytic site that is involved in precursor HA0 cleavage. "Consensus" or "consensus sequence" as used herein means a sequence (either amino acid or nucleotide sequence) that comprises the sequence variability of related sequences based on analysis of alignment of multiple sequences, for example, subtypes of a particular influenza HA0 sequence. Consensus sequence of the influenza HA0 cleavage site may include influenza A consensus hemagglutinin amino acid sequences, including for example consensus H1, consensus H3, consensus H5, or influenza B consensus hemagglutinin amino acid sequences, for example but not limited to B Florida, B Malaysia, B Wisconsin and B Massachusetts. Non limiting examples of sequences of the proteoloytic loop region are shown in FIGS. 15 and 18B of U.S. provisional application No. 61/806,227 (filed Mar. 28, 2013, which is incorporated herein by reference; also see Bianchi et al., 2005, Journal of Virology, 79:7380-7388; incorporated herein by reference).

Residues in the proteolytic loop or cleavage site might be either mutated, for example but not limited to point mutation, substitution, insertion, or deletion. The term "amino acid mutation" or "amino acid modification" as used herein is meant to encompass amino acid substitutions, deletions, insertions, and modifications. Any combination of substitution, deletion, insertion, and modification can be made as described in U.S. provisional application No. 61/806,227 (filed Mar. 28, 2013, which is incorporated herein by reference) to arrive at the final construct, provided that the final construct possesses the desired characteristics, e.g., reduced or abolished cleavage of the proteolytic loop or cleavage site by a protease.

As described herein, there is provided a nucleic acid construct (expression system) comprising an expression enhancer sequence operatively linked to a nucleotide sequence of interest encoding a protein of interest. Also provided are plant expression systems comprising an enhancer sequence as described herein. Also provided is a plant expression system comprising a plant regulatory region, in operative association with an enhancer sequence that is operatively linked to a nucleotide sequence of interest, the nucleotide sequence of interest encoding a protein of interest. The enhancer sequence may be selected from any one of SEQ ID NO's:1, 2, 24, 27, 68, 69 and 70-77, or a .nucleotide sequence that exhibits 100%, 99%, 98%, 97%, 96%, 95%, 90%, 85% or 80% identity to the sequence as set forth in any one of SEQ ID NO's:1, 2, 24, 27, 68, 69 and 70-77, wherein the expression enhancer, when operatively linked to a plant regulatory region and a plant kozak sequence as described herein, increases the level of expression of a nucleotide sequence of interest that is operatively linked to the expression enhancer when compared to the level of expression of the nucleotide sequence of interest fused to the CMPV HT (SEQ ID NO:4; prior art enhancer sequence comprising an incomplete M protein as described in Sainsbury F., and Lomonossoff G. P., 2008, Plant Physiol. 148: pp. 1212-1218; which is incorporated herein by reference) using the same plant regulatory region.

The enhancer sequence of the present invention may be used to express a protein of interest in a host organism for example a plant. In this case, the protein of interest may also be heterologous to the host organism in question and introduced into the plant cells using transformation techniques know in the art. A heterologous gene in an organism may replace an endogenous equivalent gene, i.e. one which normally performs the same or a similar function, or the inserted sequence may be additional to the endogenous gene or other sequence.

The enhancer sequence operatively linked to a nucleotide sequence of interest may also be operatively linked to promoter, or plant regulatory region, and a 3'UTR and terminator sequences. The enhancer sequence may be defined by, for example, any one of SEQ ID NO's:1, 2, 24, 27, 68, 69 and 70-77, or a .nucleotide sequence that exhibits 100%, 99%, 98%, 97%, 96%, 95%, 90%, 85% or 80% identity to the sequence as set forth in any one of SEQ ID NO's:1, 2, 24, 27, 68, 69 and 70-77. Thus, the nucleotide sequence of interest is located between the enhancer sequence and the termination sequence (see FIG. 1A). Either the expression enhancer or the nucleotide sequence of interest may comprise a plant kozak sequence.

The invention further provides an expression cassette comprising in series, a promoter or plant regulatory region, operatively linked to an expression enhancer sequence as described herein which is fused with a nucleotide sequence of interest, a 3'UTR sequence, and a terminator sequence. The enhancer sequence may be defined by, for example, any one of SEQ ID NO's:1, 2, 24, 27, 68, 69 and 70-77, or a .nucleotide sequence that exhibits 100%, 99%, 98%, 97%, 96%, 95%, 90%, 85% or 80% identity to the sequence as set forth in any one of SEQ ID NO's:1, 2, 24, 27, 68, 69 and 70-77. Either the expression enhancer or the nucleotide sequence of interest may comprise a plant kozak sequence.

As one of skill in the art would appreciate, the termination (terminator) sequence may be any sequence that is active the plant host, for example the termination sequence may be derived from the RNA-2 genome segment of a bipartite RNA virus, e.g. a comovirus, or the termination sequence may be a NOS terminator.

The constructs of the present invention can further comprise a 3' untranslated region (UTR). A 3' untranslated region contains a polyadenylation signal and any other regulatory signals capable of effecting mRNA processing or gene expression. The polyadenylation signal is usually characterized by effecting the addition of polyadenylic acid tracks to the 3' end of the mRNA precursor. Polyadenylation signals are commonly recognized by the presence of homology to the canonical form 5' AATAAA-3' although variations are not uncommon. Non-limiting examples of suitable 3' regions are the 3' transcribed non-translated regions containing a polyadenylation signal of *Agrobacterium* tumor inducing (Ti) plasmid genes, such as the nopaline synthase (Nos gene) and plant genes such as the soybean storage protein genes, the small subunit of the ribulose-1, 5-bisphosphate carboxylase gene (ssRUBISCO; U.S. Pat. No. 4,962,028; which is incorporated herein by reference), the promoter used in regulating plastocyanin expression (Pwee and Gray 1993; which is incorporated herein by reference). The termination (terminator) sequence may be obtained from the 3'UTR of the alfalfa plastocyanin gene.

By "nucleotide (or nucleic acid) sequence of interest", or "coding region of interest", it is meant any nucleotide sequence, or coding region (these terms may be used interchangeably) that is to be expressed within a host organism, for example a plant, to produce a protein of interest. Such a nucleotide sequence of interest may encode, but is not limited to, native or modified proteins, an industrial enzyme or a modified industrial enzyme, an agricultural protein or a modified agricultural protein, a helper protein, a protein supplement, a pharmaceutically active protein, a nutraceutical, a value-added product, or a fragment thereof for feed, food, or both feed and food use.

The protein of interest may comprise a native, or a non-native signal peptide; the non-native signal peptide may be of plant origin. For example, the signal peptide may be a protein disulfide isomerase signal peptide (PDI). The native signal peptide may correspond to that of the protein of interest being expressed.

The nucleotide sequence of interest, or coding region of interest may also include a nucleotide sequence that encodes a pharmaceutically active protein, for example growth factors, growth regulators, antibodies, antigens, and fragments thereof, or their derivatives useful for immunization or vaccination and the like. Such proteins include, but are not limited to a protein that is a human pathogen, a viral protein, for example but not limited to VLP-forming antigens, one or more proteins from Respiratory syncytial virus (RSV), Rotavirus, influenza virus, human immunodeficiency virus (HIV), Rabies virus, human papiloma virus (HPV), Enterovirus 71 (EV71), or interleukins, for example one or more than one of IL-1 to IL-24, IL-26 and IL-27, cytokines, Erythropoietin (EPO), insulin, G-CSF, GM-CSF, hPG-CSF, M-CSF or combinations thereof, interferons, for example, interferon-alpha, interferon-beta, interferon-gama, blood clotting factors, for example, Factor VIII, Factor IX, or tPA hGH, receptors, receptor agonists, antibodies for example but not limited to rituximab (Rituxan), neuropolypeptides, insulin, vaccines, growth factors for example but not limited to epidermal growth factor, keratinocyte growth factor, transformation growth factor, growth regulators, antigens, autoantigens, fragments thereof, or combinations thereof.

The protein of interest may also include an influenza hemagglutinin (HA; see WO 2009/009876, which is incorporated herein by reference). HA is a homotrimeric membrane type I glycoprotein, generally comprising a signal peptide, an HA1 domain, and an HA2 domain comprising a membrane-spanning anchor site at the C-terminus and a small cytoplasmic tail. Nucleotide sequences encoding HA are well known and are available (see, for example, the BioDefense and Public Health Database (Influenza Research Database; Squires et al., 2008 Nucleic Acids Research 36:D497-D503) at URL: biohealthbase.org/GSearch/home.do?decorator=Influenza; or the databases maintained by the National Center for Biotechnology Information (see URL: ncbi.nlm.nih.gov), both of which are incorporated herein by reference).

An HA protein may be of a type A influenza, a type B influenza, or is a subtype of type A influenza HA selected from the group of H1, H2, H3, H4, H5, H6, H7, H8, H9, H10, H11, H12, H13, H14, H15, and H16. In some aspects of the invention, the HA may be from a type A influenza, selected from the group H1, H2, H3, H5, H6, H7 and H9. Fragments of the HAs listed above may also be considered a protein of interest. Furthermore, domains from an HA type or subtype listed above may be combined to produce chimeric HA's (see for example WO2009/076778 which is incorporated herein by reference).

Examples of subtypes comprising HA proteins include A/New Caledonia/20/99 (H1N1), A/Indonesia/5/2006 (H5N1), A/chicken/New York/1995, A/herring gull/DE/677/88 (H2N8), A/Texas/32/2003, A/mallard/MN/33/00, A/duck/Shanghai/1/2000, A/northern pintail/TX/828189/02, A/Turkey/Ontario/6118/68(H8N4), A/shoveler/Iran/G54/03, A/chicken/Germany/N/1949(H10N7), A/duck/England/56(H11N6), A/duck/Alberta/60/76(H12N5), A/Gull/Maryland/704/77 (H13N6), A/Mallard/Gurjev/263/82, A/duck/Australia/341/83 (H15N8), A/black-headed gull/Sweden/5/99(H16N3), B/Lee/40, C/Johannesburg/66, A/PuertoRico/8/34 (H1N1), A/Brisbane/59/2007 (H1N1), A/Solomon Islands 3/2006 (H1N1), A/Brisbane 10/2007 (H3N2), A/Wisconsin/67/2005 (H3N2), B/Malaysia/2506/2004, B/Florida/4/2006, A/Singapore/1/57 (H2N2), A/Anhui/1/2005 (H5N1), A/Vietnam/1194/2004 (H5N1), A/Teal/HongKong/W312/97 (H6N1), A/Equine/Prague/56 (H7N7), A/HongKong/1073/99 (H9N2)).

The HA protein may be an H1, H2, H3, H5, H6, H7 or H9 subtype. For example, the H1 protein may be from the A/New Caledonia/20/99 (H1N1), A/PuertoRico/8/34 (H1N1), A/Brisbane/59/2007 (H1N1), A/Solomon Islands 3/2006 (H1N1), A/California/04/2009 (H1N1) or A/California/07/2009 (H1N1) strain. The H3 protein may also be from the A/Brisbane 10/2007 (H3N2), A/Wisconsin/67/2005 (H3N2), A/Victoria/361/2011 (H3N2), A/Texas/50/2012 (H3N2), A/Hawaii/22/2012 (H3N2), A/New York/39/2012 (H3N2), or A/Perth/16/2009 (H3N2) strain. In a further aspect of the invention, the H2 protein may be from the A/Singapore/1/57 (H2N2) strain. The H5 protein may be from the A/Anhui/1/2005 (H5N1), A/Vietnam/1194/2004 (H5N1), or A/Indonesia/5/2005 strain. In an aspect of the invention, the H6 protein may be from the A/Teal/HongKong/W312/97 (H6N1) strain. The H7 protein may be from the A/Equine/Prague/56 (H7N7) strain, or H7 A/Hangzhou/1/2013, A/Anhui/1/2013 (H7N9), or A/Shanghai/2/2013 (H7N9) strain. In an aspect of the invention, the H9 protein is from the A/HongKong/1073/99 (H9N2) strain. In a further aspect of the invention, the HA protein may be from an influenza virus may be a type B virus, including B/Malaysia/2506/2004, B/Florida/4/2006, B/Brisbane/60/08, B/Massachusetts/2/2012-like virus (Yamagata lineage), or B/Wisconsin/1/2010 (Yamagata lineage). Non-limiting examples of amino acid sequences of the HA proteins from H1, H2, H3, H5, H6, H7, H9 or B subtypes include sequences as described in WO 2009/009876, WO 2009/076778, WO 2010/003225 (which are incorporated herein by reference). The influenza virus HA protein may be H5 Indonesia.

The HA may also be a chimeric HA, wherein a native transmembrane domain of the HA is replaced with a heterologous transmembrane domain. The transmembrane domain of HA proteins is highly conserved (see for example FIG. 1C of WO 2010/148511; which is incorporated herein by reference). The heterologous transmembrane domain may be obtained from any HA transmembrane domain, for example but not limited to the transmembrane domain from H1 California, B/Florida/4/2006 (GenBank Accession No. ACA33493.1), B/Malaysia/2506/2004 (GenBank Accession No. ABU99194.1), H1/Bri (GenBank Accession No. ADE28750.1), H1 A/Solomon Islands/3/2006 (GenBank Accession No. ABU99109.1), H1/NC (GenBank Accession No. AAP34324.1), H2 A/Singapore/1/1957 (GenBank Accession No. AAA64366.1), H3 A/Brisbane/10/2007 (GenBank Accession No. AC 126318.1), H3 A/Wisconsin/67/2005 (GenBank Accession No. AB037599.1), H5 A/Anhui/1/2005 (GenBank Accession No. ABD28180.1), H5 A/Vietnam/1194/2004 (GenBank Accession No. ACR48874.1), H5-Indo (GenBank Accession No. ABW06108.1). The transmembrane domain may also be defined by the following consensus amino acid sequence:

(SEQ ID NO: 78)
iLXiYystvAiSslXlXXmlagXsXwmcs

The HA may comprise a native, or a non-native signal peptide; the non-native signal peptide may be of plant origin. The native signal peptide may correspond to that of the hemagglutinin being expressed, or may correspond to a second hemagglutinin. Additionally, the signal peptide may be from a structural protein or hemagglutinin of a virus other than influenza. Non-limiting examples of a signal peptide that may be used is that of alfalfa protein disulfide isomerase (PDI SP; nucleotides 32-103 of Accession No. Z11499), or the patatin signal peptide (PatA SP; located nucleotides 1738-1806 of GenBank Accession number A08215). The nucleotide sequence of PatA SP for this accession number is:

(SEQ ID NO: 79)
ATGGCAACTACTAAAACTTTTTTAATTTTATTTTTTATGATATTAGCAA
CTACTAGTTCAACATGTGCT the amino acid sequence of patatin A signal peptide is:

(SEQ ID NO: 80)
MATTKTFLILFFMILATTSSTCA

The present invention also provides nucleic acid molecules comprising sequences encoding an HA protein. The nucleic acid molecules may further comprise one or more regulatory regions operatively linked to the sequence encoding an HA protein. The nucleic acid molecules may comprise a sequence encoding an H1, H2, H3, H4, H5, H6, H7, H8, H9, H10, H11, H12, H13, H14, H15, H16 or HA from type B influenza. For example, the HA protein encoded by the nucleic acid molecule may be an H1, H2, H3, H5, H6, H7, H9 subtype an HA from type B. The H1 protein encoded by the nucleic acid may be from the A/New Caledonia/20/99 (H1N1), A/PuertoRico/8/34 (H1N1), A/Brisbane/59/2007 (H1N1), A/Solomon Islands 3/2006 (H1N1), A/California/

04/2009 (H1N1) or A/California/07/2009 (H1N1) strain. The H3 protein encoded by the nucleic acid molecule may be from the A/Brisbane 10/2007 (H3N2), A/Wisconsin/67/2005 (H3N2), A/Victoria/361/2011 (H3N2), A/Texas/50/2012 (H3N2), A/Hawaii/22/2012 (H3N2), A/New York/39/2012 (H3N2), or A/Perth/16/2009 (H3N2) strain. The H2 protein encoded by the nucleic acid molecule may be from the A/Singapore/1/57 (H2N2) strain. The H5 protein encoded by the nucleic acid molecule A/Anhui/1/2005 (H5N1), A/Vietnam/1194/2004 (H5N1), or A/Indonesia/5/2005 strain. The H6 protein encoded by the nucleic acid molecule may be from the A/Teal/HongKong/W312/97 (H6N1) strain. The H7 protein encoded by the nucleic acid molecule may be from the A/Equine/Prague/56 (H7N7) strain, or H7 A/Hangzhou/1/2013, A/Anhui/1/2013 (H7N9), or A/Shanghai/2/2013 (H7N9) strain. Additional, the H9 protein encoded by the nucleic acid molecule may be from the A/HongKong/1073/99 (H9N2) strain. The HA protein encoded by the nucleic acid molecule may be from an influenza virus type B virus, including B/Malaysia/2506/2004, B/Florida/4/2006, B/Brisbane/60/08, B/Massachusetts/2/2012-like virus (Yamagata lineage), or B/Wisconsin/1/2010 (Yamagata lineage). Non-limiting examples of amino acid sequences of the HA proteins from H1, H2, H3, H5, H6, H7, H9 or B subtypes include sequences as described in WO 2009/009876, WO 2009/076778, WO 2010/003225 (which are incorporated herein by reference). The influenza virus HA protein may be H5 Indonesia.

TABLE 1

Examples of constructs that have been prepared as described herein:

| Construct # | SP[1] | Sequence of Interest | Example |
|---|---|---|---|
| | | CMPV-HT based constructs (constructs comprising SEQ ID NO: 4; prior art) | |
| 484 | PDI[2] | H1 California | 5 |
| 489 | WT[3] | H5 Indonesia | 6 |
| 2140 | PDI | H7 Hangzhou | 7 |
| 2130 | PDI | H7 Hangzhou + H5 Indonesia TMCT[4] | 8 |
| 1039 | PDI | B Brisbane(Prl-) | 9 |
| 1067 | PDI | B Brisbane(PrL-) + Hi California TMCT | 10 |
| 2072 | PDI | B Massachussetts (PrL-) | 11 |
| 2074 | PDI | B Massachussetts (PrL-) + H1 California TMCT | 12 |
| 1445 | WT | B Wisconsin (PrL-) | 13 |
| 1454 | WT | B Wisconsin (PrL-) + H1 California TMCT | 14 |
| 5001 | WT | HC rituximab (Rituxan) | 15 |
| 5002 | PDI | HC rituximab (Rituxin) | 16 |
| 5021 | WT | LC rituximab (Rituxin) | 17 |
| 5022 | PDI | LC rituximab (Rituxin) | 18 |
| | | CPMV160 + based constructs (constructs comprising SEQ ID NO: 2) | |
| 1800 | PDI | H3 Victoria | 2 |
| 1897 | PDI | H1 California | 5 |
| 1880 | WT | H5 Indonesia | 6 |
| 2168 | PDI | H7 Hangzhou | 7 |
| 2188 | PDI | H7 Hangzhou + H5 Indonesia TMCT | 8 |
| 1937 | PDI | B Brisbane(Prl-) | 9 |
| 1977 | PDI | B Brisbane(PrL-) + Hi California TMCT | 10 |
| 2050 | PDI | B Massachussetts (PrL-) | 11 |
| 2060 | PDI | B Massachussetts (PrL-) + H1 California TMCT | 12 |
| 1975 | WT | B Wisconsin (PrL-) | 13 |
| 1893 | WT | B Wisconsin (PrL-) + H1 California TMCT | 14 |

TABLE 1-continued

Examples of constructs that have been prepared as described herein:

| Construct # | SP[1] | Sequence of Interest | Example |
|---|---|---|---|
| 2100 | WT | HC rituximab (Rituxan) | 15 |
| 2109 | PDI | HC rituximab (Rituxin) | 16 |
| 2120 | WT | LC rituximab (Rituxin) | 17 |
| 2129 | PDI | LC rituximab (Rituxin) | 18 |
| | | CPMV160 based constructs (constructs comprising SEQ ID NO: 1) | |
| 1935 | PDI | H3 Victoria | 3 |
| 1885 | WT | H5 Indonesia | 6 |

[1]SP—signal peptide
[2]PDI—alfalfa protein disulfide isomerise
[3]WT—wild type or native
[4]TMCT—transmembrane domain and cytoplasmic tail If the nucleic acid sequence of interest encodes a product that is directly or indirectly toxic to the plant, then such toxicity may be reduced by selectively expressing the nucleotide sequence of interest within a desired tissue or at a desired stage of plant development.

The coding region of interest or the nucleotide sequence of interest may be expressed in any suitable plant host which is either transformed or comprises the nucleotide sequences, or nucleic acid molecules, or genetic constructs, or vectors of the present invention. Examples of suitable hosts include, but are not limited to, *Arabidopsis*, agricultural crops including for example canola, *Brassica* spp., maize, *Nicotiana* spp., (tobacco) for example, *Nicotiana benthamiana*, alfalfa, potato, sweet potato (*Ipomoea batatus*), ginseng, pea, oat, rice, soybean, wheat, barley, sunflower, cotton, corn, rye (*Secale cereale*), sorghum (*Sorghum bicolor, Sorghum vulgare*), safflower (*Carthamus tinctorius*).

The terms "biomass" and "plant matter" as used herein refer to any material derived from a plant. Biomass or plant matter may comprise an entire plant, or part of plant including the leaf, root, stem, flower, seed, it may also include any tissue of the plant, any cells of the plant, or any fraction of the plant, part or the plant, tissue or cell. Further, biomass or plant matter may comprise intracellular plant components, extracellular plant components, liquid or solid extracts of plants, or a combination thereof. Further, biomass or plant matter may comprise plants, plant cells, tissue, a liquid extract, or a combination thereof, from plant leaves, stems, fruit, roots or a combination thereof. A portion of a plant may comprise plant matter or biomass.

By "regulatory region" "regulatory element" or "promoter" it is meant a portion of nucleic acid typically, but not always, upstream of the protein coding region of a gene, which may be comprised of either DNA or RNA, or both DNA and RNA. When a regulatory region is active, and in operative association, or operatively linked, with a gene of interest, this may result in expression of the gene of interest. A regulatory element may be capable of mediating organ specificity, or controlling developmental or temporal gene activation. A "regulatory region" includes promoter elements, core promoter elements exhibiting a basal promoter activity, elements that are inducible in response to an external stimulus, elements that mediate promoter activity such as negative regulatory elements or transcriptional enhancers. "Regulatory region", as used herein, also includes elements that are active following transcription, for example, regulatory elements that modulate gene expression such as translational and transcriptional enhancers, translational and transcriptional repressors, upstream activating sequences, and mRNA instability determinants. Several of these latter elements may be located proximal to the coding region.

In the context of this disclosure, the term "regulatory element" or "regulatory region" typically refers to a sequence of DNA, usually, but not always, upstream (5') to the coding sequence of a structural gene, which controls the expression of the coding region by providing the recognition for RNA polymerase and/or other factors required for transcription to start at a particular site. However, it is to be understood that other nucleotide sequences, located within introns, or 3' of the sequence may also contribute to the regulation of expression of a coding region of interest. An example of a regulatory element that provides for the recognition for RNA polymerase or other transcriptional factors to ensure initiation at a particular site is a promoter element. Most, but not all, eukaryotic promoter elements contain a TATA box, a conserved nucleic acid sequence comprised of adenosine and thymidine nucleotide base pairs usually situated approximately 25 base pairs upstream of a transcriptional start site. A promoter element may comprise a basal promoter element, responsible for the initiation of transcription, as well as other regulatory elements (as listed above) that modify gene expression.

There are several types of regulatory regions, including those that are developmentally regulated, inducible or constitutive. A regulatory region that is developmentally regulated, or controls the differential expression of a gene under its control, is activated within certain organs or tissues of an organ at specific times during the development of that organ or tissue. However, some regulatory regions that are developmentally regulated may preferentially be active within certain organs or tissues at specific developmental stages, they may also be active in a developmentally regulated manner, or at a basal level in other organs or tissues within the plant as well. Examples of tissue-specific regulatory regions, for example see-specific a regulatory region, include the napin promoter, and the cruciferin promoter (Rask et al., 1998, J. Plant Physiol. 152: 595-599; Bilodeau et al., 1994, Plant Cell 14: 125-130). An example of a leaf-specific promoter includes the plastocyanin promoter (see U.S. Pat. No. 7,125,978, which is incorporated herein by reference).

An inducible regulatory region is one that is capable of directly or indirectly activating transcription of one or more DNA sequences or genes in response to an inducer. In the absence of an inducer the DNA sequences or genes will not be transcribed. Typically the protein factor that binds specifically to an inducible regulatory region to activate transcription may be present in an inactive form, which is then directly or indirectly converted to the active form by the inducer. However, the protein factor may also be absent. The inducer can be a chemical agent such as a protein, metabolite, growth regulator, herbicide or phenolic compound or a physiological stress imposed directly by heat, cold, salt, or toxic elements or indirectly through the action of a pathogen or disease agent such as a virus. A plant cell containing an inducible regulatory region may be exposed to an inducer by externally applying the inducer to the cell or plant such as by spraying, watering, heating or similar methods. Inducible regulatory elements may be derived from either plant or non-plant genes (e.g. Gatz, C. and Lenk, I. R. P., 1998, Trends Plant Sci. 3, 352-358; which is incorporated by reference). Examples, of potential inducible promoters include, but not limited to, tetracycline-inducible promoter (Gatz, C., 1997, Ann. Rev. Plant Physiol. Plant Mol. Biol. 48, 89-108; which is incorporated by reference), steroid inducible promoter (Aoyama, T. and Chua, N. H., 1997, Plant J. 2, 397-404; which is incorporated by reference) and ethanol-inducible promoter (Salter, M. G., et al, 1998, Plant Journal 16, 127-132; Caddick, M. X., et al, 1998, Nature Biotech. 16, 177-180, which are incorporated by reference) cytokinin inducible IB6 and CKI1 genes (Brandstatter, I. and Kieber, J. J., 1998, Plant Cell 10, 1009-1019; Kakimoto, T., 1996, Science 274, 982-985; which are incorporated by reference) and the auxin inducible element, DRS (Ulmasov, T., et al., 1997, Plant Cell 9, 1963-1971; which is incorporated by reference).

A constitutive regulatory region directs the expression of a gene throughout the various parts of a plant and continuously throughout plant development. Examples of known constitutive regulatory elements include promoters associated with the CaMV 35S transcript. (p35S; Odell et al., 1985, Nature, 313: 810-812), the rice actin 1 (Zhang et al, 1991, Plant Cell, 3: 1155-1165), actin 2 (An et al., 1996, *Plant J.,* 10: 107-121), or tms 2 (U.S. Pat. No. 5,428,147, which is incorporated herein by reference), and triosephosphate isomerase 1 (Xu et. al., 1994, Plant Physiol. 106: 459-467) genes, the maize ubiquitin 1 gene (Cornejo et al, 1993, Plant Mol. Biol. 29: 637-646), the *Arabidopsis* ubiquitin 1 and 6 genes (Holtorf et al, 1995, Plant Mol. Biol. 29: 637-646), the tobacco translational initiation factor 4A gene (Mandel et al, 1995 Plant Mol. Biol. 29: 995-1004). the Cassava Vein Mosaic Virus promoter, pCAS, (Verdaguer et al., 1996); the promoter of the small subunit of ribulose biphosphate carboxylase, pRbcS: (Outchkourov et al., 2003), the pUbi (for monocots and dicots).

As described herein, regulatory regions comprising enhancer sequences with demonstrated efficiency in leaf expression, have been found to be effective in transient expression. Without wishing to be bound by theory, attachment of upstream regulatory elements of a photosynthetic gene by attachment to the nuclear matrix may mediate strong expression. For example up to −784 from the translation start site of pea plastocyanin (U.S. Pat. No. 7,125,978, which is incorporated herein by reference) may be used mediate strong reporter gene expression.

The term "constitutive" as used herein does not necessarily indicate that a nucleotide sequence under control of the constitutive regulatory region is expressed at the same level in all cell types, but that the sequence is expressed in a wide range of cell types even though variation in abundance is often observed.

The expression constructs as described above may be present in a vector. The vector may comprise border sequences which permit the transfer and integration of the expression cassette into the genome of the organism or host. The construct may be a plant binary vector, for example a binary transformation vector based on pPZP (Hajdukiewicz, et al. 1994). Other example constructs include pBin19 (see Frisch, D. A., L. W. Harris-Haller, et al. 1995, *Plant Molecular Biology* 27: 405-409).

If desired, the constructs of this invention may be further manipulated to include selectable markers. However, this may not be required. Useful selectable markers include enzymes that provide for resistance to chemicals such as an antibiotic for example, gentamycin, hygromycin, kanamycin, or herbicides such as phosphinothrycin, glyphosate, chlorosulfuron, and the like. Similarly, enzymes providing for production of a compound identifiable by colour change such as GUS (beta-glucuronidase), or luminescence, such as luciferase or GFP, may be used.

A vector may also include a expression enhancer as described herein. The expression enhancer may be positioned on a T-DNA which also contains a suppressor of gene silencing and NPTII. The polylinker may also encode one or two sets of 6× Histidine residues to allow the inclusion of N- or C-terminal His-tags to the protein of interest to facilitate protein purification.

Post-transcriptional gene silencing (PTGS) may be involved in limiting expression of transgenes in plants, and co-expression of a suppressor of silencing from the potato virus Y (HcPro) may be used to counteract the specific degradation of transgene mRNAs (Brigneti et al., 1998, *EMBO J.* 17, 6739-6746, which is incorporated herein by reference). Alternate suppressors of silencing are well known in the art and may be used as described herein (Chiba et al., 2006, Virology 346:7-14; which is incorporated herein by reference), for example but not limited to, TEV-p1/HC-Pro (Tobacco etch virus-p1/HC-Pro), BYV-p21, p19 of Tomato bushy stunt virus (TBSV p19; the construction of p19 is described in described in WO 2010/0003225, which is incorporated herein by reference), capsid protein of Tomato crinkle virus (TCV-CP), 2b of Cucumber mosaic virus; CMV-2b), p25 of Potato virus X (PVX-p25), p11 of Potato virus M (PVM-p11), p11 of Potato virus S (PVS-p11), p16 of Bluebeffy scorch virus, (BScV p16), p23 of Citrus tristeza virus (CTV-p23), p24 of Grapevine leafroll-associated virus-2, (GLRaV-2 p24), p10 of Grapevine virus A, (GVA-p10), p14 of Grapevine virus B (GVB-p14), p10 of Heracleum latent virus (HLV-p10), or p16 of Garlic common latent virus (GCLV-p16).

Therefore, one or more suppressors of silencing, for example, but not limited to, HcPro, TEV-p1/HC-Pro, BYV-p21, TBSV p19, TCV-CP, CMV-2b, PVX-p25, rgscam, B2 protein from FHV, the small coat protein of CPMV, and coat protein from TCV, PVM-p11, PVS-p11, BScV-p16, CTV-p23, GLRaV-2 p24, GBV-p14, HLV-p10, GCLV-p16, or GVA-p10 may be co-expressed along with the comovirus-based expression cassette, geminivirus-derived amplification element, and the nucleic acid sequence encoding the protein of interest to further ensure high levels of protein production within a plant.

The constructs of the present invention can be introduced into plant cells using Ti plasmids, Ri plasmids, plant virus vectors, direct DNA transformation, micro-injection, electroporation, etc. For reviews of such techniques see for example Weissbach and Weissbach, *Methods for Plant Molecular Biology*, Academy Press, New York VIII, pp. 421-463 (1988); Geierson and Corey, *Plant Molecular Biology*, 2d Ed. (1988); and Miki and Iyer, *Fundamentals of Gene Transfer in Plants*. In *Plant Metabolism,* 2d Ed. D T. Dennis, D H Turpin, D D Lefebrve, D B Layzell (eds), Addison Wesly, Langmans Ltd. London, pp. 561-579 (1997). Other methods include direct DNA uptake, the use of liposomes, electroporation, for example using protoplasts, micro-injection, microprojectiles or whiskers, and vacuum infiltration. See, for example, Bilang, et al. (1991, *Gene* 100: 247-250), Scheid et al. (1991, *Mol. Gen. Genet.* 228: 104-112), Guerche et al. (1987, *Plant Science* 52: 111-116), Neuhause et al. (1987, *Theor. Appl Genet.* 75: 30-36), Klein et al., (2987, *Nature* 327: 70-73); Freeman et al. (1984, *Plant Cell Physiol.* 29: 1353), Howell et al. (1980, *Science* 208: 1265), Horsch et al. (1985, *Science* 227: 1229-1231), DeBlock et al., (1989, *Plant Physiology* 91: 694-701), Methods for Plant Molecular Biology (Weissbach and Weissbach, eds., Academic Press Inc., 1988), Methods in Plant Molecular Biology (Schuler and Zielinski, eds., Academic Press Inc., 1989), WO 92/09696, WO 94/00583, EP 331083, EP 175966, Liu and Lomonossoff (2002, *J Virol Meth,* 105:343-348), EP 290395; WO 8706614; U.S. Pat. Nos. 4,945,050; 5,036,006; and 5,100,792, U.S. patent application Ser. No. 08/438,666, filed May 10, 1995, and Ser. No. 07/951,715, filed Sep. 25, 1992, (all of which are hereby incorporated by reference).

Transient expression methods may be used to express the constructs of the present invention (see D'Aoust et al., 2009, *Methods in molecular biology*, Vol 483, page 541-50; Liu and Lomonossoff, 2002, *Journal of Virological Methods,* 105:343-348; which is incorporated herein by reference). Alternatively, a vacuum-based transient expression method, as described by Kapila et al., (1997, *Plant Sci.* 122, 101-108; which is incorporated herein by reference), or WO 00/063400, WO 00/037663 (which are incorporated herein by reference) may be used. These methods may include, for example, but are not limited to, a method of Agro-inoculation or Agro-infiltration, syringe infiltration, however, other transient methods may also be used as noted above. With Agro-inoculation, Agro-infiltration, or syringe infiltration, a mixture of *Agrobacteria* comprising the desired nucleic acid enter the intercellular spaces of a tissue, for example the leaves, aerial portion of the plant (including stem, leaves and flower), other portion of the plant (stem, root, flower), or the whole plant. After crossing the epidermis the *Agrobacteria* infect and transfer t-DNA copies into the cells. The t-DNA is episomally transcribed and the mRNA translated, leading to the production of the protein of interest in infected cells, however, the passage oft-DNA inside the nucleus is transient.

Also considered part of this invention are transgenic plants, plant cells or seeds containing the gene construct of the present invention that may be used as a platform plant suitable for transient protein expression described herein. Methods of regenerating whole plants from plant cells are also known in the art (for example see Guerineau and Mullineaux (1993, Plant transformation and expression vectors. In: Plant Molecular Biology Labfax (Croy RRD ed) Oxford, BIOS Scientific Publishers, pp 121-148). In general, transformed plant cells are cultured in an appropriate medium, which may contain selective agents such as antibiotics, where selectable markers are used to facilitate identification of transformed plant cells. Once callus forms, shoot formation can be encouraged by employing the appropriate plant hormones in accordance with known methods and the shoots transferred to rooting medium for regeneration of plants. The plants may then be used to establish repetitive generations, either from seeds or using vegetative propagation techniques. Transgenic plants can also be generated without using tissue culture. Methods for stable transformation, and regeneration of these organisms are established in the art and known to one of skill in the art. Available techniques are reviewed in Vasil et al., (Cell Culture and Somatic Cell Genetics of Plants, Vol I, II and III, Laboratory Procedures and Their Applications, Academic Press, 1984), and Weissbach and Weissbach, (Methods for Plant Molecular Biology, Academic Press, 1989). The method of obtaining transformed and regenerated plants is not critical to the present invention.

If plants, plant portion or plant cell are to be transformed or co-transformed by two or more nucleic acid constructs, the nucleic acid construct may be introduced into the *Agrobacterium* in a single transfection event the nucleic acids are pooled, and the bacterial cells transfected as described. Alternately, the constructs may be introduced serially. In this case, a first construct is introduced to the *Agrobacterium* as described, the cells grown under selective conditions (e.g. in the presence of an antibiotic) where only the singly transformed bacteria can grow. Following this first selection step, a second nucleic acid construct is introduced to the *Agro-*

*bacterium* as described, and the cells grown under doubly-selective conditions, here only the doubly-transformed bacteria can grow. The doubly-transformed bacteria may then be used to transform a plant, plant portion or plant cell as described herein, or may be subjected to a further transformation step to accommodate a third nucleic acid construct.

Alternatively, if plants, a plant portion, or a plant cell are to be transformed or co-transformed by two or more nucleic acid constructs, the nucleic acid construct may be introduced into the plant by co-infiltrating a mixture of *Agrobacterium* cells with the plant, plant portion, or plant cell, each *Agrobacterium* cell may comprise one or more constructs to be introduced within the plant. In order to vary the relative expression levels within the plant, plant portion or plant cell, of a nucleotide sequence of interest within a construct, during the step of infiltration, the concentration of the various *Agrobacteria* populations comprising the desired constructs may be varied.

The present disclosure further provides a transgenic plant comprising the expression system as defined herein, wherein the heterologous nucleic acid of interest in the cassette is expressed at an enhanced level when compared to other analogous expression systems that lack one or more components of the expression system as described herein, for example CMPV HT (SEQ ID NO:4).

The present disclosure further comprises a method for generating a protein of interest, comprising the steps of providing a plant, or plant part, that expresses the expression system as described herein, harvesting, at least, a tissue in which the protein of interest has been expressed and optionally, isolating the protein of interest from the tissue.

Thus in various aspects, and without limitation, the invention provides:

an expression enhancer, comprising a comovirus 5'UTR selected from any one of SEQ ID NO's:1, 2, 24, 27, 68, 69 and 70-77, or a .nucleotide sequence that exhibits 100%, 99%, 98%, 97%, 96%, 95%, 90%, 85% or 80% identity to the sequence as set forth in any one of SEQ ID NO's:1, 2, 24, 27, 68, 69 and 70-77, wherein the expression enhancer, when operatively linked to a plant regulatory region and a plant kozak sequence as described herein, increases the level of expression of a nucleotide sequence of interest that is operatively linked to the expression enhancer when compared to the level of expression of the nucleotide sequence of interest fused to the CMPV HT (SEQ ID NO:4; prior art enhancer sequence comprising an incomplete M protein as described in Sainsbury F., and Lomonossoff G. P., 2008, Plant Physiol. 148: pp. 1212-1218; which is incorporated herein by reference) using the same plant regulatory region.

one or more expression systems comprising a comovirus-based expression enhancer or expression cassette as defined above, a promoter (regulatory region), optionally a polylinker, a kozak sequence, a nucleic acid encoding a protein of interest, and a terminator.

methods of expressing a protein of interest, in a host organism such as a plant using one or more expression systems or vectors as described herein.

host cells and organisms expressing proteins of interest from the one or more expression systems or vectors of the invention and methods of producing the hosts and organisms.

TABLE 2 list of sequences

| SEQ ID NO | Description | SEQ ID NO | Description |
|---|---|---|---|
| 1 | CPMV160 | 41 | Nucleotide sequence of native H5 Indonesia |
| 2 | CPMV160+ | 42 | Amino acid sequence of native H5 Indonesia |
| 3 | Consensus kozak sequence (A/-)A(A/G)(A/G)(A/C)A | 43 | Nucleotide sequence of PDISP/H7 Hangzhou |
| 4 | CPMV HT (prior art 5'UTR) | 44 | Amino acid sequence of PDISP/H7 Hangzhou |
| 5 | Consensus plant kingdom kozak sequence | 45 | Nucleotide sequence of PDISP/H7 Hangzhou+H5 Indonesia TMCT |
| 6 | Consensus dicot kozak sequence | 46 | Amino acid sequence of PDISP/H7 Hangzhou+H5 Indonesia TMCT |
| 7 | Consensus Arabidopsis kozak sequence | 47 | Nucleotide sequence of PDISP/HA B Brisbane (PrL-) |
| 8 | kozak sequence AGAAA | 48 | Amino acid sequence of PDISP/HA B Brisbane (PrL-) |
| 9 | kozak sequence AGACA | 49 | Nucleotide sequence of PDISP/HA B Brisbane (PrL-)+ H1 California TMCT |
| 10 | kozak sequence AGGAA | 50 | Amino acid sequence of PDISP/HA B Brisbane (PrL-)+ H1 California TMCT |

TABLE 2-continued list of sequences

| SEQ ID NO | Description | SEQ ID NO | Description |
|---|---|---|---|
| 11 | kozak sequence AAAAA | 51 | Nucleotide sequence of PDISP/HA B Massachussetts (PrL-) |
| 12 | kozak sequence AAACA | 52 | Amino acid sequence of PDISP/HA B Massachussetts (PrL-) |
| 13 | kozak sequence AAGCA | 53 | Nucleotide sequence of PDISP/HA B Massachussetts (PrL-)+H1 California TMCT |
| 14 | kozak sequence AAGAA | 54 | Amino acid sequence of PDISP/HA B Massachussetts (PrL-)+H1 California TMCT |
| 15 | kozak sequence AAAGAA | 55 | Nucleotide sequence of HA B Wisconsin (PrL-) |
| 16 | kozak sequence AAAAGAA | 56 | Amino acid sequence of HA B Wisconsin (PrL-) |
| 17 | IF-H3V36111.s1-4r | 57 | Nucleotide sequence of HA B Wisconsin (PrL-)+H1 California TMCT |
| 18 | Nucleotide sequence of PDISP/H3 Victoria. | 58 | Amino acid sequence of HA B Wisconsin (PrL-)+H1 California TMC |
| 19 | Nucleotide sequence of construct 1191 | 59 | Nucleotide sequence of HC rituximab (Rituxan) |
| 20 | Nucleotide sequence of expression cassette number 1391 | 60 | Amino acid sequence of HC Rituxan |
| 21 | Amino acid sequence of PDISP/H3 Victoria | 61 | Nucleotide sequence of PDISP/HC rituximab (Rituxan) |
| 22 | IF ** (SacII)-PDI.s1+4c | 62 | Amino acid sequence of PDISP/HC rituximab (Rituxan) |
| 23 | IF-H3V36111.s1-4r | 63 | Nucleotide sequence of LC rituximab (Rituxan) |
| 24 | CPMV155 | 64 | Amino acid sequence of LC rituximab (Rituxan) |
| 25 | Nucleotide sequence of construct 2171 | 65 | Nucleotide sequence of PDISP/LC rituximab (Rituxan) |
| 26 | Nucleotide sequence of expression cassette number 1800 from 2X35S promoter to NOS terminator | 66 | Amino acid sequence of PDISP/LC rituximab (Rituxan) |
| 27 | CPMV150 | 67 | IF-PDI.S1+3c |
| 28 | IF-CPMV(fl5'UTR)_SpPDI.c | 68 | CPMV114 |
| 29 | Nucleotide sequence of construct 1190 | 69 | CPMV160, 115A |
| 30 | Nucleotide sequence of expression cassette number 1935 from 2X35S promoter to NOS terminator | 70 | CPMV155, 115A |
| 31 | IF-HT1*(-Mprot)-PDI.c | 71 | CPMV150, 115A |
| 32 | IF-HT2*(-Mprot)-PDI.c | 72 | CPMV155+ |

TABLE 2-continued

| list of sequences | | | |
|---|---|---|---|
| SEQ ID NO | Description | SEQ ID NO | Description |
| 33 | IF-HT3*(-Mprot)-PDI.c | 73 | CPMV150+ |
| 34 | IF-HT4*(-Mprot)-PDI.c | 74 | CPMV114+ |
| 35 | IF-HT5*(-Mprot)-PDI.c | 75 | CPMV160+, 115A |
| 36 | IF-HT6*(-Mprot)-PDI.c | 76 | CPMV155+, 115A |
| 37 | IF-HT7*(-Mprot)-PDI.c | 77 | CPMV150+, 115A |
| 38 | IF-HT8*(-Mprot)-PDI.c | 78 | Transmembrane domain consensus amino acid |
| 39 | Nucleotide sequence of PDISP/H1 California | 79 | Patatin signal peptide; nucleic acid sequence |
| 40 | Amino acid sequence of PDISP/H1 California | 80 | Patatin signal peptide; amino acid sequence |

Example 1

2X35S/CPMV-HT/PDISP/H3 Victoria/NOS (Construct Number 1391)

A sequence encoding H3 from Influenza A/Victoria/361/2011 in which the native signal peptide has been replaced by that of alfalfa protein disulfide isomerase (PDISP/H3 Victoria) was cloned into 2X35S-CPMV-HT-NOS expression system (original CMPV-HT) using the following PCR-based method. A fragment containing the PDISP/H3 Victoria coding sequence was amplified using primers IF-PDI.S1+3c (FIG. 6A, SEQ ID NO: 67) and IF-H3V36111.s1-4r (FIG. 6B, SEQ ID NO: 17), using PDISP/H3 Victoria sequence (FIG. 6C, SEQ ID NO:18) as template. The PCR product was cloned in 2X35S/CPMV-HT/NOS expression system using In-Fusion cloning system (Clontech, Mountain View, Calif.). Construct number 1191 (FIG. 6D) was digested with SacII and StuI restriction enzyme and the linearized plasmid was used for the In-Fusion assembly reaction. Construct number 1191 is an acceptor plasmid intended for "In Fusion" cloning of genes of interest in a CPMV-HT-based expression cassette. It also incorporates a gene construct for the co-expression of the TBSV P19 suppressor of silencing under the alfalfa Plastocyanin gene promoter and terminator. The backbone is a pCAMBIA binary plasmid and the sequence from left to right t-DNA borders is presented in FIG. 6E (SEQ ID NO: 19). The resulting construct was given number 1391 (FIG. 6F, SEQ ID NO: 20). The amino acid sequence of mature H3 from Influenza A/Victoria/361/2011 fused with PDISP is presented in FIG. 6G (SEQ ID NO: 21). A representation of plasmid 1391 is presented in FIG. 6H.

Example 2

2X35S/CPMV160+/PDISP/H3 Victoria/NOS (Construct Number 1800)

Figure 7F:
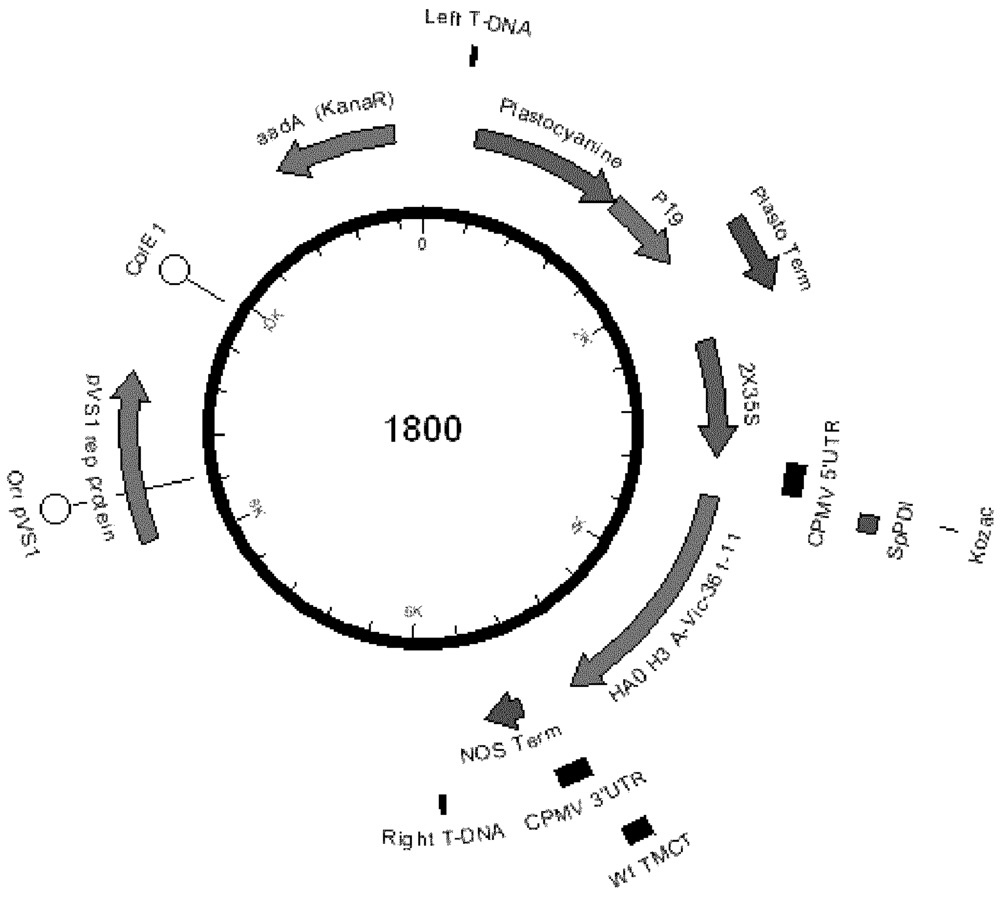

A sequence encoding H3 from Influenza A/Victoria/361/2011 in which the native signal peptide has been replaced by that of alfalfa protein disulfide isomerase (PDISP/H3 Victoria) was cloned into 2X35S/CPMV160+/NOS expression system (CPMV160+) using the following PCR-based method. A fragment containing the PDISP/H3 Victoria coding sequence was amplified using primers IF(SacII)-PDI.s1+4c (FIG. 7A, SEQ ID NO: 22) and IF-H3V36111.s1-4r (FIG. 7B, SEQ ID NO: 23), using PDISP/H3 Victoria sequence (FIG. 7C, SEQ ID NO: 24) as template. The PCR product was cloned in 2X35S/CPMV160+/NOS expression system using In-Fusion cloning system (Clontech, Mountain View, Calif.). Construct number 2171 (FIG. 7D) was digested with SacII and StuI restriction enzyme and the linearized plasmid was used for the In-Fusion assembly reaction. Construct number 2171 is an acceptor plasmid intended for "In Fusion" cloning of genes of interest in a CPMV160+ based expression cassette. It also incorporates a gene construct for the co-expression of the TBSV P19 suppressor of silencing under the alfalfa Plastocyanin gene promoter and terminator. The backbone is a pCAMBIA binary plasmid and the sequence from left to right t-DNA borders is presented in FIG. 7E (SEQ ID NO: 25). The resulting construct was given number 1800 (FIG. 7F, SEQ ID NO: 26). The amino acid sequence of mature H3 from Influenza A/Victoria/361/2011 fused with PDISP is presented in FIG. 7G (SEQ ID NO: 27). A representation of plasmid 1800 is presented in FIG. 7**H.

Example 3

2X35S/CPMV160/PDISP/H3 Victoria/NOS (Construct Number 1935)

A sequence encoding H3 from Influenza A/Victoria/361/2011 in which the native signal peptide has been replaced by that of alfalfa protein disulfide isomerase (PDISP/H3 Victoria) was cloned into 2X35S-CPMV160-NOS expression using the following PCR-based method. A fragment containing the PDISP/H3 Victoria coding sequence was amplified using primers IF-CPMV(fl5'UTR)_SpPDI.c (FIG. 8A, SEQ ID NO: 28) and IF-H3V36111.s1-4r (FIG. 7B, SEQ ID NO: 23), using PDISP/H3 Victoria sequence (FIG. 7C, SEQ ID NO: 24) as template. The PCR product was cloned in 2X35S/CPMV160/NOS expression system using In-Fusion cloning system (Clontech, Mountain View, Calif.). Construct number 1190 (FIG. 8B) was digested with SacII and StuI restriction enzyme and the linearized plasmid was used for the In-Fusion assembly reaction. Construct number 1190 is an acceptor plasmid intended for "In Fusion" cloning of genes of interest in a CPMV160-based expression cassette. It also incorporates a gene construct for the co-expression of the TBSV P19 suppressor of silencing under the alfalfa Plastocyanin gene promoter and terminator. The backbone is a pCAMBIA binary plasmid and the sequence from left to right t-DNA borders is presented in FIG. 8C (SEQ ID NO: 29). The resulting construct was given number 1935 (FIG. 8D, SEQ ID NO: 30). The amino acid sequence of mature H3 from Influenza A/Victoria/361/2011 fused with PDISP is presented in FIG. 7G (SEQ ID NO: 27). A representation of plasmid 1935 is presented in FIG. 8E.

Example 4

Variation of Sequence Between SacII Restriction Site and ATG of PDISP/H3 Victoria in 2X35S/CPMV160+/NOS Expression System (Constructs Number 1992 to 1999)

Eight constructs comprising sequence variations between SacII restriction site and the ATG of PDISP/H3 Victoria in 2X35S/CPMV160+/NOS expression system were created using the same PCR-based method as for construct no 1800 (see Example 2) using a modified forward primer and keeping all other components the same. Variant HT1* to HT8* were amplified using the primers listed in FIGS. 9A-9H, primers:

IF-HT1*(-Mprot)-PDI.c (FIG. 9A, SEQ ID NO: 31),
IF-HT2*(-Mprot)-PDI.c (FIG. 9B, SEQ ID NO: 32),
IF-HT3*(-Mprot)-PDI.c (FIG. 9C, SEQ ID NO: 33)
IF-HT4*(-Mprot)-PDI.c (FIG. 9D, SEQ ID NO: 34)
IF-HT5*(-Mprot)-PDI.c (FIG. 9E, SEQ ID NO: 35)
IF-HT6*(-Mprot)-PDI.c (FIG. 9F, SEQ ID NO: 36)
IF-HT7*(-Mprot)-PDI.c (FIG. 9G, SEQ ID NO: 37) and
IF-HT8*(-Mprot)-PDI.c (FIG. 9H, SEQ ID NO: 38), to create construct no 1992 to 1999, respectively. Representations of plasmid 1992 is presented in FIG. 9I. Analogous features were used to prepare constructs 1993-1999.

Example 5

2X35S/CPMV HT (Construct No 484) and 2X35S/CPMV160+ (Construct No 1897) for PDISP/H1 California A coding sequence corresponding to H1 from Influenza A/California/7/2009 in which the native signal peptide has been replaced by that of alfalfa protein disulfide isomerase (PDISP/H1 California) (FIG. 10A, SEQ ID NO: 39) was cloned into original CPMV-HT and CPMV160 using the same PCR-based method as construct 1391 (see Example 1) and 1800 (see Example 2), respectively, but with modified PCR primers specifically designed for PDISP/H1 California. The amino acid sequence of mature H1 from Influenza A/California/7/2009 fused with PDISP is presented in FIG. 10B (SEQ ID NO: 40). Representations of plasmid 484 and 1897 are presented in FIGS. 10C and 10D.

Example 6

2X35S/CPMV HT (Construct No 489), 2X35S/CPMV160+ (Construct No 1880) and 2X35S/CPMV160 (Construct No 1885) for H5 Indonesia A coding sequence corresponding to native H5 from Influenza A/Indonesia/5/2005 (FIG. 11A, SEQ ID NO: 41) was cloned into original CPMV-HT, CPMV160+ and CPMV160 using the same PCR-based method as construct 1391 (see Example 1), 1800 (see Example 2) and 1935 (see Example 3), respectively but with modified PCR primers specifically designed for H5 Indonesia. The amino acid sequence of native H5 from Influenza A/Indonesia/5/2005 is presented in FIG. 11B (SEQ ID NO: 42). Representations of plasmid 489, 1880 and 1885 are presented in FIG. 11C to FIG. 11E.

Example 7

2X35S/CPMV HT (Construct No 2140) and 2X35S/CPMV160+ (Construct No 2168) for PDISP-H7 Hangzhou A coding sequence corresponding to H7 from Influenza A/Hangzhou/1/2013 in which the native signal peptide has been replaced by that of alfalfa protein disulfide isomerase (PDISP/H7 Hangzhou) (FIG. 12A, SEQ ID NO:43) was cloned into original CPMV-HT and CPMV160+ using the same PCR-based method as construct 1391 (see Example 1) and 1800 (see Example 2), respectively, but with modified PCR primers specifically designed for PDISP/H7 Hangzhou. The amino acid sequence of mature H7 from Influenza A/Hangzhou/1/2013 fused with PDISP is presented in FIG. 12B (SEQ ID NO:44). Representations of plasmid 2140 and 2168 are presented in FIGS. 12C and 12D.

Example 8

2X35S/CPMV HT (Construct No 2130) and 2X35S/CPMV160+ (Construct No 2188) for PDISP/H7 Hangzhou+H5 Indonesia TMCT A chimer hemagglutinin coding sequence corresponding to the ectodomain of H7 from Influenza A/Hangzhou/1/2013 fused to the transmembrane domain and cytoplasmic tail (TMCT) of H5 from influenza A/Indonesia/5/2005 and with the signal peptide of alfalfa protein disulfide isomerase (PDISP/H7 Hangzhou+H5 Indonesia TMCT) (FIG. 13A, SEQ ID NO:45) was cloned into original CPMV-HT and CPMV160+ using the same PCR-based method as construct 1391 (see Example 1) and 1800 (see Example 2), respectively, but with modified PCR primers specifically designed for the PDISP/H7 Hangzhou+H5 Indonesia TMCT. The amino acid sequence of H7 Hangzhou+H5 Indonesia TMCT fused with PDISP is presented in FIG. 13B (SEQ ID NO: 46). Representations of plasmid 2130 and 2188 are presented in FIGS. 13C and 13D.

Example 9

2X35S/CPMV HT (Construct No 1039) and 2X35S/CPMV160+ (Construct No 1937) for PDISP/HA B Brisbane (PrL-)

A coding sequence corresponding to HA from Influenza B/Brisbane/60/2008 with deleted proteolytic loop (PrL-) (see U.S. provisional application No. 61/806,227 Filed Mar. 28, 2013, which is incorporated herein by reference, for additional information re: deleted proteolytic loop regions in HA sequences) in which the native signal peptide has been replaced by that of alfalfa protein disulfide isomerase (PDISP/HA B Brisbane (PrL-)) (FIG. 14A, SEQ ID NO: 47) was cloned into original CPMV-HT and CPMV160+ using the same PCR-based method as construct 1391 (see Example 1) and 1800 (see Example 2), respectively, but with modified PCR primers specifically designed for PDISP/HA B Brisbane (PrL-). The amino acid sequence of mature HA B Brisbane (PrL-) fused with PDISP is presented in FIG. 14B (SEQ ID NO: 48). Representations of plasmid 1039 and 1937 are presented in FIG. 14C and FIG. 14D.

Example 10

2X35S/CPMV HT (Construct No 1067) and 2X35S/CPMV160+ (Construct No 1977) for PDISP/HA B Brisbane (PrL-)+H1 California TMCT A chimer hemagglutinin coding sequence corresponding to the ectodomain of HA from Influenza B/Brisbane/60/08 with deleted proteolytic loop (PrL-) (see U.S. provisional application No. 61/806,227 Filed Mar. 28, 2013, which is incorporated herein by reference, for additional information re: deleted proteolytic loop regions in HA sequences) fused to the transmembrane domain and cytoplasmic tail (TMCT) of H1 from influenza A/California/7/2009 and with the signal peptide of alfalfa protein disulfide isomerase (PDISP/HA B Brisbane (PrL-)+H1 California TMCT) (FIG. 15A, SEQ ID NO: 49) was cloned into original CPMV-HT and CPMV160+ using the same PCR-based method as construct 1391 (see Example 1) and 1800 (see Example 2), respectively, but with modified PCR primers specifically designed for PDISP/HA B Brisbane (PrL-)+H1 California TMCT. The amino acid sequence of mature HA B Brisbane (PrL-)+H1 California TMCT fused with PDISP is presented in FIG. 15B (SEQ ID NO: 50). Representations of plasmid 1067 and 1977 are presented in FIG. 15C and FIG. 15D.

Example 11

2X35S/CPMV HT (Construct No 2072) and 2X35S/CPMV160+ (Construct No 2050) for PDISP/HA B Massachussetts (PrL-)

A coding sequence corresponding to HA from Influenza B/Massachussetts/2/2012 with deleted proteolytic loop (PrL-) (see U.S. provisional application No. 61/806,227 Filed Mar. 28, 2013 for additional information re: deleted proteolytic loop regions in HA sequences, which is incorporated herein by reference) in which the native signal peptide has been replaced by that of alfalfa protein disulfide isomerase (PDISP/HA B Massachussetts (PrL-)) (FIG. 16A, SEQ ID NO: 51) was cloned into original CPMV-HT and CPMV160+ using the same PCR-based method as construct 1391 (see Example 1) and 1800 (see Example 2), respectively, but with modified PCR primers specifically designed for PDISP/HA B Massachussetts (PrL-). The amino acid sequence of mature HA B Massachussetts (PrL-) fused with PDISP is presented in FIG. 16B (SEQ ID NO: 52). Representations of plasmid 2072 and 2050 are presented in FIG. 16C and FIG. 16D.

Example 12

2X35S/CPMV HT (Construct No 2074) and 2X35S/CPMV160+ (Construct No 2060) for PDISP/HA B Massachussetts (PrL-)+H1 California TMCT A chimer hemagglutinin coding sequence corresponding to the ectodomain of HA from Influenza B/Massachussetts/2/2012 with deleted proteolytic loop (PrL-) (see U.S. provisional application No. 61/806,227 Filed Mar. 28, 2013 for additional information re: deleted proteolytic loop regions in HA sequences, which is incorporated herein by reference) fused to the transmembrane domain and cytoplasmic tail (TMCT) of H1 from influenza A/California/7/2009 and with the signal peptide of alfalfa protein disulfide isomerase (PDISP/HA B Massachussetts (PrL-)+H1 California TMCT) (FIG. 17A, SEQ ID NO: 53) was cloned into original CPMV-HT and CPMV160+ using the same PCR-based method as construct 1391 (see Example 1) and 1800 (see Example 2), respectively, but with modified PCR primers specifically designed for PDISP/HA B Massachussetts (PrL-)+H1 California TMCT. The amino acid sequence of mature HA B Massachussetts (PrL-)+H1 California TMCT fused with PDISP is presented in FIG. 17B (SEQ ID NO: 54). Representations of plasmid 2074 and 2060 are presented in FIGS. 17C and 17D.

Example 13

2X35S/CPMV HT (Construct No 1445), 2X35S/CPMV160+ (Construct No 1820) and CPMV160 (Construct No 1975) for HA B Wisconsin (PrL-)

A coding sequence corresponding to HA from Influenza B/Wisconsin/1/2010 with deleted proteolytic loop (PrL-) (see U.S. provisional application No. 61/806,227 Filed Mar. 28, 2013 for additional information re: deleted proteolytic loop regions in HA sequences, which is incorporated herein by reference) with his native signal peptide (HA B Wisconsin (PrL-)) (FIG. 18A, SEQ ID NO: 55) was cloned into original CPMV-HT, CPMV160+, and CPMV160 using the same PCR-based method as construct 1391 (see Example 1), 1800 (see Example 2) and 1935 (see Example 3), respectively, but with modified PCR primers specifically designed for HA B Wisconsin (PrL-). The amino acid sequence of HA B Wisconsin (PrL-) with his native signal peptide is presented in FIG. 18B (SEQ ID NO: 56). Representations of plasmid 1445, 1820 and 1975 are presented in FIGS. 18C, 18D and 18E, respectively.

Example 14

2X35S/CPMV HT (Construct No 1454) and 2X35S/CPMV160+ (Construct No 1893) for HA B Wisconsin (PrL-)+H1 California TMCT A chimer hemagglutinin coding sequence corresponding to the ectodomain of HA from Influenza B/Wisconsin/2/2012 with deleted proteolytic loop (PrL-) (see U.S. provisional application No. 61/806,227 Filed Mar. 28, 2013 for additional information re: deleted proteolytic loop regions in HA sequences, which is incorporated herein by reference) fused to the transmembrane domain and cytoplasmic tail (TMCT) of H1 from influenza A/California/7/2009 with the native signal peptide of HA B Wisconsin (HA B Wisconsin (PrL-)+H1 California TMCT) (FIG. 19A, SEQ ID NO: 57) was cloned into original CPMV-HT and CPMV160+ using the same PCR-based method as construct 1391 (see Example 1), and 1800 (see Example 2), respectively, but with modified PCR primers specifically designed for HA B Wisconsin (PrL-)+H1 California TMCT. The amino acid sequence of HA B Wisconsin (PrL-)+H1 California TMCT is presented in FIG. 19B (SEQ ID NO: 58). Representations of plasmid 1454 and 1893 are presented in FIGS. 19C and 19D.

Example 15

2X35S/CPMV HT (Construct No 5001) and 2X35S/CPMV160+ (Construct No 2100) for HC Rituximab (Rituxan)

A coding sequence corresponding to the heavy chain of monoclonal IgG1 antibody Rituximab (HC rituximab (Rituxan); FIG. 20A, SEQ ID NO: 59) was cloned into original CPMV-HT and CPMV160+ using the same PCR-based method as construct 1391 (see Example 1), and 1800 (see Example 2), respectively but with modified PCR primers specifically designed for HC rituximab (Rituxan). The amino acid sequence of HC rituximab (Rituxan) is presented in FIG. 20B (SEQ ID NO:60). Representations of plasmid 5001 and 2100 are presented in FIG. 20C and FIG. 20D.

Example 16

2X35S/CPMV HT (Construct No 5002) and 2X35S/CPMV160+ (Construct No 2109) for PDISP/HC Rituximab (Rituxan)

A coding sequence corresponding to the heavy chain of monoclonal IgG1 antibody Rituximab in which the native signal peptide has been replaced by that of alfalfa protein disulfide isomerase (PDISP/HC rituximab (Rituxan); FIG. 21A, SEQ ID NO: 61) was cloned into original CPMV-HT and CPMV160+ using the same PCR-based method as construct 1391 and 1800, respectively but with modified PCR primers specifically designed for PDISP/HC rituximab (Rituxan). The amino acid sequence of mature HC rituximab (Rituxan) fused with PDISP is presented in FIG. 21B (SEQ ID NO: 62). Representations of plasmid 5002 and 2109 are presented in FIG. 21C and FIG. 21D.

Example 17

2X35S/CPMV-HT (Construct No 5021) and 2X35S/CPMV160+ (Construct No 2120) for LC Rituximab (Rituxan)

A coding sequence corresponding to the light chain of monoclonal IgG1 antibody Rituximab (LC rituximab (Rituxan; FIG. 22A, SEQ ID NO: 63) was cloned into original CPMV-HT and CPMV160+ using the same PCR-based method as construct 1391 and 1800, respectively but with modified PCR primers specifically designed for LC rituximab (Rituxan). The amino acid sequence of LC rituximab (Rituxan) is presented in FIG. 22B (SEQ ID NO: 64). Representations of plasmid 5021 and 2120 are presented in FIG. 22C and FIG. 22D.

Example 18

2X35S/CPMV-HT (Construct No 5022) and 2X35S/CPMV160+ (Construct No 2129) for PDISP/LC Rituximab (Rituxan)

A coding sequence corresponding to the light chain of monoclonal IgG1 antibody Rituximab in which the native signal peptide has been replaced by that of alfalfa protein disulfide isomerase (PDISP/LC rituximab (Rituxan; FIG. 23A, SEQ ID NO: 65) was cloned into original CPMV-HT and CPMV160+ using the same PCR-based method as construct 1391 and 1800, respectively but with modified PCR primers specifically designed for PDISP/LC rituximab (Rituxan). The amino acid sequence of mature LC rituximab (Rituxan) fused with PDISP is presented in FIG. 23B (SEQ ID NO: 66). Representations of plasmid 5022 and 2129 are presented in FIG. 23C and FIG. 23D.

Example 19

*Agrobacterium* Transfection

*Agrobacterium* strain AGL1 was transfected by electroporation with the DNA constructs using the methods described by D'Aoust et al 2008 (*Plant Biotechnology Journal* 6:930-940). Transfected *Agrobacterium* were grown in YEB medium supplemented with 10 mM 2-(N-morpholino)ethanesulfonic acid (MES), 20 μM acetosyringone, 50 μg/ml kanamycin and 25 μg/ml of carbenicillin pH5.6 to an $OD_{600}$ between 0.6 and 1.6. *Agrobacterium* suspensions were centrifuged before use and resuspended in infiltration medium (10 mM $MgCl_2$ and 10 mM MES pH 5.6).

Preparation of Plant Biomass, Inoculum and Agroinfiltration

*Nicotiana benthamiana* plants were grown from seeds in flats filled with a commercial peat moss substrate. The plants were allowed to grow in the greenhouse under a 16/8 photoperiod and a temperature regime of 25° C. day/20° C. night. Three weeks after seeding, individual plantlets were picked out, transplanted in pots and left to grow in the greenhouse for three additional weeks under the same environmental conditions.

*Agrobacteria* transfected with each construct were grown in a YEB medium supplemented with 10 mM 2-(N-morpholino)ethanesulfonic acid (MES), 20 μM acetosyringone, 50 μg/ml kanamycin and 25 μg/ml of carbenicillin pH5.6 until they reached an $OD_{600}$ between 0.6 and 1.6. *Agrobacterium* suspensions were centrifuged before use and resuspended in infiltration medium (10 mM $MgCl_2$ and 10 mM MES pH 5.6) and stored overnight at 4° C. On the day of infiltration, culture batches were diluted in 2.5 culture volumes and allowed to warm before use. Whole plants of *N. benthamiana* were placed upside down in the bacterial suspension in an air-tight stainless steel tank under a vacuum of 20-40 Torr for 2-min. Plants were returned to the greenhouse for a 2-6 day incubation period until harvest.

Leaf Harvest and Total Protein Extraction

Following incubation, the aerial part of plants was harvested, frozen at −80° C. and crushed into pieces. Total soluble proteins were extracted by homogenizing (Polytron) each sample of frozen-crushed plant material in 3 volumes of cold 50 mM Tris pH 8.0, 0.15 M NaCl, 0.1% Triton X-100 and 1 mM phenylmethanesulfonyl fluoride. After homogenization, the slurries were centrifuged at 10,000 g for 10 min at 4° C. and these clarified crude extracts (supernatant) kept for analyses.

Example 20

Protein Analysis and Immunoblotting

The total protein content of clarified crude extracts was determined by the Bradford assay (Bio-Rad, Hercules, Calif.) using bovine serum albumin as the reference standard. Proteins were separated by SDS-PAGE and electrotransferred onto polyvinylene difluoride (PVDF) membranes (Roche Diagnostics Corporation, Indianapolis, Ind.) for immunodetection. Prior to immunoblotting, the membranes were blocked with 5% skim milk and 0.1% Tween-20 in Tris-buffered saline (TBS-T) for 16-18 h at 4° C.

Immunoblotting was performed with a first incubation with a primary antibody (Table 4 presents the antibodies and conditions used for the detection of each HA), in 2 μg/ml in 2% skim milk in TBS-Tween 20 0.1%. Secondary antibodies used for chemiluminescence detection were as indicated in Table 4, diluted as indicated in 2% skim milk in TBS-Tween 20 0.1% Immunoreactive complexes were detected by chemiluminescence using luminol as the substrate (Roche Diagnostics Corporation).

TABLE 4

Electrophoresis conditions, antibodies, and dilutions for immunoblotting of expressed proteins.

| HA subtype | Influenza strain | Electrophoresis condition | Primary antibody | Dilution | Secondary antibody | Dilution |
|---|---|---|---|---|---|---|
| B | B/Brisbane/60/2008 | Non-reducing | NIBSC 10/146 | 1:20000 | Rabbit anti-sheep (JIR 313-035-045) | 1:10 000 |
| B | B/Wisconsin/1/2010 | Non-reducing | NIBSC 07/356 | 1:2000 | Rabbit anti-sheep (JIR 313-035-045) | 1:10 000 |
| B | B/ Massachussetts/2/2012 | Non-reducing | NIBSC 07/356 | 1:2000 | Rabbit anti-sheep (JIR 313-035-045) | 1:10 000 |
| H7 | A/ Hangzhou/1/2013 (H7N9)) | Non-reducing | ITC, IT-003-008M6 | 1:5000 | Goat anti-mouse (JIR 115-035-146) | 1:5 000 |
| H3 | A/Victoria/361/2011 | Non-reducing | TGA, AS400 | 1:20000 | Rabbit anti-sheep (JIR 313-035-045) | 1:10 000 |
| H1 | A/California/07/2009 (H1N1) | Reducing | NIBSC 11/110 | 1 μg/ml | Rabbit anti-sheep (JIR 313-035-045 | 1:7 500 |
| H5 | A/Indonesia/05/2005 (H5N1) | Reducing | CBER, S-7858 | 1:4000 | Rabbit anti-sheep (JIR 313-035-045) | 1:10 000 |

JIR: Jackson ImmunoResearch, West Grove, PA, USA;
CBER: Center for Biologics Evaluation and Research, Rockville, MD, USA.
Sino: Sino Biological inc., Beijing, China.
TGA: Therapeutic Goods Administration, Australia.
NIBSC: National Institute for Biological Standards and Control, United Kingdom
ITC: Immune Technology Corp., New York, NY, USA

Example 21

Hemagglutination Assay

Hemagglutination assay was based on a method described by Nayak and Reichl (2004). Briefly, serial double dilutions of the test samples (100 μL) were made in V-bottomed 96-well microtiter plates containing 100 μL PBS, leaving 100 μL of diluted sample per well. One hundred microliters of a 0.25% turkey red blood cells suspension (Bio Link Inc., Syracuse, N.Y.; for all B strains, H1, H5 and H7) or 0.5% guinea pig red blood cells suspension (for H3) were added to each well, and plates were incubated for 2 h at room temperature. The reciprocal of the highest dilution showing complete hemagglutination was recorded as HA activity.

All citations are hereby incorporated by reference.

The present invention has been described with regard to one or more embodiments. However, it will be apparent to persons skilled in the art that a number of variations and modifications can be made without departing from the scope of the invention as defined in the claims.

What is claimed is:

1. A nucleic acid molecule comprising:

a first portion consisting of nucleotides 1-160 of SEQ ID NO:1 having a substitution of G1 15A, and a second portion encoding a heterologous protein of interest, the second portion operatively linked to and fused immediately to the 3' end of the first portion, wherein transient expression of the nucleic acid molecule in a *Nicotiana benthamiana* plant increases a yield of the heterologous protein of interest, compared to transient expression of a comparative nucleic acid molecule comprising a corresponding first portion consisting of SEQ ID NO:4 in a comparative plant.

2. A plant expression system comprising the nucleic acid molecule of claim 1 or a vector comprising the nucleic acid molecule of claim 1.

3. The plant expression system of claim 2, wherein the nucleic acid molecule or vector further comprises a comovirus 3' UTR.

4. The plant expression system of claim 2, wherein the heterologous protein of interest is a viral protein or an antibody.

5. The plant expression system of claim 4, wherein the viral protein is an influenza hemagglutinin selected from the group consisting of H1, H2, H3, H4, H5, H6, H7, H8, H9, H10, H11, H12, H13, H14, H15, H16, and influenza type B hemagglutinin.

6. A method of producing a protein of interest in a plant or in a portion of a plant comprising, introducing into the plant or in the portion of a plant the plant expression system of claim 2, and incubating the plant or the portion of a plant under conditions that permit expression of the heterologous protein of interest.

7. A plant or portion of a plant transiently transfected or stably transformed with the plant expression system of claim 2.

8. The nucleic acid molecule of claim 1, wherein the heterologous protein of interest is a viral protein or an antibody.

9. The nucleic acid molecule of claim 8, wherein the viral protein is an influenza hemagglutinin selected from the group consisting of H1, H2, H3, H4, H5, H6, H7, H8, H9, H10, H11, H12, H13, H14, H15, H16, and influenza type B hemagglutinin.

10. The plant expression system of claim 2, further comprising a second nucleic acid molecule, the second nucleic acid molecule comprising a nucleotide sequence encoding a suppressor of silencing.

11. The plant expression system of claim 10 wherein the suppressor of silencing is selected from the group HcPro and p19 suppressor of silencing.

* * * * *

UNITED STATES PATENT AND TRADEMARK OFFICE
CERTIFICATE OF CORRECTION

| | |
|---|---|
| PATENT NO. | : 11,441,150 B2 |
| APPLICATION NO. | : 15/110696 |
| DATED | : September 13, 2022 |
| INVENTOR(S) | : Pierre-Olivier Lavoie et al. |

It is certified that error appears in the above-identified patent and that said Letters Patent is hereby corrected as shown below:

In the Specification

Column 4, Line 39, "GOT" should be --GOI--.

Column 4, Line 54, "GOT" should be --GOI--.

Column 5, Line 57, "GOT" should be --GOI--.

Column 13, Line 31, "+1-10%" should be --+/-10%--.

Column 25, Line 29, "GOT" should be --GOI--.

Column 25, Line 55, "GOT" should be --GOI--.

Column 27, Line 41, "(GOT)" should be --(GOI)--.

Column 38, Line 8, "DRS" should be --DR5--.

Column 39, Line 22, "Bluebeffy" should be --Blueberry--.

Column 41, Line 2, "here" should be --where--.

Signed and Sealed this
Fifteenth Day of November, 2022

Katherine Kelly Vidal
*Director of the United States Patent and Trademark Office*